(12) United States Patent
Claremon et al.

(10) Patent No.: US 9,868,748 B2
(45) Date of Patent: Jan. 16, 2018

(54) THIAZOLOPYRROLIDINE INHIBITORS OF ROR-γ

(71) Applicant: Vitae Pharmaceuticals, Inc., Fort Washington, PA (US)

(72) Inventors: David A. Claremon, Maple Glen, PA (US); Lawrence Wayne Dillard, Yardley, PA (US); Chengguo Dong, Staten Island, NY (US); Yi Fan, Doylestown, PA (US); Lanqi Jia, Horsham, PA (US); Stephen D. Lotesta, Burlington, NJ (US); Andrew Marcus, Media, PA (US); Suresh B. Singh, Kendall Park, NJ (US); Colin M. Tice, Maple Glen, PA (US); Jing Yuan, Lansdale, PA (US); Wei Zhao, North Potomac, MD (US); Yajun Zheng, Hockessin, DE (US); Linghang Zhuang, Chalfont, PA (US)

(73) Assignee: Vitae Pharmaceuticals, Inc., Parsippany, NJ (US)

( * ) Notice: Subject to any disclaimer, the term of this patent is extended or adjusted under 35 U.S.C. 154(b) by 0 days.

(21) Appl. No.: 14/888,129

(22) PCT Filed: May 1, 2014

(86) PCT No.: PCT/US2014/036361
§ 371 (c)(1),
(2) Date: Oct. 30, 2015

(87) PCT Pub. No.: WO2014/179564
PCT Pub. Date: Nov. 6, 2014

(65) Prior Publication Data
US 2017/0008910 A1 Jan. 12, 2017

Related U.S. Application Data

(60) Provisional application No. 61/818,266, filed on May 1, 2013.

(51) Int. Cl.
C07D 513/04 (2006.01)
C07D 519/00 (2006.01)

(52) U.S. Cl.
CPC ......... C07D 513/04 (2013.01); C07D 519/00 (2013.01)

(58) Field of Classification Search
CPC .................................................... C07D 513/04
USPC .................................................... 514/210.21
See application file for complete search history.

(56) References Cited

FOREIGN PATENT DOCUMENTS

| EP | 2327704 A1 | 6/2011 |
|---|---|---|
| WO | 03/062241 A1 | 7/2003 |
| WO | 2007087231 A2 | 8/2007 |
| WO | 2012/100734 A1 | 8/2012 |
| WO | 2015101928 A | 7/2015 |

OTHER PUBLICATIONS

Hynes J. et al. "The discrobery of (R)-2-(sec-butylamino)-N-(2-methyl-5-(methylcarbamoyl)phenyl) thiazole-5-carboxamide (BMS-640994)—A potent and efficacious p38alpha MAP kinase inhibitor", Bioorg Med Chem Lett, 18, Mar. 15, 2008, pp. 1762-1767.

Primary Examiner — Taofiq A Solola
(74) Attorney, Agent, or Firm — McCarter & English, LLP; Steven G. Davis; Michael J. DeGrazia

(57) ABSTRACT

Provided are novel compounds of Formula (I): pharmaceutically acceptable salts thereof, and pharmaceutical compositions thereof, which are useful in the treatment of diseases and disorders mediated by RORγ. Also provided are pharmaceutical compositions comprising the novel compounds of Formula (I) and methods for their use in treating one or more inflammatory, metabolic, autoimmune and other diseases or disorders.

19 Claims, No Drawings

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
aaagtaggtc a                                                          11

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 2

His His His His His His
1               5
```

THIAZOLOPYRROLIDINE INHIBITORS OF ROR-γ

REFERENCE TO RELATED APPLICATIONS

This application is a 35 U.S.C. §371 national stage filing of International Application No. PCT/US2014/036361, filed May 1, 2014, which claims the benefit of U.S. Provisional Application No. 61/818,266, filed May 1, 2013, the entire content of each of which is incorporated herein by reference.

SEQUENCE LISTING

The instant application contains a Sequence Listing which has been submitted electronically in ASCII format and is hereby incorporated by reference in its entirety. Said ASCII copy, created on Mar. 14, 2016, is named 121374-00302_SL.txt and is 766 bytes in size.

TECHNICAL FIELD OF THE INVENTION

The present invention is directed to novel retinoic acid receptor-related orphan receptor gamma ("RORγ" or "ROR-gamma") inhibitors, processes for their preparation, pharmaceutical compositions containing these inhibitors, and their use in the treatment of inflammatory, metabolic, autoimmune and other diseases mediated by RORγ.

BACKGROUND OF THE INVENTION

Retinoic acid receptor-related orphan receptors (RORs) are a subfamily of transcription factors in the steroid hormone nuclear receptor superfamily (Jetten & Joo (2006) Adv. Dev. Biol. 2006, 16, 313-355). The ROR family consists of ROR alpha (RORα), ROR beta (RORβ) and ROR gamma (RORγ), each encoded by a separate gene (in human: RORA, RORB and RORC, respectively; in mouse: rora, rorb and rorc, respectively). RORs contain four principal domains shared by the majority of nuclear receptors: an N-terminal domain, a highly conserved DNA-binding domain (DBD) consisting of two zinc finger motifs, a hinge domain, and a ligand binding domain (LBD). Each ROR gene generates several isoforms, differing only in their N-terminal domains. RORγ has two isoforms: RORγ1 and RORγ2 (also known as RORγt). RORγ refers to RORγ1 and/or RORγt. RORγ1 is expressed in a variety of tissues including thymus, muscle, kidney and liver, but RORγt is exclusively expressed in the cells of the immune system, has a critical role in thymopoiesis and the development of several secondary lymphoid tissues, and is a key regulator of Th17 cell differentiation (Jetten, 2009, Nucl. Recept. Signal., 7:e003, doi:10.1621/nrs.07003. Epub 2009 Apr. 3).

Th17 cells are a subset of T helper cells which preferentially produce the pro-inflammatory cytokines IL-17A, IL-17F, IL-21 and IL-22. Th17 cells and their effector molecules, such as IL-17, IL-21, IL-22, GM-CSF and CCL20, are associated with the pathogenesis of several autoimmune and inflammatory diseases, such as rheumatoid arthritis, systemic lupus erythematosus, multiple sclerosis, psoriasis, inflammatory bowel disease, allergy and asthma (Maddur et al., 2012, Am. J. Pathol., 181:8-18). Recent findings support a role for IL17 and Th17 cells in the pathogenesis of acne (Thiboutot et al., 2014, J. Invest. Dermatol., 134(2):307-10, doi: 10.1038/jid.2013.400; Agak et al., 2014, J. Invest. Dermatol., 134(2):366-73, doi: 10.1038/jid.2013.334, Epub 2013 Aug. 7). Th17 cells are also potent inducers of inflammation associated with endometriosis, a chronic inflammatory disease (Hirata et al., 2010, Endocrinol., 151:5468-5476; Hirata et al., 2011, Fertil Steril., July; 96(1):113-7, doi: 10.1016/j.fertnstert.2011.04.060, Epub 2011 May 20). Additionally, Th17 cells have a key role in the mouse autoimmune models of experimental autoimmune encephalomyelitis (EAE), collagen-induced arthritis (CIA) and adjuvant-induced arthritis (AIA) (Bedoya et al., 2013, Clin. Dev. Immunol., 2013: 986789. Epub 2013 Dec. 26. Th17 cells are activated during inflammatory and autoimmune disease processes and are responsible for recruiting other inflammatory cell types, particularly neutrophils, to mediate pathology in target tissues (Miossec & Kolls, 2012, Nature Rev., 11:763-776; Korn et al., 2009, Annu. Rev. Immunol., 27:485-517). Aberrant Th17 cell function has been implicated in a variety of autoimmune diseases, including multiple sclerosis and rheumatoid arthritis. Autoimmune disease is believed to arise from the disruption of the equilibrium between effector and regulatory T cells (Solt et al., ACS Chem Biol. 2012 Sep. 21; 7(9):1515-1519, Epub 2012 July 9). The importance of RORγt to Th17 cell differentiation and the pathogenic role of Th17 cells is evidenced by the fact that RORγt-deficient mice have very few Th17 cells and have a reduction in severity of EAE (Ivanov et al., 2006, Cell, 126:1121-1133).

Circadian rhythms are daily cycles of behavioral and physiological changes that are regulated by endogenous circadian clocks. A number of studies have established links between nuclear receptor (including RORγ) function and expression, the circadian regulatory circuitry, and the regulation of various physiological processes (Jetten (2009) op. cit.).

Obstructive sleep apnea syndrome (OSAS) is a chronic inflammatory disease regulated by T lymphocytes. OSAS patients have a significant increase in peripheral Th17 cell frequency, IL-17 and RORγt levels (Ye et al., 2012, Mediators Inflamm., 815308, doi: 10.1155/2012/815308, Epub 2012 Dec. 31).

A number of studies have provided evidence of a role of RORs in cancer. Mice deficient in the expression of RORγ exhibit a high incidence of thymic lymphomas that metastasize frequently to liver and spleen. High expression of Th17-associated genes (including RORγ) and high levels of Th17 cells in the tumor microenvironment has been shown to correlate with a poor prognosis in various cancers, including lung, gastric, breast and colon cancer (Tosolini et al., 2011, Cancer Res., 71:1263-1271, doi: 10.1158/0008-5472.CAN-10-2907, Epub 2011 Feb. 8; Su et al., 2014, Immunol. Res., 58:118-124, doi: 10.1007/s12026-013-8483-y, Epub 2014 Jan. 9; Carmi et al., 2011, J. Immunol., 186:3462-3471, doi: 10.4049/jimmunol.1002901, Epub 2011 Feb. 7; Chen et al., 2013, Histopathology, 63:225-233, doi: 10.1111/his.12156, Epub 2013 Jun. 6).

RORγ has also been identified to have a regulatory role in lipid/glucose homeostasis, and has been implicated in metabolic syndrome, obesity (Meissburger et al., 2011, EMBO Mol. Med., 3:637-651), hepatosteatosis, insulin resistance and diabetes.

Further support for the role of RORγ in the pathogenesis of inflammatory, metabolic, circadian effect, cancer, and autoimmune diseases and disorders can be found in the following references: Chang et al., 2012, J. Exp. Pharmacol., 4:141-148; Jetten et al., 2013, Frontiers Endocrinol., 4:1-8; Huh & Littman, 2012, Eur. J. Immunol., 42:2232-2237; Martinez et al., 2008, Ann. N.Y. Acad. Sci., 1143:188-211; Pantelyushin et al., 2012, J. Clin. Invest., 122:2252-2256;

Jetten & Ueda, 2002, Cell Death Differen., 9:1167-1171; Solt et al., 2010, Curr. Opin. Lipidol., 21:204-211.

In light of the role that RORγ plays in disease pathogenesis, inhibition of RORγ activity and Th17 cell differentiation and activity will be of significant therapeutic benefit. It is therefore desirable to prepare compounds that inhibit RORγ activity and hence have utility in the treatment of inflammatory, autoimmune, metabolic, circadian effect, cancer, and other diseases mediated by RORγ, such as e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus, scleroderma, psoriasis, psoriatic arthritis, steroid resistant asthma and rheumatoid arthritis.

SUMMARY OF THE INVENTION

It has now been found that compounds described herein, and pharmaceutically acceptable compositions thereof, are effective inhibitors of RORγ. Such compounds include those of Formula (I):

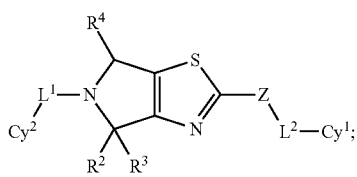

or a pharmaceutically acceptable salt thereof, wherein each of Z, $R^2$, $R^3$, $R^4$, $L^1$, $L^2$, $Cy^1$, and $Cy^2$ are as defined and described herein.

The provided compounds, and pharmaceutically acceptable compositions thereof, are inverse agonists or antagonists of RORγ and are useful for treating a variety of diseases, disorders or conditions. Such diseases, disorders, or conditions include those described herein.

The provided compounds can be used alone (i.e., as a monotherapy) or in combination with one or more other therapeutic agent effective for treating any of the indications described herein.

DETAILED DESCRIPTION OF CERTAIN EMBODIMENTS

1. General Description of Compounds of the Invention

In certain embodiments, the present invention provides a compound of Formula (I):

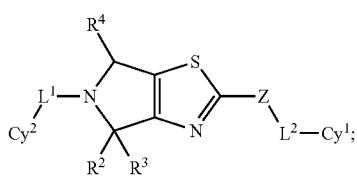

or a pharmaceutically acceptable salt thereof, wherein:
Z is —C(O)NR$^1$—, —NR$^1$C(O)—, —NR$^1$—, or NR$^1$SO$_2$;

$R^1$ is hydrogen or ($C_1$-$C_3$)alkyl;
$L^1$ and $L^2$ are each independently a bond or ($C_1$-$C_3$) alkylene optionally substituted with ($C_1$-$C_2$)alkyl or spirocyclopropane;
$R^2$ is ($C_1$-$C_6$)alkyl, halo($C_1$-$C_6$)alkyl, phenyl, benzyl, heteroaryl, monocyclic cycloalkyl or monocyclic heterocyclyl, each optionally substituted with 1 to 2 groups independently selected from CN, halo, hydroxyl, ($C_1$-$C_6$)alkyl, halo($C_1$-$C_6$)alkyl, ($C_1$-$C_6$)alkoxy, oxo, and halo($C_1$-$C_6$)alkoxy;
$R^3$ is hydrogen or ($C_1$-$C_3$)alkyl;
$Cy^1$ is aryl or heteroaryl, each of which is optionally substituted with 1 to 3 groups independently selected from $R^5$;
$R^4$ is hydrogen or ($C_1$-$C_3$)alkyl; and
$Cy^2$ is aryl, heteroaryl, monocyclic cycloalkyl, or monocyclic heterocyclyl, wherein the aryl and heteroaryl are each optionally fused with a monocyclic heterocyclyl or monocyclic cycloalkyl, and wherein $Cy^2$ is optionally substituted with 1 to 3 groups independently selected from $R^6$; and
$R^5$ and $R^6$ are each independently selected from halo, cyano, nitro, amino, hydroxy, carboxy, ($C_1$-$C_6$)alkyl, heterocyclyl, hydroxy($C_1$-$C_6$)alkyl, $CO_2H$, $(CH_2)_{1-3}COOH$, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy ($C_2$-$C_6$)alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$) cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkylsulfinyl, ($C_3$-$C_6$)cycloalkylsulfinyl, ($C_4$-$C_7$)cycloalkylalkylsulfinyl, halo($C_1$-$C_6$)alkylesulfinyl, halo($C_3$-$C_6$)cycloalkylsulfinyl, halo($C_4$-$C_7$)cycloalkylalkylsulfinyl, ($C_1$-$C_6$)alkylsulfonyl, ($C_3$-$C_6$) cycloalkylsulfonyl, ($C_4$-$C_7$)cycloalkylalkylsulfonyl, halo ($C_1$-$C_6$)alkylsulfonyl, halo($C_3$-$C_6$)cycloalkylsulfonyl, halo ($C_4$-$C_7$)cycloalkylalkylsulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$) alkylaminosulfonyl, heterocyclylsulfonyl, ($C_1$-$C_6$) alkylcarbonylamino, ($C_1$-$C_6$)alkyl-carbonylamino($C_1$-$C_6$) alkyl, ($C_1$-$C_6$)alkylsulfonylamino, ($C_1$-$C_6$) alkylsulfonylamino($C_1$-$C_6$)alkyl, ($C_1$-$C_6$)alkoxycarbonyl ($C_1$-$C_6$)alkoxy, ($C_1$-$C_6$)alkoxy($C_1$-$C_6$)alkyl, halo($C_1$-$C_6$) alkoxy($C_1$-$C_6$)alkyl, hydroxy($C_1$-$C_6$)alkoxy, aryl, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$) alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$) cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylamino sulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl ($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl.

2. Compounds and Definitions

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example, N (as in 3,4-dihydro-2H-pyrrolyl), NH (as in pyrrolidinyl) or NR$^+$ (as in N-substituted pyrrolidinyl)).

The terms "halo" and "halogen" as used herein refer to an atom selected from fluorine (fluoro, —F), chlorine (chloro, —Cl), bromine (bromo, —Br), and iodine (iodo, —I).

The term "alkyl", used alone or as a part of a larger moiety such as e.g., "haloalkyl", means a saturated monovalent straight or branched hydrocarbon radical having, unless otherwise specified, 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like. "Monovalent" means attached to the rest of the molecule at one point.

The term "haloalkyl" or "halocycloalkyl" include mono, poly, and perhaloalkyl groups where the halogens are independently selected from fluorine, chlorine, and bromine.

The term "alkylene" means a bivalent saturated straight or branched hydrocarbon radical. Unless otherwise indicated, an alkylene group has 1-3 carbon atoms. "Bivalent" means attached to the rest of the molecule at two points.

The terms "cycloalkyl", "cycloaliphatic", "carbocycle", "carbocyclyl", "carbocyclo", or "carbocyclic", used alone or as part of a larger moiety, refer to a saturated cyclic aliphatic monocyclic or bicyclic ring system, as described herein, having from, unless otherwise specified, 3 to 10 carbon ring atoms. Monocyclic cycloalkyl groups include, without limitation, cyclopropyl, cyclobutyl, cyclopentyl, cyclopentenyl, cyclohexyl, cyclohexenyl, cycloheptyl, cycloheptenyl, and cyclooctyl.

The term "aryl" used alone or as part of a larger moiety as in "aralkyl", "aralkoxy", or "aryloxyalkyl", refers to an aromatic carbocyclic ring system having, unless otherwise specified, a total of 6 to 10 ring members. The term "aryl" may be used interchangeably with the term "aryl ring". In certain embodiments of the present invention, "aryl" refers to an aromatic ring system which includes, but is not limited to, phenyl (abbreviated as "Ph"), naphthyl and the like.

The term "heteroaryl" means a 5-10-membered aromatic radical containing 1-4 heteroatoms selected from N, O, and S and includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl rings, where the radical or point of attachment is on the heteroaromatic ring. Nonlimiting examples include indolyl, indazolyl, benzimidazolyl, benzthiazolyl, quinolyl, quinazolinyl, and quinoxalinyl. A heteroaryl group may be mono- or bicyclic. The term "heteroaryl" may be used interchangeably with the terms "heteroaryl ring", "heteroaryl group", or "heteroaromatic".

The term "heterocyclyl" means a 4-, 5-, 6- and 7-membered saturated or partially unsaturated heterocyclic ring containing 1 to 4 heteroatoms independently selected from N, O, and S. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, tetrahydropyranyl, pyrrolidinyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, and tetrahydropyrimidinyl. The terms "heterocycle", "heterocyclyl", "heterocyclyl ring", "heterocyclic group", "heterocyclic moiety", and "heterocyclic radical", are used interchangeably herein. A heterocyclyl group may be mono- or bicyclic.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "St," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, e.g., the acetate, benzenesulfonate, benzoate, bicarbonate, bitartrate, carbonate, citrate, dihydrochloride, gluconate, glutamate, glycollylarsanilate, hexylresorcinate, hydrobromide, hydrochloride, malate, maleate, malonate, mesylate, nitrate, salicylate, stearate, succinate, sulfate, tartrate, and tosylate.

3. Description of Exemplary Compounds

In a first embodiment, the present invention provides a compound of Formula (I):

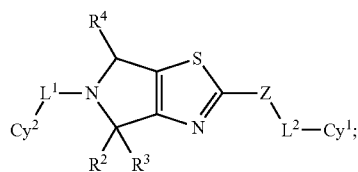
(I)

or a pharmaceutically acceptable salt thereof, wherein variables are as described above.

In a third embodiment, the compound of Formula (I) is of Formula (Ia):

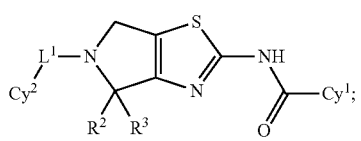
(Ia)

or a pharmaceutically acceptable salt thereof, wherein the variables in structural Formula (Ia) are as described for Formula (I).

In a fourth embodiment, the compound of Formula (I) is of Formula (Ia'):

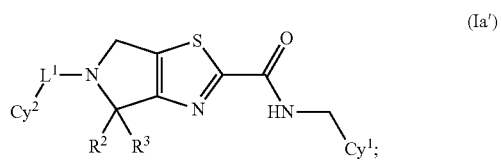
(Ia')

or a pharmaceutically acceptable salt thereof, wherein the variables in structural Formula (Ia') are as described for Formula (I).

In a fifth embodiment, the compound of Formula (I) is of Formula (Ib):

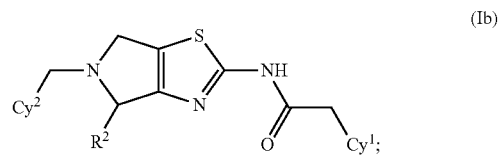
(Ib)

or a pharmaceutically acceptable salt thereof, wherein the variables in structural Formulae (Ib) are as described for Formula (I).

In a sixth embodiment, the compound of Formula (I) is of Formula (Ib'):

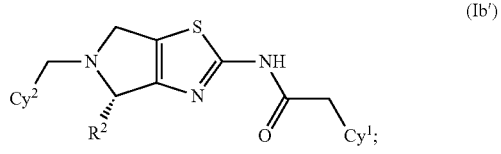
(Ib')

or a pharmaceutically acceptable salt thereof, wherein the variables in structural Formulae (Ib') are as described for Formula (I).

In a seventh embodiment, the compound of Formula (I) is of Formula (Ib"):

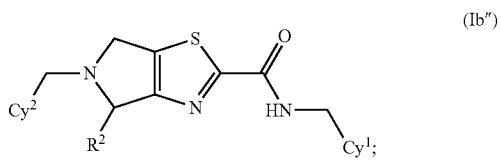
(Ib")

or a pharmaceutically acceptable salt thereof, wherein the variables in structural Formulae (Ib") are as described for Formula (I).

In an eighth embodiment, the compound of Formula (I) is of Formula (Ib'''):

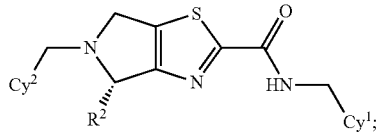
(Ib''')

or a pharmaceutically acceptable salt thereof, wherein the variables in structural Formulae (Ib''') are as described for Formula (I).

In a ninth embodiment, $Cy^1$ in Formulas (I), (Ia), (Ia'), (Ib), (Ib'), (Ib''), and (Ib''') is phenyl, pyridinyl, or pyrimidinyl, each of which is optionally substituted with 1 to 3 groups independently selected from $R^5$, wherein the remainder of the variables are as described in Formula (I).

In a tenth embodiment, $Cy^2$ in Formulas (I), (Ia), (Ia'), (Ib), (Ib'), (Ib''), and (Ib''') is phenyl, pyridinyl, pyrimidinyl, cyclohexyl, or oxadiazolyl, each of which are optionally substituted with 1 to 3 groups independently selected from $R^6$, wherein the remainder of the variables are as described in Formula (I) and the ninth embodiment.

In an eleventh embodiment, $R^5$ in Formulas (I), (Ia), (Ia'), (Ib), (Ib'), (Ib''), and (Ib''') is selected from halo, cyano, $(C_1-C_3)$alkyl, halo$(C_1-C_3)$alkyl, hydroxy$(C_1-C_3)$alkyl, $(C_1-C_6)$alkoxy, halo$(C_1-C_6)$alkoxy, $CO_2H$, $(CH_2)_{1-3}COOH$, and $(C_1-C_3)$alkylsulfonyl, wherein the remainder of the variables are as described in Formula (I) and the ninth and tenth embodiment.

In a twelfth embodiment, $R^2$ in Formulas (I), (Ia), (Ia'), (Ib), (Ib'), (Ib''), and (Ib''') is isopropyl, isobutyl, sec-butyl, phenyl, benzyl, cyclopropyl, tetrahydrofuranyl, or tetrahydropyranyl, wherein the phenyl and benzyl are each optionally substituted with 1 to 2 groups independently selected from CN, halo, $(C_1-C_6)$alkyl, halo$(C_1-C_6)$alkyl, $(C_1-C_6)$alkoxy, and halo$(C_1-C_6)$alkoxy, wherein the remainder of the variables are as described in Formula (I) and the ninth, tenth, and eleventh embodiment.

In a thirteenth embodiment, $Cy^1$ in Formulas (I), (Ia), (Ia'), (Ib), (Ib'), (Ib''), and (Ib''') is phenyl, 2-pyridinyl, or 2-pyrimidinyl, each of which is optionally substituted with 1 to 2 groups independently selected from halo, $(C_1-C_3)$ alkyl, $(CH_2)_{1-3}COOH$, $(C_1-C_3)$alkylsulfonyl, cyano, or hydroxy$(C_1-C_3)$alkyl; and $R^2$ is isopropyl, isobutyl, sec-butyl, phenyl, benzyl, or cyclopropyl, wherein the phenyl and benzyl are each optionally substituted with 1 to 2 groups independently selected from CN, halo, $(C_1-C_3)$alkyl, and $(C_1-C_3)$alkoxy, wherein the remainder of the variables are as described in Formula (I) and the ninth, tenth, eleventh, and twelfth embodiment.

In a fourteenth embodiment, $Cy^1$ in Formulas (I), (Ia), (Ia'), (Ib), (Ib'), (Ib''), and (Ib''') is phenyl optionally substituted with 1 to 2 groups independently selected from halo, $(C_1-C_3)$alkyl, $CH_2COOH$, $(C_1-C_3)$alkylsulfonyl, cyano, or hydroxy$(C_1-C_3)$alkyl; and $R^2$ is isopropyl, isobutyl, sec-butyl, phenyl, benzyl, or cyclopropyl, wherein the phenyl and benzyl are each optionally substituted with 1 to 2 groups independently selected from CN, halo, $(C_1-C_3)$alkyl, and $(C_1-C_3)$alkoxy, wherein the remainder of the variables are as described in Formula (I) and the ninth, tenth, eleventh, twelfth, and thirteenth embodiment.

In a fifteenth embodiment, the compound of Formula (I) is of Formula (Ic) or (Ic'):

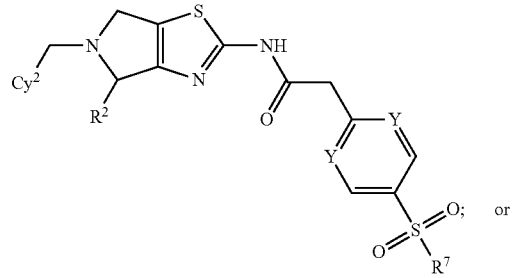
(Ic)

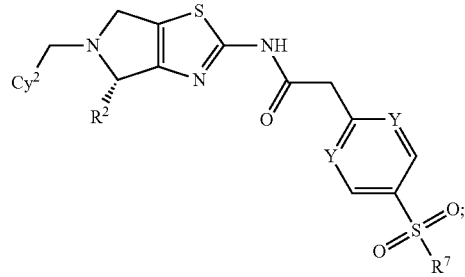
(Ic')

or a pharmaceutically acceptable salt thereof, wherein each Y in Formulas (Ic) and (Ic') is independently CH, $CR^5$ or N; and $R^7$ is $(C_1-C_3)$alkyl, wherein the remaining variables of structural Formula (Ic) and (Ic') are as described in Formula (I) and the ninth, tenth, eleventh, twelfth, thirteenth, and fourteenth embodiment.

In a sixteenth embodiment, the compound of Formula (I) is of Formula (Ic'') or (Ic'''):

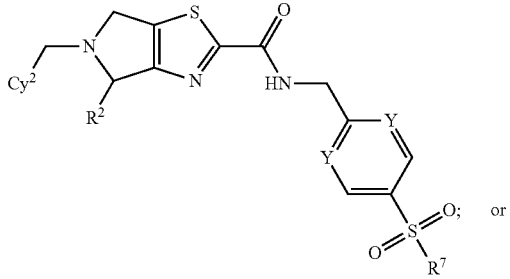
(Ic'')

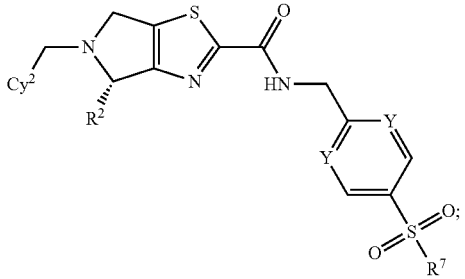
(Ic''')

or a pharmaceutically acceptable salt thereof, wherein each Y in Formulas (Ic'') and (Ic''') is independently CH, $CR^5$ or N; and $R^7$ is $(C_1-C_3)$alkyl, wherein the remaining variables of structural Formula (Ic'') and (Ic''') are as described in Formula (I) and the ninth, tenth, eleventh, twelfth, thirteenth, and fourteenth embodiment.

In a seventeenth embodiment, compounds having the formulae described above are of Formula (Id) or (Id'):

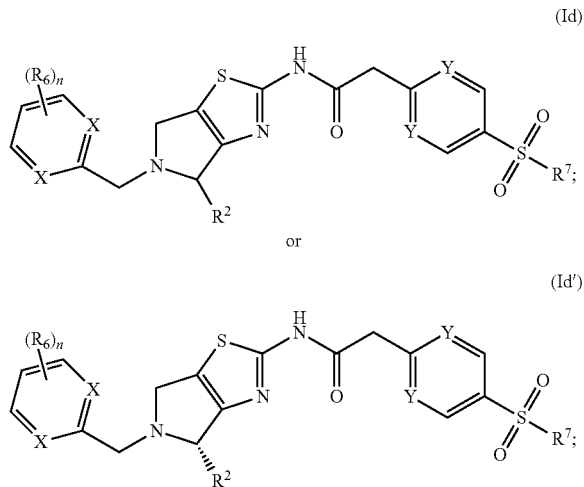

(Id)

or (Id')

or a pharmaceutically acceptable salt thereof, wherein: each X in Formulas (Id) and (Id') is independently CH, CR$^6$, or N; each Y in Formulas (Id) and (Id') is independently CH, CR$^5$ or N; n is 0, 1, or 2; and R$^7$ is (C$_1$-C$_3$)alkyl, wherein the remaining variables of structural Formula (Id) and (Id') are as described in Formula (I) and the ninth, tenth, eleventh, twelfth, thirteenth, fourteenth, and fifteenth embodiment.

In an eighteenth embodiment, compounds having the formulae described above are of Formula (Id") or (Id'"):

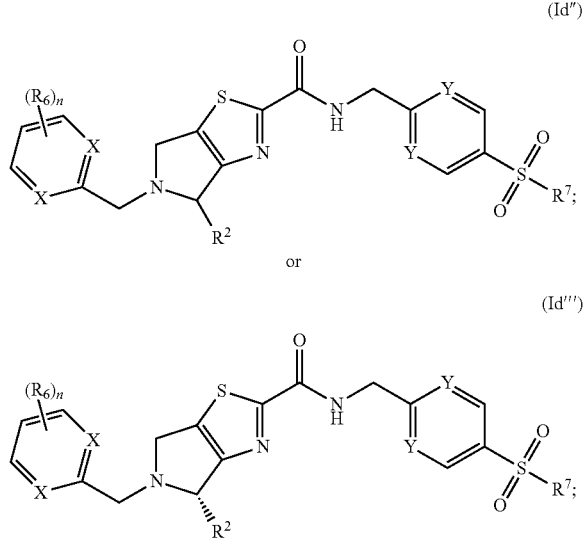

(Id")

or (Id'")

or a pharmaceutically acceptable salt thereof, wherein: each X in Formulas (Id") and (Id'") is independently CH, CR$^6$, or N; each Y in Formulas (Id") and (Id'") is independently CH, CR$^5$ or N; n is 0, 1, or 2; and R$^7$ is (C$_1$-C$_3$)alkyl, wherein the remaining variables of structural Formula (Id") and (Id'") are as described in Formula (I) and the ninth, tenth, eleventh, twelfth, thirteenth, fourteenth, and sixteenth embodiment.

In a nineteenth embodiment, R$^2$ is isopropyl, cyclopropyl, isobutyl, or sec-butyl, wherein the remaining variables are as described in the first, second, third, fourth, fifth, sixth, seventh, eighth, ninth, tenth, eleventh, twelfth, thirteenth, fourteenth, fifteenth, sixteenth, and eighteenth embodiment. Alternatively, R$^2$ is isopropyl and the remaining variables are as described in the first, second, third, fourth, fifth, sixth, seventh, eighth, ninth, tenth, eleventh, twelfth, thirteenth, fourteenth, fifteenth, sixteenth, seventeenth, and eighteenth embodiment.

In a twentieth embodiment, R$^6$ is selected from halo, cyano, nitro, amino, hydroxy, carboxy, (C$_1$-C$_6$)alkyl, hydroxy(C$_1$-C$_6$)alkyl, (C$_2$-C$_6$)alkenyl, halo(C$_2$-C$_6$)alkenyl, hydroxy(C$_2$-C$_6$)alkenyl, halo(C$_1$-C$_6$)alkyl, (C$_1$-C$_6$)alkoxy, halo(C$_1$-C$_6$)alkoxy, (C$_1$-C$_6$)alkylsulfinyl, halo(C$_1$-C$_6$)alkyl-sulfinyl, (C$_1$-C$_6$)alkylsulfonyl, halo(C$_1$-C$_6$)alkylsulfonyl, H$_2$NCO, oxo, amino(C$_1$-C$_6$)alkyl, (C$_1$-C$_6$)alkylcarbonyl, and aminocarbonyl(C$_1$-C$_6$)alkyl, wherein the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, and nineteenth embodiment. Alternatively, R$^6$ is selected from halo, cyano, nitro, amino, hydroxy, carboxy, (C$_1$-C$_6$)alkyl, hydroxy(C$_1$-C$_6$)alkyl, (C$_2$-C$_6$)alkenyl, halo (C$_1$-C$_6$)alkyl, (C$_1$-C$_6$)alkoxy, and halo(C$_1$-C$_6$)alkoxy, wherein the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, and nineteenth embodiment. In another alternative, R$^6$ is halo, cyano, halo(C$_1$-C$_3$)alkyl, or halo(C$_1$-C$_3$)alkoxy, wherein the remaining variables are as described in the first, second, third, fourth, fifth, sixth, seventh, eighth, ninth, tenth, eleventh, twelfth, thirteenth, fourteenth, fifteenth, sixteenth, seventeenth, eighteenth, and nineteenth embodiment.

Specific examples of compounds of the invention are provided in the EXEMPLIFICATION. Pharmaceutically acceptable salts as well as the neutral forms of these compounds are included in the invention.

In certain embodiments, the present invention provides a method of treating a patient (e.g., a human) with a disorder mediated by RORγ comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a patient (e.g., a human) with a disorder mediated by RORγ using a composition comprising a compound of Formula (I) and a pharmaceutically acceptable carrier, adjuvant, or vehicle. In certain embodiments, the amount of compound of Formula (I) in a provided composition is such that it is effective as an inverse agonist or antagonist to RORγ in a biological sample or in a patient. In certain embodiments, a provided composition is formulated for administration to a patient in need of such composition. In some embodiments, a provided composition is formulated for oral administration to a patient.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of RORγ. Thus, in some embodiments, the present invention provides a method of treating inflammatory, metabolic and autoimmune diseases or disorders mediated by RORγ, comprising administering a provided compound or composition. More particularly, the compounds and compositions described herein act as inverse agonists or antagonists of RORγ.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

Diseases and conditions treatable according to the methods of the invention include, but are not limited to, inflammatory, metabolic and autoimmune diseases or disorders mediated by RORγ. These diseases and conditions include, for example, asthma, chronic obstructive pulmonary disease (COPD), bronchitis, allergic rhinitis, atopic dermatitis, contact dermatitis, acne, uticaria, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to lung cancer, gastric cancer, breast cancer and colon cancer.

Also included are diseases or disorders which are implicated by the regulation of the circadian rhythm of individuals and include, e.g., major depression, seasonal affective disorder, post-traumatic stress disorder (PTSD), bipolar disorder, autism, epilepsy, Alzheimer's and other central nervous system (CNS) disorders associated with altered sleep and/or circadian rhythms.

In one embodiment, a human patient is treated with a compound of Formula (I) and a pharmaceutically acceptable carrier, adjuvant, or vehicle, wherein said compound is present in an amount to treat or ameliorate one or more of the diseases and conditions recite above. In an alternative embodiment, the diseases and conditions treated or ameliorated by a compound of Formula (I) include, e.g., asthma, atopic dermatitis, acne, Crohn's disease, regional enteritis, ulcerative colitis, Sjögren's syndrome, uveitis, Behçet's disease, dermatomyositis, multiple sclerosis, ankylosing spondylitis, systemic lupus erythematosus (SLE), scleroderma, psoriasis, psoriatic arthritis (PsA), steroid resistant asthma and rheumatoid arthritis in the patient.

The invention further relates to a combination therapy for treating or ameliorating a disease or a disorder described herein. In some embodiments, the combination therapy comprises administering at least one compound represented by Structural Formula I in combination with one or more agents for treating or ameliorating inflammatory, metabolic and autoimmune diseases or disorders mediated by RORγ. In some embodiments, the combination therapy comprises administering at least one compound represented by Structural Formula I in combination with one or more agents for the treatment of diseases including asthma, chronic obstructive pulmonary disease (COPD), bronchitis, allergic rhinitis, atopic dermatitis, contact dermatitis, acne, uticaria, cystic fibrosis, allograft rejection, multiple sclerosis, scleroderma, arthritis, rheumatoid arthritis, juvenile rheumatoid arthritis, osteoarthritis, ankylosing spondylitis, systemic lupus erythematosus (SLE), psoriasis, Hashimoto's disease, pancreatitis, autoimmune diabetes, type I diabetes, autoimmune ocular disease, ulcerative colitis, Crohn's disease, regional enteritis, inflammatory bowel disease (IBD), inflammatory bowel syndrome (IBS), Sjögren's syndrome, optic neuritis, obesity, hepatosteatosis, adipose tissue-associated inflammation, insulin resistance, type II diabetes, neuromyelitis optica, myasthenia gravis, age related macular degeneration, dry eye, uveitis, Guillain-Barré syndrome, psoriasis, psoriatic arthritis (PsA), steroid resistant asthma, Graves' disease, scleritis, major depression, seasonal affective disorder, PTSD, bipolar disorder, autism, epilepsy, Alzheimer's, CNS disorders associated with altered sleep and/or circadian rhythms, endometriosis, obstructive sleep apnea syndrome (OSAS), Behçet's disease, dermatomyositis, polymyocitis, graft versus host disease, primary biliary cirrhosis, liver fibrosis, non-alcoholic fatty liver disease (NAFLD), sarcoidosis, primary sclerosing cholangitis, autoimmune thyroid disease, autoimmune polyendocrine syndrome type I, autoimmune polyendocrine syndrome type II, celiac disease, neuromyelitis, juvenile idiopathic arthritis, systemic sclerosis, myocardial infarction, pulmonary hypertension, osteoarthritis, cutaneous leishmaniasis, sinonasal polyposis, and cancer, including but not limited to, lung cancer, gastric cancer, breast cancer and colon cancer.

The compounds according to the invention may also be used in combination with immunotherapies for the treatment of a disease or disorder disclosed herein.

Combination therapy includes e.g., co-administration of a compound of the invention and one or more other agent, sequential administration of a compound of the invention and one or more other agent, administration of a composition containing a compound of the invention and one or more other agent, or simultaneous administration of separate compositions containing a compound of the invention and one or more other agent.

The invention further provides a method of treating a subject, such as a human, suffering from one of the above-mentioned disorders or diseases.

The invention further relates to the use of provided compounds for the production of pharmaceutical compositions which are employed for the treatment and/or prophylaxis and/or amelioration of the diseases and disorders mentioned herein.

Compounds or compositions described herein may be administered using any amount and any route of administration effective for treating or lessening the severity of one or more of the diseases and conditions described herein. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

The amount of both, a provided compound and additional therapeutic agent (in those compositions which comprise an additional therapeutic agent as described above) that may be combined with the carrier materials to produce a single dosage form will vary depending upon the host treated and the particular mode of administration.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent.

The amount of additional therapeutic agent present in the compositions of this disclosure will be no more than the amount that would normally be administered in a composition comprising that therapeutic agent as the only active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Description of Synthesis

The compounds of the present invention can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. In these reactions, it is also possible to make use of variants which are themselves known to those of ordinary skill in the art, but are not mentioned in greater detail. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxy, thiol and carboxylic acid groups, that may interfere with the desired reaction, it may be advantageous to employ protected forms of the intermediate. Methods for the selection, introduction and subsequent removal of protecting groups are well known to those skilled in the art. In the discussion below variables have the meanings indicated above unless otherwise indicated. The abbreviations used in these experimental details are listed below and additional ones should be known to a person skilled in the art of synthesis. In addition, one can refer to the following references for suitable methods of synthesis as described in March, Advanced Organic Chemistry, 3rd edition, John Wiley & Sons, 1985, Greene and Wuts, Protective Groups in Organic Synthesis, 2$^{nd}$ edition, John Wiley & Sons, 1991, and Richard Larock, Comprehensive Organic Transformations, 4$^{th}$ edition, VCH publishers Inc., 1989.

Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

Where NMR data are presented, spectra were obtained on a Varian 400 (400 MHz) or 300 (300 MHz) and are reported as ppm downfield from tetramethylsilane with number of proton, multiplicities and coupling constants indicated parenthetically along with reference to deuterated solvent.

The chiral purity of compounds described herein was determined by analytical chiral HPLC, which was carried out using Chiralcel® or Chiralpak® columns, using CO$_2$, together with from 5% to 40% methanol, ethanol or isopropanol, containing 0.05% DEA as eluents. Representative HPLC methods are as follows.

The invention is illustrated by way of the following examples, in which the following abbreviations may be employed.

| Abbreviation | Meaning |
| --- | --- |
| ACN, MeCN, CH$_3$CN | acetonitrile |
| aq | aqueous |
| Boc | tert-butoxy carbonyl, t-butoxy carbonyl, or tert-butylcarbamate |
| brine | saturated aqueous NaCl |
| Cbz | benzyloxy carbonyl or benzylcarbamate |
| CeCl$_3$ | ceric chloride |
| Cs$_2$CO$_3$ | cesium carbonate |
| CuI | cuprous iodide |
| DCM or CH$_2$Cl$_2$ | methylene chloride |
| DIEA | diisopropyl ethyl amine |
| DMF | dimethyl formamide |
| DMS/Me$_2$S | dimethyl sulfide |
| DMSO | dimethyl sulfoxide |
| EDCI | 1-(3-dimethylaminopropyl)-3-ethylcarbodiiimide hydrochloride |
| EtI | ethyl iodide |
| Et | ethyl |

| Analytical Chiral HPLC | |
| --- | --- |
| Method | Detailed information |
| OJ-H_3_5_40_2.35ML | Column: Chiralcel ® OJ-H 250 × 4.6 mm I.D., 5 µm Mobile phase: methanol (0.05% DEA) in CO$_2$ from 5% to 40% Flow rate: 2.35 mL/min Wavelength: 220 nm |
| OJ-H_3_5_40_2.5ML | Column: Chiralcel ® OJ-H 250 × 4.6 mm I.D., 5 µm Mobile phase: methanol (0.05% DEA) in CO$_2$ from 5% to 40% Flow rate: 2.5 mL/min Wavelength: 220 nm |
| AS-H_3_5_40_2.35ML | Column: Chiralpak ® AS-H 250 × 4.6 mm I.D., 5 µm Mobile phase: methanol (0.05% DEA) in CO$_2$ from 5% to 40% Flow rate: 2.35 mL/min Wavelength: 220 nm |
| AS-H_4_5_40_2.5ML | Column: Chiralpak ® AS-H 250 × 4.6 mm I.D., 5 µm Mobile phase: iso-propanol (0.05% DEA) in CO$_2$ from 5% to 40% Flow rate: 2.5 mL/min Wavelength: 220 nm |
| AS-H_5_5_40_2.35ML | Column: Chiralpak ® AS-H 250 × 4.6 mm I.D., 5 µm Mobile phase: ethanol (0.05% DEA) in CO$_2$ from 5% to 40% Flow rate: 2.35 mL/min Wavelength: 220 nm |
| AS-H_3_5_40_2.5ML | Column: Chiralpak ® AS-H 250 × 4.6 mm I.D., 5 µm Mobile phase: methanol (0.05% DEA) in CO$_2$ from 5% to 40% Flow rate: 2.5 mL/min Wavelength: 220 nm |
| AD-H_3_5_40_2.35ML | Column: Chiralpak ® AD-H 250 × 4.6 mm I.D., 5 µm Mobile phase: methanol (0.05% DEA) in CO$_2$ from 5% to 40% Flow rate: 2.35 mL/min Wavelength: 220 nm |
| AD-H_5_5_40_2.35ML | Column: Chiralpak ® AD-H 250 × 4.6 mm I.D., 5 µm Mobile phase: ethanol (0.05% DEA) in CO$_2$ from 5% to 40% Flow rate: 2.35 mL/min Wavelength: 220 nm |
| OD-3_3_5_40_2.5ML | Column: Chiralcel ® OD-3 150 × 4.6 mm I.D., 3 µm Mobile phase: methanol (0.05% DEA) in CO$_2$ from 5% to 40% Flow rate: 2.5 mL/min Wavelength: 220 nm |
| OD-3_4_5_40_2.5ML | Column: Chiralcel ® OD-3 150 × 4.6 mm I.D., 3 µm Mobile phase: iso-propanol (0.05% DEA) in CO$_2$ from 5% to 40% Flow rate: 2.5 mL/min Wavelength: 220 nm |
| OD-3_5_5_40_2.5ML | Column: Chiralcel ® OD-3 150 × 4.6 mm I.D., 3 µm Mobile phase: ethanol (0.05% DEA) in CO$_2$ from 5% to 40% Flow rate: 2.5 mL/min Wavelength: 220 nm |
| AD-3_3_5_40_2.5ML | Column: Chiralpak ® AD-3 150 × 4.6 mm I.D., 3 µm Mobile phase: methanol (0.05% DEA) in CO$_2$ from 5% to 40% Flow rate: 2.5 mL/min Wavelength: 220 nm |
| AD-3_4_5_40_2.5ML | Column: Chiralpak ® AD-3 150 × 4.6 mm I.D., 3 µm Mobile phase:iso-propanol (0.05% DEA) in CO$_2$ from 5% to 40% Flow rate: 2.5 mL/min Wavelength: 220 nm |
| AD-3_5_5_40_2.5ML | Column: Chiralpak ® AD-3 150 × 4.6 mm I.D., 3 µm Mobile phase: ethanol (0.05% DEA) in CO$_2$ from 5% to 40% Flow rate: 2.5 mL/min Wavelength: 220 nm |
| OD-H_3_5_40_2.35ML | Column: Chiralcel ® OD-H 250 × 4.6 mm I.D., 5 µm Mobile phase: methanol (0.05% DEA) in CO$_2$ from 5% to 40% Flow rate: 2.35 mL/min Wavelength: 220 nm |
| OD-H_5_5_40_2.35ML | Column: Chiralcel ® OD-H 250 × 4.6 mm I.D., 5 µm Mobile phase: ethanol (0.05% DEA) in CO$_2$ from 5% to 40% Flow rate: 2.35 mL/min Wavelength: 220 nm |

| Abbreviation | Meaning |
| --- | --- |
| Et$_2$O | ethyl ether |
| Et$_3$SiH | triethylsilane |
| Et$_3$N | triethylamine |
| EtOAc, EA, AcOEt | ethyl acetate |
| EtOH | ethanol |
| FeCl$_3$ | ferric chloride |
| h, hr | hour(s) |
| HATU | O-(7-azabenzotriazol-1-yl)-N,N,N',N'-tetramethyluronium-hexafluorophosphate |
| HBTU | O-benzotriazole-1-yl-N,N,N',N'-tetramethyluronium-hexafluorophosphate |
| HCl | hydrochloric acid |
| H$_2$O | water |
| H$_2$O$_2$ | hydrogen peroxide |
| HPLC | high performance liquid chromatography |
| i-BuOCOCl | iso-butoxycarbonyl chloride |
| ICl | iodochloride |
| K$_2$CO$_3$ | potassium carbonate |
| K$_3$PO$_4$ | tripotassium phosphate |
| LC-MS | liquid chromatography-mass spectrometry |
| LDA | lithium diiisopropylamide |
| LiCl | lithium chloride |
| LiOH | lithium hydroxide |
| MCPBA, m-CPBA | meta-chloroperoxybenzoic acid |
| MeOH | methanol |
| MeI | methyl iodide |
| Me | methyl |
| mg | milligram |
| MgSO$_4$ | magnesium sulfate (anhydrous) |
| min | minute(s) |
| mL | milliliters |
| mmol | millimoles |
| mp, m.p. | melting point |
| MS | mass spectrometry |
| MW | microwave |
| NaBH$_4$ | sodium borohydride |
| NaBH$_3$CN | sodium cyanoborohydride |
| NaH | sodium hydride |
| NaHCO$_3$ | sodium bicarbonate |
| NaOH | sodium hydroxide |
| NaOMe | sodium methoxide |
| Na$_2$S$_2$O$_3$ | sodium thiosulfate |
| Na$_2$S$_2$O$_5$ | sodium dithionate |
| Na$_2$SO$_4$ | sodium sulfate |
| NH$_4$OH | ammonium hydroxide |
| (NH$_4$)$_2$CO$_3$ | ammonium carbonate |
| NH$_4$Cl | ammonium chloride |
| Na$_2$CO$_3$ | sodium carbonate |
| NaHCO$_3$ | sodium bicarbonate |
| NaH | sodium hydride |
| n-BuLi | n-butyllithium |
| NMM | N-methyl-morpholine |
| NMP | N-methyl-pyrrolidin-2-one |
| OTf | trifluoromethanesulfonate |
| OTs | tosylate |
| PdCl$_2$dppf | [1,1-bis(diphenylphosphino)ferrocene]dichloropalladium(ii) |
| Pd$_2$(dba)$_3$ | tris(dibenzylideneacetone)dipalladium(0) |
| PE | petroleum ether |
| rt | room temperature |
| sat. | saturated |
| SFC | supercritical fluid chromatography |
| t-BuOK | potassium tert butoxide |
| t-BuLi | tert butyl lithium |
| t-BuOOH | tert butyl peroxide |
| TBAF | tetrabutylammonium fluoride |
| TFA | trifluoroacetic acid |
| THF | tetrahydrofuran |
| TLC | thin layer chromatography |
| Ti(OEt)$_4$ | titanium tetra ethoxide |
| Zn | zinc |
| Zn(CN)$_2$ | zinc cyanide |

Compounds according to Formula (I), can be prepared by reacting an intermediate compound of Formula (II) with an alkyl or aryl halide, according to reaction Scheme 1, a reaction that is performed in a polar aprotic solvent, such as, for example, acetonitrile, in the presence of a suitable base, such as, for example, N,N-diisopropylethylamine or potassium carbonate. Alternatively, the final compounds according to Formula (I), can be prepared by reacting an intermediate compound of Formula (II) with an aldehyde or ketone, according to reaction Scheme 1, following art-known reductive amination procedure, in the typical solvent, such as, for example, dichloroethane or dichloromethane; in the presence of suitable reducing reagent, such as sodium cyanoborohydride or sodium triacetoxyborohydride. In reaction Scheme 1, all variables are defined as in Formula (I).

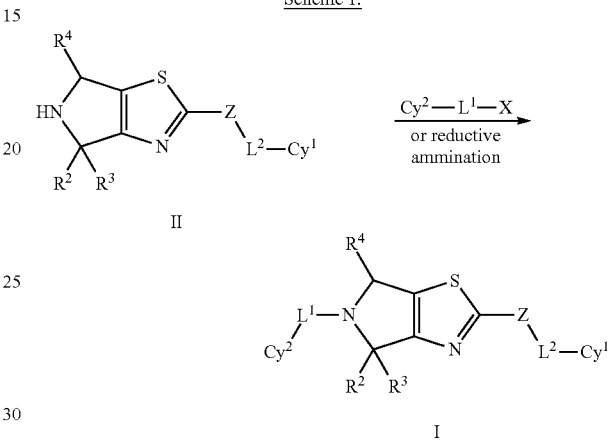

Scheme 1.

Intermediate compound of Formula (II) can be can be prepared by deprotecting an intermediate compound of Formula (III), wherein Pg is a suitable nitrogen protecting group (Greene and Wuts, 1991, op. cit.), e.g., Pg=tert-butylcarbamate, removed with trifluoroacetic acid according to Scheme 2. In reaction Scheme 2, all variables are defined as in Formula (I).

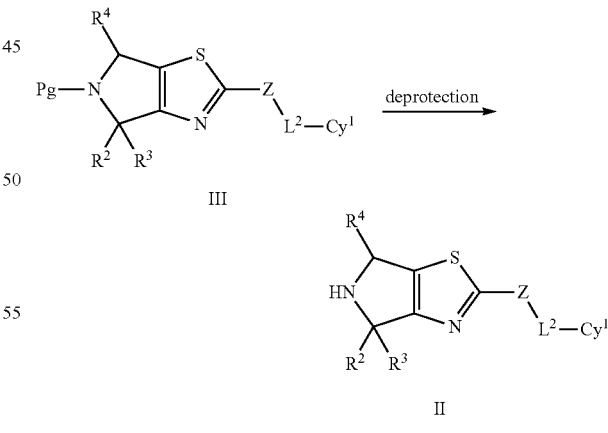

Scheme 2.

Intermediate compound of Formula (III) wherein Z is —NR$^1$C(O)—, can be prepared from amine (IV) and a carboxylic acid ((V) wherein Q is CO and X is OH), according to Scheme 3. The reaction is conveniently carried out in the presence of an activating reagent, for example, 1-propanephosphonic acid cyclic anhydride (T$_3$P) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-diisopropylethylamine or triethylamine, at a temperature, for example in the range from 0 to 60° C. Alternatively, intermediate compound of Formula (III) wherein Z is —NR$^1$SO$_2$, can be prepared from amine (IV) and a sulfonyl halide ((V) wherein Q is SO$_2$ and X is Cl or F), according to Scheme 3. The reaction is conveniently carried out in the presence of a base, e.g., pyridine or triethylamine, in an organic solvent, for example, dichloromethane, at a temperature, for example in the range from 0 to 60° C. Accordingly, in reaction Scheme 3, all variables are defined as in Formula (I), Z is —NR$^1$C(O)— or —NR$^1$SO$_2$—, and X-Q is —COOH or —SO$_2$Cl.

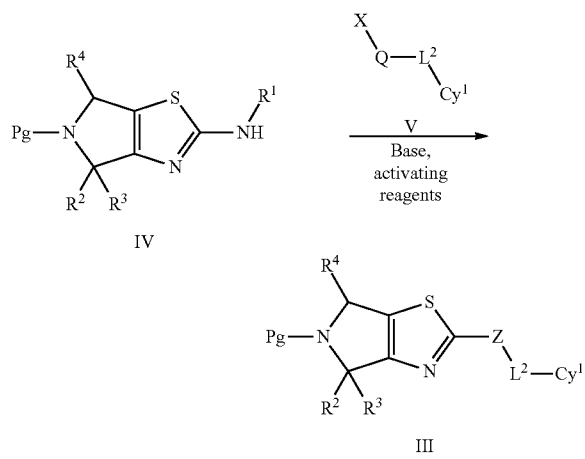

Scheme 3.

Intermediate compound of Formula (VI) wherein R$_5$ represents amide, can be prepared from amine (VIII) and an acid (VII). The reaction is conveniently carried out in the presence of an activating reagent, for example, 1-propanephosphonic acid cyclic anhydride (T3P) or O-(7-azabenzotriazol-1-yl)-N,N,N',N'-tetramethyluronium hexafluorophosphate (HATU), in an organic solvent, for example, N,N-dimethylformamide or dichloromethane, optionally in the presence of a base, e.g., N,N-Diisopropylethylamine or triethylamine, at a temperature, for example in the range from 0 to 60° C. (Scheme 4).

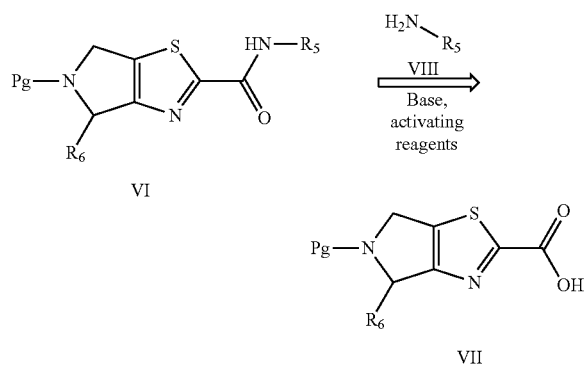

Scheme 4.

Intermediate compound of Formula (VII) wherein R$_6$ can be lower alkyl group, can be prepared from halide (IX) wherein X represents a halogen atom, preferably a bromine atom, by halogen-lithium exchange using an organometallic reagent, such as n-BuLi (Scheme 5). The reaction is generally carried out in an etherate solvent such as THF or diethyl ether at about −78° C. to form an organometallic reagent intermediate. It was quenched with carbon dioxide followed by water to yield the carboxylic acid (VII).

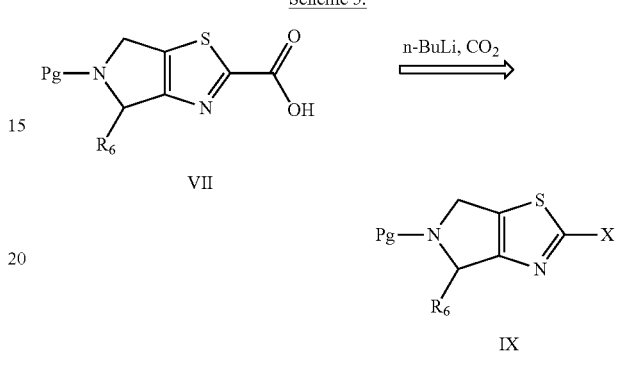

Scheme 5.

Intermediate compound of Formula (IX) wherein R$_6$ can be lower alkyl group, can be prepared from an intermediate compound of Formula (IV-A) by Sandmeyer reaction as shown in Scheme 6.

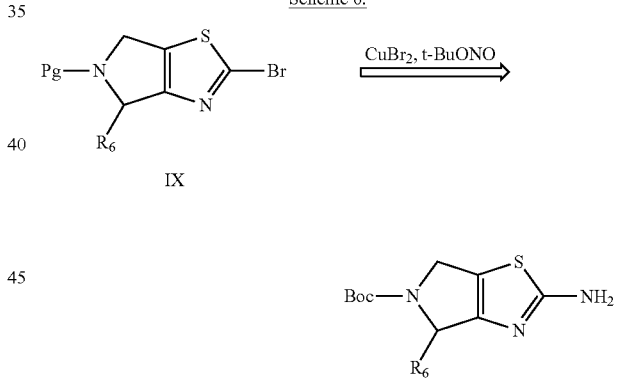

Scheme 6.

Preparation of Intermediates

Tert-butyl (S)-2-amino-4-isopropyl-4,6-dihydro-5H-pyrrolo[3,4-d]thiazole-5-carboxylate (IV-1)

As a representative example, intermediate compound of Formula (IV) wherein R$^1$ is H, R$^2$ is isopropyl, R$^3$ is H and R$^4$ is H, Pg is tert-butylcarbamate (IV-1), can be prepared by following the reaction steps shown in the reaction Scheme 7. An intermediate compound of Formula (IV) with variable R$^1$, R$^2$, R$^3$, and R$^4$, can be prepared readily according to the Scheme 7, or modifications thereof, using readily available starting materials and reagents.

Scheme 7.

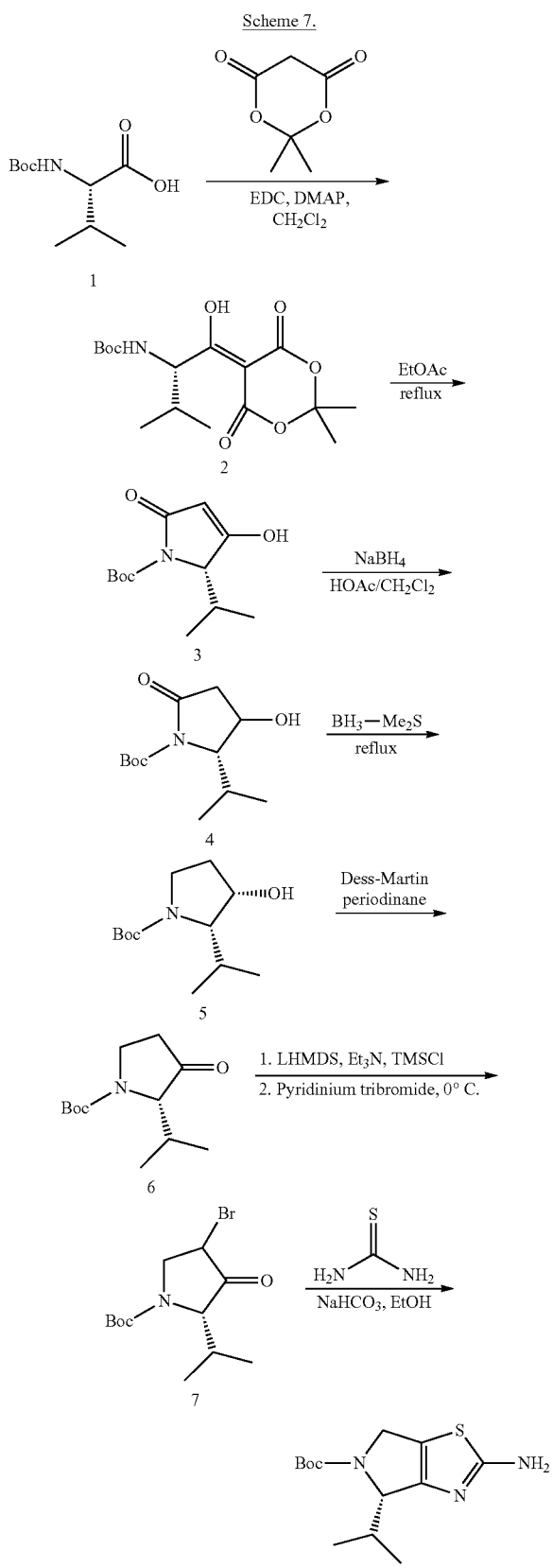

At 0° C., to a mixture of compound 1 (20 g, 92 mmol) and EDC (26.45 g, 138 mol) in dry CH$_2$Cl$_2$ (250 mL) was added Meldrum's acid (14.57 g, 101 mmol) followed by addition of DMAP (16.84 g, 138 mmol). The mixture was stirred at rt for 10 h. The mixture was filtered and the filtrate was washed with 1N HCl (3×200 mL), water (3×200 mL) and brine (300 mL). The organic layer was dried over anhydrous Na$_2$SO$_4$, filtered and concentrated under vacuum to afford the crude compound 2 (31 g, 100% crude yield) as a yellow solid. LC-MS $t_R$=1.75 min in 2 min chromatography, MS (ESI) m/z 344 [M+H]$^+$.

A mixture of compound 2 (31 g, 90 mmol) from above in EtOAc (650 mL) was refluxed for 3 h under N$_2$. The mixture was concentrated under reduced pressure to afford crude compound 3 (21.6 g, 100% crude yield) as a tan oil, which was used for next step directly without further purification. LC-MS $t_R$=1.25 min in 2 min chromatography, MS (ESI) m/z 186 [M−56+H]$^+$.

At 0° C., to a stirred solution of compound 3 (1.65 g, crude, assumed 6.8 mmol) in CH$_2$Cl$_2$ (30 mL) was added acetic acid (4 mL). NaBH$_4$ (775 mg, 20.40 mmol) was added portionwise while stirring and maintaining the temperature at 0° C. The resulting mixture was stirred at 0° C. for 1 h then warmed to rt overnight. 20 mL of 5% aq citric acid was added at 0° C. The organic layer was collected, washed with brine (40 mL), dried over Na$_2$SO$_4$, filtered and concentrated under reduced pressure. The crude compound 4 was purified by flash chromatography over silica gel eluting with EtOAc/hexanes (50/50) to afford 1.0 g of compound 4 as a colorless oil. LC-MS $t_R$=1.13 min in 2 min chromatography, MS (ESI) m/z 188 [M−56+H]$^+$.

At rt, to a solution of compound 4 (1.00 g, 4.1 mmol) in THF (16 mL) under N$_2$ was added a solution of BH$_3$-Me$_2$S (7.4 mL, 16 mmol) slowly then the mixture was refluxed for 1 h. The mixture was cooled to rt and quenched with sat. aq NH$_4$Cl solution (20 mL) at 0° C. slowly. The mixture was extracted with ethyl acetate (3×50 mL). The combined organic layers were dried over anhydrous Na$_2$SO$_4$, filtered and concentrated under reduced pressure. The residue was purified by column chromatography on silica gel (eluting with hexanes/EtOAc=35/65) to give compound 5 (375 mg, 25% yield over 2 steps) as a colorless oil. LC-MS $t_R$=1.30 min in 2 min chromatography, MS (ESI) m/z 174 [M−56+H]$^+$. $^1$H NMR (CDCl$_3$ 400 MHz): δ 4.47-4.40 (m, 1H), 3.70-3.66 (m, 1H), 3.50-3.43 (m, 1H), 3.35-3.29 (m, 1H), 2.14-2.05 (m, 2H), 1.89-1.80 (m, 1H), 1.71-1.70 (m, 1H), 1.45 (s, 9H), 1.05 (d, J=6.8 Hz, 3H), 0.96 (d, J=7.2 Hz, 3H).

To a solution of compound 5 (1.80 g, 7.9 mmol) in CH$_2$Cl$_2$ (40 mL) was added Dess-Martin periodinane (4.00 g, 9.4 mmol) portion wise at 0° C. The mixture was stirred at rt for 1 h. The mixture was quenched with sat. aq Na$_2$S$_2$O$_3$ solution (30 mL) at 0° C. The organic layer was separated and washed with sat. NaHCO$_3$ solution (30 mL), brine (50 mL), dried over anhydrous Na$_2$SO$_4$, filtered and concentrated under reduced pressure. The residue was purified by column chromatography on silica gel (eluting with hexanes/EtOAc=10/1) to give compound 6 (1.45 g, 80% yield) as a colorless oil. LC-MS $t_R$=1.48 min in 2 min chromatography, MS (ESI) m/z 172 [M−56+H]$^+$. $^1$H NMR (CDCl$_3$ 400 MHz): δ 4.14-4.07 (m, 1H), 3.81-3.79 (m, 1H), 3.56-3.54 (m, 1H), 2.62-2.52 (m, 1H), 2.47-2.40 (m, 1H), 2.39-2.24 (m, 1H), 1.48 (s, 9H), 1.00 (d, J=6.8 Hz, 3H), 0.95 (d, J=7.2 Hz, 3H).

At −78° C., to a solution of compound 6 (310 mg, 1.35 mmol) in dry THF (10 mL) was added 1.0 M LiHMDS in THF (2.7 mL, 2.7 mmol) slowly under nitrogen. The reaction mixture was stirred at −78° C. for 30 min. Et$_3$N (380 μL, 2.7 mmol) was added followed by TMSCl (345 μL, 2.7 mmol) and the resulting mixture was stirred at −78° C. for 1 h. It was quenched by addition of H$_2$O (10 mL) and extracted with ethyl acetate (2×40 mL). The organic phase was washed with brine, dried over anhydrous Na$_2$SO$_4$, filtered and concentrated under reduced pressure to afford crude silyl enol ether, which was used directly for the next step without further purification.

At 0° C., to a solution of the crude silyl enol ether (1.35 mmol) in THF (10 mL) was added pyridinium tribromide (430 mg, 1.5 mmol) and the mixture was stirred for 20 min at 0° C. The reaction was quenched with sat. aq Na$_2$S$_2$O$_3$ solution (10 mL) at 0° C. and extracted with ethyl acetate (2×30 mL). The organic phase was washed with brine, dried over anhydrous Na$_2$SO$_4$, filtered and concentrated under reduced pressure. The residue was purified by column chromatography on silica gel eluting with hexanes/ethyl acetate 10/1 to afford compound 7 (390 mg, 90%) as a pale yellow oil. LC-MS $t_R$=1.69 min in 2 min chromatography, MS (ESI) m/z 250 [M−56+H]$^+$.

To a solution of compound 7 (650 mg, 2.0 mmol) in EtOH (8 mL) was added thiourea (620 mg, 8.0 mmol) and NaHCO$_3$ (506 mg, 6.0 mmol). The mixture was stirred at 70° C. for 10 h and concentrated under reduced pressure. H$_2$O (15 mL) and ethyl acetate (30 mL) were added to the mixture and separated. The aqueous layer was extracted with ethyl acetate (3×20 mL). The combined organic layers were washed with brine (30 mL), dried over anhydrous Na$_2$SO$_4$, filtered and concentrated under reduced pressure. The residue was purified by column chromatography on silica gel eluting with hexanes/ethyl acetate 1/1 to afford compound IV-1 (550 mg, 90%) as an off-white solid. LC-MS $t_R$=1.22 min in 2 min chromatography, MS (ESI) m/z 284 [M+H]$^+$.

$^1$H NMR (CD$_3$OD, 400 MHz): δ 4.87-4.60 (m, 1H), 4.52 (d, J=12 Hz, 1H), 4.37-4.28 (m, 1H), 2.40-2.32 (m, 1H), 1.50 (s, 9H), 1.07-1.03 (m, 3H), 0.72-0.68 (m, 3H).

Tert-butyl (S)-2-amino-4-((S)-sec-butyl)-4,6-di-hydro-5H-pyrrolo[3,4-d]thiazole-5-carboxylate (IV-2)

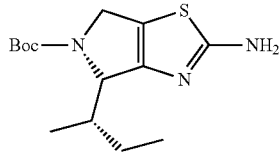

IV-2

Intermediate compound of Formula (IV) wherein R$^1$ is H, R$^2$ is sec-butyl, R$^3$ is H and R$^4$ is H, Pg is tert-butylcarbamate (IV-2), can be prepared following analogous methods used in Scheme 7 using Boc-L-Isoleucine instead of compound 1. LC-MS $t_R$=1.34 min in 2 min chromatography, MS (ESI) m/z 298.3 [M+H]$^+$. $^1$H NMR (CD$_3$OD, 400 MHz): δ 4.69-4.52 (m, 1H), 4.50 (d, J=13.2 Hz, 1H), 4.38-4.29 (m, 1H), 2.15-2.11 (m, 1H), 1.68-1.62 (m, 1H), 1.51 (s, 9H), 1.39-1.32 (m, 1H), 1.00 (t, J=7.6 Hz, 3H), 0.63 (d, J=6.8 Hz, 3H)

Benzyl (S)-2-amino-4-isopropyl-4-methyl-4,6-di-hydro-5H-pyrrolo[3,4-d]thiazole-5-carboxylate (IV-3)

Alternatively, intermediate compound of Formula (IV) wherein R$^1$ is H, R$^2$ is isopropyl, R$^3$ is Me and R$^4$ is H, Pg is benzylcarbamate (IV-3), can be prepared by following the reaction steps shown in the reaction Scheme 8.

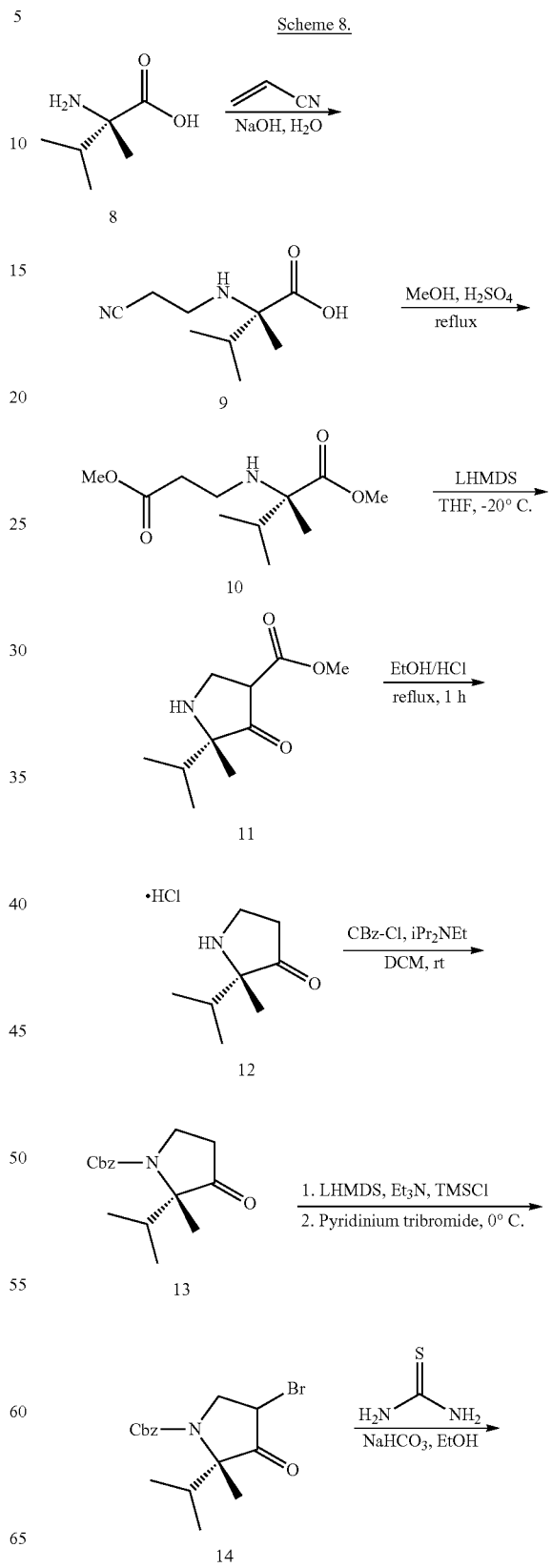

Scheme 8.

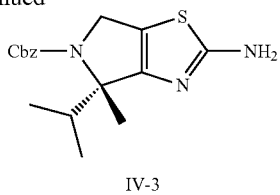

IV-3

To a suspension of compound 8 (5 g, 38.17 mmol) in H$_2$O (15 mL) was added powdered NaOH in one portion at 0° C. The mixture was allowed to warm to room temperature and stirred for 1 h at which point a homogeneous solution had formed. This solution was cooled back down to 0° C. and acrylonitrile (2.66 mL, 40.08 mmol) was added dropwise. The reaction was allowed to warm to rt and stirred for 1 day. AcOH (5 mL) was added at rt causing a white precipitate to form. The reaction was then placed in a 0° C. refrigerator for 1 h before filtering off the white precipitate, washing with EtOH and drying under high vacuum to afford nearly pure crude compound 9 as a white powder (6.78 g, 97% yield). LC-MS $t_R$=0.298 min in 2 min chromatography, MS (ESI) m/z 185.19 [M+H]$^+$.

A solution of crude compound 9 (6.78 g, 36.84 mmol) in a mixture of MeOH (30 mL) and conc. H$_2$SO$_4$ (10 mL) was refluxed for 7 days. The solution was cooled to 0° C. and a saturated aqueous solution of NaHCO$_3$ was carefully added to the mixture until the bubbling subsided. The mixture was extracted using DCM (2×150 mL). The DCM layers were combined, dried over Na$_2$SO$_4$ and evaporated to afford nearly pure crude compound 10 (4.70 g, 55% yield). LC-MS $t_R$=0.557 min in 2 min chromatography, MS (ESI) m/z 232.25 [M+H]$^+$.

To a solution of crude compound 10 (4.70 g, 20.35 mmol) in dry THF (25 mL) was added a 1M solution of LHMDS in THF (42.75 mL, 42.75 mmol) dropwise at −20° C. under N$_2$. The reaction stirred for 10 minutes at −20° C. and was quenched by adding sat. NH$_4$Cl (20 mL) at −20° C. The mixture was extracted using EtOAc (3×50 mL). The organic layers were combined, dried over Na$_2$SO$_4$ and evaporated to afford nearly pure crude compound 11, which was used directly for the next step without further purification. LC-MS $t_R$=0.497 min in 2 min chromatography, MS (ESI) m/z 200.24 [M+H]$^+$.

A solution of crude compound 11 (taken on directly from previous reaction) in a mixture of EtOH (15 mL) and conc. HCl (15 mL) was refluxed for 5 h. The solvents were evaporated and the resulting white solid material was dried under high vacuum to afford nearly pure compound 12 (3.39 g, 95% yield over 2 steps). LC-MS $t_R$=0.328 min in 2 min chromatography, MS (ESI) m/z 142.23 [M+H]$^+$.

To a solution of crude compound 12 (98 mg, 0.552 mmol) and iPr$_2$NEt (0.50 mL, 2.76 mmol) in DCM (3 mL) was added a 3M solution of benzyl chloroformate in toluene (0.40 mL, 1.20 mmol) at rt. The reaction stirred for 1 h at rt before adding sat. NH$_4$Cl (3 mL). The mixture was extracted with DCM (2×10 mL). The organic layers were combined, washed with brine (10 mL), dried over Na$_2$SO$_4$, filtered and concentrated under reduced pressure. The crude compound 13 was purified by flash chromatography over silica gel eluting with 20% EtOAc/hexanes to afford 122 mg of compound 13 as a colorless oil (80% yield). LC-MS $t_R$=1.602 min in 2 min chromatography, MS (ESI) m/z 276.39 [M+H]$^+$. $^1$H NMR (CDCl$_3$) δ 7.38-7.30 (m, 5H), 5.16 (s, 2H), 3.78-3.73 (m, 2H), 2.66-2.43 (m, 3H), 1.51 (s, 3H), 0.99 (s, 3H), 0.86 (s, 3H).

At −78° C., to a solution of compound 13 (122 mg, 0.44 mmol) in dry THF (5 mL) was added 1.0 M LiHMDS in THF (0.89 mL, 0.89 mmol) slowly under nitrogen. The reaction mixture was stirred at −78° C. for 30 min. Et$_3$N (0.12 mL, 0.89 mmol) was added followed by TMSCl (0.11 mL, 0.89 mmol) and the resulting mixture was stirred at −78° C. for 1 h. It was quenched by addition of H$_2$O (10 mL) and extracted with ethyl acetate (2×20 mL). The organic phase was washed with brine, dried over anhydrous Na$_2$SO$_4$, filtered and concentrated under reduced pressure to afford crude compound silyl enol ether as yellow oil, which was used directly for the next step without further purification.

At 0° C., to a solution of crude silyl enol ether (0.44 mmol) in THF (10 mL) was added pyridinium tribromide (170 mg, 0.53 mmol) and the mixture was stirred for 20 min at 0° C. The reaction was quenched with saturated aqueous Na$_2$S$_2$O$_3$ solution (5 mL) at 0° C. and extracted with ethyl acetate (2×20 mL). The organic phase was washed with brine, dried over anhydrous Na$_2$SO$_4$, filtered and concentrated under reduced pressure to afford nearly pure crude compound 14 as an oil, which was used directly for the next step without further purification. LC-MS $t_R$=1.772 min in 2 min chromatography, MS (ESI) m/z 354.30 and 356.28 [M+H]$^+$.

To a solution of compound 14 (0.44 mmol) in EtOH (5 mL) was added thiourea (87 mg, 1.32 mmol) and NaHCO$_3$ (150 mg, 1.76 mmol). The mixture was stirred at 70° C. for 10 h and concentrated under reduced pressure. H$_2$O (10 mL) and ethyl acetate (20 mL) were added to the mixture and separated. The aqueous layer was extracted with ethyl acetate (3×10 mL). The combined organic layers were washed with brine (15 mL), dried over anhydrous Na$_2$SO$_4$, filtered and concentrated under reduced pressure. The residue was purified by column chromatography on silica gel eluting with hexanes/ethyl acetate 1/1 to afford compound IV-3 (48 mg, 31% yield over 3 steps) as an off-white solid. LC-MS $t_R$=1.352 min in 2 min chromatography, MS (ESI) m/z 348.36 [M+H]$^+$.

Benzyl 2-amino-4-(3-bromobenzyl)-4,6-dihydro-5H-pyrrolo[3,4-d]thiazole-5-carboxylate (IV-4)

Intermediate compound of Formula (IV) wherein $R^1$ is H, $R^2$ is 3-bromobenzyl, $R^3$ is H and $R^4$ is H, Pg is benzylcarbamate (IV-4), can be prepared by following the reaction steps shown in the reaction Scheme 9.

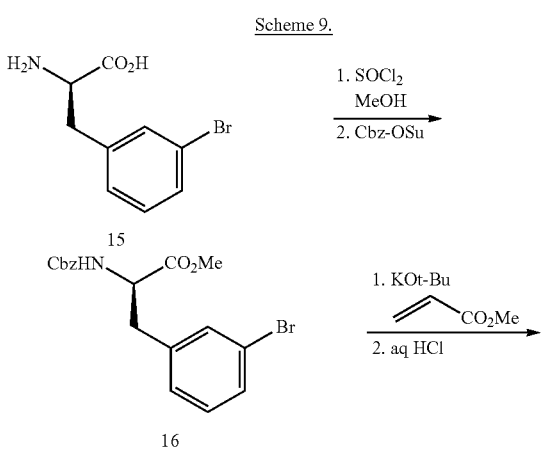

Scheme 9.

-continued

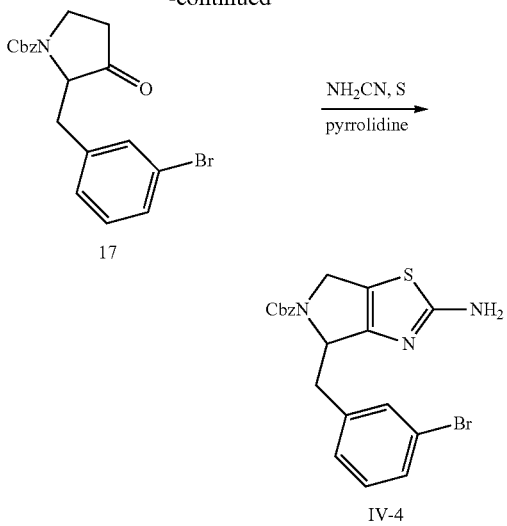

2-(4-(Ethylsulfonyl)phenyl)acetic acid (V-1)

Carboxylic acid V-1 was prepared following the synthetic route shown in Scheme 10.

Scheme 10.

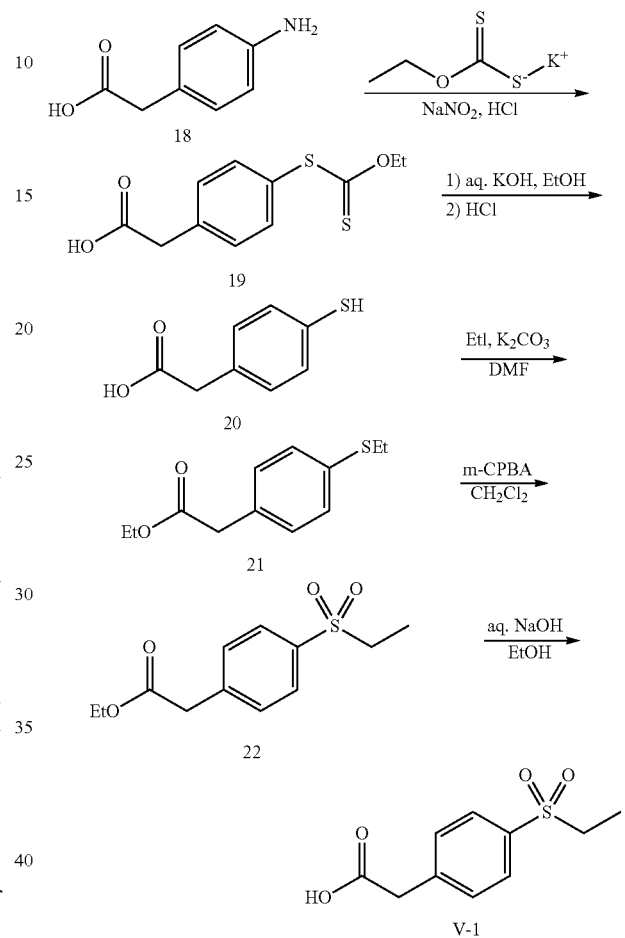

To a stirred solution of 15 (5.0 g, 20.5 mmol) in MeOH (100 mL) SOCl$_2$ (5 mL) was added dropwise slowly. The mixture was stirred overnight at rt, heated at reflux for 1 d and concentrated to afford a tan solid. This material was stirred vigorously with THF (50 mL) and 10% aq K$_2$CO$_3$ (50 mL). Cbz-OSu (6.40 g, 26.0 mmol) was added and stirring was continued for 16 h. The mixture was concentrated under reduced pressure to remove THF. The aqueous residue was extracted with EtOAc (2×45 mL). The combined EtOAc layer was washed with brine (10 mL), dried over Na$_2$SO$_4$ and concentrated to leave an amber oil. Chromatography on an 80-g silica cartridge, eluted with a 0-60% EtOAc in hexanes gradient, gave 16 (6.48 g, 81%) as a white solid. LC-MS $t_R$=0.96 min in 1.5 min chromatography, MS (ESI) m/z 394, 392 [M+H]$^+$.

To a stirred solution of compound 16 (6.48 g, 16.5 mmol) in dry THF (80 mL) was added solid KOt-Bu (2.04 g, 18.1 mmol). The mixture was stirred for 15 min and a solution of methyl acrylate (1.5 mL, 16.5 mmol) in dry THF (10 mL) was added dropwise over 2 min. The mixture was heated at reflux for 2.5 h, cooled, diluted with 5% aq HCl (30 mL) and concentrated to remove THF. The aqueous residue was extracted with EtOAc (150 mL). The organic layer was washed with brine (25 mL), dried over Na$_2$SO$_4$ and concentrated to leave an orange oil. This material was stirred vigorously at reflux with 1% aq HCl (50 mL) for 4 d. The mixture was cooled and extracted with ether (175 mL). The ether layer was washed with sat. aq NaHCO$_3$ (10 mL) and brine (20 mL), and dried over Na$_2$SO$_4$. Removal of the solvent left an orange oil (5.93 g). Chromatography on an 80-g silica cartridge, eluted with a 0-50% EtOAc in hexanes gradient, afforded product 17 (3.52 g, 55%). LC-MS $t_R$=1.01 min in 1.5 min chromatography, MS (ESI) m/z 390, 388 [M+H]$^+$.

A stirred mixture of 17 (446 mg, 1.15 mmol), cyanamide (49 mg, 1.15 mmol), sulfur (37 mg, 1.15 mmol), pyrrolidine (9 μL, 0.12 mmol) and i-PrOH (5 mL) was heated at 60° C. for 1 d. The mixture was concentrated and the residue was purified by chromatography on a 40-g silica cartridge, eluted with a 0-100% EtOAc in hexanes gradient to afford product IV-4 (134 mg, 26%) as an oil. LC-MS $t_R$=0.94 min in 1.5 min chromatography, MS (ESI) m/z 446, 444 [M+H]$^+$.

A solution of sodium nitrite (18.4 g, 0.267 mol) in 133 mL of water was added dropwise to a suspension of compound 18 (40.3 g, 0.267 mol) in water (133 mL) and conc. HCl (54 mL, 0.65 mol) at 0° C. After addition, the reaction mixture was stirred at the same temperature for 45 minutes. A solution of cold diazonium salt was then added dropwise to a mixture of potassium ethylxanthate (49.3 g, 0.31 mol), water (80 mL) and aqueous sodium carbonate solution (200 mL, 2 M) at rt. After addition, the mixture was allowed to warm to 45° C. and stirred at this temperature until gas evolution ceased (about 3 h to overnight). The mixture was cooled to rt and adjusted to pH 1 with conc. HCl. The aqueous layer was extracted with ethyl acetate (3×300 mL). The combined organic layers were dried over anhydrous Na$_2$SO$_4$, filtered and concentrated under reduced pressure to afford crude compound 19 (50 g, 73%) as a dark red liquid, which was used for next step directly without further purification. $^1$H NMR (purified by pre-TLC, CDCl$_3$ 300 MHz): δ 7.40 (d, J=7.5 Hz, 2H), 7.28 (d, J=7.8 Hz, 2H), 4.54 (q, J=6.9 Hz, 2H), 3.63 (s, 2H), 1.26 (t, J=6.9 Hz, 3H).

To a solution of compound 19 (50.0 g, crude, 0.195 mol) in EtOH (180 mL) was added a solution of KOH (40.5 g, 0.724 mol) in water (180 mL). The mixture was stirred at reflux overnight. The mixture was concentrated under reduced pressure to remove EtOH. The aqueous phase was adjusted to pH 1-2 with conc. HCl. Then the aqueous phase was extracted with ethyl acetate (3×200 mL). The combined organic layers were dried over anhydrous Na₂SO₄, filtered and concentrated under reduced pressure to afford crude compound 20 (32.0 g, 98%) as a gray solid, which was used for next step directly without further purification. ¹H NMR (purified by pre-TLC, CD₃OD 400 MHz): δ 7.23 (d, J=8.4 Hz, 2H), 7.15 (d, J=8.0 Hz, 2H), 3.54 (s, 2H).

To a solution of compound 20 (32 g, crude, 0.19 mol) in dry DMF (300 mL) was added K₂CO₃ (105 g, 0.76 mol) and EtI (118 g, 0.76 mol). The reaction mixture was stirred at rt overnight. Ethyl acetate (800 mL) and water (600 mL) was added to the mixture. After partition, the aqueous layer was extracted with ethyl acetate (3×500 mL). The combined organic layers were washed with brine (2×800 mL), dried over anhydrous Na₂SO₄, filtered and concentrated under reduced pressure. The residue was purified by column chromatography on silica gel eluting with petroleum ether/ethyl acetate 30/1 to give compound 21 (15.3 g, 36%) as a yellow oil. LC-MS $t_R$=0.881 min in 5-95AB_1.5 min chromatography (Welch Xtimate C18, 2.1*30 mm, 3 um), MS (ESI) m/z 224.8 [M+H]⁺. ¹H NMR (CDCl₃ 300 MHz): δ 7.02 (d, J=8.1 Hz, 2H), 6.94 (d, J=8.1 Hz, 2H), 3.89 (q, J=7.2 Hz, 2H), 3.31 (s, 2H), 2.67 (q, J=7.5 Hz, 2H), 1.07-0.97 (m, 6H).

To a solution of compound 21 (7.8 g, 35 mmol) in DCM (100 mL) was added m-CPBA (21 g, 123 mmol) in portions at 0° C. The reaction mixture was stirred for 16 h at rt. The reaction mixture was filtered. 200 mL of DCM was added to the filtrate and then the mixture was quenched with sat. Na₂SO₃ solution (200 mL). After partition, the organic layer was washed with sat. Na₂SO₃ solution (200 mL) and then sat. Na₂CO₃ solution (300 mL). The combined aqueous phases were extracted with DCM (3×400 mL). The combined organic layers were washed with brine (500 mL), dried over anhydrous Na₂SO₄, filtered and concentrated under reduced pressure. The residue was purified by column on silica gel eluting with petroleum ether/ethyl acetate 3/1 to 5/1 to afford compound 22 (7.0 g, 78%) as a white solid. LC-MS $t_R$=0.807 min in 5-95AB_2 min chromatography (Welch Xtimate C18, 2.1*30 mm, 3 um), MS (ESI) m/z 256.8 [M+H]⁺. ¹H NMR (CDCl₃ 400 MHz): δ 7.87 (d, J=8.4 Hz, 2H), 7.50 (d, J=8.0 Hz, 2H), 4.18 (q, J=6.8 Hz, 2H), 3.72 (s, 2H), 3.11 (q, J=7.6 Hz, 2H), 1.30-1.25 (m, 6H).

To a solution of compound 22 (10.0 g, 39 mmol) in EtOH (100 mL) was added a solution of NaOH (5.7 g, 142.5 mmol) in water (100 mL). The reaction mixture was stirred at rt for 16 h. EtOH was removed under reduced pressure. The aqueous layer was adjusted to pH 1 with 6 N aq HCl and extracted with ethyl acetate (3×100 mL). The combined organic layers were washed with brine (2×100 mL), dried over anhydrous Na₂SO₄, filtered and concentrated under reduced pressure to give the desired product V-1 (7.3 g, 82%) as a white solid. LC-MS $t_R$=0.573 min in 5-95AB_1.5 min chromatography (Welch Xtimate C18, 2.1*30 mm, 3 um), MS (ESI) m/z 228.8 [M+H]⁺. ¹H NMR (CDCl₃ 400 MHz): δ 7.88 (d, J=8.0 Hz, 2H), 7.50 (d, J=8.4 Hz, 2H), 3.77 (s, 2H), 3.12 (q, J=7.6 Hz, 2H), 1.28 (t, J=7.6 Hz, 3H).

Tert-butyl (S)-2-(2-(4-(ethylsulfonyl)phenyl)acetamido)-4-isopropyl-4,6-dihydro-5H-pyrrolo[3,4-d]thiazole-5-carboxylate (III-1)

Amide (III-1) was prepared following the synthetic route shown in Scheme 11.

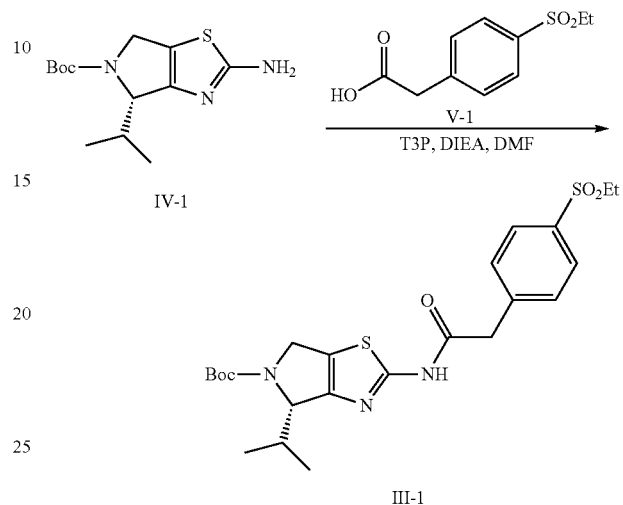

At 0° C., to a solution of compound (IV-1) (278 mg, 1.0 mmol) in DMF (6 mL) was added carboxylic acid (V-1) (342 mg, 1.5 mmol), N,N-diisopropylethylamine (350 μL, 2.5 mmol) followed by propylphosphonic anhydride solution (T3P, 50 wt. % in ethyl acetate, 1.2 mL, 2 mmol). The mixture was allowed to stir at rt for 6 h and diluted with H₂O (20 mL) and ethyl acetate (30 mL). The aqueous phase was extracted with ethyl acetate (3×20 mL). The combined organic layers were washed with brine (30 mL), dried over anhydrous Na₂SO₄, filtered and concentrated under reduced pressure. The residue was purified by column chromatography on silica gel eluting with Hexanes/ethyl acetate (1/1) to afford compound (III-1) (390 mg, 80%) as a white solid. LC-MS $t_R$=1.62 min in 2 min chromatography, MS (ESI) m/z 494 [M+H]⁺. ¹H NMR (CD₃OD, 400 MHz): δ 7.89 (d, J=8.4 Hz, 2H), 7.62 (d, J=8.4 Hz, 2H), 4.73-4.64 (m, 3H), 4.51-4.43 (m, 2H), 3.92 (s, 2H), 3.20 (q, J=7.6 Hz, 2H), 2.48-2.40 (m, 1H), 1.51 (s, 9H), 1.22 (t, J=7.6 Hz, 3H), 1.14-1.11 (m, 3H), 0.64-0.60 (m, 3H).

(S)-2-(4-(Ethylsulfonyl)phenyl)-N-(4-isopropyl-5,6-dihydro-4H-pyrrolo[3,4-d]thiazol-2-yl)acetamide (II-1)

Free amine (II-1) was prepared following the synthetic route shown in Scheme 12.

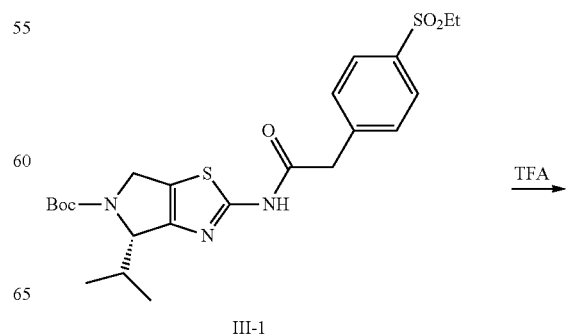

-continued

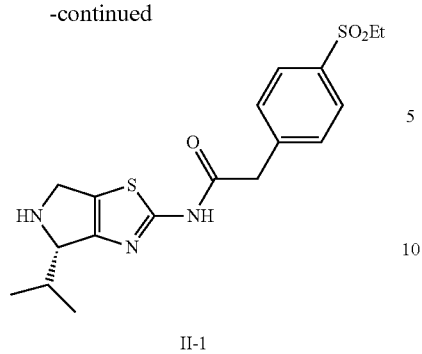

II-1

To a solution of compound III-1 (135 mg, 0.27 mmol) in CH$_2$Cl$_2$ (5 mL) was added TFA (1 mL). The mixture was stirred at rt for 2 h and neutralized with sat. NaHCO$_3$ solution. The separated aqueous phase was extracted with CH$_2$Cl$_2$ (3×15 mL). The organic layer was dried over anhydrous Na$_2$SO$_4$, filtered and concentrated under reduced pressure to afford crude compound II-1 as a brown oil, which was used directly for the next step without further purification. LC-MS t$_R$=0.67 min in 2 min chromatography, MS (ESI) m/z 394 [M+H]$^+$.

N—((S)-4-((S)-sec-butyl)-5,6-dihydro-4H-pyrrolo[3,4-d]thiazol-2-yl)-2-(4-(methylsulfonyl)phenyl)acetamide (II-2)

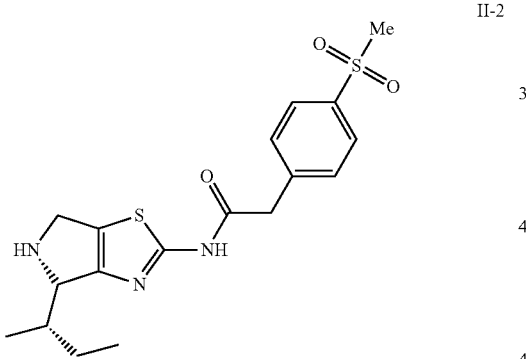

II-2

Intermediate compound of Formula (II-2) can be prepared following analogous methods used in Schemes 1 and 12 using compound (IV-2) instead of compound (IV-1). LC-MS t$_R$=0.70 min in 2 min chromatography, MS (ESI) m/z 394.2 [M+H]$^+$.

(S)-2-(4-(ethylsulfonyl)phenyl)-N-(4-isopropyl-4-methyl-5,6-dihydro-4H-pyrrolo[3,4-d]thiazol-2-yl)acetamide (II-3)

Scheme 13.

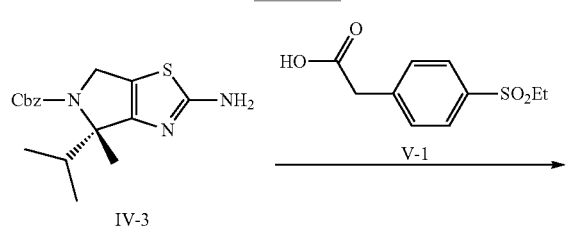

-continued

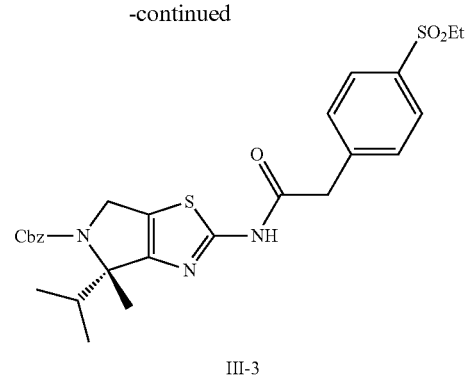

III-3

To a solution of compound IV-3 (48 mg, 0.124 mmol) in THF (6 mL) was added carboxylic acid V-1 (42 mg, 0.185 mmol) and Et$_3$N (0.03 mL, 0.25 mmol) at rt. To this solution was added a propylphosphonic anhydride solution (T3P, 50 wt. % in ethyl acetate, 0.11 mL, 0.185 mmol) dropwise at rt. The reaction turned a red color upon addition of T3P. The mixture was allowed to stir at rt for 30 min and was then diluted with H$_2$O (10 mL) and ethyl acetate (20 mL). The aqueous phase was extracted with ethyl acetate (3×10 mL). The combined organic layers were washed with sat. NaHCO$_3$ (10 mL), brine (10 mL), dried over anhydrous Na$_2$SO$_4$, filtered and concentrated under reduced pressure to afford nearly pure crude compound III-3 as an oil, which was used directly for the next step without further purification. LC-MS t$_R$=1.676 min in 2 min chromatography, MS (ESI) m/z 542.53 [M+H]$^+$.

Scheme. 14.

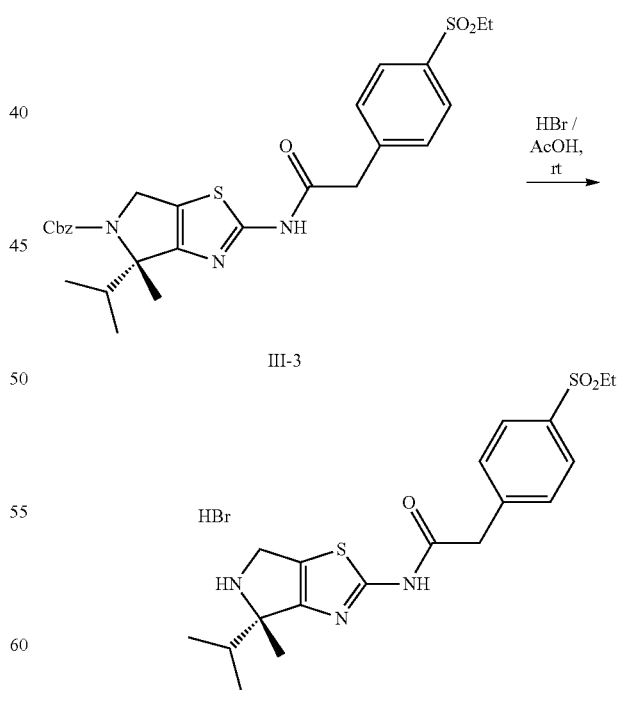

To a solution of crude compound III-3 (0.124 mmol) in AcOH (2 mL) was added a 33% solution of HBr in AcOH (2 mL) at rt. The mixture was stirred at rt for 30 min and neutralized with a saturated NaHCO₃ solution. The separated aqueous phase was extracted with CH₂Cl₂ (3×10 mL). The organics was dried over anhydrous Na₂SO₄, filtered and concentrated under reduced pressure to afford crude compound II-3 as an oil, which was used directly for the next step without further purification. LC-MS $t_R$=0.703 min in 2 min chromatography, MS (ESI) m/z 408.41 [M+H]⁺.

N-(4-(3-bromobenzyl)-5,6-dihydro-4H-pyrrolo[3,4-d]thiazol-2-yl)-2-(4-(ethylsulfonyl)phenyl)acetamide (II-8)

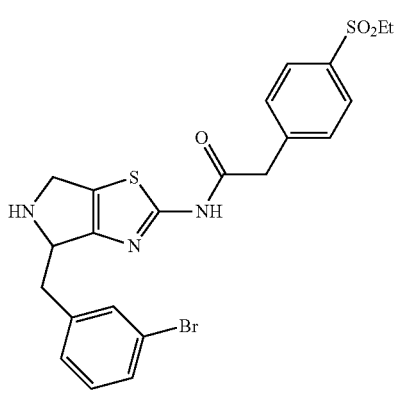

Intermediate compound of Formula (II-8) can be prepared following analogous methods used in Schemes 13 and 14 using compound (IV-4) instead of compound (IV-3). LC-MS $t_R$=0.58 min in 1.5 min chromatography, MS (ESI) m/z 520, 522 [M+H]⁺.

(S)-5-(tert-butoxycarbonyl)-4-isopropyl-5,6-dihydro-4H-pyrrolo[3,4-d]thiazole-2-carboxylic acid (VII-1)

Carboxylic acid (VII-1) was prepared following the synthetic route shown in Scheme 15.

Scheme 15.

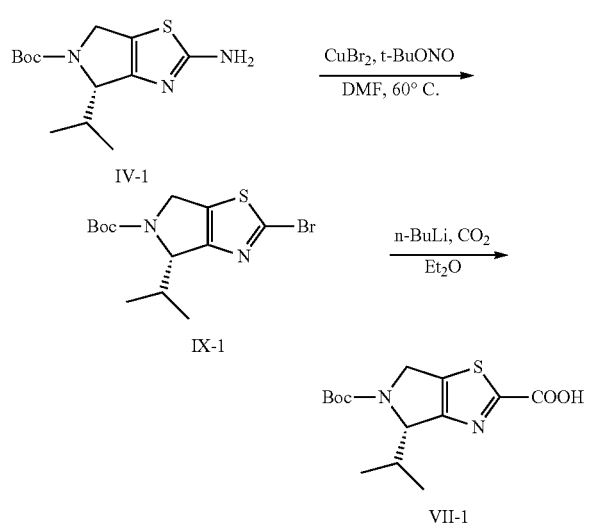

To a solution of IV-1 (3.0 g, 10.60 mmol) in CH₃CN (65 mL) was added ᵗBuONO (3.3 g, 31.80 mmol) at 0° C. under N₂ atmosphere. The mixture was stirred at 0° C. for 20 min. CuBr (3.0 g, 21.20 mmol) was added to the mixture in portions at 0° C. The mixture was allowed to warm to rt and stirred for 30 min at rt. The mixture was quenched with water (80 mL) at 0° C. The mixture was filtered and the filtrate was concentrated under reduced pressure to remove CH₃CN. The aqueous layer was extracted with ethyl acetate (3×50 mL). The combined organic layers were washed with brine (50 mL), dried over anhydrous sodium sulfate, filtered and concentrated under reduced pressure. The residue was purified by column chromatography on silica gel eluting with petroleum ether/ethyl acetate 10/1 to afford IX-1 (1.9 g, 52%) as a pink oil. LC-MS $t_R$=0.971 min in 5-95AB_1.5 min chromatography (Welch MK RP-18e 25-2 mm), MS (ESI) m/z 290.6 [M−56+H]⁺. LC-MS $t_R$=1.57 min in 2 min chromatography, MS (ESI) m/z 480 [M+H]⁺.

To a solution of IX-1 (2.0 g, 5.76 mmol) in anhydrous THF (35 mL) was added n-BuLi (3.5 mL, 8.64 mmol, 2.5M in hexane) dropwise at −78° C. under N₂. The resulting suspension was allowed to warm to 0° C. and stirred at 0° C. for 30 min. The mixture was then recooled to −78° C. and a stream of CO₂ gas (from gas bag) was bubbled into the reaction for 5 min. The reaction mixture was then slowly allowed to warm to rt and stirred for an additional 2 h at rt. The mixture was concentrated under reduced pressure. The residue was dissolved in MeOH (20 mL) and adjusted to pH=5 with 4N HCl/MeOH (2.2 mL) solution. The residue was concentrated under reduced pressure and purified by column chromatography on silica gel eluting with CH₂Cl₂/MeOH 20/1 to afford VII-1 (1.32 g, 74%) as a red solid. LC-MS $t_R$=0.822 min in 5-95AB_1.5 min chromatography (Welch MK RP-18e 25-2 mm), MS (ESI) m/z 312.9 [M+H]⁺. ¹H NMR (CD₃OD): δ 4.86-4.82 (m, 1H), 4.81-4.67 (m, 1H), 4.61-47 (m, 1H), 2.48-2.38 (m, 1H), 1.52 (s, 9H), 1.12-1.08 (m, 3H), 0.69-0.65 (m, 3H). Isomer SFC $t_R$=3.68 min in 15 min chromatography (Column: AS-H; Method Name: AS-H_3_5_40_2.5 ml.met, ee=100%).

Tert-butyl (S)-2-((4-(ethylsulfonyl)benzyl)carbamoyl)-4-isopropyl-4,6-dihydro-5H-pyrrolo[3,4-d]thiazole-5-carboxylate (VI-1)

Amide (VI-1) was prepared following the synthetic route shown in Scheme 16.

Scheme 16.

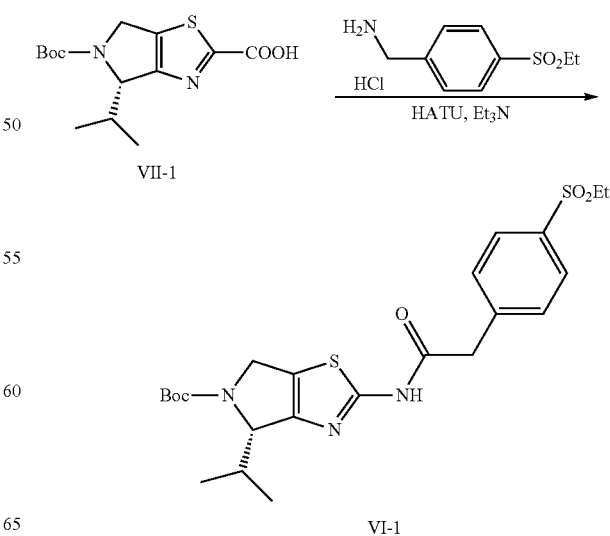

To a solution of VII-1 (568 mg, 1.82 mmol) in DMF (10 mL) was added (4-(ethylsulfonyl)phenyl)methanamine HCl salt (514 mg, 2.18 mmol), HATU (1.38 g, 3.64 mmol) and Et₃N (552 mg, 5.45 mmol). The mixture was stirred at rt for 4 h. Ethyl acetate (20 mL) and water (20 mL) were added to the mixture. After partition, the aqueous layer was extracted with ethyl acetate (3×20 mL). The combined organic layers were washed successively with water (3×20 mL) and brine (30 mL), dried over sodium sulfate, filtered and concentrated under reduced pressure. The residue was purified by column chromatography on silica gel eluting with petroleum ether/ethyl acetate 1/1 to afford VI-1 (256 mg, 29%) as a pale yellow solid. LC-MS $t_R$=0.906 min in 5-95AB_1.5 min chromatography (Welch MK RP-18e 25-2 mm), MS (ESI) m/z 494.1 [M+H]⁺. Isomer SFC $t_R$=7.75 min in 15 min chromatography (Column: AD-3; Method Name: AD-3_4_5_40_2.5 ml.met, ee=96.27%).

(S)—N-(4-(ethylsulfonyl)benzyl)-4-isopropyl-5,6-dihydro-4H-pyrrolo[3,4-d]thiazole-2-carboxamide (VI-2)

Free amine (VI-2) was prepared following the synthetic route shown in Scheme 17.

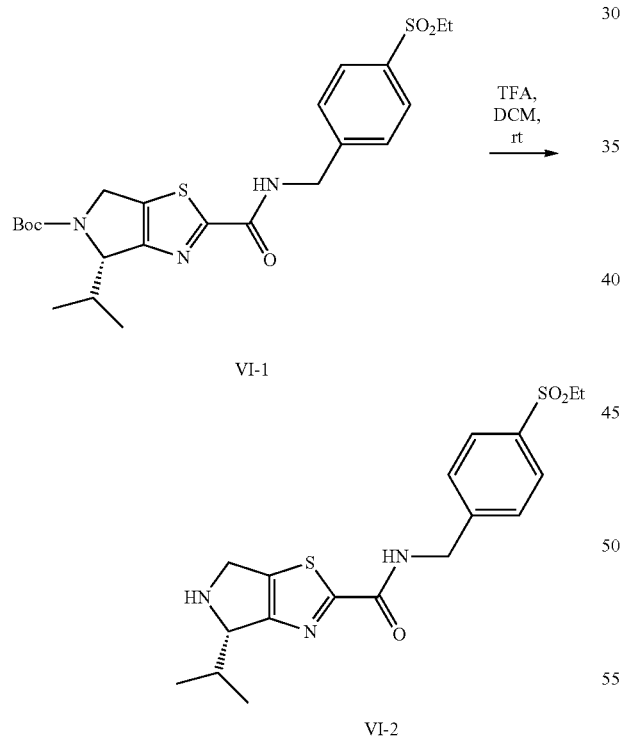

To a solution of VI-1 (256 mg, 0.523 mmol) in CH₂Cl₂ (4 mL) was added TFA (1 mL). The mixture was stirred at rt for 2 h. The mixture was concentrated under reduced pressure to afford crude VI-2 (crude 394 mg, 100%) as a brown oil, which was used for the next step directly without further purification. LC-MS $t_R$=0.623 min in 5-95AB_1.5 min chromatography (Welch MK RP-18e 25-2 mm), MS (ESI) m/z 393.9 [M+H]⁺.

Tert-butyl (S)-4-isopropyl-2-((4-(methylsulfonyl)benzyl)carbamoyl)-4,6-dihydro-5H-pyrrolo[3,4-d]thiazole-5-carboxylate (VI-3)

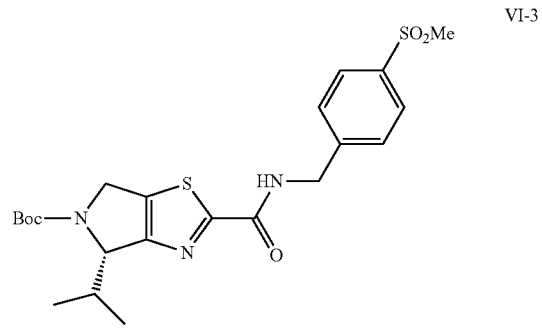 [SMILES: CC(C)[C@H]1c2nc(C(=O)NCc3ccc(S(C)(=O)=O)cc3)sc2CN1C(=O)OC(C)(C)C]

Intermediate compound of Formula (VI-3) can be prepared following analogous methods used in Scheme 16 using (4-(methylsulfonyl)phenyl)methanamine HCl salt instead of (4-(ethylsulfonyl)phenyl)methanamine. LC-MS $t_R$=0.875 min in 5-95AB_1.5 min chromatography (Welch MK RP-18e 25-2 mm), MS (ESI) m/z 480.0 [M+H]⁺. Isomer SFC $t_R$=4.247 min in 12 min chromatography (Column: OJ-3; Method Name: OJ-3_B2_5_40_25 ML, ee=97.0%).

Tert-butyl (S)-2-(((5-(ethylsulfonyl)pyridin-2-yl)methyl)carbamoyl)-4-isopropyl-4,6-dihydro-5H-pyrrolo[3,4-d]thiazole-5-carboxylate (VI-4)

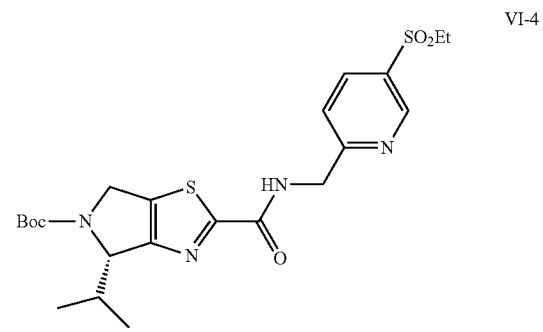

Intermediate compound of Formula (VI-4) can be prepared following analogous methods used in Scheme 16 using (5-(ethylsulfonyl)pyridin-2-yl)methanamine HCl salt instead of (4-(ethylsulfonyl)phenyl)methanamine. LC-MS $t_R$=0.880 min in 5-95AB_1.5 min chromatography (Welch MK RP-18e 25-2 mm), MS (ESI) m/z 495.1 [M+H]⁺.

The following are the preparations of intermediates on the left-hand side.

Trans-4-(trifluoromethyl)cyclohexane-1-carbaldehyde (Intermediate a)

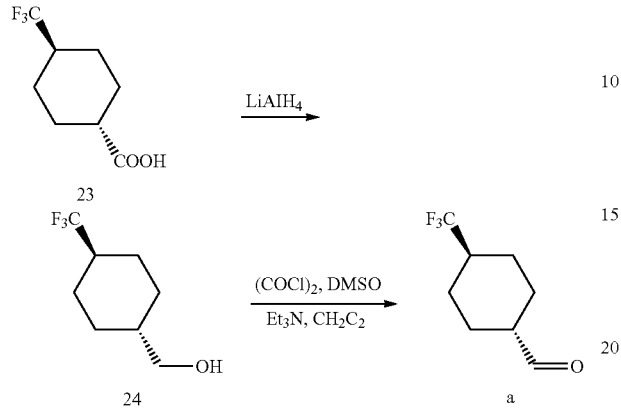

A solution of trans-4-(trifluoromethyl)cyclohexanecarboxylic acid 23 (1.0 g, 5.1 mmol) in anhydrous THF (10 mL) was added into a mixture of LiAlH$_4$ (0.4 g, 10.5 mmol) in anhydrous THF (5 mL) dropwise at 0° C. under N$_2$. The mixture was stirred at rt for 2 h. The mixture was added water (0.4 mL) and 10% aqueous NaOH solution (0.4 mL) carefully at 0° C. The mixture was filtered and the filtrate was dried over anhydrous Na$_2$SO$_4$, filtered and concentrated under reduced pressure to afford crude alcohol 24 (900 mg, 97%) as a colorless oil, which was used for the next step without further purification. $^1$H NMR (CDCl$_3$): δ 3.52-3.49 (m, 2H), 2.03-1.92 (m, 5H), 1.54-1.46 (m, 1H), 1.37-1.33 (m, 3H), 1.03-0.97 (m, 2H).

To a solution of oxalyl dichloride (419 mg, 3.3 mmol) in anhydrous CH$_2$Cl$_2$ (8 mL) was added DMSO (515 mg, 6.6 mmol) at −78° C. under N$_2$. After being stirred for 30 mins, a solution of 24 (200 mg, 1.1 mmol) in anhydrous CH$_2$Cl$_2$ (1 mL) was added dropwise. The mixture was stirred at −78° C. for 30 mins, a solution of Et$_3$N (1.1 g, 11.0 mmol) in anhydrous CH$_2$Cl$_2$ (1 mL) was added carefully. After being stirred at −78° C. for 1 h, the mixture was warmed to rt and stirred overnight. The reaction mixture was added with CH$_2$Cl$_2$ (10 mL) and washed with water (20 mL×3) and brine (20 mL), dried over anhydrous Na$_2$SO$_4$, filtered and concentrated under reduced pressure. The residue was purified by preparative TLC with petroleum ether/ethyl acetate 5/1 to afford the aldehyde a (100 mg, 50%) as a yellow oil. $^1$H NMR (DMSO-d$_6$): δ 9.57 (s, 1H), 2.33-2.12 (m, 3H), 2.03-1.92 (m, 3H), 1.33-1.24 (m, 4H).

Trans-4-(5-methyl-1,3,4-oxadiazol-2-yl)cyclohexane-1-carbaldehyde (Intermediate b)

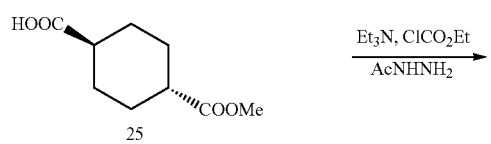

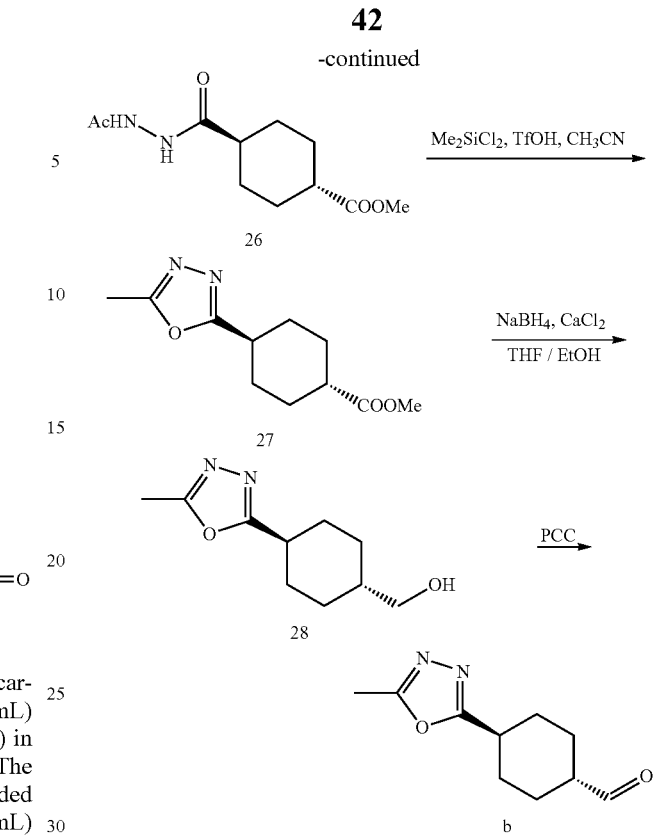

To a solution of 25 (2.0 g, 10.7 mmol) in anhydrous THF (30 mL) was added Et$_3$N (2.17 g, 21.5 mmol) and ClCO$_2$Et (2.74 g, 14.8 mmol) at 0-5° C. under N$_2$. The mixture was stirred at 0-5° C. for 1 h. After 1 h, the precipitated ammonium salts were removed by filtration. To the filtrate was added a solution of AcNHNH$_2$ (0.83 g, 11.8 mmol) in anhydrous THF (10 mL). The mixture was stirred at rt for 48 h. The reaction mixture was added with water (30 mL) and extracted with EtOAc (3×30 mL). The combined organic layers were washed with brine (30 mL), dried over anhydrous Na$_2$SO$_4$, filtered and concentrated under reduced pressure to afford crude 26 (1.55 g, 60%) as a white solid, which was used for the next step directly without further purification. $^1$H NMR (CD$_3$OD): δ 3.67 (s, 3H), 2.36-2.23 (m, 2H), 2.08-2.02 (m, 2H), 1.99 (s, 3H), 1.98-1.92 (m, 2H), 1.61-1.41 (m, 4H).

To a solution of 26 (1.5 g, 6.20 mmol) in CH$_3$CN (60 mL) was added TfOH (2.42 g, 16.1 mmol) and Me$_2$SiCl$_2$ (880 mg, 6.82 mmol) under N$_2$. The mixture was stirred at 80° C. for 16 h. After cooled to rt, the mixture was poured into ice. The reaction mixture was adjusted to pH=3 with 1N aqueous sodium hydroxide solution (6.2 mL). The mixture was added with water (20 mL) and extracted with EtOAc (3×20 mL). The combined organic layers were washed with brine (20 mL), dried over anhydrous Na$_2$SO$_4$, filtered and concentrated under reduced pressure. The residue was purified by column chromatography on silica gel eluting with (petroleum ether: ethyl acetate=5:1 to 2:1) to afford 27 (480 mg, 35%) as a pale yellow solid.

To a solution of CaCl$_2$ (982 mg, 8.93 mmol) in anhydrous THF/EtOH (1:1, 6 mL) was added NaBH$_4$ (679 mg, 17.9 mmol) at 0° C. under N$_2$. The mixture was stirred at 0° C. for 30 min. Then 27 (100 mg, 0.45 mmol) in anhydrous THF/EtOH (1:1, 4 mL) was added to above mixture. The mixture was stirred at rt for 2 h. The reaction mixture was concentrated under reduced pressure. The reaction mixture was added with water (10 mL) and extracted with EtOAc (3×10 mL). The combined organic layers were washed with brine (10 mL), dried over anhydrous $Na_2SO_4$, filtered and concentrated under reduced pressure to afford crude alcohol 28 (80 mg, 92%) as a pale yellow oil, which was used for the next step directly without further purification.

To a solution of alcohol 28 (50 mg, 0.26 mmol) in anhydrous $CH_2Cl_2$ (5 mL) was added PCC (96 mg, 0.38 mmol) under $N_2$. The mixture was stirred at rt for 2 h. The reaction was added with water (10 mL) and extracted with $CH_2Cl_2$ (3×10 mL). The combined organic layers were washed with brine (10 mL), dried over anhydrous $Na_2SO_4$, filtered and concentrated under reduced pressure to afford the aldehyde b (49 mg, 99%) as a pale yellow oil, which was used for the next step directly without further purification.

4-Methoxy-4-methylcyclohexane-1-carbaldehyde (Intermediate c)

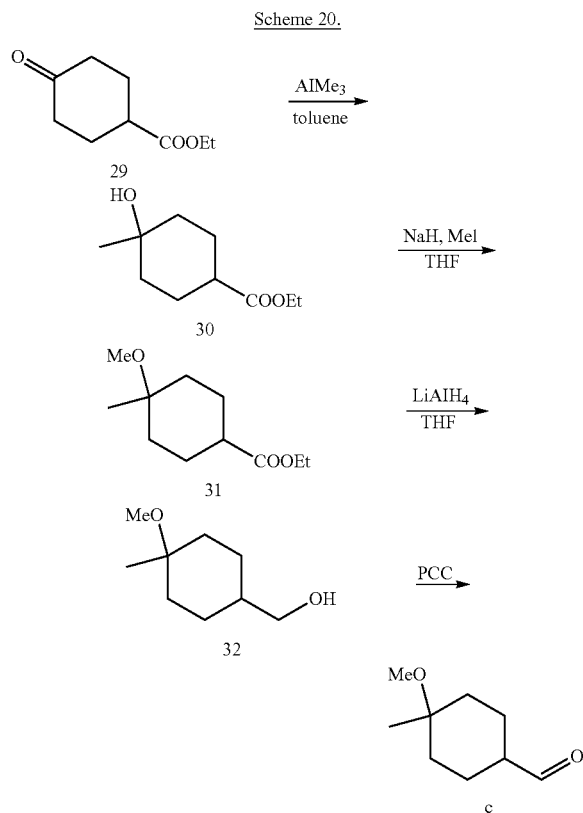

To a solution of ester 29 (2 g, 11.76 mmol) in anhydrous toluene (25 mL) was added $AlMe_3$ (11.8 mL, 23.5 mmol, 2 M in toluene) dropwise at 0° C. The mixture was stirred at rt for 3 h. The reaction was quenched by the addition of saturated $NH_4Cl$ solution (50 mL) at 0° C. The mixture was filtered and concentrated under reduced pressure. The aqueous layer was extracted with ethyl acetate (3×30 mL). The combined organic layers were washed with brine (50 mL), dried over anhydrous sodium sulfate, filtered and concentrated under reduced pressure. The residue was purified by column chromatography on silica gel eluting with petroleum ether/ethyl acetate 5/1 to afford tertiary alcohol 30 (1.0 g, 46%) as a colorless oil. $^1$H NMR ($CDCl_3$): δ 4.13 (q, J=7.2 Hz, 2H), 2.38-2.17 (m, 1H), 1.98-1.88 (m, 1H), 1.86-1.76 (m, 2H), 1.74-1.64 (m, 2H), 1.45-1.38 (m, 3H), 1.26-1.21 (m, 6H).

To a solution of 30 (500 mg, 3.16 mmol) in anhydrous THF (8 mL) was added NaH (253 mg, 6.32 mmol, 60% in mineral oil) in portions at 0° C. The mixture was stirred at 0° C. for 40 min. Then MeI (914 mg, 3.79 mmol) was added to the mixture via syringe at 0° C. After addition, the mixture was stirred at rt for 3 h. The reaction was quenched by the addition of saturated $NH_4Cl$ solution (20 mL) at 0° C. The mixture was concentrated under reduced pressure. The aqueous layer was extracted with ethyl acetate (3×25 mL). The combined organic layers were washed with brine (30 mL), dried over anhydrous sodium sulfate, filtered and concentrated under reduced pressure to afford crude 31 (crude 350 mg, 55%) as a pale yellow oil, which was used for the next step directly without further purification. $^1$H NMR ($CDCl_3$): δ 4.13 (q, J=7.2 Hz, 2H), 3.21 (s, 3H), 2.40-2.36 (m, 1H), 1.93-1.86 (m, 2H), 1.71-1.62 (m, 4H), 1.57-1.48 (m, 2H), 1.26 (t, J=7.2 Hz, 3H), 1.16 (s, 3H).

To a solution of 31 (crude 350 mg, 1.75 mmol) in THF (5 mL) was added $LiAlH_4$ (2.62 mL, 5.25 mmol, 2 M in THF) dropwise at 0° C. The mixture was stirred at rt for 3 h. The reaction was quenched successively with water (0.2 mL) and 10% NaOH solution (0.2 mL) at 0° C. The mixture was filtered and concentrated under reduced pressure. Water (15 mL) and ethyl acetate (15 mL) were added to the mixture. After partition, the aqueous layer was extracted with ethyl acetate (3×15 mL). The combined organic layers were washed with brine (20 mL), dried over anhydrous sodium sulfate, filtered and concentrated under reduced pressure. The residue was purified by column chromatography on silica gel eluting with petroleum/ethyl acetate 5/1 to afford the alcohol 32 (80 mg, 29%) as a colorless oil. $^1$H NMR ($CDCl_3$): δ 3.52 (d, J=6.4 Hz, 2H), 3.25 (s, 3H), 1.80-1.71 (m, 4H), 1.51-1.47 (m, 5H), 1.18 (s, 3H).

To a solution of 32 (40 mg, 0.253 mmol) in $CH_2Cl_2$ (3 mL) was added PCC (110 mg, 0.506 mmol). The mixture was stirred at rt for 2 h. Water (15 mL) was added to the mixture. The aqueous layer was extracted with $CH_2Cl_2$ (3×15 mL). The combined organic layers were washed successively with water (3×15 mL) and brine (20 mL), dried over anhydrous sodium sulfate, filtered and concentrated under reduced pressure to afford the aldehyde c (crude 40 mg, 100%) as a pale yellow oil, which was used for the next step directly without further purification.

4-(1-Methyl-2-oxo-1,2-dihydropyridin-4-yl)benzyl methanesulfonate (Intermediate d)

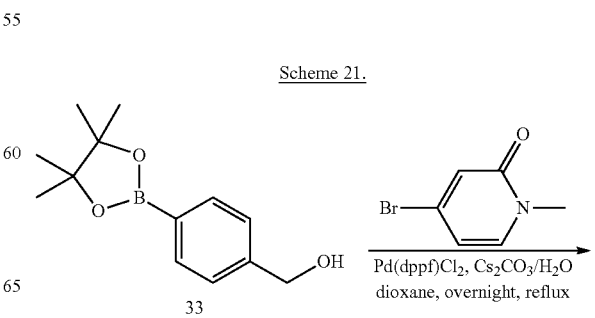

-continued

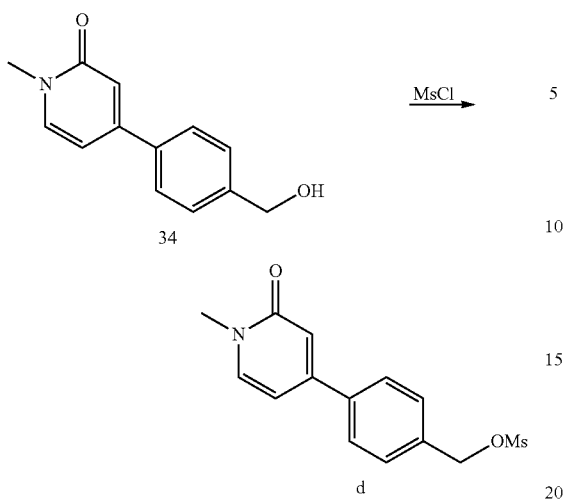

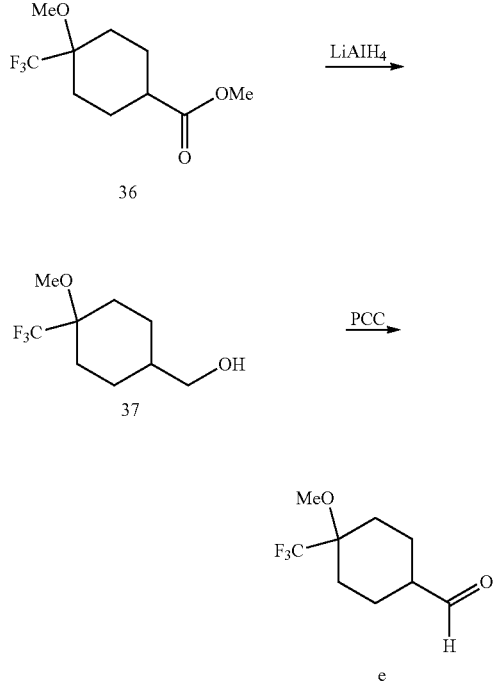

A mixture of 4-bromo-1-methylpyridin-2(1H)-one (80 mg, 0.43 mmol), 33 (100 mg, 0.43 mmol) and Cs$_2$CO$_3$ (419 mg, 1.29 mmol) in dioxane/H$_2$O (3/1, 8 mL) was added Pd(dppf)Cl$_2$ (62 mg, 0.085 mmol) at rt under N$_2$. After addition, the mixture was stirred at 100° C. overnight. The mixture was concentrated under reduced pressure. The residue was added ethyl acetate (5 mL) and filtered. The filtrate was dried over anhydrous Na$_2$SO$_4$, filtered, concentrated and purified by preparative TLC with dichloromethane/methanol 10/1 to afford 34 (90 mg, 98%) as a grey solid. LC-MS $t_R$=0.589 min in 5-95 AB_1.5 min chromatography (Welch Xtimate MK RP-18e 25-2 mm), MS (ESI) m/z 215.9 [M+H]$^+$.

To a solution of 34 (30 mg, 0.14 mmol) in anhydrous dichloromethane (2 mL) was added triethylamine (71 mg, 0.70 mmol) and methanesulfonyl chloride (80 mg, 0.70 mmol) at 0° C. under N$_2$. After addition, the mixture was stirred at rt for 1 h. The mixture was added with dichloromethane (5 mL) and washed with water (3×5 mL) and brine (5 mL), dried over anhydrous Na$_2$SO$_4$, filtered and concentrated under reduced pressure to afford crude intermediate d (40 mg, 100%) as a gray oil, which was used for the next step directly without further purification. LC-MS $t_R$=0.692 min in 5-95 AB_1.5 min chromatography (Welch Xtimate MK RP-18e 25-2 mm), MS (ESI) m/z 293.8 [M+H]$^+$.

4-Methoxy-4-(trifluoromethyl)cyclohexane-1-carbaldehyde (Intermediate e)

Scheme 22.

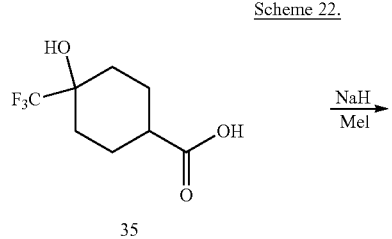

To a solution of 35 (200 mg, 0.94 mmol) in anhydrous DMF/THF (1:1, 6 mL) was added NaH (113 mg, 2.83 mmol, 60% in mineral oil) at 0° C. under N$_2$. The mixture was stirred at 0° C. for 30 min, then MeI (399 mg, 2.83 mmol) was added at 0° C. under N$_2$. The mixture was stirred at rt for 5 h. The reaction mixture was quenched with sat. NH$_4$Cl solution (10 mL) and water (10 mL) at 0° C. and extracted with EtOAc (3×10 mL). The combined organic layers were washed with brine (10 mL), dried over anhydrous Na$_2$SO$_4$, filtered and concentrated under reduced pressure to afford crude 36 (210 mg, 93%) as a pale yellow oil, which was used for the next step directly without further purification. $^1$H NMR (CDCl$_3$): δ 3.67 (d, J=8.0 Hz, 3H), 3.39 (s, 3H), 2.31-2.24 (m, 1H), 2.09-2.01 (m, 2H), 1.93-1.68 (m, 5H), 1.57-1.51 (m, 1H).

To a solution of 36 (100 mg, 0.42 mmol) in anhydrous THF (5 mL) was added LiAlH$_4$ (0.42 mL, 0.83 mmol, 2M in THF) dropwise at 0° C. under N$_2$. The mixture was stirred at 0° C. for 2 h. The reaction mixture was quenched by the addition of water (0.03 mL) and with 10% aqueous NaOH solution (0.03 mL) at 0° C. The mixture was filtered and concentrated under reduced pressure to afford crude alcohol 37 (61 mg, 69%) as a pale yellow solid, which was used for the next step directly without further purification.

To a solution of 37 (60 mg, 0.28 mmol) in anhydrous CH$_2$Cl$_2$ (5 mL) was added PCC (122 mg, 0.57 mmol) under N$_2$. The mixture was stirred at rt for 2 h. The reaction mixture was added with water (10 mL) and extracted with CH$_2$Cl$_2$ (3×10 mL). The combined organic layers were washed with brine (10 mL), dried over anhydrous Na$_2$SO$_4$, filtered and concentrated under reduced pressure to afford crude intermediate e (45 mg, 79%) as a pale yellow oil, which was used for the next step directly without further purification.

4-(2-Methyl-2H-tetrazol-5-yl)benzaldehyde (Intermediate f)

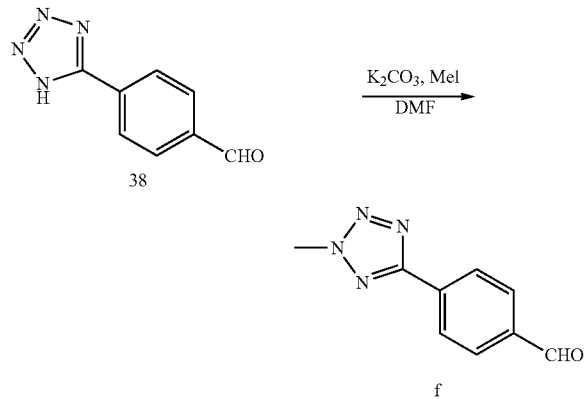

Scheme 23.

To a solution of 38 (100 mg, 0.575 mmol) in anhydrous DMF (5 mL) was added MeI (3.37 g, 23.7 mmol) and K$_2$CO$_3$ (396 mg, 2.875 mmol). The mixture was stirred at rt for 1 h. The mixture was quenched with water (10 mL) and extracted with ethyl acetate (3×10 mL). The combined organic layers were washed with brine (30 mL), dried over anhydrous Na$_2$SO$_4$, filtered and concentrated under reduced pressure to afford aldehyde f (60 mg, 56%) as a white solid. $^1$H NMR (CDCl$_3$): δ 10.09 (s, 1H), 8.33 (d, J=8.0 Hz, 2H), 8.02 (d, J=8.0 Hz, 2H), 4.45 (s, 3H).

6-(Trifluoromethyl)tetrahydro-2H-pyran-3-carbaldehyde (Intermediate g)

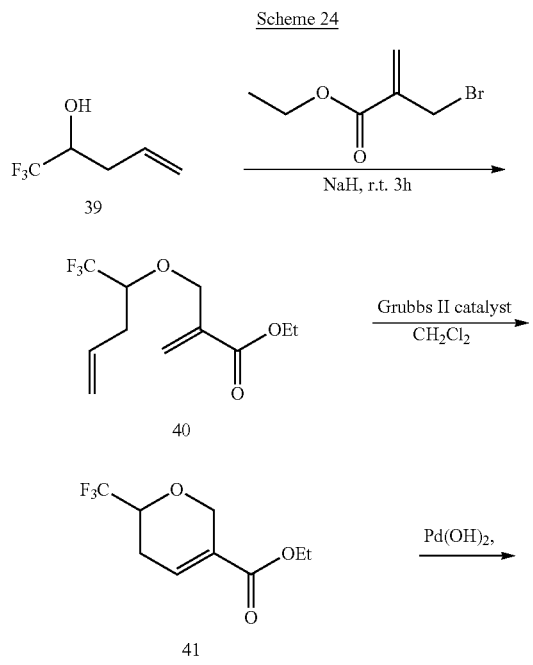

Scheme 24

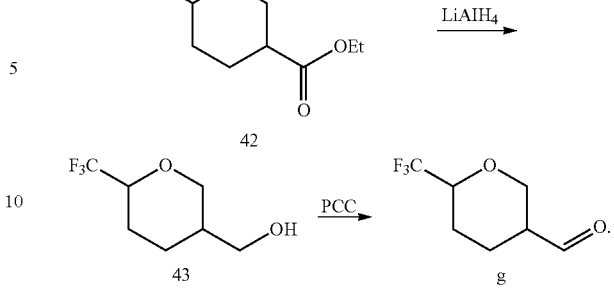

To a solution of 39 (2 g, 14.28 mmol) in anhydrous DMF (25 mL) was added NaH (685 mg, 17.13 mmol, 60% in mineral oil) in portions at 0° C. The mixture was stirred at 0° C. for 30 min and ethyl 2-(bromomethyl)acrylate (2.76 g, 14.28 mmol) was added to the resulting mixture via syringe at 0° C. After addition, the mixture was stirred at rt for 6 h. The reaction was quenched with water (30 mL) at 0° C. The mixture was extracted with ethyl acetate (3×40 mL). The combined organic layers were washed successively with water (3×50 mL), brine (50 mL), dried over anhydrous sodium sulfate, filtered and concentrated under reduced pressure. The residue was purified by column chromatography on silica gel eluting with petroleum ether/ethyl acetate 40/1 to afford compound 40 (1.08 g, 30%) as a colorless oil. $^1$H NMR (CDCl$_3$): δ 6.33 (s, 1H), 5.91 (s, 1H), 5.83-5.77 (m, 1H), 5.21-5.12 (m, 2H), 4.48 (d, J=13.6 Hz, 1H), 4.32 (d, J=13.2 Hz, 1H), 4.23 (q, J=7.2 Hz, 2H), 3.83-3.72 (m, 1H), 2.46-2.40 (m, 2H), 1.31 (t, J=7.2 Hz, 3H).

To a solution of 40 (300 mg, 1.19 mmol) in CH$_2$Cl$_2$ (120 mL) was added Grubbs II catalyst (101 mg, 0.119 mmol) under N$_2$. The mixture was stirred at rt for 3 h. Water (100 mL) was added to the mixture to quench the reaction. The organic layer was washed successively with water (3×100 mL) and brine (100 mL), dried over anhydrous sodium sulfate, filtered and concentrated under reduced pressure. The residue was purified by preparative TLC eluting with petroleum ether/ethyl acetate 10/1 to afford 41 (240 mg, 90%) as a grey oil. $^1$H NMR (CDCl$_3$): δ 7.04 (d, J=3.2 Hz, 1H), 4.63 (d, J=16.4 Hz, 1H), 4.41-4.40 (m, 1H), 4.23 (q, J=7.2 Hz, 2H), 3.93-3.90 (m, 1H), 2.52-2.49 (m, 1H), 2.41-2.36 (m, 1H), 1.31 (t, J=7.2 Hz, 3H).

A mixture of ethyl 41 (380 mg, 1.70 mmol) and Pd(OH)$_2$/C (210 mg, 10% w/w) in anhydrous THF (10 mL) was stirred at rt overnight under H$_2$ (30 psi). The mixture was filtered and the filtrate was concentrated under reduced pressure to afford crude compound 42 (crude 380 mg, 99%) as a colorless oil, which was used for the next step directly without further purification. $^1$H NMR (CDCl$_3$): δ 4.52 (d, J=12.0 Hz, 1H), 4.21 (q, J=7.2 Hz, 2H), 3.76-3.66 (m, 2H), 2.53 (s, 1H), 2.52-2.38 (m, 1H), 1.89-1.69 (m, 3H), 1.28 (t, J=7.2 Hz, 3H).

To a solution of 42 (crude 280 mg, 1.24 mmol) in anhydrous THF (4 mL) was added LiAlH$_4$ (1.9 mL, 3.72 mmol, 2 M in THF) dropwise at 0° C. After addition, the mixture was stirred at rt for 3 h. The reaction was quenched successively with water (0.15 mL) and 10% aqueous NaOH solution (0.15 mL) at 0° C. The mixture was filtered and the filtrate was concentrated under reduced pressure. The residue was purified by column chromatography on silica gel eluting with petroleum ether/ethyl acetate 5/1 to alcohol 43 (160 mg, 70%) as a colorless oil. $^1$H NMR (CDCl$_3$): δ 4.11

(d, J=11.6 Hz, 1H), 3.87-3.85 (m, 1H), 3.75-3.64 (m, 3H), 1.94-1.85 (m, 1H), 1.78-1.71 (m, 4H).

To a solution of 43 (120 mg, 0.652 mmol) in CH₂Cl₂ (5 mL) was added PCC (281 mg, 1.304 mmol). The mixture was stirred at rt for 2 h. Water (20 mL) was added to the mixture to quench the reaction. The mixture was extracted with CH₂Cl₂ (3×20 mL). The combined organic layers were washed successively with water (3×20 mL), brine (30 mL), dried over anhydrous sodium sulfate, filtered and concentrated under reduced pressure to afford crude aldehyde g (crude 120 mg, 100%) as a pale yellow oil, which was used for the next step directly without further purification.

4-(Bromomethyl)-2-chlorobenzonitrile (Intermediate h)

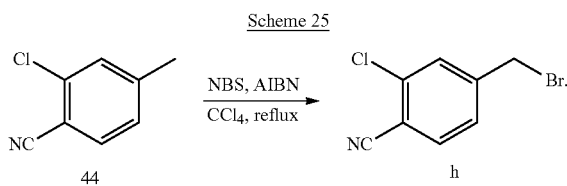

Scheme 25

To a solution of 44 (160 mg, 1.05 mmol) in CCl₄ (5 mL) was added NBS (224 mg, 1.26 mmol), AIBN (183 mg, 1.05 mmol). The mixture was stirred at 70° C. for 6 h. The mixture was concentrated under reduced pressure. The residue was purified by preparative TLC (petroleum ether/ethyl acetate=10:1) to give intermediate h (110 mg, 45%) as a white solid.

Trans-4-(difluoromethoxy)cyclohexyl)methyl methanesulfonate (Intermediate i)

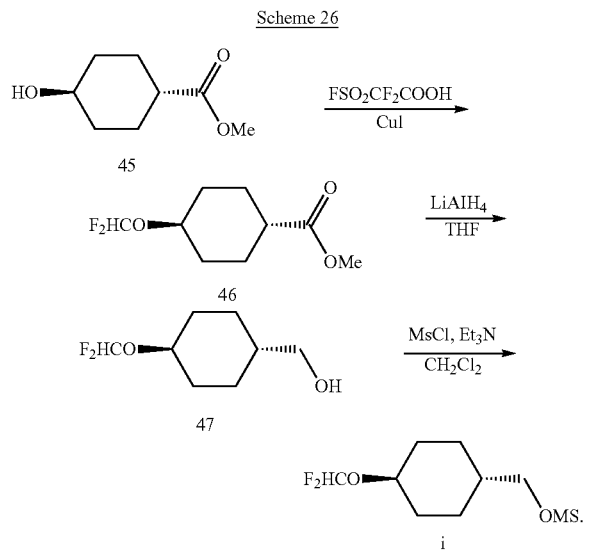

Scheme 26

To a solution of 45 (200 mg, 1.27 mmol) in CH₃CN (20.5 mL) was added a mixture of CuI (48 mg, 0.25 mmol) and FSO₂CF₂COOH (451 mg, 2.53 mmol) in CH₃CN (1.3 mL) dropwise at 50° C. under N₂. The reaction mixture was stirred at 50° C. for 1 h. The mixture was quenched with water (20 mL) and extracted with ethyl acetate (3×20 mL). The combined organic layers were washed with brine (20 mL), dried over anhydrous sodium sulfate, filtered and concentrated under reduced pressure to afford 46 (crude 180 mg, 68%) as a yellow oil, which was used for the next step without further purification. ¹H NMR (CDCl₃): δ 6.23 (t, J=75.2 Hz, 1H), 4.11-4.04 (m, 1H), 3.68 (s, 3H), 2.32-2.29 (m, 1H), 1.60-1.25 (m, 8H).

To a solution of 46 (180 mg, 0.87 mmol) in anhydrous THF (5 mL) was added LiAlH₄ (66 mg, 1.73 mmol) in portions at 0° C. under N₂. The mixture was stirred at rt for 2 h. The mixture was quenched with water (0.066 mL) and 10% aqueous NaOH solution (0.066 mL) at 0° C. The mixture was filtered and the filtrate was concentrated under reduced pressure to afford alcohol 47 (crude 150 mg, 96%) as a yellow oil, which was used for the next step without further purification. ¹H NMR (CDCl₃): δ 6.23 (t, J=75.2 Hz, 1H), 4.08-3.96 (m, 1H), 3.46 (d, J=6.0 Hz, 2H), 2.11-2.02 (m, 2H), 1.91-1.81 (m, 2H), 1.48-1.39 (m, 3H), 1.28-1.22 (m, 1H), 1.08-0.96 (m, 2H).

To a solution of 47 (150 mg, 0.86 mmol) in anhydrous CH₂Cl₂ (3 mL) was added Et₃N (261 mg, 2.58 mmol) and MsCl (196 mg, 1.72 mmol) at 0° C. under N₂. The mixture was stirred at rt overnight. The mixture was quenched with water (10 mL) at 0° C. and extracted with CH₂Cl₂ (3×10 mL). The combined organic layers were washed with brine (30 mL), dried over anhydrous Na₂SO₄, filtered and concentrated under reduced pressure. The residue was purified by preparative TLC with petroleum ether/ethyl acetate 3/1 to afford intermediate i (86 mg, 40%) as a yellow oil. ¹H NMR (CDCl₃): δ 6.23 (t, J=75.2 Hz, 1H), 4.06-3.98 (m, 3H), 3.01 (s, 3H), 2.12-2.05 (m, 2H), 1.89-1.82 (m, 2H), 1.78-1.69 (m, 1H), 1.49-1.38 (m, 2H), 1.17-1.08 (m, 2H).

(1-Methyl-6-(trifluoromethyl)piperidin-3-yl)methyl 4-methylbenzenesulfonate (Intermediate j)

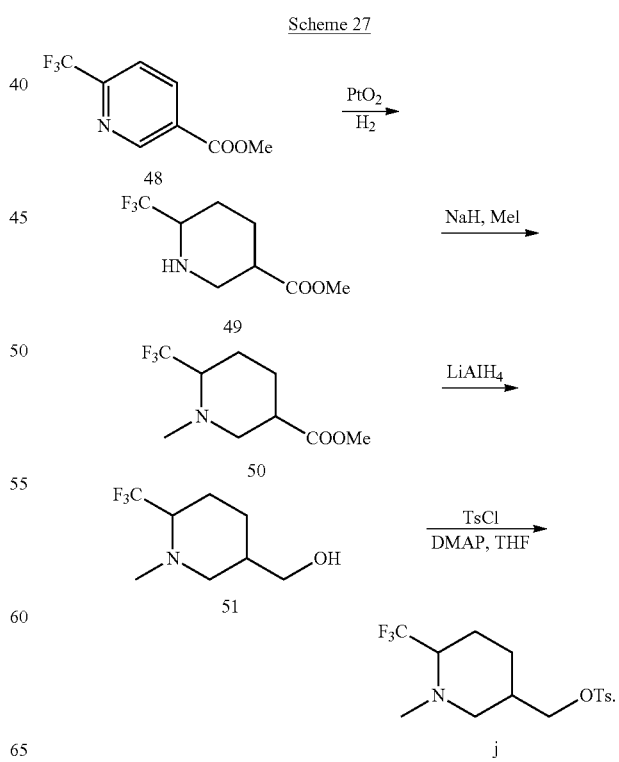

Scheme 27

To a solution of 48 (1.25 g, 6.1 mmol) in MeOH/AcOH (1:1, 20 mL) was added PtO$_2$ (138 mg, 0.61 mmoL), followed by 2 N HCl (2.5 mL) into a Parr Shaker. The mixture was stirred at rt overnight under a 55 psi H$_2$ atmosphere. The mixture was filtered through a Celite pad and the filtrate was concentrated under reduced pressure to afford crude 49 (1.2 g, 93%) as a yellow oil, which was used for the next step without further purification.

To a solution of 49 (1.0 g, 4.44 mmol) in THF/DMF (13:8, 22 mL) was added NaH (266 mg, 6.66 mmol, 60% in mineral oil) at 0° C., followed by MeI (946 mg, 6.66 mmol). The mixture was stirred at 0° C. for 0.5 h then slowly warmed up to rt and stirred overnight. It was treated with water (20 mL) and extracted with ethyl acetate (3×20 mL). The combined organics layers were washed with brine (40 mL), dried over anhydrous sodium sulfate, filtered and concentrated under reduced pressure to afford 50 (1.07 g, 100%) as a yellow oil, which was used for the next step without further purification.

To a solution of 50 (1.098 g, 4.88 mmol) in anhydrous THF (40 mL) was added LiAlH$_4$ (3.7 mL, 7.32 mmol, 2 M in THF) dropwise at 0° C. under N$_2$. The mixture was stirred at 0° C. for 0.5 h under N$_2$. It was treated with sodium sulphate decahydratewater at 0° C. and warmed up to room temperature, filtered through a Celited pad and the filtrate was concentrated under reduced pressure to afford the alcohol 51 (800 mg, 83%) as a yellow oil, which was used for the next step without further purification. $^1$H NMR (CDCl$_3$): δ 3.70-3.55 (m, 2H), 2.93-3.02 (m, 1H), 2.76-2.66 (m, 2H), 2.54 (s, 3H), 2.05-1.95 (m, 2H), 1.67-1.60 (m, 2H), 1.54-1.44 (m, 1H).

To a solution of 51 (280 mg, 1.42 mmol) in anhydrous THF (10 mL) was added Et$_3$N (460 mg, 4.56 mmoL) and TsCl (543 mg, 2.84 mmol), followed by DMAP (17 mg, 0.14 mmol). The mixture was stirred at rt overnight under N$_2$ atmosphere. The mixture was diluted with ethyl acetate (30 mL) and washed with water (30 mL). The organic layer was dried over anhydrous sodium sulfate, filtered and concentrated under reduced pressure. The residue was purified by preparative TLC with petroleum ether/ethyl acetate 3/1 to afford intermediate j (120 mg, 24%) as a colourless oil.

(6-Methoxy-5-(trifluoromethyl)pyridin-2-yl)methyl methanesulfonate (Intermediate k)

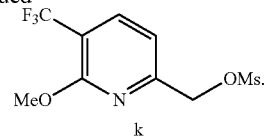

To a solution of 52 in CHCl$_3$ (4 mL) was added Ag$_2$CO$_3$ (299 mg, 1.08 mmol) followed by MeI (153 mg, 1.08 mmol). The mixture was stirred at rt for 20 h. The mixture was filtered and the filtrate was concentrated under vacuum to afford 53 (120 mg, 94% yield) as a white solid, which was used for the next step directly without further purification.

A solution of 53 (20 mg, 0.085 mmol) in dry THF (2 mL) was cooled to 0° C. under N$_2$. LiAlH$_4$ (0.13 mL, 0.255 mmol, 2 M in THF) was added dropwise to above solution at 0° C. The resulting mixture was stirred at 0° C. for 2 h. The mixture was quenched with ice water (0.13 mL) at 0° C. and then stirred for 20 mins at rt. EtOAc (5 mL) was added to the mixture, followed by anhydrous Na$_2$SO$_4$ (400 mg). The mixture was filtered and the filtrate was concentrated under reduced pressure. The residue was purified by preparative TLC (petroleum ether/ethyl acetate=3/1) to afford 54 (12 mg, 67%) as a colorless oil. $^1$H NMR (CDCl$_3$): δ 7.85 (d, J=7.6 Hz, 1H), 7.93 (d, J=7.6 Hz, 1H), 4.73 (s, 2H), 4.06 (s, 3H), 3.18 (s, 1H).

To a solution of 54 (15 mg, 0.07 mmol) in DCM (2 mL) was added triethylamine (21 mg, 0.21 mmol). The mixture was cooled to 0° C. MsCl (25 mg, 0.21 mmol) was added. The mixture was stirred at 0° C. for 1 h and then allowed to warm to rt for 20 h. TLC showed the starting material was consumed completely. Water (5 mL) and DCM (3 mL) were added to the mixture. After partition, the aqueous layer was extracted with DCM (3×3 mL). The combined organic layers were washed with brine (5 mL), dried over anhydrous sodium sulfate, filtered and concentrated under reduced pressure. The residue was purified by preparative TLC (petroleum ether/ethyl acetate=4/1) to afford intermediate k (5 mg, 25%) as a white solid. LC-MS $t_R$=0.819 min in 5-95AB_1.5 min chromatography (Welch MK RP-18e 25-2 mm), MS (ESI) m/z 285.8 [M+H]$^+$.

6-(Bromomethyl)-2-methyl-3-(trifluoromethyl)pyridine (Intermediate l)

Scheme 28

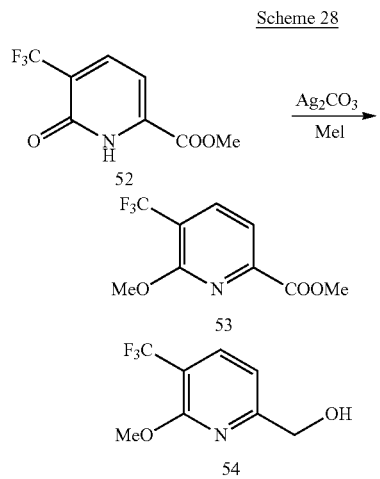

Scheme 29

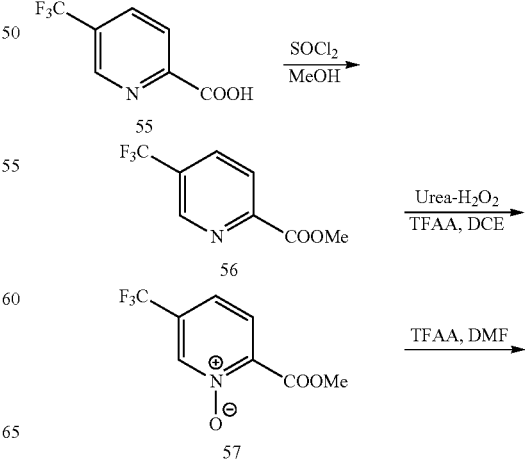

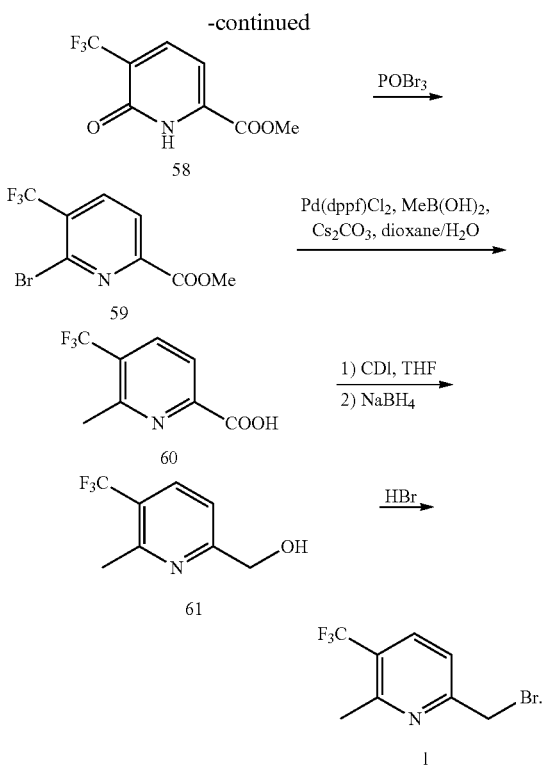

SOCl$_2$ (1.1 mL, 15.7 mmol) was added dropwise slowly to a solution of acid 55 (0.6 g, 3.1 mmol) in anhydrous methanol (40 mL). The mixture was stirred at reflux under N$_2$ for 18 h. The solvent was removed under reduced pressure. Water (5 mL) and EtOAc (5 mL) were added to the mixture. The mixture was basified with sat. NaHCO$_3$ solution to pH=7-8. After partition, the aqueous layer was extracted with EtOAc (3×3 mL), the combined organic layers were washed with brine (5 mL), dried over anhydrous sodium sulfate, filtered and concentrated under reduced pressure to afford 56 (510 mg, 80%) as a pale yellow solid, which was used for the next step directly without further purification.

Urea-H$_2$O$_2$ (161 mg, 1.72 mmol) was added into a solution of 56 (100 mg, 0.49 mmol) in DCE (4 mL). Trifluoroacetic anhydride (281 mg, 1.35 mmol) was added at −10° C. for 2 h. The reaction mixture was stirred at 0° C. for 2 h and then at rt overnight. The mixture was poured into ice-water (10 mL) and adjusted to pH 6-7 with 30% sodium hydroxide solution. The mixture was extracted with ethyl acetate (5 mL×3). The combined organic layers were dried over anhydrous Na$_2$SO$_4$, filtered and concentrated under reduced pressure to afford 57 (50 mg, 46%) as a yellow solid, which was used for the next step directly without further purification. LC-MS t$_R$=0.372 min in 5-95AB_1.5 min chromatography (Welch MK RP-18e 25-2 mm), MS (ESI) m/z 221.8 [M+H]$^+$.

Trifluoroacetic anhydride (0.4 mL, 2.3 mmol) was added dropwise to a mixture of 57 (50 mg, 0.23 mmol) in DMF (1 mL) at 0° C. for 3.5 h. The reaction mixture was stirred at 45-50° C. for 2.5 h. The mixture was poured into ice-water (10 mL) and adjusted to pH 5-6 with 30% sodium hydroxide solution. The mixture was extracted with ethyl acetate (5 mL×3). The combined organic layers were dried over anhydrous Na$_2$SO$_4$, filtered and concentrated under reduced pressure to afford 58 (20 mg, 40%) as a white solid, which was used for the next step directly without further purification. $^1$H NMR (CDCl$_3$): δ 7.90 (d, J=6.8 Hz, 1H), 7.02 (d, J=6.8 Hz, 1H), 4.04 (s, 3H).

Compound 58 (200 mg, 0.9 mmol) together with phosphoryl tribromide (320 mg, 1.1 mmol) in the presence of a cat. DMF (one drop) in toluene (5 mL) was heated to 110° C. for 2 h. The reaction mixture was then cooled to rt. The mixture was poured into ice-water (10 mL) slowly. The resulting mixture was extracted with ethyl acetate (10 mL×3). The combined organic layers were dried over anhydrous Na$_2$SO$_4$, filtered and concentrated under reduced pressure. The residue was purified by preparative TLC to afford 59 (200 mg, 80%) as a white solid. $^1$H NMR (CDCl$_3$): δ 8.21 (d, J=8.0 Hz, 1H), 8.15 (d, J=8.0 Hz, 1H), 4.06 (s, 3H).

To a solution of 59 (130 mg, 0.46 mmol) and methylboronic acid (55 mg, 0.92 mmol) in dioxane/H$_2$O (3 mL/0.3 mL) was added Cs$_2$CO$_3$ (450 mg, 1.38 mmol) followed by Pd(dppf)Cl$_2$ (34 mg, 0.046 mmol) under N$_2$ with stirring. The mixture was stirred at reflux for 20 h until the material was disappeared. The reaction mixture was cooled to rt. Water (10 mL) was added and the mixture was extracted with ethyl acetate (2×5 mL). The aqueous layer was acidified by 2 N HCl to pH=5-6. The mixture was extracted with ethyl acetate (3×5 mL). The combined organic layers were dried over anhydrous Na$_2$SO$_4$, filtered and concentrated under reduced pressure to afford crude 60 (100 mg, 100% yield) as a yellow solid, which was used for the next step directly without further purification.

To a solution of 60 (80 mg, 0.4 mmol) in dry THF (4 mL) was added carbonyldiimidazole (81 mg, 0.5 mmol) at rt. The initial suspension was stirred for 20 h at rt at which point the reaction became homogeneous. TLC showed the starting material was consumed completely. In a separate flask, a solution of NaBH$_4$ (61 mg, 1.6 mmol) in THF/H$_2$O (1:1, 2 mL) was stirred at 0° C. The above imidazolide reaction mixture was then added dropwise to the NaBH$_4$ solution at 0° C. The resulting mixture was then allowed to warm to rt for 4 h at which point the TLC showed complete conversion to the desired alcohol. Water (10 mL) was added. The mixture was adjusted to pH=6 with 1 N HCl and then extracted with ethyl acetate (5 mL). The organic layer was washed with 10% NaOH solution (5×5 mL) and then dried over anhydrous Na$_2$SO$_4$, filtered and concentrated under reduced pressure. The residue was purified by preparative TLC (petroleum ether/ethyl acetate=2/1) to afford the alcohol 61 (40 mg, 53%) as a colorless oil. LC-MS t$_R$=0.616 min in 5-95AB_1.5 min chromatography (Welch MK RP-18e 25-2 mm), MS (ESI) m/z 191.8 [M+H]$^+$.

A solution of 61 (40 mg, 0.21 mmol) in HBr/H$_2$O (2 mL, 48%) was heated to 110° C. for 20 h. The solvent was removed under reduced pressure at 50° C. to afford crude bromide 1 HBr salt (45 mg, 100%) as a yellow oil, which was used for the next step directly without further purification. LC-MS t$_R$=0.844 min in 5-95AB_1.5 min chromatography (Welch MK RP-18e 25-2 mm), MS (ESI) m/z 253.6 [M+H]$^+$.

Trans-4-(((methylsulfonyl)oxy)methyl)cyclohexyl acetate (Intermediate m)

Scheme 30

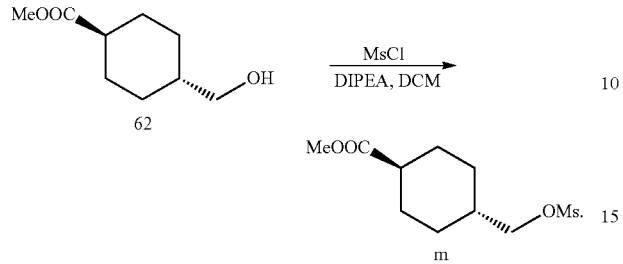

To a solution of 62 (300 mg, 1.74 mmol) in anhydrous CH$_2$Cl$_2$ (10 mL) at 0° C. was treated with DIPEA (675 mg, 5.23 mmol) followed by MsCl (800 mg, 6.98 mmol). The mixture was stirred at rt for 1 h. The reaction was quenched with the addition of water (15 mL) at 0° C. The aqueous layer was extracted with CH$_2$Cl$_2$ (3×25 mL). The combined organic layers were washed successively with water (3×25 mL) and brine (30 mL), dried over anhydrous sodium sulfate, filtered and concentrated under reduced pressure to afford crude intermediate m (crude 300 mg, 69%) as a pale yellow oil, which was used for the next step directly without further purification. $^1$H NMR (CDCl$_3$): δ 4.03 (d, J=6.4 Hz, 2H), 3.66 (s, 3H), 3.00 (s, 3H), 2.31-2.17 (m, 1H), 2.06-1.97 (m, 2H), 1.92-1.87 (m, 2H), 1.46-1.42 (m, 3H), 1.08-1.05 (m, 2H).

2-(Bromomethyl)-5-(trifluoromethyl)benzonitrile (Intermediate n)

Scheme 31

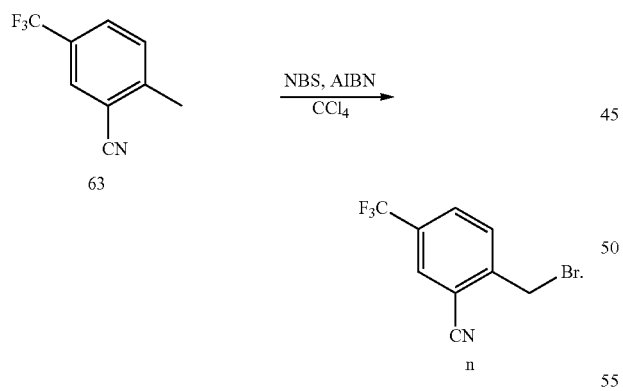

To a solution of 63 (100 mg, 0.54 mmol) in anhydrous CCl$_4$ (2 mL) was added NBS (96 mg, 0.54 mmol) and AIBN (94 mg, 0.54 mmol). The mixture was stirred at reflux under N$_2$ for 6 h. Water (5 mL) and dichloromethane (3 mL) were added to the mixture. After partition, the aqueous layer was extracted with dichloromethane (3×3 mL). The combined organic layers were washed with brine (5 mL), dried over anhydrous sodium sulfate, filtered and concentrated under reduced pressure. The residue was purified by column chromatography on silica gel eluting with petroleum/ethyl acetate 8/1 to afford bromide n (60 mg, 42%) as a colorless oil. $^1$H NMR (CDCl$_3$): δ 7.94 (s, 1H), 7.86 (dd, J=1.6, 8.4 Hz, 1H), 7.73 (d, J=8.0 Hz, 1H), 4.67 (s, 2H).

4-(2-Methyl-2H-tetrazol-5-yl)benzaldehyde (Intermediate o)

Scheme 32

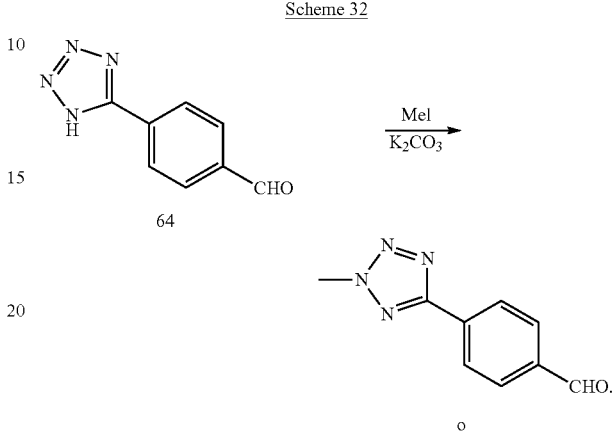

To a mixture of 64 (100 mg, 0.617 mmol) in anhydrous DMF (40 mL) was added K$_2$CO$_3$ (3.83 g, 11.8 mmol) and MeI (261 mg, 1.851 mmol). The reaction mixture was stirred at rt for 1 h. TLC (petroleum ether/ethyl acetate 1/1) showed that the reaction was completed. Water (20 mL) and ethyl acetate (20 mL) were added to the mixture. After partition, the aqueous layer was extracted with ethyl acetate (3×20 mL). The combined organic layers were washed with brine (3×70 mL), dried over anhydrous sodium sulfate, filtered and concentrated under reduced pressure. The residue was purified by preparative TLC with petroleum ether/ethyl acetate 1/1 to afford aldehyde o (80 mg, 74%) as a white solid. $^1$H NMR (CDCl$_3$): δ 10.11 (s, 1H), 8.34 (d, J=8.4 Hz, 2H), 8.03 (d, J=8.4 Hz, 2H), 4.46 (s, 3H).

4-Acetyl-3-chlorobenzonitrile (Intermediate p)

Scheme 33

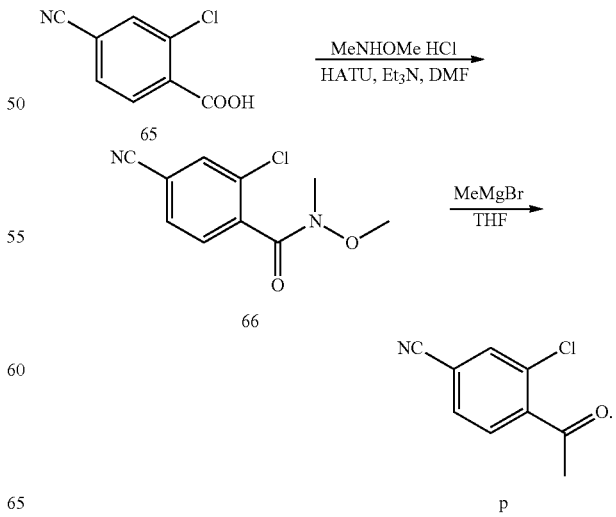

To a solution of 65 (300 mg, 1.66 mmol) in anhydrous DMF (20 mL) was added MeNHOMe.HCl (318 mg, 3.32 mmol), HATU (1.89 g, 4.98 mmol) and Et$_3$N (0.7 mL, 4.98 mmol). The mixture was stirred at rt overnight. The reaction was quenched with water (20 mL). The aqueous layer was extracted with ethyl acetate (3×20 mL). The combined organic layers were washed with brine (3×20 mL), dried over anhydrous Na$_2$SO$_4$, filtered and concentrated under reduced pressure. The residue was purified by column chromatography on silica gel eluting with petroleum ether/ethyl acetate 1/1 to afford 66 (370 mg, 99%) as a yellow oil. LC-MS t$_R$=0.735 min in 5-95AB_1.5 min chromatography (Welch MK RP-18e 25-2 mm), MS (ESI) m/z 224.8 [M+H]$^+$.

To a solution of 66 (70 mg, 0.31 mmol) in anhydrous THF (1 mL) was added MeMgBr (0.52 mL, 1.55 mmol, 3M in Et$_2$O) at 0° C. under N$_2$. The mixture was stirred at rt overnight under N$_2$. The mixture was quenched with sat. NH$_4$Cl solution (10 mL). The aqueous layer was extracted with ethyl acetate (3×10 mL). The combined organic layers were washed with brine (20 mL), dried over anhydrous Na$_2$SO$_4$, filtered and concentrated under reduced pressure. The residue was purified by preparative TLC with petroleum ether/ethyl acetate 3/1 to afford ketone p (40 mg, 72%) as a white solid. $^1$H NMR (CD$_3$OD): δ 7.92 (d, J=1.2 Hz, 1H), 7.78 (dd, J=1.6, 8.0 Hz, 1H), 7.73 (d, J=7.6 Hz, 1H), 2.62 (s, 3H).

5-Bromo-2-(chloromethyl)-3-fluoropyridine (Intermediate q)

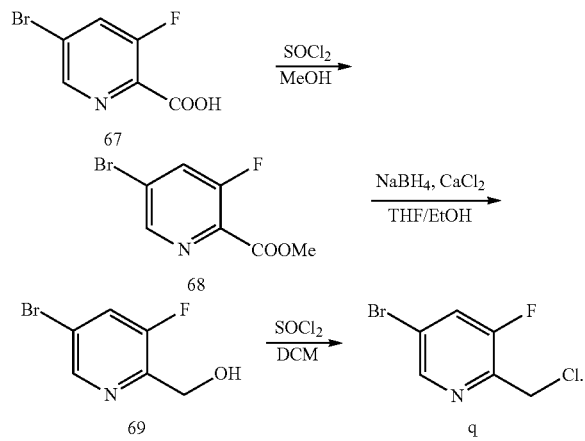

Scheme 34

To a solution of acid 67 (250 mg, 1.14 mmol) in anhydrous MeOH (4 mL) was added sulfonyl chloride (682 mg, 5.68 mmol) at rt under N$_2$. The mixture was stirred at 70° C. for 4 h. The mixture was concentrated under reduced pressure to afford crude 68 (280 mg, HCl salt, 100%) as a pale yellow solid, which was used for the next step directly without further purification.

Calcium chloride (500 mg, 4.5 mmol) in anhydrous THF/EtOH (1/1, 10 mL) was stirred at rt under N$_2$ until dissolved completed. The solution was cooled to 0° C. and NaBH$_4$ (342 mg, 9.0 mmol) was added. After being stirred at 0° C. for 30 min, a solution of 68 (350 mg, 1.49 mmol) in anhydrous THF/EtOH (1/1, 6 mL) was added. The mixture was warmed to rt and stirred overnight. The reaction mixture was quenched with sat. NH$_4$Cl solution (10 mL). The mixture was filtered and the filtrate was extracted with ethyl acetate (20 mL×3). The combined organic layers were washed with water (50 mL×3) and brine (50 mL), dried over anhydrous Na$_2$SO$_4$, filtered and concentrated under reduced pressure. The residue was purified by preparative TLC with petroleum ether/ethyl acetate 3/1 to afford to afford alcohol 69 (150 mg, 49%) as a white solid.

To a solution of 69 (90 mg, 0.44 mmol) in anhydrous CH$_2$Cl$_2$ (1 mL) was added sulfonyl chloride (0.2 mL) at rt under N$_2$. The mixture was stirred at reflux for 3 h. The mixture was concentrated under reduced pressure to afford crude chloride q (HCl salt, 100 mg, 100%) as a yellow solid, which was used for the next step directly without further purification. LC-MS t$_R$=0.796 min in 5-95 AB_1.5 min chromatography (Welch Xtimate MK RP-18e 25-2 mm), MS (ESI) m/z 223.6 [M+H]$^+$.

4-Acetyl-2-fluorobenzonitrile (Intermediate r)

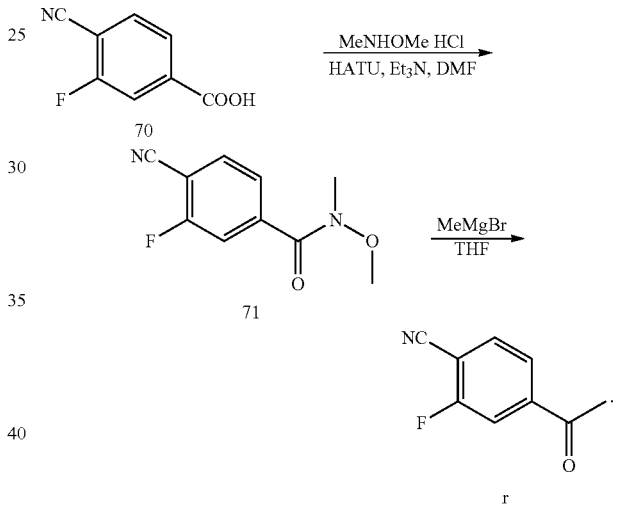

Scheme 35

A mixture of 70 (3.0 g, 17.18 mmol), N,O-dimethylhydroxylamine hydrochloride (1.9 g, 19.99 mmol), HATU (5.3 g, 21.82 mmol) and triethylamine (5.5 g, 54.54 mmol) in anhydrous DMF (30.0 mL) was stirred at rt overnight. The mixture was quenched with sat. NH$_4$Cl solution (20 mL). The solution was extracted with ethyl acetate (3×20 mL). The combined organic layers were washed with water (3×20 mL), brine (20 mL), dried over anhydrous Na$_2$SO$_4$, filtered and concentrated under reduced pressure. The residue was purified by chromatography column on silica gel eluting with dichloromethane/methanol 5/1 to give 71 (3.70 g, 98%) as a colorless oil.

To a mixture of 71 (1.70 g, 8.17 mg) in anhydrous THF (10.0 mL) was added MeMgBr (8.17 mL, 24.52 mmol, 3.0 M in Et$_2$O) at −78° C. under N$_2$. The mixture was stirred at −78° C. for 2 h. The mixture was quenched with sat. NH$_4$Cl solution (20 mL). The solution was extracted with ethyl acetate (3×20 mL). The combined organic layers were washed with water (3×20 mL), brine (30 mL), dried over anhydrous Na$_2$SO$_4$, filtered and concentrated under reduced pressure. The residue was purified by chromatography column on silica gel eluting with dichloromethane/methanol 3/1 to give ketone r (1.30 g, 96%) as a yellow oil.

3-(Chloromethyl)-2-methyl-6-(trifluoromethyl)pyridine (Intermediate s)

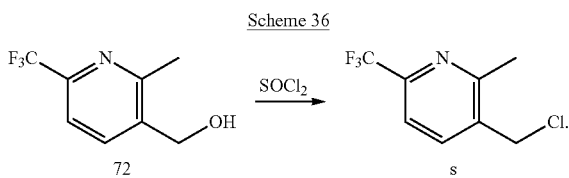

Scheme 36

To a solution of 72 (96 mg, 0.5 mmol) in CH$_2$Cl$_2$ (1.5 mL) was added SOCl$_2$ (0.5 mL). The mixture was stirred at reflux for 5 h. The mixture was concentrated under reduced pressure to afford crude chloride s (104 mg, 100%) as a yellow oil, which was used for the next step directly without further purification.

6-(Chloromethyl)-4-methylnicotinonitrile (Intermediate t)

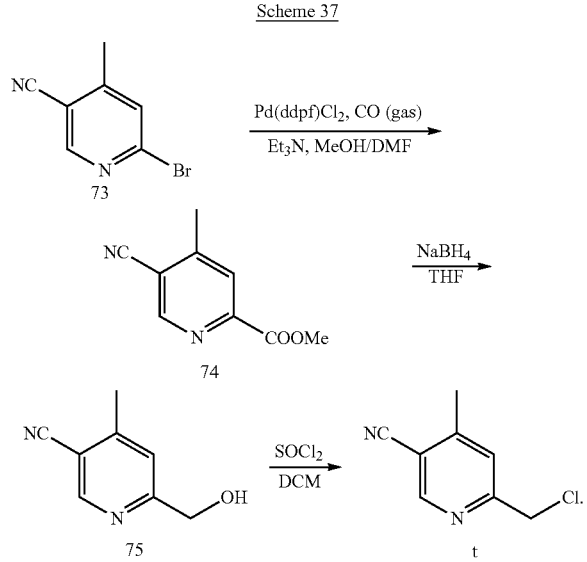

Scheme 37

To a solution of 73 (200 mg, 1.02 mmol) in anhydrous MeOH (2 mL) and DMF (2 mL) was added Et$_3$N (206 mg, 2.04 mmol) and Pd(dppf)Cl$_2$ (149 mg, 0.204 mmol). The mixture was stirred at 60° C. under CO gas (50 psi) overnight. The mixture was filtered and the filtrate was added with water (15 mL). The mixture was extracted with ethyl acetate (3×25 mL). The combined organic layers were washed with water (2×20 mL) and brine (20 mL), dried over anhydrous Na$_2$SO$_4$, filtered and concentrated under reduced pressure. The residue was purified by preparative TLC (petroleum ether/ethyl acetate=1/1) to give 74 (110 mg, 61%) as a white solid.

To a solution of CaCl$_2$ (377 mg, 3.40 mmol) in THF/EtOH (1:1, 10 mL) was added NaBH$_4$ (129 mg, 3.40 mmol) at 0° C. under N$_2$ atmosphere. The mixture was stirred at 0° C. for 1 h. Then a solution of 74 (60 mg, 0.34 mmol) in THF/EtOH (1:1, 1 mL) was added to the reaction mixture at 0° C. The mixture was allowed to warm to rt and stirred at rt overnight. The mixture was quenched with sat. NH$_4$Cl solution (10 mL). The mixture was filtered and the filtrate was concentrated under reduced pressure. Water (15 mL) and ethyl acetate (30 mL) were added to the residue. After partition, the aqueous layer was extracted with ethyl acetate (3×30 mL). The combined organic layers were washed with water (30 mL), dried over anhydrous Na$_2$SO$_4$, filtered and concentrated under reduced pressure. The residue was purified by preparative TLC (petroleum ether/ethyl acetate=1/1) to give 75 (35 mg, 70%) as a white solid.

To a solution of 75 (20 mg, 0.14 mmol) in anhydrous DCM (0.5 mL) was added SOCl$_2$ (50 mg, 0.42 mmol). The mixture was stirred at reflux for 3 h. The mixture was concentrated under reduced pressure to afford chloride t (25 mg, 114%) as a yellow oil, which was used for the next step directly without further purification.

6-(Chloromethyl)-2-methylnicotinonitrile (Intermediate u)

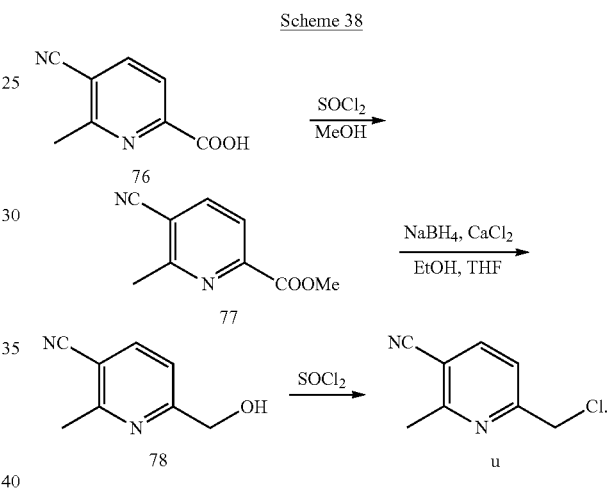

Scheme 38

A solution of 76 (200.0 mg, 1.234 mmol) in anhydrous MeOH (2.0 mL) was added sulfonyl chloride (440.0 mg, 3.703 mmol) at 0° C. under N$_2$. The solution was stirred at reflux for 2 h. The solution was concentrated under reduced pressure to afford crude 77 (200 mg, 93%) as a brown solid, which was used for next step directly without further purification. LC-MS $t_R$=0.252 min in 5-95AB_1.5 min chromatography (Welch Chromolith Flash RP-18e, 25-2 mm), MS (ESI) m/z 148.8 [M+H]$^+$.

CaCl$_2$ (1.26 g, 11.36 mmol) in anhydrous ethanol/THF (1:1, 4 mL) was added NaBH$_4$ (840.0 mg, 22.72 mmol) at 0° C. The mixture was stirred at 0° C. for 30 mins. To the mixture was added a solution of 77 (200.0 mg, 1.15 mmol) in anhydrous ethanol (1.0 mL) at 0° C. The mixture was stirred at rt overnight. The mixture was quenched with sat. NH$_4$Cl solution (50 mL). The solution was extracted with ethyl acetate (3×10 mL). The combined organic layers were washed with water (3×10 mL), brine (15 mL), dried over anhydrous Na$_2$SO$_4$, filtered and concentrated under reduced pressure. The residue was purified by preparative TLC with petroleum ether/ethyl acetate 1/1 to afford 78 (90.0 mg, 54%) as a white solid.

To a solution of 78 (50.0 mg, 0.338 mmol) in sulfonyl chloride (120.0 mg, 1.014 mmol) was stirred at 40° C. for 2 h. The solution was concentrated under reduced pressure to give crude chloride u (HCl salt, 50 mg, 89%) as a brown oil, which was used for next step directly without further purification.

6-(Bromomethyl)-2-methoxynicotinonitrile (Intermediate v)

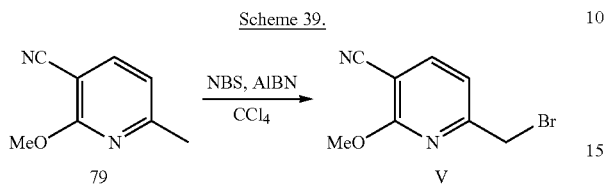

Scheme 39.

To a solution of 79 (20 mg, 0.135 mmol) in CCl$_4$ (2 mL) was added NBS (15 mg, 0.270 mmol) and AIBN (61 mg, 0.405 mmol). The mixture was stirred at 80° C. for 3 h. The mixture was concentrated under reduced pressure to afford crude bromide v (35 mg, 100%) as a white solid, which was used for the next step directly without further purification.

5-Chloro-2-(1-chloroethyl)-3-fluoropyridine (Intermediate w)

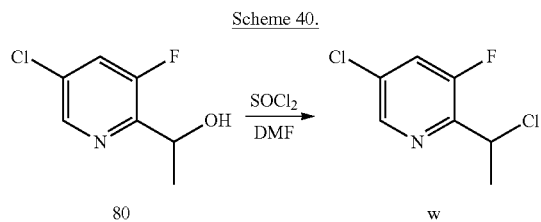

Scheme 40.

A solution of 80 (200 mg, 1.14 mmol) in SOCl$_2$ (3 mL) was added DMF (0.05 mL). The mixture was stirred at 60° C. for 4 h. The mixture was concentrated under reduced pressure to afford crude intermediate w (210 mg, 95%) as a tan solid, which was used for the next step without directly further purification. LC-MS $t_R$=0.849 min in 5-95AB_1.5 min chromatography (MK RP-18e, 25-2 mm), MS (ESI) m/z 193.8 [M+H]$^+$.

2-(Bromomethyl)-5-(difluoromethoxy)pyridine (Intermediate x)

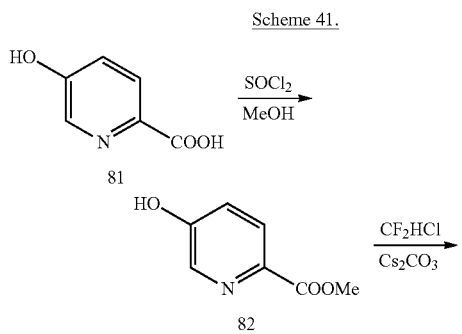

Scheme 41.

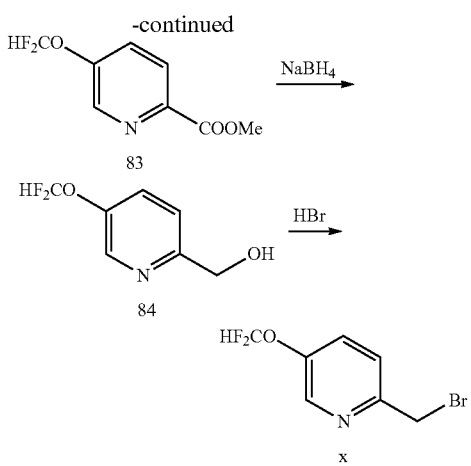

To solution of 81 (1 g, 7.19 mmol) in anhydrous MeOH (20 mL) was added SOCl$_2$ (4 mL) at 0° C. The mixture was stirred at reflux overnight under N$_2$. TLC (ethyl acetate) showed that the reaction was completed. The mixture was concentrated under reduced pressure to afford crude 82 (1.1 g, 100%) as a white solid, which was used for the next step directly without further purification.

To a mixture of 82 (600 mg, 3.92 mmol) in anhydrous DMF (40 mL) was added Cs$_2$CO$_3$ (3.83 g, 11.8 mmol). HCF$_2$Cl gas was bubbled into the mixture and the reaction mixture was stirred at rt for 2 h. TLC (ethyl acetate) showed that the reaction was completed. Water (20 mL) and ethyl acetate (20 mL) were added to the mixture. After partition, the aqueous layer was extracted with ethyl acetate (3×20 mL). The combined organic layers were washed with brine (3×70 mL), dried over anhydrous sodium sulfate, filtered and concentrated under reduced pressure to afford 83 (350 mg, 44%) as a dark yellow oil, which was used for the next step directly without further purification. LC-MS $t_R$=0.664 min in 5-95AB_1.5 min chromatography (Welch MK RP-18e, 25-2 mm), MS (ESI) m/z 203.8 [M+H]$^+$.

To a solution of CaCl$_2$ (541 mg, 4.92 mmol) in THF/EtOH (1:1, 10 mL) was added NaBH$_4$ (374 mg, 9.84 mmol) at 0° C. under N$_2$. The mixture was stirred at 0° C. for 1 h under N$_2$. Then a solution of 83 (100 mg, 0.49 mmol) in THF/EtOH (1:1, 4 mL) was added to the reaction mixture at 0° C. The mixture was allowed to warm to rt and stirred at rt overnight under N$_2$. The mixture was quenched with sat. NH$_4$Cl solution (50 mL) slowly at 0° C. The mixture was filtered and concentrated under reduced pressure. Water (30 mL) and ethyl acetate (30 mL) were added to the residue. After partition, the aqueous layer was extracted with ethyl acetate (3×30 mL). The combined organic layers were washed with water (100 mL), dried over anhydrous anhydrous sodium sulfate, filtered and concentrated under reduced pressure to afford crude 84 (86 mg, 100%) as a pale yellow oil, which was used for the next step directly without further purification. LC-MS $t_R$=0.225 min in 5-95AB_1.5 min chromatography (Welch MK RP-18e, 25-2 mm), MS (ESI) m/z 175.8 [M+H]$^+$.

A mixture of 84 (50 mg, 0.286 mmol) in HBr/H$_2$O solution (5 mL, 48%) was stirred at reflux overnight. The mixture was concentrated under reduced pressure to afford crude bromide x HBr salt (91 mg, 100%) as a orange solid, which was used for the next step directly without further purification. LC-MS $t_R$=0.747 min in 5-95AB_1.5 min chromatography (Welch MK RP-18e, 25-2 mm), MS (ESI) m/z 237.6 [M+H]$^+$.

1-(Chloromethyl)-4-cyclopropylbenzene
(Intermediate y)

Scheme 42.

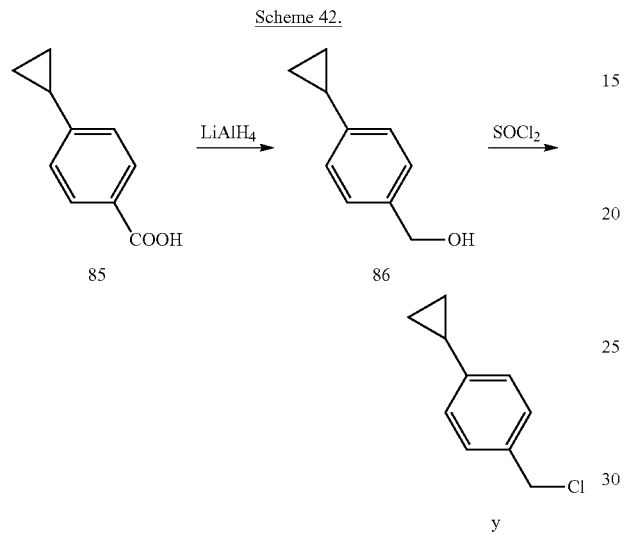

To a solution of 85 (100 mg, 0.617 mmol) in anhydrous THF (4 mL) was added LiAlH$_4$ (70 mg, 1.850 mmol) in portions at 0° C. under N$_2$. The mixture was stirred at rt for 3 h. The mixture was quenched successively with water (0.07 mL) and 10% aqueous NaOH solution (0.07 mL) at 0° C. The mixture was filtered and the filtrate was concentrated under reduced pressure. Water (15 mL) and ethyl acetate (15 mL) were added to the mixture. After partition, the aqueous layer was extracted with ethyl acetate (3×15 mL). The combined organic layers were washed with brine (25 mL), dried over anhydrous sodium sulfate, filtered and concentrated under reduced pressure. The residue was purified by preparative TLC with petroleum ether/ethyl acetate 5/1 to afford 86 (80 mg, 88%) as a colorless oil. $^1$H NMR (CDCl$_3$): δ 7.28 (d, J=8.0 Hz, 2H), 7.10 (d, J=8.0 Hz, 2H), 4.66 (s, 2H), 1.96-1.91 (m, 1H), 1.01-0.97 (m, 2H), 0.73-0.71 (m, 2H).

A mixture of 86 (40 mg, 0.27 mmol) in SOCl$_2$ (3 mL) was stirred at 50° C. for 2 h. The mixture was concentrated under reduced pressure to afford crude chloride y (45 mg, 100%) as a colorless oil, which was used directly for the next step directly without further purification.

Preparation of Compounds of Formula I

Compounds of Formula (I) were prepared from compound II-1 by method A, method B or method C, which are exemplified by compound I-A1 (Scheme 43), compound I-A2 (Scheme 44) and compound I-A17 (Scheme 45), respectively, using an appropriate halide or aldehyde/ketone.

Method A. (S)—N-(5-(4-(difluoromethoxy)benzyl)-4-isopropyl-5,6-dihydro-4H-pyrrolo[3,4-d]thiazol-2-yl)-2-(4-(ethylsulfonyl)phenyl)acetamide (Compound I-A1)

Scheme 43.

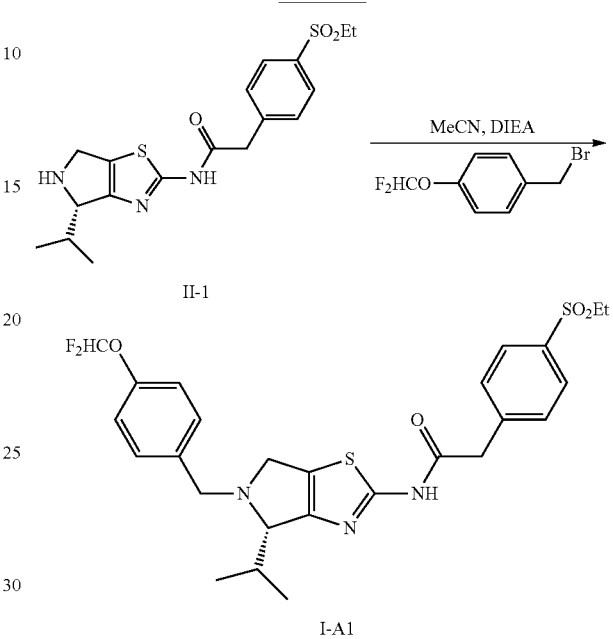

To a solution of compound II-1 (10 mg) in CH$_3$CN (0.5 mL) was added 4-(difluoromethoxy)benzyl bromide (1.3 equiv.) and N,N-diisopropylethylamine (2.5 equiv.). The mixture was stirred at rt for 2 h. The solvent was removed in vacuo to give the crude product which was purified on reverse phase prep-HPLC to yield the final compound I-A1. LC-MS $t_R$=1.01 min in 2 min chromatography, MS (ESI) m/z 550.5 [M+H]$^+$. $^1$H NMR (CD$_3$OD, 400 MHz): δ 7.89 (d, J=8.8 Hz, 2H), 7.67 (d, J=8.4 Hz, 2H), 7.62 (d, J=8.4 Hz, 2H), 7.28 (d, J=8.8 Hz, 2H), 6.93 (t, J=73.6 Hz, 1H), 4.86-4.79 (m, 1H), 4.70-4.61 (m, 4H), 3.94 (s, 2H), 3.23 (q, J=7.6 Hz, 2H), 2.15-2.05 (m, 1H), 1.22 (t, J=7.6 Hz, 3H), 1.13 (d, J=6.8 Hz, 3H), 0.88 (d, J=6.8 Hz, 3H).

Method B. (S)-2-(4-(ethylsulfonyl)phenyl)-N-(4-isopropyl-5-(4-(trifluoromethyl)benzyl)-5,6-dihydro-4H-pyrrolo[3,4-d]thiazol-2-yl)acetamide (Compound I-A2)

Scheme 44.

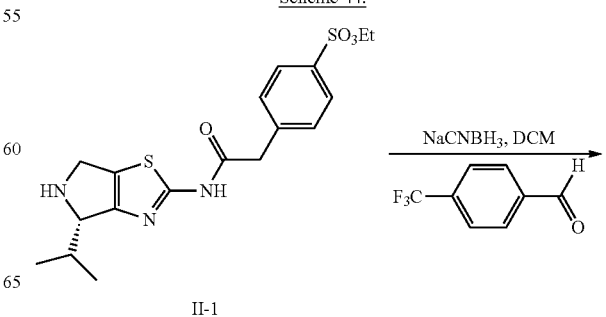

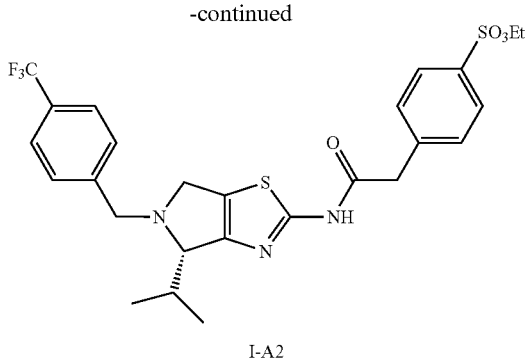

I-A2

To a solution of compound II-1 (10 mg) in dichloromethane (0.4 mL) was added 4-(trifluoromethyl)benzaldehyde (1.3 equiv.) followed by NaCNBH₃ (1.5 equiv.). The mixture was stirred at rt for 2 h. The solvent was removed in vacuo to give the crude product which was purified on reverse phase prep-HPLC to yield the final compound I-A2. LC-MS $t_R$=1.18 min in 2 min chromatography, MS (ESI) m/z 552.4 [M+H]⁺. ¹H NMR (CD₃OD, 400 MHz): δ 7.90 (d, J=8.8 Hz, 2H), 7.83 (m, 4H), 7.62 (d, J=8.8 Hz, 2H), 4.86-4.79 (m, 1H), 4.91-4.61 (m, 5H), 3.94 (s, 2H), 3.21 (q, J=7.6 Hz, 2H), 2.16-2.05 (m, 1H), 1.22 (t, J=7.6 Hz, 3H), 1.15 (d, J=6.8 Hz, 3H), 0.90 (d, J=6.8 Hz, 3H).

Method C. 2-(4-(ethylsulfonyl)phenyl)-N—((S)-4-isopropyl-5-((trans-4-(trifluoromethyl)cyclohexyl)methyl)-5,6-dihydro-4H-pyrrolo[3,4-d]thiazol-2-yl)acetamide (Compound I-A17)

Scheme 45.

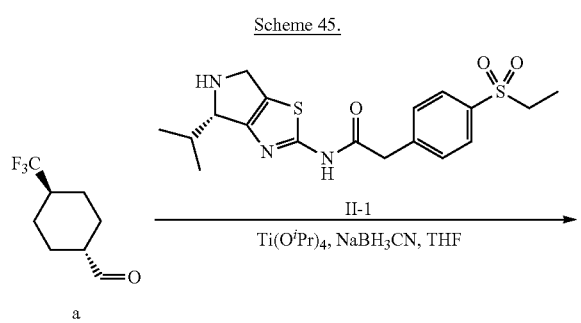

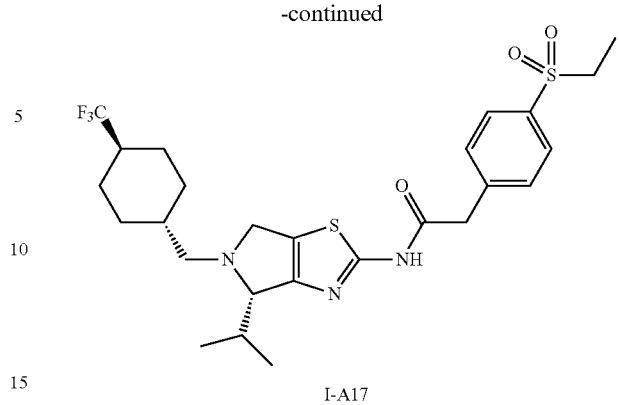

I-A17

A mixture of aldehyde a (50 mg, 0.28 mmol), compound II-1 (50 mg, 0.13 mmol) and tetraisopropoxytitanium (111 mg, 0.39 mmol) in anhydrous THF (3 mL) was stirred at reflux under N₂ for 3.5 h. After being cooled to rt, NaBH₃CN (41 mg, 0.65 mmol) was added. The mixture was stirred at reflux for 3 h. The mixture was added with water (5 mL) and filtered. The filtrate was extracted with ethyl acetate (3×5 mL) and the combined organic layers were washed with water (3×10 mL), dried over anhydrous Na₂SO₄, filtered and concentrated under reduced pressure. The residue was purified by preparative TLC with petroleum ether/ethyl acetate 1/1 and separated by SFC and HCl preparative HPLC to afford the title compound I-A17 (10.60 mg, HCl salt, 23.6%) as a white solid. LC-MS $t_R$=0.767 min in 5-95 AB_1.5 min chromatography (Welch Xtimate MK RP-18e 25-2 mm), MS (ESI) m/z 558.1 [M+H]⁺. 1H NMR (CD₃OD): δ 7.91 (d, J=8.4 Hz, 2H), 7.64 (d, J=8.4 Hz, 2H), 4.65-4.60 (m, 3H), 3.96 (s, 2H), 3.43-3.38 (m, 1H), 3.23 (q, J=7.2 Hz, 2H), 2.23-2.18 (m, 2H), 2.06-2.02 (m, 4H), 1.45-1.42 (m, 3H), 1.34-1.30 (m, 7H), 1.24 (t, J=7.6 Hz, 3H), 1.11-1.08 (m, 2H). Isomer SFC $t_R$=1.507 min in 3 min chromatography (Column: AD-H; Method Name: AD-H_3 UM_5_5_40_4 ML_3 MIN.M, ee=99.11%).

(S)-2-(4-(ethylsulfonyl)phenyl)-N-(4-isopropyl-5-(4-(1-methyl-2-oxo-1,2-dihydropyridin-4-yl)benzyl)-5,6-dihydro-4H-pyrrolo[3,4-d]thiazol-2-yl)acetamide (Compound I-A18)

Scheme 46.

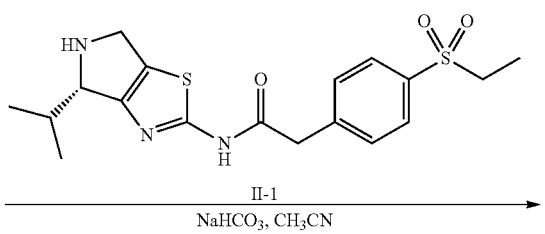

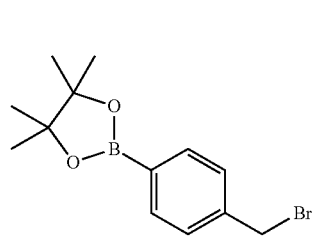

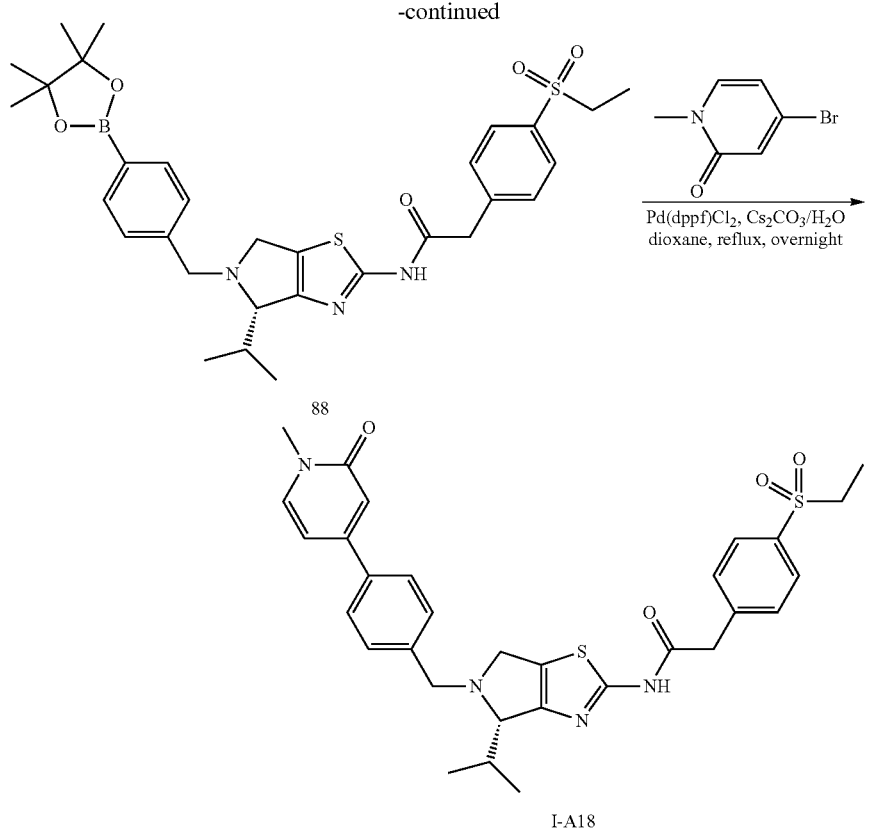

To a solution of compound II-1 (50 mg, 0.13 mmol) in CH₃CN (2 mL) was dioxaborolane 87 (60 mg, 0.19 mmol) and NaHCO₃ (55 mg, 0.65 mmol). The mixture was stirred at rt overnight. The reaction mixture was filtered, concentrated and purified by preparative TLC (petroleum ether: ethyl acetate=1:1) to afford the compound 88 (50 mg, 63%) as a colorless oil. LCMS: $t_R$=0.842 min in 5-95AB_1.5 min chromatography (MK RP18e 25-2 mm), MS (ESI) m/z 610.0 [M+H]⁺.

To a solution of 88 (50 mg, 0.082 mmol) in dioxane (1.5 mL) was added 4-bromo-1-methylpyridin-2(1H)-one (20 mg, 0.098 mmol), Pd(dppf)Cl₂ (10 mg, 0.01 mmol), Cs₂CO₃ (85 mg, 0.25 mmol) and water (0.3 mL) under N₂. The mixture was stirred at 100° C. overnight. The reaction mixture was filtered, concentrated, purified by preparative TLC (ethyl acetate) and HCl preparative HPLC to afford the compound I-A18 (HCl salt, 5.6 mg, 11%) as a white solid. LCMS: $t_R$=0.727 min in 5-95AB_1.5 min chromatography (MK RP18e 25-2 mm), MS (ESI) m/z 591.3 [M+H]⁺. ¹H NMR (CD₃OD): δ 7.87 (d, J=8.0 Hz, 2H), 7.82 (d, J=8.4 Hz, 2H), 7.76 (d, J=8.4 Hz, 3H), 7.61 (d, J=8.4 Hz, 2H), 6.81 (d, J=2.0 Hz, 1H), 6.73 (dd, J=2.0, 7.2 Hz, 1H), 4.80-4.65 (m, 5H), 3.93 (s, 2H), 3.61 (s, 3H), 3.20 (q, J=7.2 Hz, 2H), 2.10-2.00 (m, 1H), 1.20 (t, J=7.2 Hz, 3H), 1.12 (d, J=6.8 Hz, 3H), 0.88 (d, J=6.4 Hz, 3H). Isomer SFC $t_R$=1.872 min in 3 min chromatography (Column: OJ-H; Method Name: OJ-H_3 UM_5_5_40_4 mL_3 min, ee=100.00%).

(S)-2-(4-(ethylsulfonyl)phenyl)-N-(4-isopropyl-5-(4-(1-methyl-6-oxo-1,6-dihydropyridin-3-yl)benzyl)-5,6-dihydro-4H-pyrrolo[3,4-d]thiazol-2-yl)acetamide (Compound I-A19)

Scheme 47.

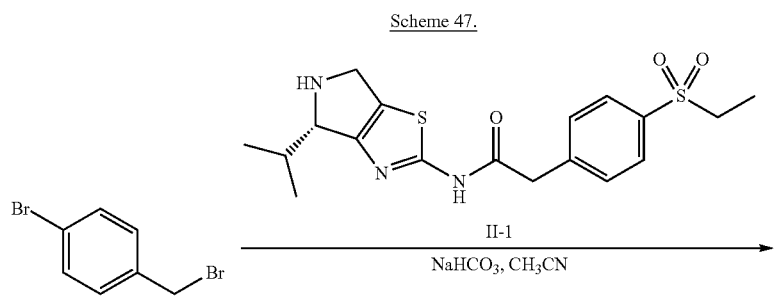

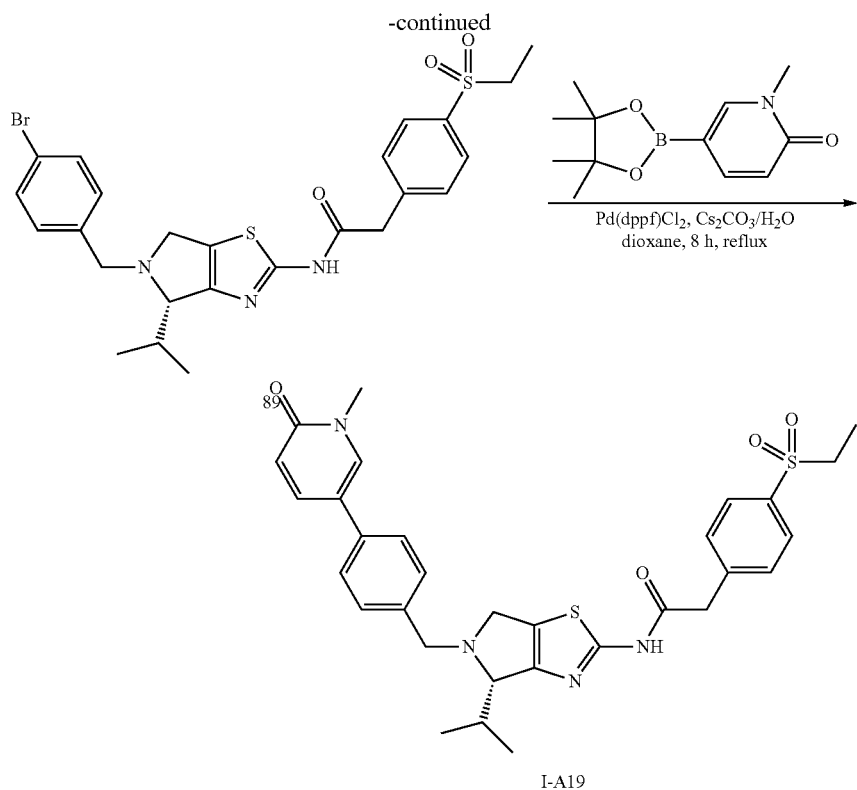

I-A19

To a solution of compound II-1 (100 mg, 0.25 mmol) in CH$_3$CN (2 mL) was added 1-bromo-4-(bromomethyl)benzene (76 mg, 0.31 mmol) and NaHCO$_3$ (105 mg, 1.25 mmol). The mixture was stirred at rt overnight. TLC (petroleum ether:ethyl acetate=2:1) showed that the reaction was good. The reaction mixture was filtered and the filtrate was concentrated and purified by preparative TLC (petroleum ether: ethyl acetate=2:1) to afford (S)—N-(5-(4-bromobenzyl)-4-isopropyl-5,6-dihydro-4H-pyrrolo[3,4-d]thiazol-2-yl)-2-(4-(ethylsulfonyl)phenyl)acetamide 89 (110 mg, 78%) as a colorless oil. LCMS: t$_R$=0.785 min in 5-95AB_1.5 min chromatography (MK RP18e 25-2 mm), MS (ESI) m/z 562.0 [M+H]$^+$. $^1$H NMR (CD$_3$OD): δ 7.86 (d, J=8.4 Hz, 2H), 7.60 (d, J=8.0 Hz, 2H), 7.45 (d, J=8.4 Hz, 2H), 7.32 (d, J=8.0 Hz, 2H), 4.09-4.02 (m, 2H), 3.83 (s, 2H), 3.81-3.69 (m, 2H), 3.58-3.52 (m, 1H), 3.18 (q, J=7.6 Hz, 2H), 1.98-1.91 (m, 1H), 1.19 (t, J=7.6 Hz, 3H), 1.06 (d, J=6.8 Hz, 3H), 0.89 (d, J=6.4 Hz, 3H).

To a solution of 89 (60 mg, 0.11 mmol) in dioxane (2 mL) was added 1-methyl-5-(4,4,5,5-tetramethyl-1,3,2-dioxaborolan-2-yl)pyridin-2(1H)-one (50 mg, 0.21 mmol), Pd(dppf)Cl$_2$ (15 mg, 0.02 mmol), Cs$_2$CO$_3$ (98 mg, 0.33 mmol) and H$_2$O (0.2 mL) under N$_2$. The mixture was stirred at 100° C. for 8 h. The mixture was added with water (10 mL) and extracted with EtOAc (5 mL×3). The combined organic layers were dried over sodium sulfate, filtered, concentrated, purified by preparative TLC (petroleum ether: ethyl acetate=1:8) and separated by HCl preparative HPLC to afford the compound I-A19 (HCl salt, 10.4 mg, 15%) as a white solid. LCMS: t$_R$=0.727 min in 5-95AB_1.5 min chromatography (MK RP18e 25-2 mm), MS (ESI) m/z 591.1 [M+H]$^+$. $^1$H NMR (CD$_3$OD): δ 8.12 (d, J=2.0 Hz, 1H), 7.95 (dd, J=2.4, 9.2 Hz, 1H), 7.91 (d, J=8.4 Hz, 2H), 7.73 (s, 4H), 7.65 (d, J=8.4 Hz, 2H), 6.68 (d, J=9.6 Hz, 1H), 4.80-4.60 (m, 5H), 3.97 (s, 2H), 3.69 (s, 3H), 3.23 (q, J=7.2 Hz, 2H), 2.13-2.00 (m, 1H), 1.24 (t, J=7.2 Hz, 3H), 1.12 (d, J=6.8 Hz, 3H), 0.89 (d, J=6.8 Hz, 3H). Isomer SFC t$_R$=3.807 min in 8 min chromatography (Column: AS-H; Method Name: AS-H_S_5_40_3 mL_8 min_15 cm, ee=96.10%).

(S)-2-(4-(ethylsulfonyl)phenyl)-N-(4-isopropyl-5-((1-(2,2,2-trifluoroethyl)piperidin-4-yl)methyl)-5,6-dihydro-4H-pyrrolo[3,4-d]thiazol-2-yl)acetamide (Compound I-A20)

Scheme 48.

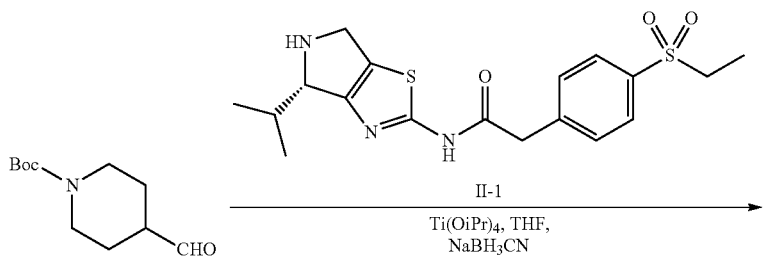

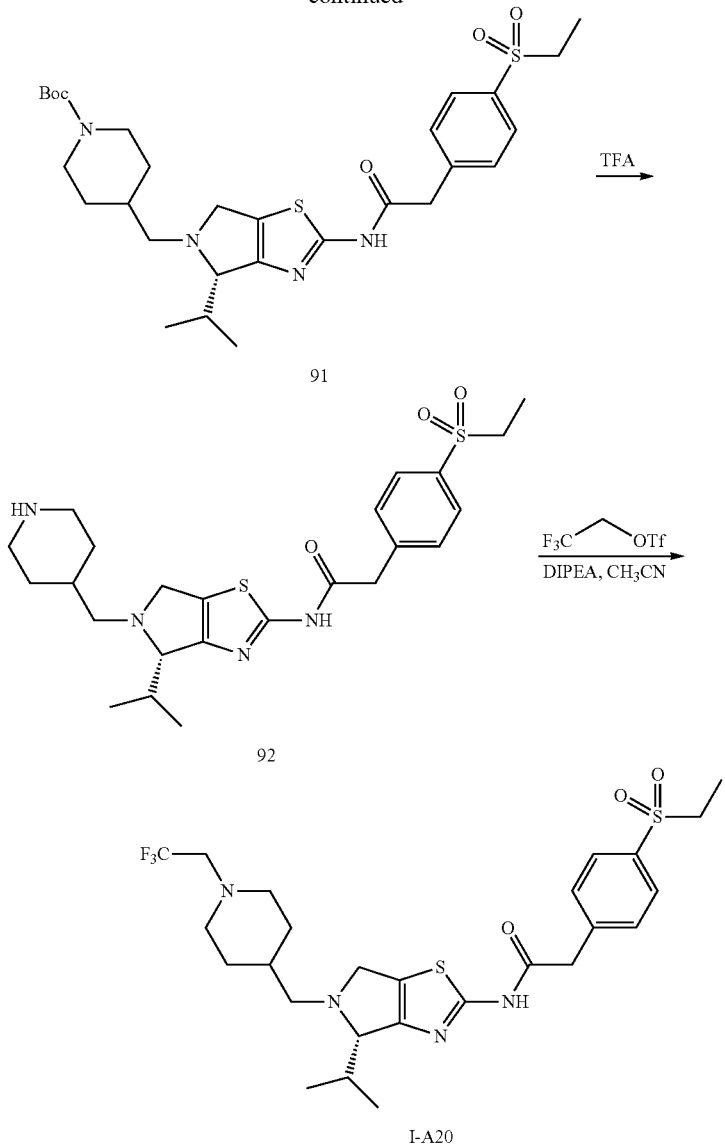

To a solution of aldehyde 90 (52 mg, 0.2 mmol) and compound II-1 (50 mg, 0.127 mmol) in anhydrous THF (3 mL) was added Ti(O$^i$Pr)$_4$ (180 mg, 0.635 mmol). The mixture was stirred at reflux overnight under N$_2$. The mixture was cooled to rt, then NaBH$_3$CN (24 mg, 0.381 mmol) was added to the reaction mixture. The mixture was stirred at reflux for another 2 h under N$_2$. TLC (petroleum ether/ethyl acetate 1/1) showed that a new spot was observed. The mixture was quenched with water (20 mL) and filtered. The filtrate was extracted with ethyl acetate (3×20 mL). The combined organic layers were dried over anhydrous sodium sulfate, filtered and concentrated under reduced pressure. The residue was purified by preparative TLC with petroleum ether/ethyl acetate 1/1 to afford product 91 (60 mg, 66%) as a yellow oil. LC-MS t$_R$=0.757 min in 5-95AB_1.5 min chromatography (Welch MK RP-18e, 25-2 mm), MS (ESI) m/z 591.1 [M+H]$^+$.

To a solution of 91 (60 mg, 0.102 mmol) in DCM (3 mL) was added TFA (1 mL) at 0° C. The mixture was stirred at rt for 1 h. The mixture was concentrated under reduced pressure to afford crude 92 TFA salt (58 mg, 100%) as a dark yellow oil, which was used for the next step without further purification. LC-MS t$_R$=0.607 min in 5-95AB_1.5 min chromatography (Welch MK RP-18e, 25-2 mm), MS (ESI) m/z 491.0 [M+H]$^+$.

To a mixture of 92 TFA salt (58 mg, 0.099 mmol) in anhydrous CH$_3$CN (2 mL) was added 2,2,2-trifluoroethyl trifluoromethanesulfonate (44 mg, 0.204 mmol) and DIPEA (39 mg, 0.306 mmol). The mixture was stirred at rt for 1 h under N$_2$. The mixture was diluted with ethyl acetate (20 mL). The organic layer was washed with water (20 mL), dried over anhydrous sodium sulfate, filtered and concentrated under reduced pressure. The residue was purified by HCl preparative HPLC separation to afford the compound I-A20 (HCl salt, 24.90 mg, 43%) as a white solid. LC-MS t$_R$=0.651 min in 5-95AB_1.5 min chromatography (Welch MK RP-18e, 25-2 mm), MS (ESI) m/z 573.2 [M+H]$^+$. $^1$H NMR (CD$_3$OD): δ 7.91 (d, J=8.4 Hz, 2H), 7.64 (d, J=8.4 Hz, 2H), 5.12-5.02 (m, 2H), 4.55-4.64 (m, 1H), 4.26 (q, J=8.8 Hz, 2H), 3.96 (s, 2H), 3.77-3.70 (m, 2H), 3.60-3.50 (m, 2H), 3.40-3.34 (m, 2H), 3.23 (q, J=7.2 Hz, 2H), 2.45-2.20 (m, 4H), 1.91-1.75 (m, 2H), 1.33 (d, J=7.2 Hz, 3H), 1.24 (t, J=7.2 Hz, 3H), 1.10 (d, J=7.2 Hz, 3H). Isomer SFC $t_R$=1.660 in 3 min chromatography (Column: AD-H; Method Name: AD-H_3 UM_3_5_40_4 ML_3 MIN.N, ee=97.80%).

The compounds I-A3 to I-A16 and I-A21 to I-A64 in Table 1 were prepared from compound II-1 using the appropriate (het)arylalkyl halide (Method A) or (het)aryl aldehyde (Method B or C).

TABLE 1

| Compound Number | R₁ | PREP method | MS | 1H NMR (400 MHz) |
|---|---|---|---|---|
| I-A3 | 4-chlorobenzyl (methyl branch) | A | m/z 519.3 [M + H]+ $t_R$ = 1.06 min | (CD3OD) δ 7.89 (d, J = 8.4 Hz, 2H), 7.62 (d, J = 8.4 Hz, 4H), 7.52 (d, J = 8.4 Hz, 2H), 4.89-4.80 (m, 1H), 4.70-4.61 (m, 4H), 3.94 (s, 2H), 3.22 (q, J = 7.6 Hz, 2H), 2.10-2.05 (m, 1H), 1.22 (t, J = 7.6 Hz, 3H), 1.13 (d, J = 6.8 Hz, 3H), 0.88 (d, J = 6.8 Hz, 3H). |
| I-A4 | 4-cyano-3-fluorobenzyl (methyl branch) | A | m/z 527.3 [M + H]+ $t_R$ = 1.23 min | (CD3OD) δ 7.90 (t, J = 6.8 Hz, 1H), 7.89 (d, J = 6.8 Hz, 2H), 7.67 (d, J = 10 Hz, 1H), 7.63-7.60 (m, 3H), 4.75-4.48 (m, 5H), 3.94 (s, 2H), 3.22 (q, J = 7.6 Hz, 2H), 2.18-2.15 (m, 1H), 1.22 (t, J = 7.6 Hz, 3H), 1.17 (d, J = 7.2 Hz, 3H), 0.91 (d, J = 6.8 Hz, 3H). |
| I-A5 | 5-cyanopyridin-2-yl (methyl branch) | A | m/z 510.3 [M + H]+ $t_R$ = 0.92 min | (CD3OD) δ 9.03 (d, J = 2.0 Hz, 1H), 8.29 (dd, J₁ = 8.4 Hz, J₂ = 2.0 Hz, 1H), 7.89 (d, J = 8.4 Hz, 2H), 7.70 (d, J = 8.4 Hz, 1H), 7.83 (d, J = 8.4 Hz, 2H), 4.99-4.94 (m, 3H), 4.72-4.68 (m, 2H), 3.94 (s, 2H), 3.22 (q, J = 7.6 Hz, 2H), 2.45-2.44 (m, 1H), 1.22 (t, J = 7.6 Hz, 3H), 1.20 (d, J = 7.2 Hz, 3H), 0.95 (d, J = 6.8 Hz, 3H). |
| I-A6 | 5-trifluoromethylpyrimidin-2-yl (methyl branch) | A | m/z 554.3 [M + H]+ $t_R$ = 1.01 min | (CD3OD) δ 9.25 (s, 2H), 7.89 (d, J = 8.4 Hz, 2H), 7.62 (d, J = 8.4 Hz, 1H), 5.10-5.06 (m, 3H), 4.82-4.77 (m, 2H), 3.94 (s, 2H), 3.22 (q, J = 7.6 Hz, 2H), 2.65-2.60 (m, 1H), 1.24 (t, J = 7.6 Hz, 3H), 1.22 (d, J = 7.2 Hz, 3H), 0.96 (d, J = 6.8 Hz, 3H). |

TABLE 1-continued

| Compound Number | R₁ | PREP method | MS | 1H NMR (400 MHz) |
|---|---|---|---|---|
| I-A7 | benzyl | A | m/z 484.0 [M + H]+ tR = 0.68 min/1.5 min | (CDCl3) δ 9.85 (brs, 1H), 7.91-7.89 (m, 2H), 7.51 (d, J = 8.4 Hz, 2H), 7.40-7.24 (m, 3H), 4.15 (d, J = 13.6 Hz, 2H), 3.88-3.75 (m, 4H), 3.63 (d, J = 13.6 Hz, 1H), 3.15 (q, J = 7.6 Hz, 2H), 2.05-1.97 (m, 1H), 1.30 (t, J = 7.6 Hz, 3H), 1.02 (d, J = 6.8 Hz, 3H), 0.93 (d, J = 6.8 Hz, 3H). |
| I-A8 | 3-CF₃-benzyl | A | m/z 551.9 [M + H]+ tR = 0.74 min/1.5 min | (CDCl3) δ 9.89 (brs, 1H), 7.89 (d, J = 8.0 Hz, 2H), 7.65 (s, 1H), 7.61-7.59 (m, 1H), 7.55-7.48 (m, 3H), 7.46-7.41 (m, 1H), 4.20-4.13 (m, 2H), 3.89-3.82 (m, 4H), 3.60 (d, J = 10.8 Hz, 1H), 3.15 (q, J = 7.6 Hz, 2H), 2.02-1.96 (m, 1H), 1.30 (t, J = 7.6 Hz, 3H), 1.03 (d, J = 7.2 Hz, 3H), 0.92 (d, J = 7.2 Hz, 3H). |
| I-A9 | 5-CF₃-1,3,4-oxadiazol-2-ylmethyl | A | m/z 544.3 [M + H]+ tR = 1.55 min | (CD3OD) δ 7.89 (d, J = 8.4 Hz, 2H), 7.61 (d, J = 8.4 Hz, 1H), 4.55-4.43 (m, 3H), 4.14-4.09 (m, 2H), 3.92 (s, 2H), 3.20 (q, J = 7.6 Hz, 2H), 2.06-2.02 (m, 1H), 1.22 (t, J = 7.6 Hz, 3H), 1.07 (d, J = 7.2 Hz, 3H), 0.88 (d, J = 6.8 Hz, 3H). |
| I-A10 | 5-Cl-3-F-pyridin-2-ylmethyl | A | m/z 537.4 [M + H]+ tR = 1.03 min | (CD3OD) δ 8.58 (s, 1H), 7.99 (d, J = 9.2 Hz, 1H), 7.89 (d, J = 8.4 Hz, 2H), 7.62 (d, J = 8.4 Hz, 2H), 4.97-4.87 (m, 3H), 4.82-4.75 (m, 2H), 3.94 (s, 2H), 3.21 (q, J = 7.6 Hz, 2H) 2.49-2.44 (m, 1H), 1.24 (t, J = 7.6 Hz, 3H), 1.21 (d, J = 7.2 Hz, 3H), 0.97 (d, J = 6.8 Hz, 3H). |
| I-A11 | 5-Cl-pyridin-2-ylmethyl | A | m/z 519.4 [M + H]+ tR = 0.96 min | (CD3OD) δ 8.70 (d, J = 2.8 Hz, 1H), 7.97 (dd, J₁ = 8.4 Hz, J₂ = 2.8 Hz, 1H), 7.89 (d, J = 8.4 Hz, 2H), 7.62 (d, J = 8.4 Hz, 2H), 7.56 (d, J = 8.4 Hz 1H), 4.95-4.92 (m, 1H), 4.82-4.80 (m, 2H), 4.73-4.70 (m, 2H), 3.94 (s, 2H), 3.21 (q, J = 7.6 Hz, 2H), 2.39-2.33 (m, 1H), 1.22 (t, J = 7.6 Hz, 3H), 1.18 (d, J = 7.2 Hz, 3H), 0.94 (d, J = 6.8 Hz, 3H). |

TABLE 1-continued

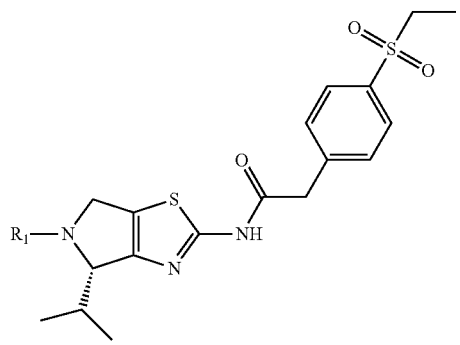

| Compound Number | R₁ | PREP method | MS | 1H NMR (400 MHz) |
|---|---|---|---|---|
| I-A12 | 5-(trifluoromethyl)pyridin-2-yl-CH(CH₃)- (CF₃ on pyridine) | A | m/z 554.4 [M + H]+ $t_R$ = 1.08 min | (CD3OD) δ 9.02 (s, 1H), 8.25 (dd, $J_1$ = 8.0 Hz, $J_2$ = 2.4 Hz, 1H), 7.89 (d, J = 8.4 Hz, 2H), 7.73 (d, J = 8.0 Hz, 1H), 7.62 (d, J = 8.0 Hz, 2H), 4.99-4.89 (m, 3H), 4.71-4.68 (m, 2H), 3.94 (s, 2H), 3.20 (q, J = 7.6 Hz, 2H), 2.44-2.42 (m, 1H), 1.22 (t, J = 7.6 Hz, 3H), 1.19 (d, J = 7.2 Hz, 3H), 0.96 (d, J = 6.8 Hz, 3H). |
| I-A13 | 4-cyano-2-fluorophenyl-CH(CH₃)- | A | m/z 527.4 [M + H]+ $t_R$ = 1.20 min | (CD3OD) δ 7.89 (d, J = 8.4 Hz, 2H), 7.88 (m, 1H), 7.78 (d, J = 9.6 Hz, 1H), 7.73 (d, J = 8.0 Hz, 1H), 7.62 (d, J = 8.4 Hz, 2H), 4.82-4.80 (m, 1H), 4.72-4.58 (m, 4H), 3.94 (s, 2H), 3.22 (q, J = 7.6 Hz, 2H), 2.28-2.24 (m, 1H), 1.24 (t, J = 7.6 Hz, 3H), 1.21 (d, J = 6.8 Hz, 3H), 1.00 (d, J = 6.8 Hz, 3H). |
| I-A14 | 4-fluorophenyl-CH(CH₃)- | A | m/z 502.0 [M + H]+ $t_R$ = 0.71 min/1.5 min | (CDCl3) δ 9.02 (brs, 1H), 7.92 (d, J = 8.8 Hz, 2H), 7.54 (d, J = 8.0 Hz, 2H), 7.36 (dd, J = 8.4, 5.6 Hz, 2H), 7.04-6.99 (m, 2H), 4.10 (d, J = 13.6 Hz, 2H), 3.88-3.85 (m, 3H), 3.76 (d, J = 14.0 Hz, 1H), 3.59 (d, J = 12.4 Hz, 1H), 3.12 (q, J = 7.2 Hz, 3H), 2.02-1.94 (m, 1H), 1.30 (d, J = 7.2 Hz, 3H), 1.02 (d, J = 6.8 Hz, 3H), 0.91 (d, J = 6.8 Hz, 3H). |
| I-A15 | 4-cyanophenyl-CH(CH₃)- | A | m/z 508.9 [M + H]+ $t_R$ = 0.68 min/1.5 min | (CDCl3) δ 9.07 (brs, 1H), 7.90 (d, J = 8.0 Hz, 2H), 7.61 (d, J = 8.4 Hz, 2H), 7.53-7.49 (m, 4H), 4.18-4.11 (m, 2H), 3.87-3.83 (m, 4H), 3.54 (dd, J = 2.8, 13.2 Hz, 1H), 3.12 (q, J = 7.6 Hz, 2H), 1.98-1.92 (m, 1H), 1.29 (t, J = 7.2 Hz, 3H), 1.00 (d, J = 6.8 Hz, 3H), 0.90 (d, J = 6.8 Hz, 3H). |

TABLE 1-continued

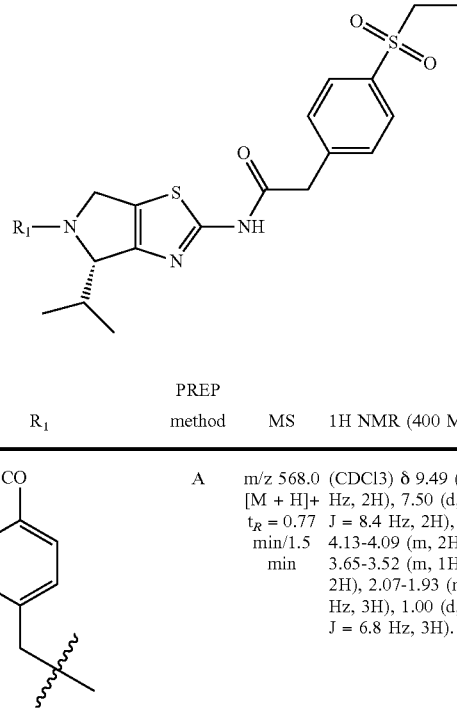

| Compound Number | R₁ | PREP method | MS | 1H NMR (400 MHz) |
|---|---|---|---|---|
| I-A16 | 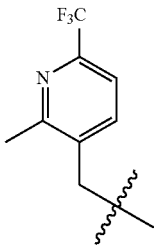 [SMILES: *Cc1ccc(C(F)(F)F)nc1C] F₃CO- | A | m/z 568.0 [M + H]+ t_R = 0.77 min/1.5 min | (CDCl3) δ 9.49 (s, 1H), 7.88 (d, J = 8.0 Hz, 2H), 7.50 (d, J = 8.4 Hz, 2H), 7.40 (d, J = 8.4 Hz, 2H), 7.15 (d, J = 8.0 Hz, 2H), 4.13-4.09 (m, 2H), 3.86-3.75 (m, 4H), 3.65-3.52 (m, 1H), 3.12 (q, J = 7.2 Hz, 2H), 2.07-1.93 (m, 1H), 1.28 (t, J = 7.2 Hz, 3H), 1.00 (d, J = 6.8 Hz, 3H), 0.90 (d, J = 6.8 Hz, 3H). |
| I-A21 | F₃C pyridine | A | m/z 567.5 [M + H]+ t_R = 1.46 min | (CD3OD) δ 8.19 (d, J = 8.0 Hz, 1H), 7.89 (d, J = 8.0 Hz, 2H), 7.75 (d, J = 8.0 Hz, 1H), 7.62 (d, J = 8.0 Hz, 2H), 4.88-4.80 (m, 1H), 4.75-4.41 (m, 4H), 3.94 (s, 2H), 3.23 (q, J = 7.6 Hz, 2H), 2.28-2.24 (m, 1H), 1.24 (t, J = 7.6 Hz, 3H), 1.21 (d, J = 6.8 Hz, 3H), 0.94 (d, J = 6.8 Hz, 3H). |
| I-A22 | F₃C N-methylpiperidine | A | m/z 573.5 [M + H]+ t_R = 0.87 min | (CD3OD) δ 7.90 (d, J = 8.4 Hz, 2H), 7.62 (d, J = 8.4 Hz, 2H), 5.08-4.98 (m, 1H), 4.66-4.56 (m, 3H), 4.13-3.96 (m, 1H), 3.94 (s, 2H), 3.48-3.46 (m, 1H), 3.21 (q, J = 7.6 Hz, 2H), 3.01 (s, 3H), 2.58 (m, 1H), 2.39 (m, 1H), 2.31-2.76 (m, 2H), 2.20-2.15 (m, 1H), 2.01-1.94 (m, 1H), 1.23 (t, J = 7.6 Hz, 3H), 1.05 (m, 3H), 0.90 (m, 3H). |
| I-A23 | methyl-oxadiazole-cyclohexyl | B | m/z 572.1 (M + H) | (CD3OD) δ 7.88 (d, J = 8.4 Hz, 2H), 7.61 (d, J = 8.4 Hz, 2H), 4.98-4.92 (m, 1H), 4.64-4.53 (m, 2H), 3.93 (s, 2H), 3.43-3.38 (m, 2H), 3.18 (q, J = 7.2 Hz, 2H), 2.96-2.86 (m, 1H), 2.49 (s, 3H), 2.34-2.26 (m, 1H), 2.26-2.17 (m, 2H), 2.13-1.93 (m, 3H), 1.71-1.58 (m, 2H), 1.38-1.31 (m, 2H), 1.29 (d, J = 6.8 Hz, 3H), 1.20 (t, J = 7.2 Hz, 3H), 1.07 (d, J = 6.8 Hz, 3H). |

TABLE 1-continued

| Compound Number | R₁ | PREP method | MS | 1H NMR (400 MHz) |
|---|---|---|---|---|
| I-A24 | 4-Br, 2-F phenyl with (S)-1-methylethyl linker | B | m/z 593.7 (M + H) | (CD3OD) δ 7.89 (d, J = 8.4 Hz, 2H), 7.75-7.67 (m, 1H), 7.61 (d, J = 8.4 Hz, 2H), 7.52-7.45 (m, 2H), 5.20-5.14 (m, 1H), 4.83-4.67 (m, 3H), 3.93 (s, 2H), 3.21 (q, J = 7.2 Hz, 2H), 2.05-1.95 (m, 1H), 1.80-1.70 (m, 3H), 1.22 (t, J = 7.2 Hz, 3H), 1.15-1.13 (m, 3H), 0.95-0.85 (m, 3H). |
| I-A25 | 4-Br, 2-F phenyl with (R)-1-methylethyl linker | B | m/z 593.7 (M + H) | (CD3OD) δ 7.88 (d, J = 8.8 Hz, 2H), 7.75-7.71 (m, 1H), 7.61 (d, J = 8.4 Hz, 2H), 7.50-7.40 (m, 2H), 5.25-5.19 (m, 1H), 4.83-4.73 (m, 3H), 3.92 (s, 2H), 3.20 (q, J = 7.2 Hz, 2H), 2.25-2.15 (m, 1H), 1.75-1.65 (m, 3H), 1.21 (t, J = 7.2 Hz, 3H), 1.15-1.10 (m, 3H), 0.90-0.80 (m, 3H). |
| I-A26 | 2-CF3 tetrahydropyran-4-yl with methyl linker (cis) | B | m/z 560.1 (M + H) | (CD3OD) δ 7.90 (d, J = 8.0 Hz, 2H), 7.63 (d, J = 8.4 Hz, 2H), 5.06-4.93 (m, 2H), 4.86-4.76 (m, 1H), 4.69-4.53 (m, 2H), 4.26-4.16 (m, 1H), 3.93-3.82 (m, 4H), 3.22 (q, J = 7.2 Hz, 2H), 2.42-2.14 (m, 3H), 1.94-1.86 (m, 1H), 1.74-1.62 (m, 1H), 1.54-1.39 (m, 1H), 1.33-1.26 (m, 3H), 1.22 (t, J = 7.2 Hz, 3H), 1.12-0.96 (m, 3H). |
| I-A27 | 2-CF3 tetrahydropyran-4-yl with methyl linker (trans) | B | m/z 560.1 (M + H) | (CD3OD) δ 7.90 (d, J = 8.0 Hz, 2H), 7.63 (d, J = 8.4 Hz, 2H), 5.06-4.92 (m, 3H), 4.86-4.76 (m, 2H), 4.68-4.53 (m, 1H), 4.29-4.21 (m, 1H), 3.93-3.78 (m, 3H), 3.22 (q, J = 7.2 Hz, 2H), 2.41-2.07 (m, 3H), 1.96-1.86 (m, 1H), 1.74-1.44 (m, 2H), 1.33-1.26 (m, 3H), 1.22 (t, J = 7.2 Hz, 3H), 1.11-0.94 (m, 3H). |

TABLE 1-continued

| Compound Number | R₁ | PREP method | MS | 1H NMR (400 MHz) |
|---|---|---|---|---|
| I-A28 | OCHF₂ (cyclohexyl-CH) | A | m/z 556.1 (M + H) | (CD3OD) δ 7.89 (d, J = 8.0 Hz, 2H), 7.62 (d, J = 8.4 Hz, 2H), 6.40 (t, J = 76.0 Hz, 1H), 4.99-4.93 (m, 2H), 4.60-4.52 (m, 2H), 4.09-4.05 (m, 1H), 3.95 (s, 2H), 3.45-3.34 (m, 1H), 3.23 (q, J = 7.6 Hz, 2H), 2.32-2.28 (m, 1H), 2.13-1.85 (m, 5H), 1.57-1.45 (m, 2H), 1.28 (d, J = 6.8 Hz, 3H), 1.27-1.24 (m, 2H), 1.22 (t, J = 7.6 Hz, 3H), 1.08 (d, J = 6.0 Hz, 3H). |
| I-A29 | CF₃ (N-methylpiperidinyl) | A | m/z 573.0 (M + H) | (CD3OD) δ 7.91 (d, J = 8.4 Hz, 2H), 7.64 (d, J = 8.4 Hz, 2H), 5.13-5.02 (m, 1H), 4.72-4.53 (m, 2H), 4.23-4.12 (m, 1H), 3.97 (s, 2H), 3.88-3.78 (m, 1H), 3.56-3.44 (m, 2H), 3.23 (q, J = 7.2 Hz, 2H), 3.20-3.11 (m, 1H), 3.08 (s, 3H), 2.73-2.60 (m, 1H), 2.52-2.40 (m, 1H), 2.48-2.29 (m, 2H), 2.08-1.95 (m, 1H), 1.65-1.48 (m, 1H), 1.33 (d, J = 5.6 Hz, 3H), 1.24 (t, J = 7.2 Hz, 3H), 1.07 (d, J = 5.6 Hz, 3H). |
| I-A30 | CF₃ (N-methylpiperidinyl) | A | m/z 573.0 (M + H) | (CD3OD) δ 7.89 (d, J = 8.0 Hz, 2H), 7.62 (d, J = 8.0 Hz, 2H), 5.07-5.00 (m, 1H), 4.66-4.45 (m, 2H), 3.94 (s, 2H), 3.89-3.75 (m, 2H), 3.53-3.35 (m, 2H), 3.21 (q, J = 7.6 Hz, 2H), 3.03-2.93 (m, 4H), 2.58-2.45 (m, 1H), 2.42-2.11 (m, 3H), 2.03-1.85 (m, 1H), 1.55-1.45 (m, 1H), 1.29 (d, J = 5.6 Hz, 3H), 1.22 (t, J = 7.6 Hz, 3H), 1.04 (d, J = 5.6 Hz, 3H). |
| I-A31 | F₃C, MeO-pyridinyl | A | m/z 583.1 (M + H) | (CD3OD) δ 8.06-8.04 (m, 1H), 7.89 (d, J = 8.4 Hz, 2H), 7.62 (d, J = 8.4 Hz, 2H), 7.27 (d, J = 7.6 Hz, 1H), 5.03-4.80 (m, 5H), 4.01 (s, 3H), 3.93 (s, 2H), 3.21 (q, J = 7.6 Hz, 2H), 2.05-2.41 (m, 1H), 1.30-1.05 (m, 6H), 0.96 (d, J = 5.2 Hz, 3H). |

TABLE 1-continued

| Compound Number | R₁ | PREP method | MS | 1H NMR (400 MHz) |
|---|---|---|---|---|
| I-A32 | 4-chloro-2,6-difluorophenyl sec-butyl | C | m/z 568.0 (M + H) | (CD₃OD) δ 7.89 (d, J = 8.4 Hz, 2H), 7.62 (d, J = 8.4 Hz, 2H), 7.37 (d, J = 9.6 Hz, 2H), 5.26-5.13 (m, 1H), 4.76-4.53 (m, 3H), 3.94 (s, 3H), 3.21 (q, J = 7.6 Hz, 2H), 2.13-1.97 (m, 1H), 1.84 (d, J = 6.4 Hz, 3H), 1.22 (t, J = 7.6 Hz, 3H), 1.14 (d, J = 5.6 Hz, 3H), 0.91 (d, J = 6.0 Hz, 3H). |
| I-A33 | 3-trifluoromethyl-2-methylpyridin-6-yl | A | m/z 567.1 (M + H) | (CD₃OD) δ 8.18 (d, J = 8.0 Hz, 1H), 7.91 (d, J = 8.0 Hz, 2H), 7.64 (d, J = 8.4 Hz, 2H), 7.55 (d, J = 7.6 Hz, 1H), 5.03 (d, J = 14.4 Hz, 1H), 4.92 (s, 2H), 4.83-4.70 (m, 2H), 3.96 (s, 2H), 3.23 (q, J = 7.2 Hz, 2H), 2.77 (s, 3H), 2.55-2.41 (m, 1H), 1.30-1.15 (m, 6H), 0.96 (d, J = 6.4 Hz, 3H). |
| I-A34 | 4-trifluoromethylphenyl | C | m/z 566.1 (M + H) | (CD₃OD) δ 7.91 (d, J = 8.0 Hz, 2H), 7.89-7.81 (m, 4H), 7.63 (d, J = 8.0 Hz, 2H), 5.10-4.95 (m, 2H), 4.84-4.70 (m, 2H), 3.94 (s, 2H), 3.23 (q, J = 7.2 Hz, 2H), 1.96-1.70 (m, 4H), 1.23 (t, J = 7.2 Hz, 3H), 1.05 (d, J = 6.0 Hz, 3H), 0.86 (d, J = 6.4 Hz, 3H). |
| I-A35 | 4-trifluoromethylphenyl | C | m/z 566.1 (M + H) | (CD₃OD) δ 7.91 (d, J = 8.4 Hz, 2H), 7.89-7.81 (m, 4H), 7.63 (d, J = 8.4 Hz, 2H), 5.15-4.95 (m, 2H), 4.85-4.75 (m, 2H), 3.95 (s, 2H), 3.22 (q, J = 7.6 Hz, 2H), 2.18-2.00 (m, 1H), 1.87-1.65 (m, 3H), 1.23 (t, J = 7.6 Hz, 3H), 1.10 (d, J = 6.8 Hz, 3H), 0.80 (d, J = 6.8 Hz, 3H). |

TABLE 1-continued

| Compound Number | R₁ | PREP method | MS | 1H NMR (400 MHz) |
|---|---|---|---|---|
| I-A36 | 3-F, 4-(1-methyl) 4-CF₃-phenyl | C | m/z 584.1 (M + H) | (CD₃OD) δ 8.05-7.95 (m, 1H), 7.91 (d, J = 8.4 Hz, 2H), 7.76-7.66 (m, 2H), 7.63 (d, J = 8.0 Hz, 2H), 5.35-5.15 (m, 3H), 4.75-4.60 (m, 1H), 3.95 (s, 2H), 3.23 (q, J = 7.2 Hz, 2H), 2.13-1.98 (m, 1H), 1.85-1.65 (m, 3H), 1.24 (t, J = 7.2 Hz, 3H), 1.16 (d, J = 6.4 Hz, 3H), 0.94 (d, J = 6.4 Hz, 3H). |
| I-A37 | 3-F, 4-(1-methyl) 4-CF₃-phenyl | C | m/z 584.1 (M + H) | (CD₃OD) δ 8.05-7.95 (m, 1H), 7.90 (d, J = 8.0 Hz, 2H), 7.70-7.66 (m, 2H), 7.63 (d, J = 8.4 Hz, 2H), 5.35-5.15 (m, 1H), 4.75-4.55 (m, 3H), 3.94 (s, 2H), 3.23 (q, J = 7.2 Hz, 2H), 2.25-2.18 (m, 1H), 1.88-1.70 (m, 3H), 1.24 (t, J = 7.2 Hz, 3H), 1.18 (d, J = 6.4 Hz, 3H), 0.88 (d, J = 6.4 Hz, 3H). |
| I-A38 | 3-F, 4-(1-methyl) 4-Cl-phenyl | C | m/z 550.1 (M + H) | (CD₃OD) δ 7.91 (d, J = 8.0 Hz, 2H), 7.80-7.72 (m, 1H), 7.64 (d, J = 8.0 Hz, 2H), 7.46-7.36 (m, 2H), 5.18-5.03 (m, 2H), 4.78-4.63 (m, 2H), 3.95 (s, 2H), 3.23 (q, J = 7.6 Hz, 2H), 2.08-1.99 (m, 1H), 1.79-1.72 (m, 3H), 1.24 (t, J = 7.6 Hz, 3H), 1.16 (d, J = 6.0 Hz, 3H), 0.95 (d, J = 6.0 Hz, 3H). |
| I-A39 | 3-F, 4-(1-methyl) 4-Cl-phenyl | C | m/z 550.1 (M + H) | (CD₃OD) δ 7.91 (d, J = 8.8 Hz, 2H), 7.82-7.78 (m, 1H), 7.63 (d, J = 8.4 Hz, 2H), 7.41-7.32 (m, 2H), 5.25-5.12 (m, 1H), 4.92-4.89 (m, 1H), 4.78-4.65 (m, 2H), 3.95 (s, 2H), 3.23 (q, J = 7.2 Hz, 3H), 2.26-2.19 (m, 1H), 1.79-1.72 (m, 3H), 1.23 (t, J = 7.2 Hz, 3H), 1.18 (d, J = 6.4 Hz, 3H), 0.88 (d, J = 6.4 Hz, 3H). |

TABLE 1-continued

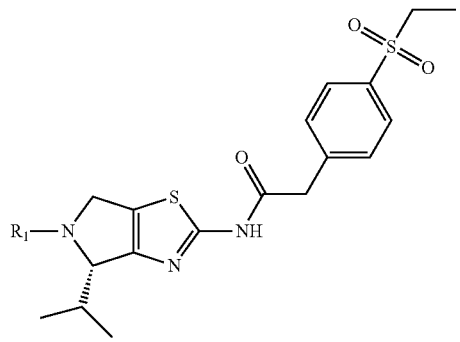

| Compound Number | R₁ | PREP method | MS | 1H NMR (400 MHz) |
|---|---|---|---|---|
| I-A40 | (tetrazole-phenyl-CMe2- group) | C | m/z 566.1 (M + H) | (CD$_3$OD) δ 7.99 (d, J = 8.4 Hz, 2H), 7.93 (d, J = 8.0 Hz, 2H), 7.91 (d, J = 8.0 Hz, 2H), 7.64 (d, J = 8.4 Hz, 2H), 4.81-4.65 (m, 5H), 4.23 (s, 3H), 3.96 (s, 2H), 3.23 (q, J = 7.6 Hz, 2H), 2.30-1.95 (m, 1H), 1.24 (t, J = 7.6 Hz, 3H), 1.17 (d, J = 6.4 Hz, 3H), 0.93 (d, J = 6.8 Hz, 3H). |
| I-A41 | (Boc-morpholine-CH2- group) | C | m/z 593.1 (M + H) | (CD$_3$OD) δ 7.89 (d, J = 8.0 Hz, 2H), 7.62 (d, J = 8.4 Hz, 2H), 4.35-4.31 (m, 1H), 4.20-4.15 (m, 1H), 3.90-3.65 (m, 6H), 3.55-3.45 (m, 2H), 3.22 (q, J = 7.2 Hz, 2H), 2.88-2.63 (m, 4H), 1.94-1.91 (m, 1H), 1.46 (s, 9H), 1.22 (q, J = 7.6 Hz, 3H), 1.08 (d, J = 6.8 Hz, 3H), 0.84 (d, J = 6.4 Hz, 3H). |
| I-A42 | (tetrazole-phenyl-CMe2- group) | C | m/z 566.1 (M + H) | (CD$_3$OD) δ 8.25 (d, J = 8.0 Hz, 2H), 7.91 (d, J = 8.4 Hz, 2H), 7.83 (d, J = 8.4 Hz, 2H), 7.64 (d, J = 8.4 Hz, 2H), 4.80-4.60 (m, 5H), 4.46 (s, 3H), 3.96 (s, 2H), 3.23 (q, J = 7.6 Hz, 2H), 2.20-1.99 (m, 1H), 1.23 (t, J = 7.2 Hz, 3H), 1.14 (d, J = 6.4 Hz, 3H), 0.91 (d, J = 6.4 Hz, 3H). |

TABLE 1-continued

| Compound Number | R₁ | PREP method | MS | 1H NMR (400 MHz) |
|---|---|---|---|---|
| I-A43 | *tert-butyl morpholine-4-carboxylate with CH2 linker* | C | m/z 593.1 (M + H) | (CD₃OD) δ 7.89 (d, J = 8.4 Hz, 2H), 7.62 (d, J = 8.4 Hz, 2H), 4.35-4.31 (m, 1H), 3.91-3.70 (m, 7H), 3.55-3.45 (m, 2H), 3.22 (q, J = 7.2 Hz, 2H), 3.01-2.87 (m, 4H), 1.95-1.90 (m, 1H), 1.46 (s, 9H), 1.22 (q, J = 7.2 Hz, 3H), 1.08 (d, J = 6.8 Hz, 3H), 0.84 (d, J = 6.8 Hz, 3H). |
| I-A44 | *methyl cyclohexanecarboxylate with CH2 linker* | A | m/z 548.1 (M + H) | (CD₃OD) δ 7.89 (d, J = 8.8 Hz, 2H), 7.62 (d, J = 8.4 Hz, 2H), 5.00-4.95 (m, 4H), 4.60-4.55 (m, 1H), 3.94 (s, 2H), 3.66 (s, 3H), 3.42-3.36 (m, 1H), 3.21 (q, J = 7.2 Hz, 2H), 2.35-2.31 (m, 2H), 2.08-1.82 (m, 6H), 1.51-1.48 (m, 2H), 1.28 (d, J = 6.8 Hz, 3H), 1.21 (t, J = 7.2 Hz, 3H), 1.07 (d, J = 6.8 Hz, 3H). |
| I-A45 | *4-CF3, 2-CN phenyl with CH2 linker* | A | m/z 577.0 (M + H) | (CD₃OD) δ 8.27 (s, 1H), 8.09 (dd, J = 9.2, 14.4 Hz, 2H), 7.88 (d, J = 8.0 Hz, 2H), 7.61 (d, J = 8.0 Hz, 2H), 4.80-4.40 (m, 5H), 3.93 (s, 2H), 3.20 (q, J = 7.6 Hz, 2H), 2.45-2.20 (m, 1H), 1.26 (d, J = 6.8 Hz, 3H), 1.20 (t, J = 7.2 Hz, 3H), 0.95 (d, J = 6.4 Hz, 3H). |
| I-A46 | *5-CN, 3-F pyridine with CH2 linker* | A | m/z 528.1 (M + H) | (CD₃OD) δ 8.88 (s, 1H), 8.26 (dd, J = 1.2, 8.0 Hz, 1H), 7.89 (d, J = 8.0 Hz, 2H), 7.63 (d, J = 8.4 Hz, 2H), 5.06-5.03 (m, 3H), 4.78-4.70 (m, 2H), 3.95 (s, 2H), 3.21 (q, J = 7.2 Hz, 2H), 2.58-2.53 (m, 1H), 1.25-1.22 (m, 6H), 0.97 (d, J = 6.8 Hz, 3H). |

TABLE 1-continued

| Compound Number | R₁ | PREP method | MS | 1H NMR (400 MHz) |
|---|---|---|---|---|
| I-A47 | 5-chloro-pyridin-2-yl with (S)-methyl-methylene linker | C | m/z 533.1 (M + H) | (CD₃OD) δ 8.68 (s, 1H), 8.01-7.97 (m, 1H), 7.91 (d, J = 8.4 Hz, 2H), 7.63 (d, J = 8.4 Hz, 2H), 7.63-7.60 (m, 1H), 4.83-4.73 (m, 4H), 3.95 (s, 2H), 3.23 (q, J = 7.2 Hz, 2H), 2.33-2.20 (m, 1H), 1.70 (d, J = 6.8 Hz, 3H), 1.24 (t, J = 7.2 Hz, 3H), 1.13 (d, J = 6.8 Hz, 3H), 0.82 (d, J = 6.8 Hz, 3H). |
| I-A48 | 5-chloro-pyridin-2-yl with methyl-methylene linker | C | m/z 533.0 (M + H) | (CD₃OD) δ 8.66 (s, 1H), 8.01-7.93 (m, 1H), 7.91 (d, J = 8.4 Hz, 2H), 7.63 (d, J = 8.4 Hz, 2H), 7.63-7.59 (m, 1H), 4.77-4.73 (m, 4H), 3.94 (s, 2H), 3.23 (q, J = 7.2 Hz, 2H), 2.17-2.08 (m, 1H), 1.69-1.78 (m, 3H), 1.25 (t, J = 7.2 Hz, 3H), 1.11 (d, J = 6.8 Hz, 3H), 0.88 (d, J = 6.8 Hz, 3H). |
| I-A49 | 5-cyano-4-methyl-pyridin-2-yl with dimethyl-methylene linker | A | m/z 524.1 (M + H) | (CDCl₃) δ 9.75-9.69 (m, 1H), 8.72 (s, 1H), 8.10-8.05 (m, 1H), 7.92 (d, J = 7.6 Hz, 2H), 7.59 (d, J = 7.2 Hz, 2H), 4.72-4.46 (m, 5H), 3.98 (s, 2H), 3.14 (q, J = 7.6 Hz, 2H), 2.63 (s, 3H), 2.18-2.10 (m, 1H), 1.31 (t, J = 7.2 Hz, 3H), 1.06 (d, J = 6.8 Hz, 3H), 0.91 (d, J = 6.8 Hz, 3H). |
| I-A50 | 3-cyano-2-methyl-pyridin-6-yl with dimethyl-methylene linker | A | m/z 524.0 (M + H) | (CDCl₃) δ 9.39 (s, 1H), 7.94-7.90 (m, 3H), 7.56 (d, J = 8.4 Hz, 3H), 4.32-4.24 (m, 2H), 4.13-4.09 (m, 1H), 3.99 (s, 1H), 3.91 (s, 2H), 3.72 (d, J = 12.4 Hz, 1H), 3.16 (q, J = 7.6 Hz, 2H), 2.77 (s, 3H), 2.05-1.95 (m, 1H), 1.32 (t, J = 7.6 Hz, 3H), 1.01 (d, J = 6.8 Hz, 3H), 0.92 (d, J = 6.8 Hz, 3H). |

TABLE 1-continued

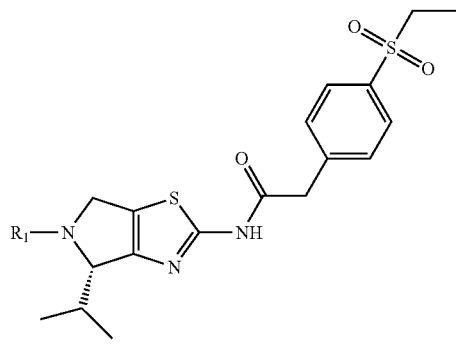

| Compound Number | R$_1$ | PREP method | MS | 1H NMR (400 MHz) |
|---|---|---|---|---|
| I-A51 | (3-cyano-2-methoxypyridin-6-yl)methyl group with MeO, NC substituents | A | m/z 540.0 (M + H) | (CDCl$_3$) δ 9.39 (s, 1H), 7.94-7.90 (m, 3H), 7.56 (d, J = 8.4 Hz, 3H), 4.32-4.24 (m, 2H), 4.13-4.09 (m, 1H), 3.99 (s, 1H), 3.91 (s, 2H), 3.72 (d, J = 12.4 Hz, 1H), 3.16 (q, J = 7.6 Hz, 2H), 2.77 (s, 3H), 2.05-1.95 (m, 1H), 1.32 (t, J = 7.6 Hz, 3H), 1.01 (d, J = 6.8 Hz, 3H), 0.92 (d, J = 6.8 Hz, 3H). |
| I-A53 | (5-chloro-3-fluoropyridin-2-yl) group | A | m/z 551.0 (M + H) | (CDCl$_3$) δ 8.73 (s, 1H), 8.34 (s, 1H), 7.93 (d, J = 8.4 Hz, 2H), 7.54 (d, J = 8.4 Hz, 2H), 7.41 (d, J = 8.4 Hz, 1H), 4.65-4.50 (m, 1H), 4.23-4.11 (m, 2H), 3.87 (s, 2H), 3.80-3.76 (m, 1H), 3.14 (q, J = 7.2 Hz, 2H), 2.05-1.95 (m, 1H), 1.40 (d, J = 6.4 Hz, 3H), 1.32 (t, J = 7.2 Hz, 3H), 0.99 (d, J = 6.8 Hz, 3H), 0.85 (d, J = 6.4 Hz, 3H). |
| I-A54 | (5-difluoromethoxypyridin-2-yl)methyl, HF$_2$CO substituent | A | m/z 551.0 (M + H) | (CD$_3$OD) δ 8.36 (s, 1H), 7.90 (d, J = 8.0 Hz, 2H), 7.72-7.66 (m, 2H), 7.64 (d, J = 8.4 Hz, 2H), 6.94 (t, J = 73.2 Hz, 1H), 4.25-4.20 (m, 2H), 4.04-4.00 (m, 1H), 3.96-3.90 (m, 3H), 3.74-3.68 (m, 1H), 3.22 (q, J = 7.6 Hz, 2H), 2.00-1.94 (m, 1H), 1.23 (t, J = 7.6 Hz, 3H), 1.08 (d, J = 7.2 Hz, 3H), 0.91 (d, J = 7.2 Hz, 3H). |
| I-A58 | (2-trifluoromethylpyrimidin-5-yl)methyl, F$_3$C substituent | C | m/z 554.0 (M + H) | (CD$_3$OD) δ 9.01 (s, 2H), 7.91 (d, J = 8.4 Hz, 2H), 7.64 (d, J = 8.4 Hz, 2H), 4.33-4.28 (m, 1H), 4.21-4.16 (m, 1H), 4.05-4.01 (m, 1H), 3.96-3.90 (m, 3H), 3.71-3.65 (m, 1H), 3.22 (q, J = 7.2 Hz, 2H), 2.06-2.01 (m, 1H), 1.23 (t, J = 7.2 Hz, 3H), 1.12 (d, J = 6.8 Hz, 2H), 0.94 (d, J = 6.8 Hz, 2H). |

TABLE 1-continued

| Compound Number | R₁ | PREP method | MS | 1H NMR (400 MHz) |
|---|---|---|---|---|
| I-A59 | 4-cyclopropylbenzyl | A | m/z 524.1 (M + H) | (CD₃OD) δ 7.87 (d, J = 8.0 Hz, 2H), 7.60 (d, J = 8.4 Hz, 2H), 7.25 (d, J = 8.0 Hz, 2H), 7.02 (d, J = 8.0 Hz, 2H), 4.08-4.03 (m, 2H), 3.89-3.83 (m, 3H), 3.73 (d, J = 13.2 Hz, 1H), 3.64-3.58 (m, 1H), 3.18 (q, J = 7.2 Hz, 2H), 1.99-1.82 (m, 2H), 1.20 (t, J = 7.2 Hz, 3H), 1.06 (d, J = 6.8 Hz, 3H), 0.93-0.91 (m, 2H), 0.89 (d, J = 6.8 Hz, 3H), 0.65-0.63 (m, 2H). |
| I-A60 | 4-(methoxycarbonyl)benzyl | A | m/z 542.0 (M + H) | (CDCl₃) δ 9.50 (brs, 1H), 8.00 (d, J = 8.4 Hz, 2H), 7.91 (d, J = 8.0 Hz, 2H), 7.53 (d, J = 8.4 Hz, 2H), 7.47 (d, J = 8.4 Hz, 2H), 4.20-4.13 (m, 2H), 3.92-3.84 (m, 7H), 3.60 (d, J = 13.2 Hz, 1H), 3.14 (q, J = 7.6 Hz, 2H), 2.03-1.95 (m, 1H), 1.30 (t, J = 7.6 Hz, 3H), 1.02 (d, J = 6.8 Hz, 3H), 0.92 (d, J = 6.8 Hz, 3H). |
| I-A61 | 4-(difluoromethyl)benzyl | A | m/z 534.0 (M + H) | (CDCl₃) δ 9.92 (s, 1H), 7.89 (d, J = 8.0 Hz, 2H), 7.52-7.45 (m, 6H), 6.64 (t, J = 56.4 Hz, 1H), 4.19-4.14 (m, 2H), 3.89-3.83 (m, 4H), 3.62-3.59 (m, 1H), 3.15 (q, J = 7.6 Hz, 2H), 2.03-1.97 (m, 1H), 1.29 (t, J = 7.6 Hz, 3H), 1.02 (d, J = 6.8 Hz, 3H), 0.92 (d, J = 6.8 Hz, 3H). |
| I-A62 | 1-(6-(trifluoromethyl)pyridin-3-yl)ethyl | A | m/z 553.1 (M + H) | (CDCl₃) δ 9.61 (brs, 1H), 8.74 (s, 1H), 7.95-7.89 (m, 3H), 7.67 (d, J = 8.0 Hz, 1H), 7.53 (d, J = 8.4 Hz, 2H), 4.23-4.15 (m, 2H), 3.97-3.90 (m, 4H), 3.65-3.55 (m, 1H), 3.14 (q, J = 7.6 Hz, 2H), 2.03-1.96 (m, 1H), 1.30 (t, J = 7.6 Hz, 3H), 1.02 (d, J = 6.8 Hz, 3H), 0.91 (d, J = 6.8 Hz, 3H). |

TABLE 1-continued

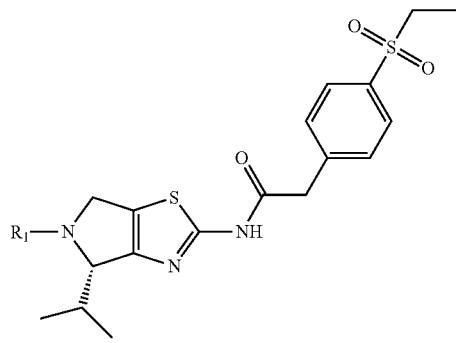

| Compound Number | R₁ | PREP method | MS | 1H NMR (400 MHz) |
|---|---|---|---|---|
| I-A63 | (4-ethylbenzyl) | A | m/z 512.0 (M + H) | (CDCl₃) δ 9.63 (s, 1H), 7.89 (d, J = 8.0 Hz, 2H), 7.52 (d, J = 8.4 Hz, 2H), 7.36-7.27 (m, 2H), 7.16 (d, J = 7.6 Hz, 2H), 4.11 (m, 2H), 3.92 (s, 2H), 3.90-3.58 (m, 3H), 3.13 (q, J = 7.6 Hz, 2H), 2.64 (q, J = 7.6 Hz, 2H), 2.07-1.97 (m, 1H), 1.30 (t, J = 7.6 Hz, 3H), 1.23 (t, J = 7.6 Hz, 3H), 1.01 (d, J = 6.8 Hz, 3H), 0.92 (d, J = 6.8 Hz, 3H). |
| I-A64 | (4-methylbenzyl) | A | m/z 498.1 (M + H) | (CDCl₃) δ 9.56 (s, 1H), 7.90 (d, J = 8.0 Hz, 2H), 7.51 (d, J = 8.4 Hz, 2H), 7.31-7.26 (m, 2H), 7.13 (d, J = 7.6 Hz, 2H), 4.13-4.09 (m, 2H), 3.91 (s, 2H), 3.86-3.80 (m, 1H), 3.76-3.56 (m, 2H), 3.13 (q, J = 7.6 Hz, 2H), 2.34 (s, 3H), 2.06-1.96 (m, 1H), 1.30 (t, J = 7.6 Hz, 3H), 1.02 (d, J = 6.8 Hz, 3H), 0.92 (d, J = 6.8 Hz, 3H). |

(S)—N-(5-(4-chlorobenzyl)-4-isopropyl-5,6-dihydro-4H-pyrrolo[3,4-d]thiazol-2-yl)-2-(4-(methylsulfonyl)phenyl)acetamide (Compound I-B1)

Compound I-B1 was prepared by following the synthetic steps shown in Schemes 49-51.

Scheme 49.

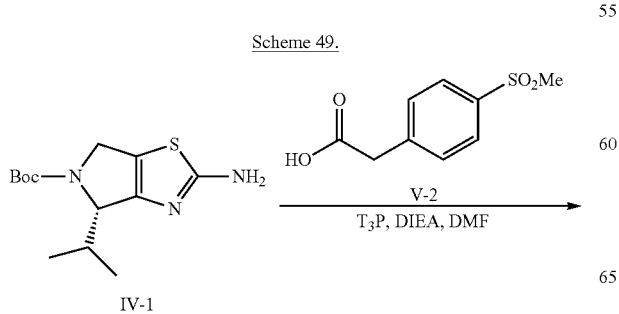

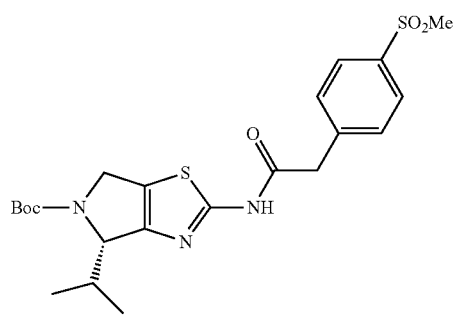

III-2

To a solution of compound IV-1 (145 mg, 0.5 mmol) in DMF (3 mL) was added carboxylic acid V-2 (214 mg, 1.0 mmol), N,N-diisopropylethylamine (210 μL, 1.0 mmol) followed by propylphosphonic anhydride solution (T3P, 50 wt. % in ethyl acetate, 0.6 mL, 1 mmol). The mixture was allowed to stir at rt for 8 h and diluted with H$_2$O (20 mL) and ethyl acetate (30 mL). The aqueous phase was extracted with ethyl acetate (3×20 mL). The combined organic layers were washed with brine (30 mL), dried over anhydrous Na$_2$SO$_4$, filtered and concentrated under reduced pressure. The residue was purified by column chromatography on silica gel eluting with Hexanes/ethyl acetate (1/1) to afford compound III-2 (156 mg, 65%) as a white solid. LC-MS $t_R$=1.57 min in 2 min chromatography, MS (ESI) m/z 480 [M+H]$^+$. $^1$H NMR (CD$_3$OD, 400 MHz): δ 7.93 (d, J=8.0 Hz, 2H), 7.61 (d, J=8.0 Hz, 2H), 4.72-4.64 (m, 3H), 4.51-4.43 (m, 2H), 3.91 (s, 2H), 3.11 (s, 3H), 2.45-2.35 (m, 1H), 1.51 (s, 9H), 1.14-1.11 (m, 3H), 0.64-0.60 (m, 3H).

pressure to afford crude compound II-2 as a brown oil, which was used directly for the next step without further purification. LC-MS $t_R$=0.62 min in 2 min chromatography, MS (ESI) m/z 380 [M+H]$^+$.

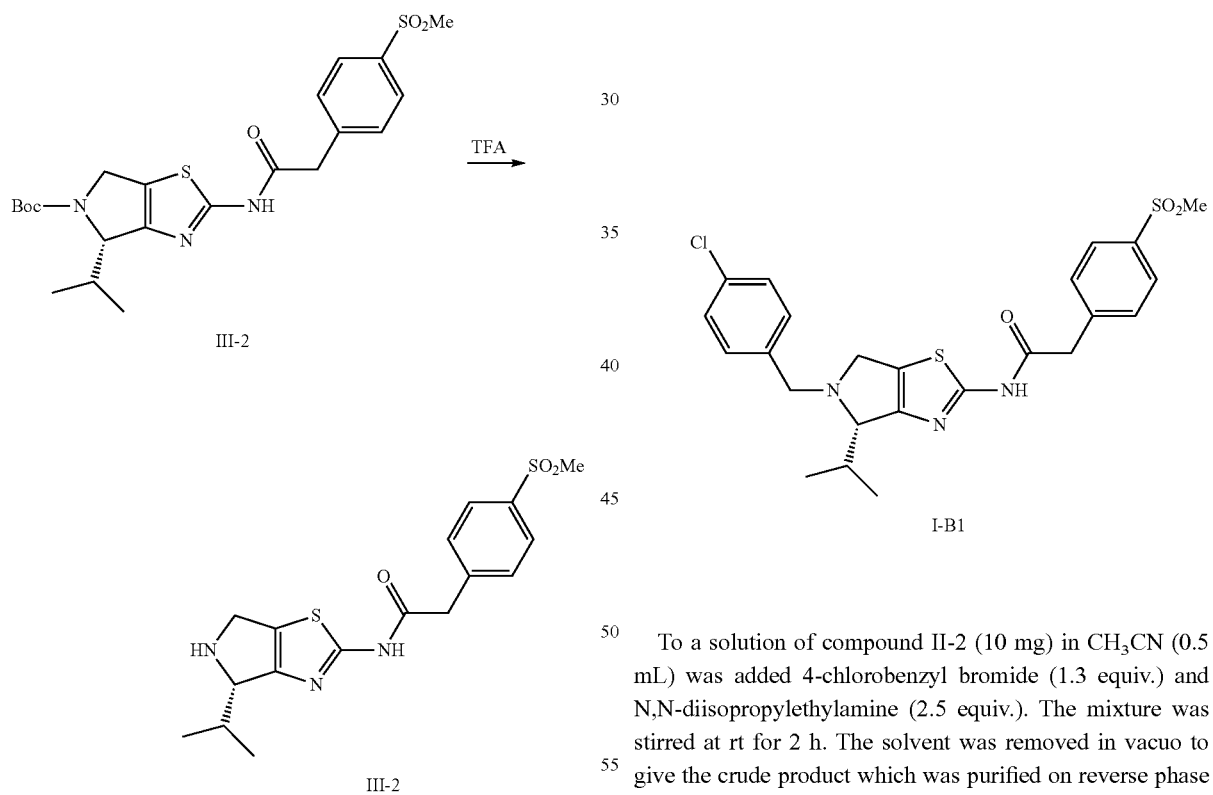

To a solution of compound III-2 (50 mg, 0.1 mmol) in CH$_2$Cl$_2$ (3.0 mL) was added TFA (0.5 mL). The mixture was stirred at rt for 1 h and neutralized with sat. NaHCO$_3$ solution. The separated aqueous phase was extracted with CH$_2$Cl$_2$ (3×15 mL). The organic layer was dried over anhydrous Na$_2$SO$_4$, filtered and concentrated under reduced To a solution of compound II-2 (10 mg) in CH$_3$CN (0.5 mL) was added 4-chlorobenzyl bromide (1.3 equiv.) and N,N-diisopropylethylamine (2.5 equiv.). The mixture was stirred at rt for 2 h. The solvent was removed in vacuo to give the crude product which was purified on reverse phase prep-HPLC to yield the final compound I-B1. LC-MS $t_R$=1.01 min in 2 min chromatography, MS (ESI) m/z 506.3 [M+H]$^+$. $^1$H NMR (CD$_3$OD, 400 MHz): δ 7.93 (d, J=8.4 Hz, 2H), 7.61 (m, 4H), 7.53 (d, J=8.4 Hz, 2H), 4.83-4.79 (m, 1H), 4.70-4.61 (m, 4H), 3.94 (s, 2H), 3.12 (s, 3H), 2.08-2.03 (m, 1H), 1.13 (d, J=6.8 Hz, 3H), 0.87 (d, J=6.8 Hz, 3H).

The compounds I-B2 to I-B19 in Table 2 were prepared from compound II-2 using the appropriate (het)arylalkyl halide (Method A) or (het)aryl aldehyde (Method B or C).

TABLE 2

| Compound Number | R₁ | PREP method | MS | 1H NMR (400 MHz) |
|---|---|---|---|---|
| I-B2 | F₂HCO-(4-phenyl)-CH< | A | m/z 537.3 [M + H]+ tR = 0.96 min | (CD3OD) δ 7.93 (d, J = 8.8 Hz, 2H), 7.66 (d, J = 8.8 Hz, 2H), 7.63 (d, J = 10 Hz, 2H), 7.27 (d, J = 8.8 Hz, 2H), 6.93 (t, J = 73.6 Hz, 1H), 4.88-4.79 (m, 1H), 4.70-4.61 (m, 4H), 3.94 (s, 2H), 3.12 (s, 3H), 2.08-2.03 (m, 1H), 1.13 (d, J = 7.2 Hz, 3H), 0.88 (d, J = 6.8 Hz, 3H). |
| I-B3 | NC-(2-F-4-phenyl)-CH< | A | m/z 514.3 [M +H] + tR = 1.16 min | (CD3OD) δ 7.94 (d, J = 8.4 Hz, 2H), 7.89 (d, J = 6.4 Hz, 1H), 7.68 (d, J = 10 Hz, 1H), 7.63-7.60 (m, 3H), 4.77-4.52 (m, 5H), 3.93 (s, 2H), 3.12 (s, 3H), 2.20-2.16 (m, 1H), 1.17 (d, J = 6.8 Hz, 3H), 0.90 (d, J = 6.8 Hz, 3H). |
| I-B4 | F₃C-(5-pyridin-2-yl)-CH< | B | m/z 539.4 [M + H]+ tR = 1.03 min | (CD3OD) δ 8.79 (s, 1H), 8.13 (d, J = 8.4 Hz, 1H), 7.92 (d, J = 8.4 Hz, 2H), 7.84 (d, J = 8.0 Hz, 1H), 7.60 (d, J = 8.4 Hz, 2H), 4.34-4.23 (m, 2H), 4.13-4.09 (m, 1H), 3.97-3.95 (m, 1H), 3.91 (s, 2H), 3.73-3.69 (m, 1H), 3.11 (s, 3H), 2.01-1.96 (m, 1H), 1.07 (d, J = 6.8 Hz, 3H), 0.90 (d, J = 6.8 Hz, 3H). |
| I-B5 | F₃C-(2-pyridin-5-yl)-CH< | A | m/z 539.4 [M + H]+ tR = 1.15 | (CD3OD) δ 8.74 (s, 1H), 8.09 (d, J = 8.0 Hz, 1H), 7.92 (d, J = 8.4 Hz, 2H), 7.80 (d, J = 8.0 Hz, 1H), 7.61 (d, J = 8.4 Hz, 2H), 4.28-4.24 (m, 2H), 4.15-4.09 (m, 1H), 4.00-3.95 (m, 1H), 3.91 (s, 2H), 3.66-3.62 (m, 1H), 3.11 (s, 3H), 2.03-1.98 (m, 1H), 1.09 (d, J = 6.8 Hz, 3H), 0.92 (d, J = 6.8 Hz, 3H). |

TABLE 2-continued

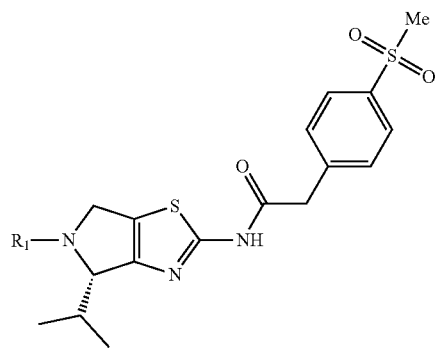

| Compound Number | R₁ | PREP method | MS | 1H NMR (400 MHz) |
|---|---|---|---|---|
| I-B6 | 5-chloro-4-methylpyridin-2-yl-methyl (Cl, Me on pyridine) | B | m/z 520.5 [M + H]+ tR = 0.96 min | (CD3OD) δ 8.38 (s, 1H), 7.93 (d, J = 8.0 Hz, 2H), 7.61 (d, J = 8.0 Hz, 2H), 7.56 (s, 1H), 4.23-4.20 (m, 1H), 4.19-4.15 (m, 1H), 3.97-3.93 (m, 1H), 3.91 (s, 2H), 3.72-3.68 (m, 1H), 3.11 (s, 3H), 2.43 (s, 3H), 1.97-1.95 (m, 1H), 1.07 (d, J = 6.8 Hz, 3H), 0.91 (d, J = 6.8 Hz, 3H). |
| I-B7 | 4-cyano-3-methylphenyl-methyl | A | m/z 509.0 (M + H) | (CD₃OD) δ 7.95 (d, J = 8.4 Hz, 2H), 7.79 (d, J = 8.0 Hz, 1H), 7.68-7.60 (m, 4H), 4.73-4.65 (m, 5H), 3.95 (s, 2H), 3.14 (s, 3H), 2.60 (s, 3H), 2.10-2.03 (m, 1H), 1.15 (d, J = 6.8 Hz, 3H), 0.92 (d, J = 6.4 Hz, 3H). |
| I-B8 | 3-chloro-4-cyanophenyl-methyl | A | m/z 529.0 (M + H) | (CD₃OD) δ 7.97-7.93 (m, 4H), 7.78-7.76 (m, 1H), 7.63 (d, J = 8.8 Hz, 2H), 5.68-5.63 (m, 5H), 3.96 (s, 2H), 3.14 (s, 3H), 2.23-2.16 (m, 1H), 1.18 (d, J = 7.2 Hz, 3H), 0.93 (d, J = 6.8 Hz, 3H). |
| I-B9 | 4-(2-methyltetrazol-5-yl)phenyl-methyl | C | m/z 552.1 (M + H) | (CD₃OD) δ 8.27 (d, J = 8.4 Hz, 2H), 7.95 d, J = 8.4 Hz, 2H), 7.83 (d, J = 8.0 Hz, 2H), 7.63 (d, J = 8.4 Hz, 2H), 4.86-4.70 (m, 5H), 4.46 (s, 3H), 3.96 (s, 2H), 3.14 (s, 3H), 2.12-2.04 (m, 1H), 1.15 (d, J = 6.8 Hz, 3H), 0.91 (d, J = 6.8 Hz, 3H). |

TABLE 2-continued

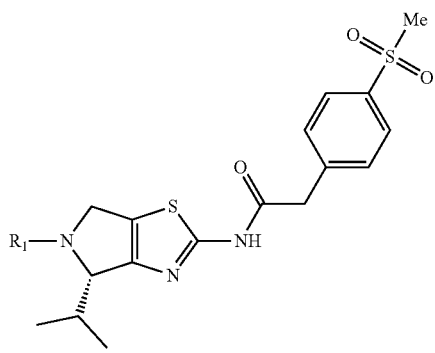

| Compound Number | R₁ | PREP method | MS | 1H NMR (400 MHz) |
|---|---|---|---|---|
| I-B10 | ![NC-phenyl-Cl with isopropyl] | C | m/z 543.0 (M + H) | (CD₃OD) δ 8.24 (d, J = 8.0 Hz, 1H), 8.02 (s, 1H), 7.93 (d, J = 8.0 Hz, 2H), 7.86 (d, J = 8.0 Hz, 1H), 7.61 (d, J = 8.4 Hz, 2H), 5.39 (q, J = 6.4 Hz, 1H), 4.80-4.73 (m, 2H), 4.57-4.40 (m, 1H), 3.94 (s, 2H), 3.11 (s, 3H), 2.52-2.35 (m, 1H), 1.86 (d, J = 6.4 Hz, 3H), 1.31-1.18 (m, 3H), 0.90 (d, J = 6.0 Hz, 3H). |
| I-B11 | ![NC-phenyl-F with isopropyl] | C | m/z 527.1 (M + H) | (CD₃OD) δ 7.95 (d, J = 8.4 Hz, 2H), 7.89 (t, J = 6.8 Hz, 1H), 7.75 (d, J = 10.0 Hz, 1H), 7.67 (d, J = 8.4 Hz, 1H), 7.62 (d, J = 8.4 Hz, 2H), 4.83-4.74 (m, 4H), 3.94 (s, 1H), 3.14 (m, 3H), 1.99-1.95 (m, 1H), 1.84 (d, J = 7.2 Hz, 3H), 1.14 (d, J = 6.4 Hz, 3H), 0.89 (d, J = 6.4 Hz, 3H). |
| I-B12 | ![NC-phenyl-F with isopropyl] | C | m/z 527.0 (M + H) | (CD₃OD) δ 7.95 (d, J = 8.4 Hz, 2H), 7.91 (t, J = 8.0 Hz, 1H), 7.82 (d, J = 8.0 Hz, 1H), 7.71 (d, J = 8.0 Hz, 1H), 7.63 (d, J = 8.8 Hz, 2H), 4.81-4.65 (m, 4H), 3.95 (s, 2H), 3.14 (s, 3H), 2.17-2.13 (m, 1H), 1.77 (d, J = 6.8 Hz, 3H), 1.15 (d, J = 6.8 Hz, 3H), 0.82 (d, J = 6.4 Hz, 3H). |
| I-B13 | ![F₃C-pyridine-Me with isopropyl] | A | m/z 553.1 (M + H) | (CD₃OD) δ 8.23 (d, J = 7.6 Hz, 1H), 7.94 (d, J = 8.4 Hz, 2H), 7.78 (d, J = 8.0 Hz, 1H), 7.62 (d, J = 8.4 Hz, 2H), 4.91-4.45 (m, 5H), 3.94 (s, 2H), 3.12 (s, 3H), 2.73 (s, 3H), 2.15-2.45 (m, 1H), 1.25 (d, J = 6.4 Hz, 3H), 0.96 (d, J = 6.8 Hz, 3H). |

TABLE 2-continued

| Compound Number | R₁ | PREP method | MS | 1H NMR (400 MHz) |
|---|---|---|---|---|
| I-B14 | 4-cyanophenyl-CH(Me)- (wedge) | C | m/z 509.1 (M + H) | (CD$_3$OD) δ 7.93 (d, J = 8.4 Hz, 2H), 7.87-7.82 (m, 4H), 7.60 (d, J = 8.4 Hz, 2H), 5.00-4.93 (m, 4H), 4.71-4.62 (m, 1H), 3.92 (s, 2H), 3.12 (s, 3H), 1.92-1.75 (m, 4H), 1.06 (d, J = 6.0 Hz, 3H), 0.85 (d, J = 6.4 Hz, 3H). |
| I-B15 | 4-cyanophenyl-CH(Me)- | C | m/z 509.0 (M + H) | (CD$_3$OD) δ 7.94 (d, J = 8.4 Hz, 2H), 7.90-7.82 (m, 4H), 7.61 (d, J = 8.0 Hz, 2H), 5.07-4.98 (m, 2H), 4.79-4.65 (m, 3H), 3.93 (s, 2H), 3.12 (s, 3H), 2.08-1.99 (m, 1H), 1.78-1.72 (m, 3H), 1.09 (d, J = 6.8 Hz, 3H), 0.78 (d, J = 6.8 Hz, 3H). |
| I-B16 | 4-cyano-2-chlorophenyl-CH(Me)CH$_2$- | A | m/z 529.0 (M + H) | (CD$_3$OD) δ 8.05 (s, 1H), 8.01-7.94 (m, 3H), 7.86 (d, J = 8.8 Hz, 1H), 7.64 (d, J = 8.4 Hz, 2H), 4.75-4.66 (m, 5H), 3.96 (s, 2H), 3.14 (s, 3H), 2.33-2.27 (m, 1H), 1.25 (d, J = 7.2 Hz, 3H), 0.98 (d, J = 6.4 Hz, 3H). |
| I-B17 | 4-cyano-2-fluorophenyl-CH(Me)CH$_2$- | A | m/z 513.0 (M + H) | (CD$_3$OD) δ 8.03 (t, J = 7.6 Hz, 1H), 7.94 (d, J = 8.0 Hz, 2H), 7.80 (d, J = 9.6 Hz, 1H), 7.75 (d, J = 7.6 Hz, 1H), 7.63 (d, J = 8.4 Hz, 2H), 4.87-4.81 (m, 3H), 4.75-4.73 (m, 2H), 3.97 (s, 2H), 3.13 (s, 3H), 2.31-2.27 (m, 1H), 1.25 (d, J = 6.8 Hz, 3H), 1.02 (d, J = 6.4 Hz, 3H). |

TABLE 2-continued

| Compound Number | R₁ | PREP method | MS | 1H NMR (400 MHz) |
|---|---|---|---|---|
| I-B18 | (4-cyanobenzyl-methyl) | A | m/z 495.0 (M + H) | (CD₃OD) δ 7.93 (d, J = 8.0 Hz, 2H), 7.70 (d, J = 8.0 Hz, 2H), 7.61 (d, J = 7.6 Hz, 4H), 4.22-4.09 (m, 2H), 3.90-3.88 (m, 4H), 3.59-3.57 (m, 1H), 3.11 (s, 3H), 1.98-1.90 (m, 1H), 1.08 (d, J = 6.8 Hz, 3H), 0.91 (d, J = 6.4 Hz, 3H). |
| I-B19 | (4-trifluoromethylbenzyl-methyl) | A | m/z 538.0 (M + H) | (CD₃OD) δ 7.93 (dd, J = 1.6, 7.6 Hz, 2H), 7.64-7.59 (m, 6H), 4.20 (d, J = 14.4 Hz, 1H), 4.11-4.08 (m, 1H), 3.90 (s, 3H), 3.89-3.86 (m, 1H), 3.60-3.55 (m, 1H), 3.10 (s, 3H), 2.02-1.98 (m, 1H), 1.08 (d, J = 7.2 Hz, 3H), 0.90 (d, J = 6.8 Hz, 3H). |

(S)—N-(5-(4-chlorobenzyl)-4-isopropyl-5,6-dihydro-4H-pyrrolo[3,4-d]thiazol-2-yl)-2-(5-(ethylsulfonyl)pyridin-2-yl)acetamide (Compound I-C1)

Compound I-C1 was prepared by following the synthetic steps shown in Schemes 52-56.

Scheme 52.

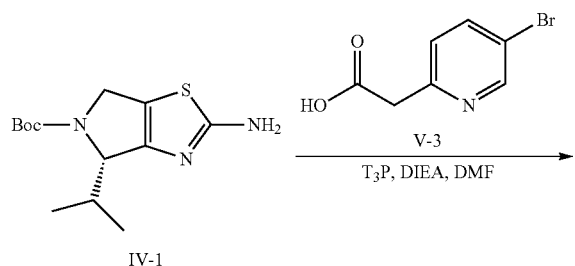

-continued

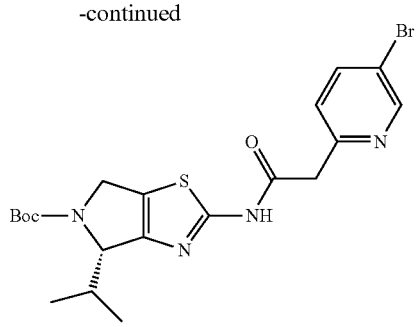

III-3

To a solution of compound IV-1 (105 mg, 0.37 mmol) in DMF (3 mL) was added carboxylic acid V-3 (120 mg, 0.56 mmol), N,N-diisopropylethylamine (130 μL, 0.93 mmol) followed by propylphosphonic anhydride solution (T₃P, 50 wt. % in ethyl acetate, 330 μL, 0.56 mmol). The mixture was allowed to stir at rt for 8 h and diluted with H₂O (20 mL) and ethyl acetate (30 mL). The aqueous phase was extracted with ethyl acetate (2×20 mL). The combined organic layers were washed with brine (30 mL), dried over anhydrous Na₂SO₄, filtered and concentrated under reduced pressure. The residue was purified by column chromatography on silica gel eluting with Hexanes/ethyl acetate (4/6) to afford compound III-3 (150 mg, 84%) as an orange solid. LC-MS $t_R$=1.77 min in 2 min chromatography, MS (ESI) m/z 480, 482 [M+H]⁺. ¹H NMR (CD₃OD, 400 MHz): δ 8.61 (s, 1H), 7.98 (d, J=8.4 Hz, 1H), 7.39 (d, J=8.4 Hz, 1H), 4.73-4.64 (m, 2H), 4.51-4.44 (m, 1H), 3.97 (s, 2H), 2.46-2.40 (m, 1H), 1.51 (s, 9H), 1.14-1.11 (m, 3H), 0.65-0.61 (m, 3H).

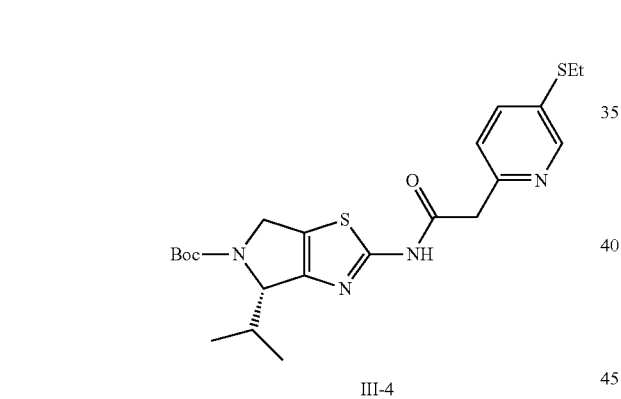

III-3

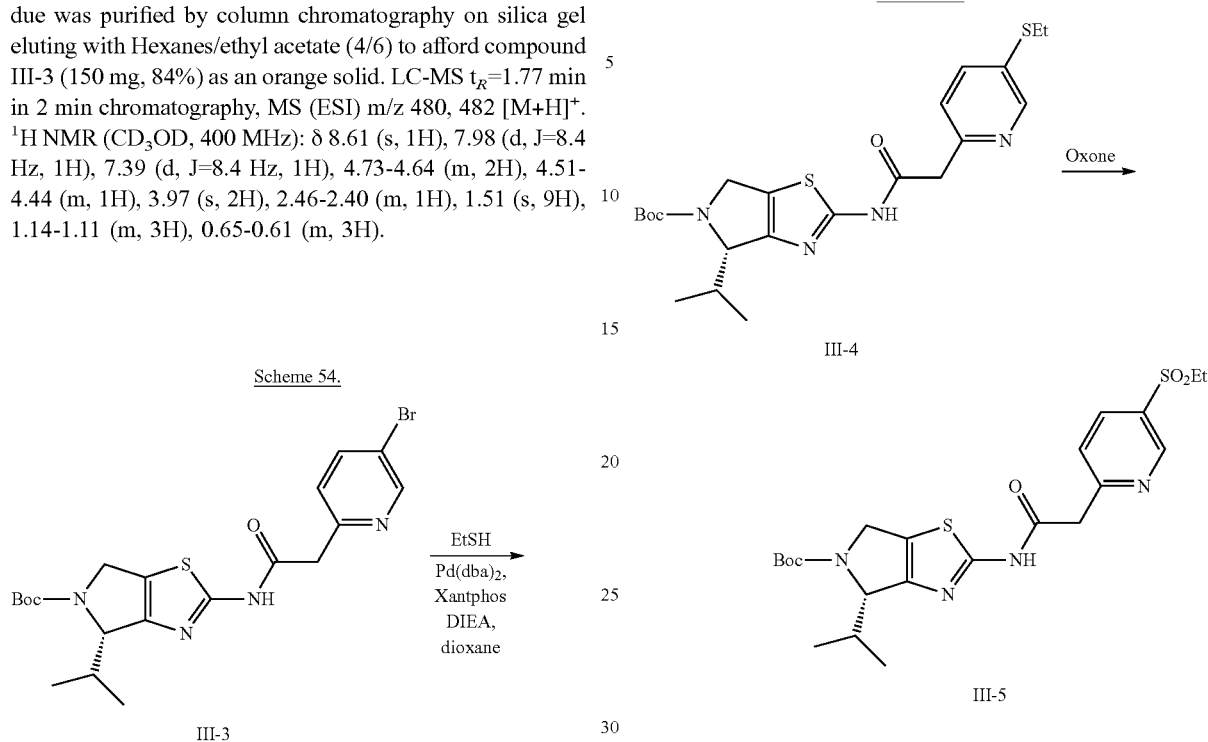

III-4

III-5

To a mixture of bromide III-3 (96 mg, 0.2 mmol), ethanethiol (23 μL, 0.3 mmol), Xantphos (12 mg, 20 μmol) and Hunig's base (60 μL, 0.4 mmol) was added dioxane (2 mL) to give a light yellow solution. Pd(dba)₂ (12 mg, 20 μmol) was added. The mixture was evacuated and filled with nitrogen, repeated three times. The reaction mixture was heated to 110° C. and stirred for 10 h under nitrogen. The mixture was cooled down to rt and diluted with EtOAc (15 mL) and H₂O (15 mL). The aqueous phase was extracted with ethyl acetate (2×15 mL). The combined organic layers were washed with brine (30 mL), dried over anhydrous Na₂SO₄, filtered and concentrated under reduced pressure. The residue was purified by column chromatography on silica gel eluting with Hexanes/ethyl acetate (6/4) to afford compound III-4 (75 mg, 80%) as a pale oil. LC-MS $t_R$=1.74 min in 2 min chromatography, MS (ESI) m/z 480, 463 [M+H]⁺.

To a stirred solution of 111-4 (75 mg, 0.16 mmol) in aq CH₃CN (4 mL, 1:1 by volume) was added Oxone (300 mg, 0.48 mmol). The mixture was stirred at rt for 1.5 h. It was diluted with EtOAc (15 mL) and H₂O (15 mL). The aqueous phase was extracted with ethyl acetate (2×15 mL). The combined organic layers were washed with brine (30 mL), dried over anhydrous Na₂SO₄, filtered and concentrated under reduced pressure. The residue was purified by column chromatography on silica gel eluting with Hexanes/ethyl acetate (3/7) to afford compound III-5 (60 mg, 76%) as a yellow oil. LC-MS $t_R$=1.54 min in 2 min chromatography, MS (ESI) m/z 480, 495 [M+H]⁺. ¹H NMR (CD₃OD, 400 MHz): δ 9.00 (s, 1H), 8.28 (d, J=8.4 Hz, 1H), 7.71 (d, J=8.4 Hz, 1H), 4.73-4.64 (m, 2H), 4.51-4.44 (m, 1H), 4.15 (s, 2H), 3.24 (q, J=7.6 Hz, 2H), 2.45-2.40 (m, 1H), 1.51 (s, 9H), 1.26 (t, J=7.6 Hz, 3H), 1.20-1.13 (m, 3H), 0.65-0.55 (m, 3H).

Scheme 55.

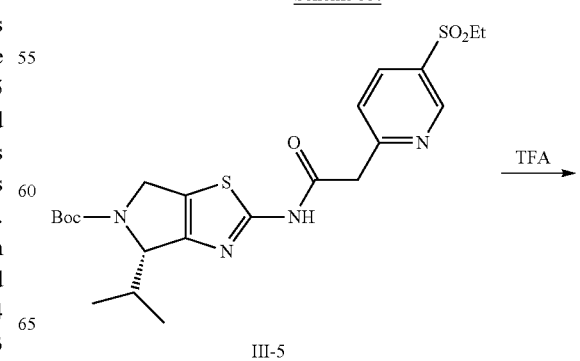

III-5

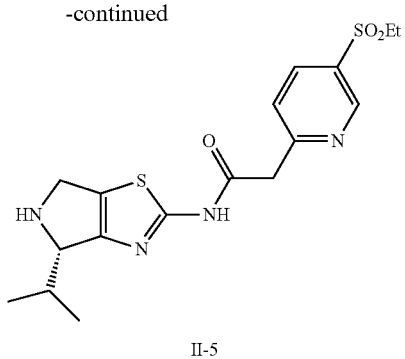

II-5

To a solution of compound III-5 (30 mg, 0.06 mmol) in CH$_2$Cl$_2$ (2.0 mL) was added TFA (0.4 mL). The mixture was stirred at rt for 1 h and neutralized with sat. NaHCO$_3$ solution. The separated aqueous phase was extracted with CH$_2$Cl$_2$ (3×15 mL). The combined organic layers were dried over anhydrous Na$_2$SO$_4$, filtered and concentrated under reduced pressure to afford crude compound II-5 as a brown oil, which was used directly for the next step without further purification. LC-MS t$_R$=0.61 min in 2 min chromatography, MS (ESI) m/z 395 [M+H]$^+$.

Scheme 56.

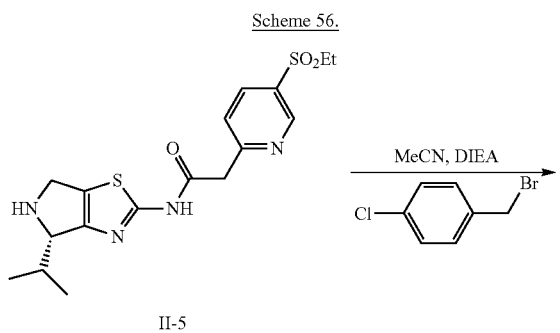

II-5

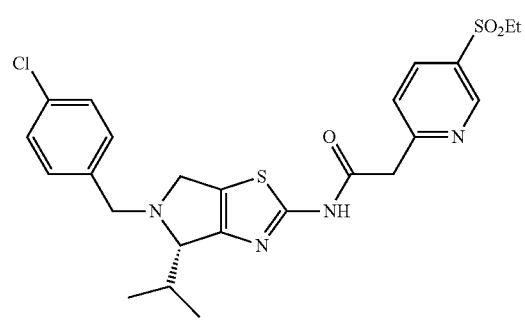

I-C1

To a solution of compound II-5 (10 mg) in CH$_3$CN (0.5 mL) was added 4-chlorobenzyl bromide (1.3 equiv.) and N,N-diisopropylethylamine (2.5 equiv.). The mixture was stirred at rt for 2 h. The solvent was removed in vacuo to give the crude product which was purified on reverse phase prep-HPLC to yield the final compound I-C1. LC-MS t$_R$=0.98 min in 2 min chromatography, MS (ESI) m/z 520.4 [M+H]$^+$. $^1$H NMR (CD$_3$OD, 400 MHz): δ 8.99 (d, J=2.4 Hz, 1H), 8.28 (dd, J$_1$=8.0 Hz, J$_2$=2.4 Hz, 1H), 7.70 (d, J=8.0 Hz, 1H), 7.40 (d, J=8.8 Hz, 2H), 7.33 (d, J=8.8 Hz, 2H), 4.14 (s, 2H), 4.13-3.88 (m, 2H), 3.87-3.85 (m, 1H), 3.79 (d, J=12.8 Hz, 1H), 3.61 (dd, J$_1$=12.8 Hz, J$_2$=3.2 Hz, 1H), 3.28 (q, J=7.6 Hz, 2H), 2.02-1.97 (m, 1H), 1.28 (t, J=7.6 Hz, 3H), 1.07 (d, J=6.8 Hz, 3H), 0.92 (d, J=6.8 Hz, 3H).

The following compounds in Table 3 were prepared from compound II-5 using the appropriate (het)arylalkyl halide (Method A) or (het)aryl aldehyde (Method B).

TABLE 3

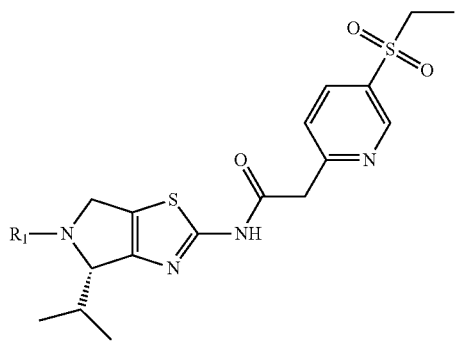

| Compound Number | R$_1$ | PREP method | MS | 1H NMR (400 MHz) |
|---|---|---|---|---|
| I-C2 | F$_2$HCO-C$_6$H$_4$-CH$_2$- | A | m/z 551.4 [M + H]$^+$ t$_R$ = 0.94 min | (CD$_3$OD) δ 8.99 (s, 1H), 8.28 (d, J = 8.0 Hz, 1H), 7.70 (d, J = 8.0 Hz, 1H), 7.46 (d, J = 8.8 Hz, 2H), 7.12 (d, J = 8.8 Hz, 2H), 6.80 (t, J = 74 Hz, 1H), 4.23-4.12 (m, 2H), 4.14 (s, 2H), 3.94-3.85 (m, 2H), 3.75-3.63 (m, 1H), 3.28 (q, J = 7.6 Hz, 2H), 2.03-1.99 (m, 1H), 1.29 (t, J = 7.6 Hz, 3H), 1.08 (d, J = 6.8 Hz, 3H), 0.93 (d, J = 6.8 Hz, 3H). |

TABLE 3-continued

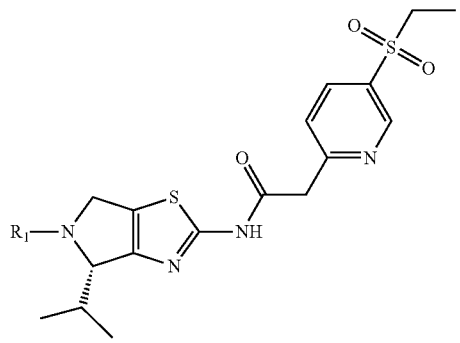

| Compound Number | R₁ | PREP method | MS | 1H NMR (400 MHz) |
|---|---|---|---|---|
| I-C3 | F₃CO-phenyl-Cl-CH(CH₃)- | A | m/z 603.5 [M + H]⁺ $t_R$ = 1.29 min | (CD₃OD) δ 8.98 (s, 1H), 8.30 (d, J = 8.0 Hz, 1H), 7.96 (s, 1H), 7.71 (d, J = 8.0 Hz, 2H), 7.59 (d, J = 8.0 Hz, 1H), 4.93-4.82 (m, 1H), 4.70-4.65 (m, 4H), 4.17 (s, 2H), 3.30 (q, J = 7.6 Hz, 2H), 2.13-2.07 (m, 1H), 1.22 (t, J = 7.6 Hz, 3H), 1.16 (d, J = 6.8 Hz, 3H), 0.92 (d, J = 6.8 Hz, 3H). |
| I-C4 | F₃C-phenyl-CH(CH₃)- | A | m/z 553.5 [M + H]⁺ $t_R$ = 1.12 min | (CD₃OD) δ 8.98 (s, 1H), 8.30 (d, J = 8.4 Hz, 1H), 7.88-7.82 (m, 4H), 7.71 (d, J = 8.4 Hz, 1H), 4.97-4.76 (m, 5H), 4.17 (s, 2H), 3.30 (q, J = 7.6 Hz, 2H), 2.13-2.07 (m, 1H), 1.26 (t, J = 7.6 Hz, 3H), 1.15 (d, J = 6.8 Hz, 3H), 0.91 (d, J = 6.8 Hz, 3H). |
| I-C5 | F₃C-phenyl-Cl-CH(CH₃)- | A | m/z 588.5 [M + H]⁺ $t_R$ = 1.37 min | (CD₃OD) δ 8.99 (s, 1H), 8.29 (d, J = 8.4 Hz, 1H), 7.95-7.91 (m, 2H), 7.76-7.74 (m, 1H), 7.71 (d, J = 8.4 Hz, 1H), 4.97-4.71 (m, 5H), 4.16 (s, 2H), 3.30 (q, J = 7.6 Hz, 2H), 2.20-2.12 (m, 1H), 1.28 (t, J = 7.6 Hz, 3H), 1.19 (d, J = 6.8 Hz, 3H), 0.89 (d, J = 6.8 Hz, 3H). |
| I-C6 | OMe-cyclohexyl-CH(CH₃)- | B | m/z 535.1 (M + H) | (CD3OD) δ 10.69 (s, 1H), 9.15 (d, J = 2.4 Hz, 1H), 8.22 (dd, J = 2.4, 8.4 Hz, 1H), 7.54 (d, J = 8.0 Hz, 1H), 4.28 (dd, J = 4.0, 12.4 Hz, 1H), 4.08 (s, 2H), 3.68 (d, J = 3.2 Hz, 1H), 3.60 (dd, J = 4.0, 12.0 Hz, 1H), 3.25 (s, 3H), 3.20 (q, J = 7.2 Hz, 2H), 2.63-2.61 (m, 2H), 2.09-1.98 (m, 1H), 1.96-1.86 (m, 1H), 1.76-1.64 (m, 3H), 1.63-1.56 (m, 2H), 1.53-1.42 (m, 3H), 1.35 (t, J = 7.2 Hz, 3H), 1.18 (s, 3H), 1.05 (d, J = 6.8 Hz, 3H), 0.86 (d, J = 6.8 Hz, 3H). |

TABLE 3-continued

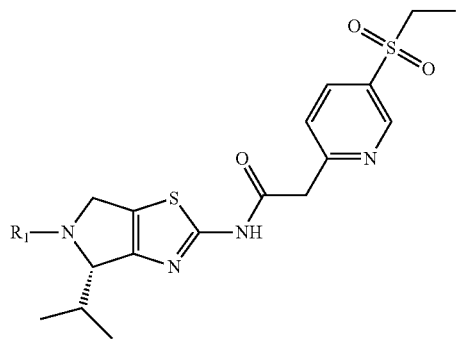

| Compound Number | R₁ | PREP method | MS | 1H NMR (400 MHz) |
|---|---|---|---|---|
| I-C7 | ![methyl pyridinone-phenyl] | A | m/z 592.1 (M + H) | (CD3OD) δ 9.02 (d, J = 2.0 Hz, 1H), 8.35 (dd, J = 2.4, 8.0 Hz, 1H), 7.88 (d, J = 7.6 Hz, 2H), 7.87 (s, 1H), 7.83 (s, 1H), 7.82 (d, J = 8.4 Hz, 1H), 7.76 (d, J = 8.0 Hz, 1H), 6.93 (s, 1H), 6.89 (dd, J = 2.0, 7.2 Hz, 1H), 4.89-4.88 (m, 3H), 4.81-4.73 (m, 4H), 3.70 (s, 3H), 3.33 (q, J = 7.2 Hz, 2H), 2.13-2.08 (m, 1H), 1.28 (t, J = 7.2 Hz, 3H), 1.16 (d, J = 6.8 Hz, 3H), 0.93 (d, J = 6.8 Hz, 3H). |
| I-C8 | F₃C, OMe cyclohexyl | B | m/z 589.2 (M + H) | (CD3OD) δ 9.01 (s, 1H), 8.35 (dd, J = 2.4, 8.0 Hz, 1H), 7.76 (d, J = 8.4 Hz, 1H), 5.01-4.96 (m, 1H), 4.65-4.58 (m, 1H), 4.56-4.54 (m, 1H), 3.55 (m, 2H), 3.39 (s, 3H), 3.32 (q, J = 7.2 Hz, 3H), 3.27-3.25 (m, 2H), 2.34-2.22 (m, 2H), 1.96-1.86 (m, 2H), 1.85-1.72 (m, 3H), 1.66-1.58 (m, 2H), 1.30-1.27 (m, 1H), 1.28 (d, J = 6.4 Hz, 3H), 1.25 (t, J = 7.2 Hz, 3H), 1.05 (d, J = 6.4 Hz, 3H). |
| I-C9 | ![methyl tetrazole-phenyl] | B | m/z 567.1 (M + H) | (CD3OD) δ 8.98 (d, J = 2.0 Hz, 1H), 8.30 (dd, J = 2.4, 6.0 Hz, 1H), 8.25 (d, J = 8.4 Hz, 2H), 7.80 (d, J = 8.4 Hz, 2H), 7.71 (d, J = 8.4 Hz, 1H), 4.85-4.82 (m, 3H), 4.76-4.72 (m, 4H), 4.45 (s, 3H), 3.31 (q, J = 7.6 Hz, 2H), 2.10-2.04 (m, 1H), 1.26 (t, J = 7.6 Hz, 3H), 1.14 (d, J = 6.8 Hz, 3H), 0.90 (d, J = 6.8 Hz, 3H). |
| I-C10 | NC, Cl phenyl | A | m/z 544.1 (M + H) | (CD3OD) δ 8.99 (d, J = 2.0 Hz, 1H), 8.31 (dd, J = 2.4 and 8.4 Hz, 1H), 8.04 (s, 1H), 7.96 (d, J = 8.0 Hz, 1H), 7.82 (d, J = 8.0 Hz, 1H), 7.43 (d, J = 8.4 Hz, 1H), 4.77-4.65 (m, 4H), 3.40-3.28 (m, 5H), 2.25-2.10 (m, 1H), 1.26 (t, J = 7.2 Hz, 3H), 1.18 (d, J = 6.4 Hz, 3H), 0.92 (d, J = 6.8 Hz, 3H). |

TABLE 3-continued

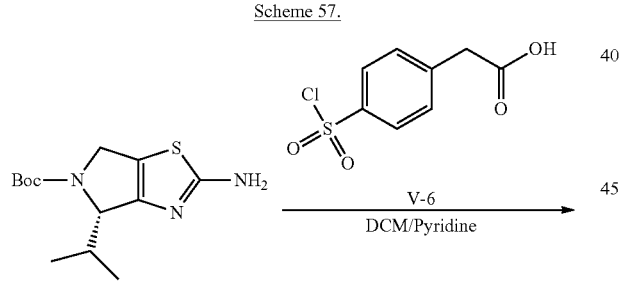

| Compound Number | R₁ | PREP method | MS | 1H NMR (400 MHz) |
|---|---|---|---|---|
| I-C11 | 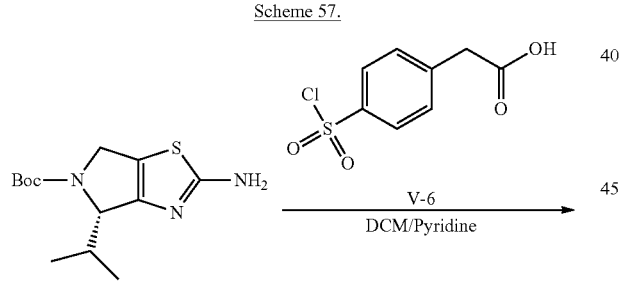 NC-phenyl-CH(CH₃)- | A | m/z 510.1 (M + H) | (CD3OD) δ 8.99 (d, J = 2.0 Hz, 1H), 8.31 (dd, J = 2.4 and 8.4 Hz, 1H), 7.91-7.84 (m, 4H), 7.72 (d, J = 8.4 Hz, 1H), 4.81-4.68 (m, 4H), 3.40-3.28 (m, 5H), 2.15-2.05 (m, 1H), 1.26 (t, J = 7.2 Hz, 3H), 1.15 (d, J = 6.4 Hz, 3H), 0.90 (d, J = 6.8 Hz, 3H). |

(S)-2-(4-(N-(5-(4-chlorobenzyl)-4-isopropyl-5,6-dihydro-4H-pyrrolo[3,4-d]thiazol-2-yl)sulfamoyl)phenyl)acetic acid (Compound I-D1)

Compound I-D1 was prepared by following the synthetic steps shown in Schemes 57-59.

[M+H]⁺. ¹H NMR (CD₃OD, 400 MHz): δ 7.82-7.79 (m, 2H), 7.43-7.40 (m, 2H), 4.74-4.64 (m, 1H), 4.56-4.47 (m, 2H), 3.82 (s, 2H), 2.45-2.40 (m, 1H), 1.51 (s, 9H), 1.14-1.10 (m, 4H), 0.65-0.61 (m, 2H).

Scheme 57.

Scheme 58.

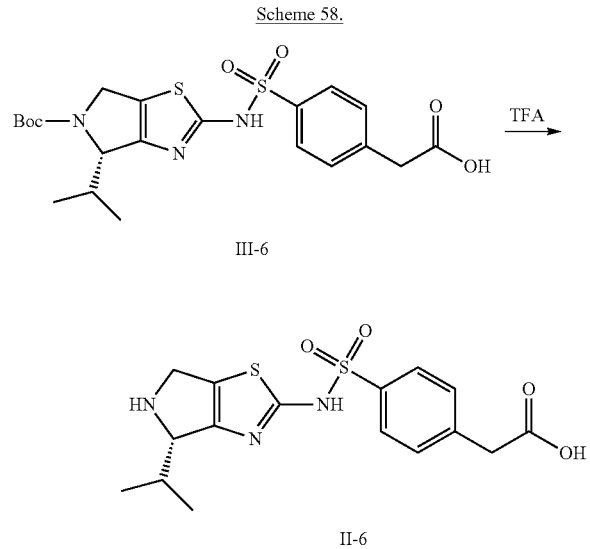

To a solution of compound IV-1 (25 mg, 0.1 mL) in CH₂Cl₂ (0.5 mL) was added pyridine (0.25 mL) and sulfonyl chloride V-6 (31 mg, 0.13 mmol, 1.3 equiv.). The mixture was stirred at rt for 8 h. The solvent was removed in vacuo to give the crude product which was purified on reverse phase prep-HPLC to yield the final compound III-6. LC-MS $t_R$=1.71 min in 2 min chromatography, MS (ESI) m/z 482

To a solution of compound III-6 (15 mg, 0.03 mmol) in CH₂Cl₂ (2.0 mL) was added TFA (0.4 mL). The mixture was stirred at rt for 1 h. The solvent was removed, and the residual TFA was removed by azeotrope with toluene to yield the TFA salt of 11-6, which was used directly for the next step without further purification. LC-MS $t_R$=0.57 min in 2 min chromatography, MS (ESI) m/z 381 [M+H]⁺.

Scheme 59.

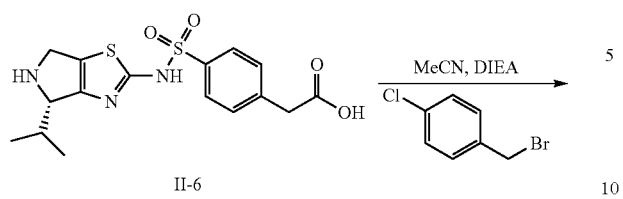

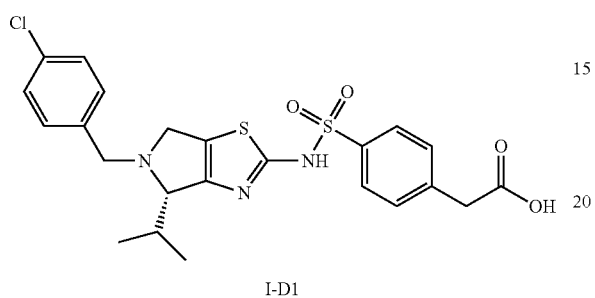

To a solution of compound II-6 (10 mg) in CH₃CN (0.5 mL) was added 4-chlorobenzyl bromide (1.3 equiv.) and N,N-diisopropylethylamine (2.5 equiv.). The mixture was stirred at rt for 2 h. The solvent was removed in vacuo to give the crude product which was purified on reverse phase prep-HPLC to yield the final compound I-D1. LC-MS $t_R$=0.96 min in 2 min chromatography, MS (ESI) m/z 507 [M+H]⁺. ¹H NMR (CD₃OD, 400 MHz): δ 7.79 (d, J=8.0 Hz, 2H), 7.61 (d, J=8.0 Hz, 2H), 7.53 (d, J=8.0 Hz, 2H), 7.40 (d, J=8.0 Hz, 2H), 4.83-4.64 (m, 5H), 3.82 (s, 2H), 2.03-1.98 (m, 1H), 1.35 (d, J=6.8 Hz, 3H), 0.87 (d, J=6.8 Hz, 3H).

(S)-2-(4-(N-(5-(4-cyano-3-fluorobenzyl)-4-isopropyl-5,6-dihydro-4H-pyrrolo[3,4-d]thiazol-2-yl)sulfamoyl)phenyl)acetic acid (Compound I-D2)

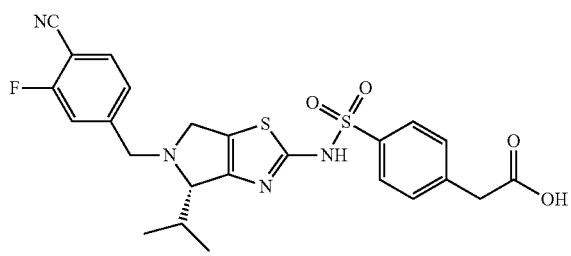

Compound I-D2 was prepared following analogous methods used in Scheme 59 using 4-(bromomethyl)-2-fluorobenzonitrile instead of 1-(bromomethyl)-4-chlorobenzene. LC-MS $t_R$=1.06 min in 2 min chromatography, MS (ESI) m/z 515 [M+H]⁺. ¹H NMR (CD₃OD, 400 MHz): δ 7.93 (t, J=8.0 Hz, 1H), 7.79 (d, J=8.4 Hz, 2H), 7.71 (d, J=9.6 Hz, 1H), 7.63 (d, J=8.0 Hz, 1H), 7.40 (d, J=8.4 Hz, 2H), 4.75-4.59 (m, 5H), 3.83 (s, 2H), 2.19-2.13 (m, 1H), 1.17 (d, J=6.8 Hz, 3H), 0.89 (d, J=6.8 Hz, 3H).

(S)—N-(5-(4-chlorobenzyl)-4-isopropyl-5,6-dihydro-4H-pyrrolo[3,4-d]thiazol-2-yl)-3-(trifluoromethyl)benzenesulfonamide (Compound I-D3)

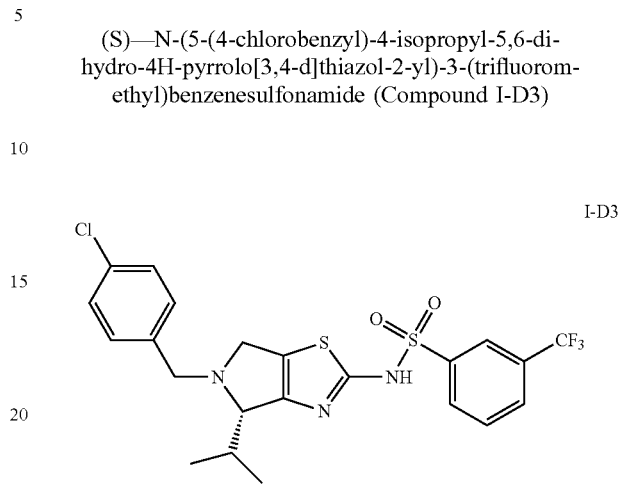

Compound I-D3 was prepared following analogous methods used in Scheme 59 using (S)—N-(4-isopropyl-5,6-dihydro-4H-pyrrolo[3,4-d]thiazol-2-yl)-3-(trifluoromethyl)benzenesulfonamide. LC-MS $t_R$=1.57 min in 2 min chromatography, MS (ESI) m/z 517 [M+H]⁺. ¹H NMR (CD₃OD, 400 MHz): δ 8.18 (d, J=6.4 Hz, 1H), 8.16 (s, 1H), 7.94 (d, J=8.0 Hz, 1H), 7.77 (7, J=8.0 Hz, 1H), 7.53 (d, J=8.0 Hz, 1H), 7.46 (d, J=8.0 Hz, 2H), 4.57-4.54 (m, 1H), 4.53-4.43 (m, 3H), 4.32-4.30 (m, 1H), 2.04-2.00 (m, 1H), 0.94 (d, J=6.8 Hz, 3H), 0.84 (d, J=6.8 Hz, 3H).

(S)—N-(5-(4-chlorobenzyl)-4-isopropyl-5,6-dihydro-4H-pyrrolo[3,4-d]thiazol-2-yl)-2-(4-cyanophenyl)acetamide (Compound I-E1)

Compound I-E1 was prepared by following the synthetic steps shown in Scheme 60.

Scheme 60.

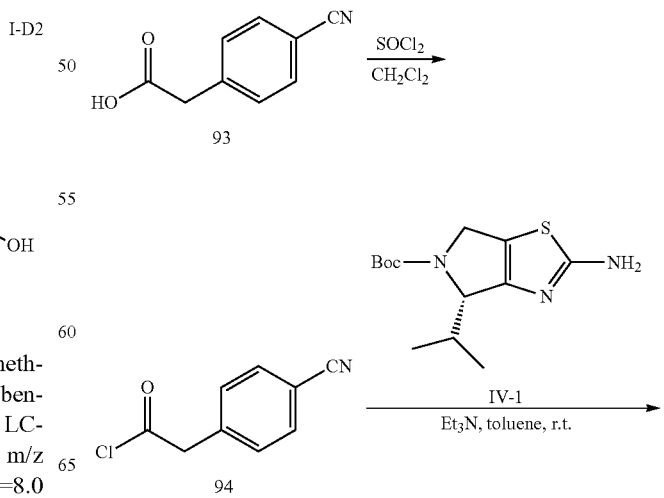

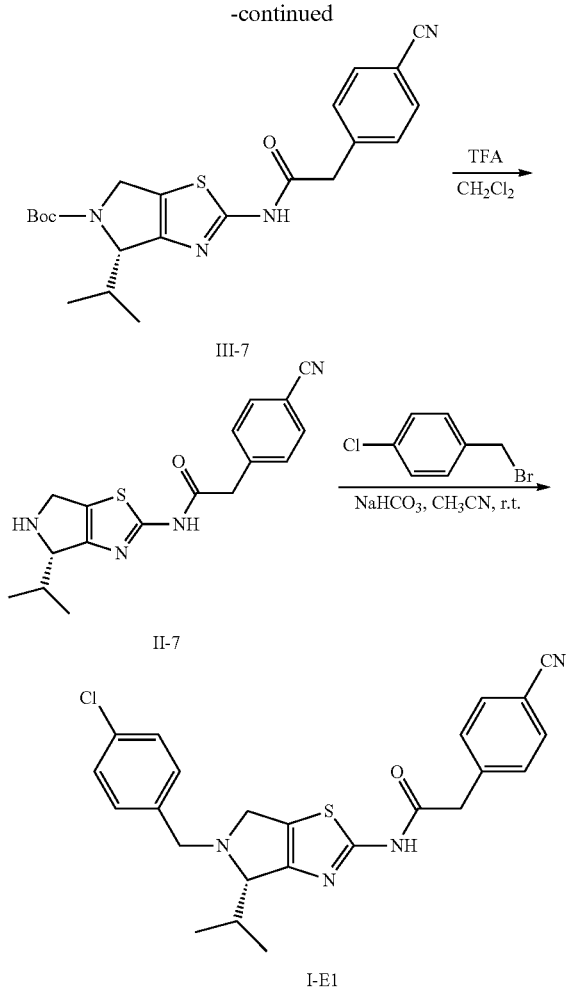

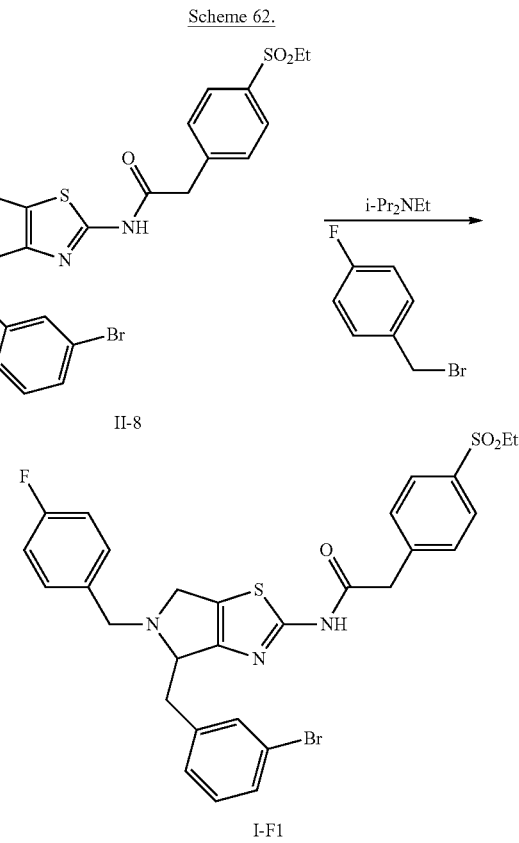

To a solution of compound 93 (100 mg, 0.62 mmol) in anhydrous CH$_2$Cl$_2$ (1 mL) was added SOCl$_2$ (0.2 mL) at rt under N$_2$. The mixture was stirred at 50° C. for 2 h. The mixture was concentrated under reduced pressure to afford crude compound 94 (120 mg, 100%) as a white solid, which was used for next step without further purification.

A mixture of compound 94 (110 mg, 0.62 mmol), compound IV-1 (100 mg, 0.35 mmol) and Et$_3$N (106 mg, 1.05 mmol) in anhydrous toluene (1.5 mL) was stirred at rt overnight. The mixture was added with ethyl acetate (5 mL) and washed with water (5 mL×3). The organic layer was dried over anhydrous Na$_2$SO$_4$, filtered and concentrated under reduced pressure. The residue was purified by preparative TLC with petroleum ether/ethyl acetate 3/1 to afford compound III-7 (120 mg, 81%) as a yellow solid. LC-MS $t_R$=0.924 min in AB 5-95_1.5 min chromatography (Welch Xtimate C18, 2.1*30 mm, 3 um), MS (ESI) m/z 427.0 [M+H]$^+$.

To a solution of compound III-7 (33 mg, 0.077 mmol) in anhydrous CH$_2$Cl$_2$ (0.8 mL) was added TFA (0.2 mL). The mixture was stirred at rt for 3 h. The mixture was concentrated under reduced pressure to give crude compound II-7 (35 mg, 100%) as a yellow oil, which was used for next step without further purification. LC-MS $t_R$=0.598 min in AB 5-95_1.5 min chromatography (Welch Xtimate C18, 2.1*30 mm, 3 um), MS (ESI) m/z 326.9 [M+H]$^+$.

A mixture of compound II-7 (35 mg, 0.077 mmol, crude TFA salt), 4-chlorobenzyl bromide (19 mg, 0.12 mmol) and NaHCO$_3$ (19 mg, 0.23 mmol) in CH$_3$CN (0.5 mL) was stirred at rt overnight. The mixture was filtered and the filter cake was washed with ethyl acetate (5 mL×2). The combined organic layers and the filtrate were washed with water (10 mL) and brine (10 mL), dried over anhydrous Na$_2$SO$_4$, filtered and concentrated under reduced pressure. The residue was purified by preparative TLC with petroleum ether/ethyl acetate (2/1) to afford I-E1 (20.30 mg, 57%) as a pink solid. LC-MS $t_R$=0.754 min in AB 5-95_1.5 min chromatography (Welch Xtimate C18 2.1*30 mm, 3 um), MS (ESI) m/z 451.0 [M+H]$^+$. $^1$H NMR (CDCl$_3$ 400 MHz): δ 9.49 (brs, 1H), 7.66 (d, J=8.0 Hz, 2H), 7.44 (d, J=7.2 Hz, 2H), 7.34-7.28 (m, 4H), 4.14-4.07 (m, 2H), 3.85-3.79 (m, 3H), 3.76 (d, J=10.4 Hz, 1H), 3.58 (dd, J=2.0 Hz, 12.8 Hz, 1H), 2.01-1.95 (m, 1H), 1.01 (d, J=6.8 Hz, 3H), 0.91 (d, J=6.8 Hz, 3H). SFC $t_R$=1.881 min in 3 min chromatography (Column: OD-H; Method Name: OD-H_3 UM_5_5_40_4 ML_3 MIN.M, ee=97.10%).

N-(4-(3-bromobenzyl)-5-(4-fluorobenzyl)-5,6-dihydro-4H-pyrrolo[3,4-d]thiazol-2-yl)-2-(4-(ethylsulfonyl)phenyl)acetamide (Compound I-F1)

Compound I-F1 was prepared by following the synthetic step shown in Scheme 62.

Scheme 62.

Compound II-8 was dissolved in MeOH (1 mL) and treated with i-Pr$_2$NEt (18 μL, 0.1 mmol) and 4-fluorobenzyl bromide (5 μL, 0.04 mmol). The mixture was stirred overnight at rt, concentrated and the residue purified by prep HPLC to afford product I-F1 as its TFA salt (5 mg, 36%). LC-MS $t_R$=0.75 min in 1.5 min chromatography, MS (ESI) m/z 630, 628 [M+H]$^+$. $^1$H NMR (CD$_3$OD, 400 MHz): (57.88

(d, J=7.2 Hz, 2H), 7.60 (d, J=7.2 Hz, 2H), 7.53-7.45 (m, 4H), 7.34-7.18 (m, 4H), 5.11-5.40 (m, 1H), 4.62 (s, 2H), 4.58-4.52 (m, 1H), 4.45-4.39 (m, 1H), 3.91 (s, 2H), 3.35-3.10 (m, 4H), 1.21 (t, J=7.2 Hz, 3H).

(S)—N-(5-(4-chlorobenzyl)-4-isopropyl-5,6-dihydro-4H-pyrrolo[3,4-d]thiazol-2-yl)-2-(4-(N-cyclopropylsulfamoyl)phenyl)acetamide (Compound I-G1)

Compound I-G1 was prepared by following the synthetic steps shown in Scheme 61.

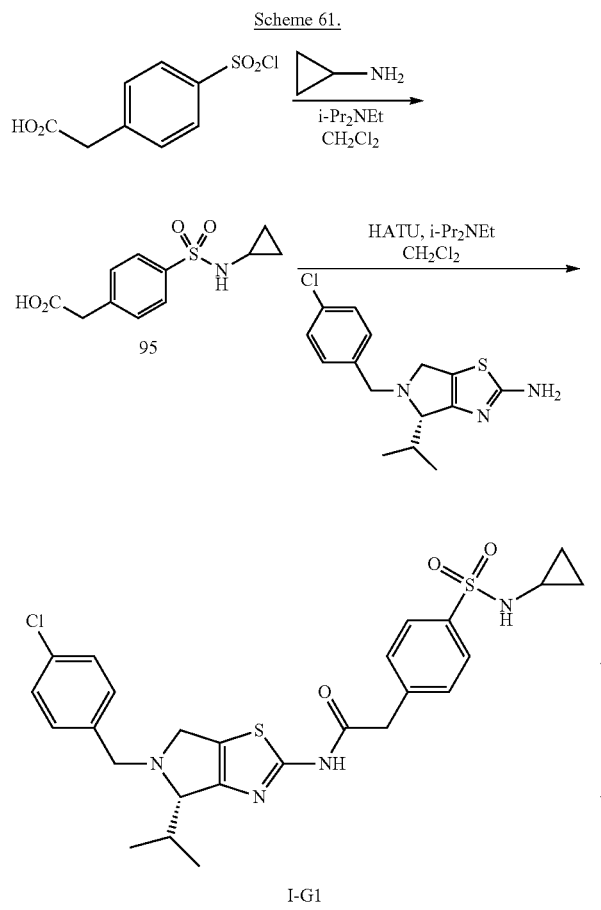

To a stirred solution of 2-(4-(chlorosulfonyl)phenyl)acetic acid (152 mg, 0.65 mmol) and i-Pr$_2$NEt (0.26 mL, 1.43 mmol) in CH$_2$Cl$_2$ (5 mL) was added cyclopropylamine (0.049 mL, 0.71 mmol). The mixture was stirred overnight at rt, diluted with EtOAc (80 mL), washed with 5% aq HCl (2×10 mL) and brine (10 mL), and dried over Na$_2$SO$_4$. Removal of the solvent left 95 (113 mg, 68%) as a white solid. LC-MS ESI m/z=256.

The reaction was performed under standard amide coupling reaction condition by using HATU and i-Pr$_2$NEt in CH$_2$Cl$_2$ at rt. The crude product was purified by prep HPLC to afford (S)—N-(5-(4-chlorobenzyl)-4-isopropyl-5,6-dihydro-4H-pyrrolo[3,4-d]thiazol-2-yl)-2-(4-(N-cyclopropylsulfamoyl)phenyl)acetamide (I-G1) as its TFA salt. LC-MS t$_R$=0.7 min in 1.5 min chromatography, MS (ESI) m/z 545 [M+H]$^+$. $^1$H NMR (CD$_3$OD, 400 MHz): δ 0.47-0.58 (m, 4H), 0.88 (d, 3H), 1.15 (d, 3H), 2.00-2.19 (m, 2H), 3.91 (s, 2H), 4.59-4.69 (m, 4H), 4.73-4.82 (m, 1H), 7.50-7.58 (m, 4H), 7.61 (d, 2H), 7.84 (d, 2H).

(S)—N-(5-(4-chlorobenzyl)-4-isopropyl-5,6-dihydro-4H-pyrrolo[3,4-d]thiazol-2-yl)-2-(4-(N-methylsulfamoyl)phenyl)acetamide (Compound I-G2)

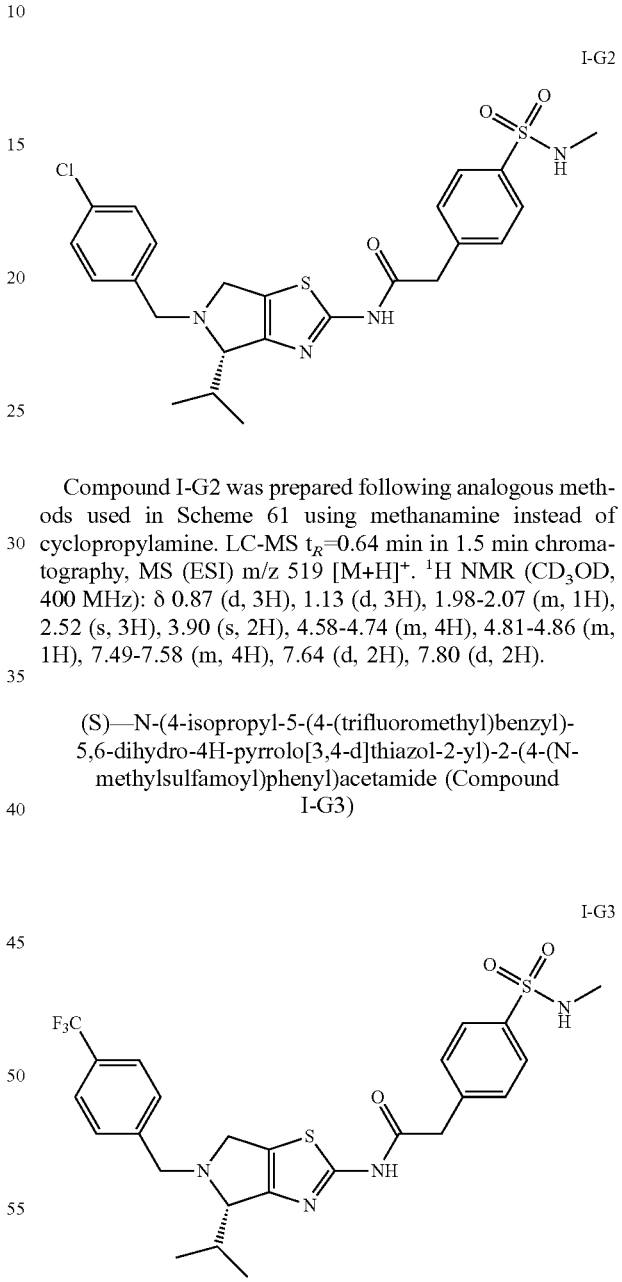

Compound I-G2 was prepared following analogous methods used in Scheme 61 using methanamine instead of cyclopropylamine. LC-MS t$_R$=0.64 min in 1.5 min chromatography, MS (ESI) m/z 519 [M+H]$^+$. $^1$H NMR (CD$_3$OD, 400 MHz): δ 0.87 (d, 3H), 1.13 (d, 3H), 1.98-2.07 (m, 1H), 2.52 (s, 3H), 3.90 (s, 2H), 4.58-4.74 (m, 4H), 4.81-4.86 (m, 1H), 7.49-7.58 (m, 4H), 7.64 (d, 2H), 7.80 (d, 2H).

(S)—N-(4-isopropyl-5-(4-(trifluoromethyl)benzyl)-5,6-dihydro-4H-pyrrolo[3,4-d]thiazol-2-yl)-2-(4-(N-methylsulfamoyl)phenyl)acetamide (Compound I-G3)

Compound I-G3 was prepared following analogous methods used in Scheme 61 using (S)-4-isopropyl-5-(4-(trifluoromethyl)benzyl)-5,6-dihydro-4H-pyrrolo[3,4-d]thiazol-2-amine. LC-MS t$_R$=0.71 min in 1.5 min chromatography, MS (ESI) m/z 553 [M+H]$^+$. $^1$H NMR (CD$_3$OD, 400 MHz): δ 0.86 (d, 3H), 1.12 (d, 3H), 2.01-2.15 (m, 1H), 2.52 (s, 3H), 3.91 (s, 2H), 4.66-4.92 (m, 3H), 4.90 (s, 2H), 7.54 (d, 2H), 7.77-7.86 (m, 4H), 7.93 (d, 2H).

N—((S)-4-((S)-sec-butyl)-5-(4-chlorobenzyl)-5,6-dihydro-4H-pyrrolo[3,4-d]thiazol-2-yl)-2-(4-(methylsulfonyl)phenyl)acetamide (I-H1)

Compound I-H1 was prepared by following the synthetic step shown in Scheme 63.

Scheme 63.

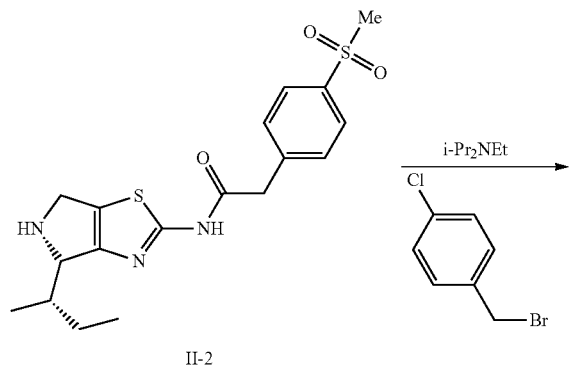

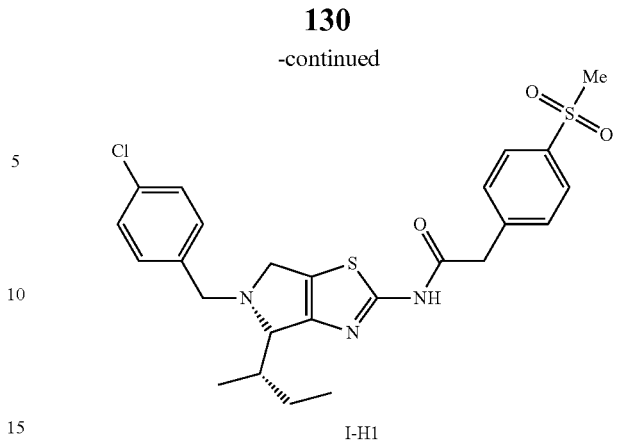

Compound II-2 was dissolved in MeOH (0.5 mL) and treated with i-Pr$_2$NEt (18 μL, 0.1 mmol) and 4-chlorobenzyl bromide (8 μL, 0.06 mmol). The mixture was stirred at rt for 2 h, concentrated and the residue purified by prep HPLC to afford product I-H1 as its TFA salt (6 mg, 36%). LC-MS $t_R$=1.06 min in 2 min chromatography, MS (ESI) m/z 518.3 [M+H]$^+$. $^1$H NMR (CD$_3$OD, 400 MHz): δ 7.93 (d, J=8.0 Hz, 2H), 7.61 (d, J=8.0 Hz, 2H), 7.63 (d, J=10 Hz, 2H), 7.37 (d, J=8.0 Hz, 2H), 7.31 (d, J=8.0 Hz, 2H), 4.11-4.07 (m, 2H), 3.91-3.89 (m, 1H), 3.89 (s, 2H), 3.76 (d, J=13.6 Hz, 1H), 3.59 (d, J=13.6 Hz, 1H), 3.11 (s, 3H), 1.69-1.56 (m, 3H), 0.94 (t, J=7.2 Hz, 3H), 0.84 (d, J=6.8 Hz, 3H).

The following compounds in Table 4 were prepared from compound II-2 using the appropriate (het)arylalkyl halide by the method shown in Scheme 63.

TABLE 4

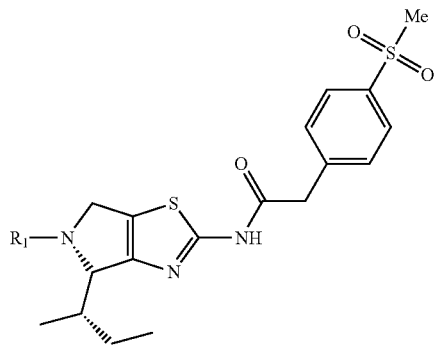

| Compound Number | R$_1$ | MS | 1H NMR (400 MHz) |
|---|---|---|---|
| I-H2 | 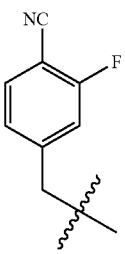 [SMILES: *Cc1ccc(C#N)c(F)c1] | m/z 527.4 [M + H]$^+$ $t_R$ = 1.21 min | (CD$_3$OD) δ 7.93 (d, J = 8.4 Hz, 2H), 7.75 (t, J = 7.2 Hz, 1H), 7.61 (d, J = 8.4 Hz, 2H), 7.58-7.51 (m, 2H), 4.18-3.98 (m, 4H), 3.90 (s, 2H), 3.66 (d, J = 13.6 Hz, 1H), 3.11 (s, 3H), 1.70-1.56 (m, 3H), 0.95 (t, J = 7.2 Hz, 3H), 0.82 (d, J = 6.8 Hz, 3H). |

TABLE 4-continued

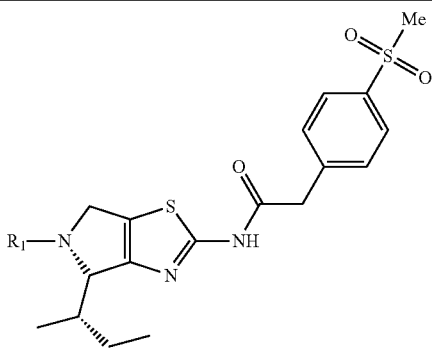

| Compound Number | R₁ | MS | 1H NMR (400 MHz) |
|---|---|---|---|
| I-H3 | ![Cl-pyridinyl-CH2] (5-chloropyridin-2-yl)methyl | m/z 519.3 [M + H]⁺ $t_R$ = 0.97 min | (CD₃OD) δ 8.47 (s, 1H), 7.93 (d, J = 8.0 Hz, 2H), 7.86 (d, J = 8.4 Hz, 1H), 7.61 (d, J = 8.0 Hz, 3H), 4.20 (d, J = 15.2 Hz, 2H), 4.00-3.96 (m, 2H), 3.90 (s, 2H), 3.71 (d, J = 12.4 Hz, 1H), 3.11 (s, 3H), 1.65-1.54 (m, 3H), 0.94 (t, J = 6.8 Hz, 3H), 0.83 (d, J = 6.8 Hz, 3H). |

(S)—N-(5-((5-cyanopyridin-2-yl)methyl)-4-isopropyl-4-methyl-5,6-dihydro-4H-pyrrolo[3,4-d]thiazol-2-yl)-2-(4-(ethylsulfonyl)phenyl)acetamide (I-I1)

Compound I-I1 was prepared by following the synthetic step shown in Scheme 64.

To a solution of crude compound II-3 (15 mg, 0.037 mmol) in CH₃CN (1 mL) was added 6-(bromomethyl) nicotinonitrile (10 mg, 0.055 mmol)) and K₂CO₃ (15 mg, 0.11 mmol). The mixture was stirred at rt for 15 h. The suspension was filtered through celite and the filtrate was evaporated to give the crude product. Purification on the reverse phase prep-HPLC afforded compound I-I1. LC-MS $t_R$=1.086 min in 2 min chromatography, MS (ESI) m/z 524.53 [M+H]⁺. ¹H NMR (CD₃OD) δ 9.04 (s, 1H), 8.34 (dd, J=8.0 Hz, 2.4 Hz, 1H), 7.89 (d, J=8.0 Hz, 2H), 7.79 (d, J=8.0 Hz, 1H), 7.62 (d, J=8.0 Hz, 2H), 4.92 (s, 2H), 4.76 (d, J=12.8 Hz, 1H), 4.67 (d, J=12.8 Hz, 1H), 3.94 (s, 2H), 3.20 (q, J=7.2 Hz, 2H), 2.49-2.45 (m, 1H), 1.31 (d, J=6.8 Hz, 3H), 1.28 (s, 3H), 1.21 (t, J=7.2 Hz, 3H), 1.15 (d, J=6.8 Hz, 3H).

Scheme 64.

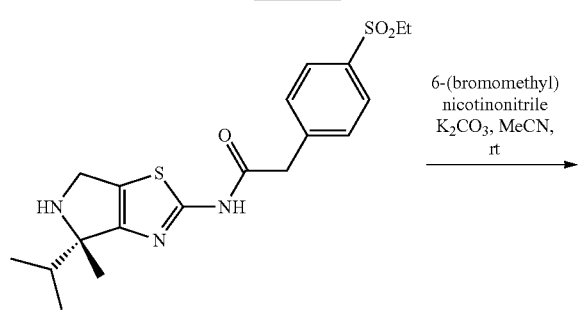

(S)-5-(4-chlorobenzyl)-N-(4-(ethylsulfonyl)benzyl)-4-isopropyl-5,6-dihydro-4H-pyrrolo[3,4-d]thiazole-2-carboxamide (I-J1)

Compound I-J1 was prepared by following the synthetic step shown in Scheme 65.

Scheme 65.

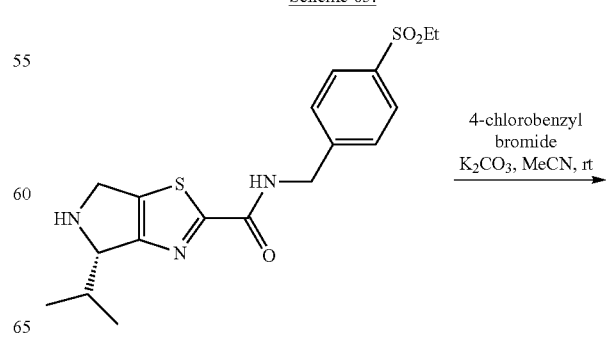

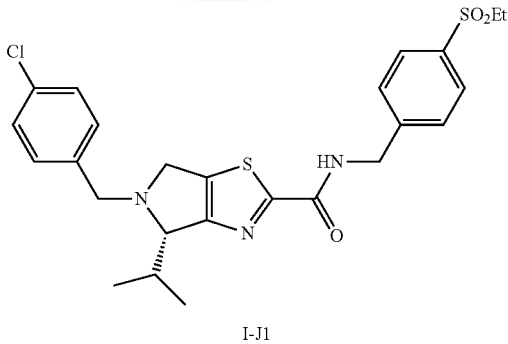

I-J1

To a solution of VI-2 (crude 20 mg, 0.05 mmol) in CH₃CN (2 mL) was added 4-chlorobenzyl bromide (21 mg, 0.10 mmol) and K₂CO₃ (14 mg, 0.10 mmol). The mixture was stirred at rt overnight. The mixture was concentrated under reduced pressure. Water (10 mL) and ethyl acetate (10 mL) were added to the mixture. After partition, the aqueous layer was extracted with ethyl acetate (3×10 mL). The combined organic layers were washed with brine (15 mL), dried over anhydrous sodium sulfate, filtered and concentrated under reduced pressure. Purification on the reverse phase prep-HPLC afforded compound I-J2. LC-MS $t_R$=1.315 min in 2 min chromatography, MS (ESI) m/z 518.38 [M]⁺. ¹H NMR (CD₃OD): δ 7.88 (d, J=8.4 Hz, 2H), 7.62 (d, J=8.4 Hz, 2H), 7.58 (d, J=8.4 Hz, 2H), 7.50 (d, J=8.4 Hz, 2H), 4.67 (s, 2H), 4.69-4.57 (m, 5H), 3.19 (q, J=7.2 Hz, 2H), 2.20-2.13 (m, 1H), 1.20 (t, J=7.2 Hz, 3H), 1.18 (d, J=6.4 Hz, 3H), 0.92 (d, J=6.4 Hz, 3H).

The following compounds in Table 5 were prepared from compound VI-2 using the appropriate (het)arylalkyl halide (Method A) or (het)aryl aldehyde (Method B or C).

TABLE 5

| Compound Number | R₁ | PREP method | LC/MS | 1H NMR (400 MHz) |
|---|---|---|---|---|
| I-J2 | (4-cyanobenzyl) | A | m/z 509.4 [M + H]⁺ $t_R$ = 1.34 min | (CD₃OD) δ 7.88 (d, J = 8.4 Hz, 2H), 8.0 (d, J = 8.4 Hz, 2H), 7.74 (d, J = 8.4 Hz, 2H), 7.61 (d, J = 8.4 Hz, 2H), 4.71-4.38 (m, 5H), 4.67 (d, J = 1.6 Hz, 2H), 3.19 (q, J = 7.2 Hz, 2H), 2.20-2.14 (1H, m), 1.20 (t, J = 7.2 Hz, 3H), 1.18 (d, J = 6.4 Hz, 3H), 0.93 (d, J = 6.4 Hz, 3H). |
| I-J3 | (4-(1-methyltetrazol-5-yl)benzyl) | C | m/z 566.0 [M + H]⁺ | (CD₃OD) δ 8.27 (d, J = 8.4 Hz, 2H), 7.90 (d, J = 8.4 Hz, 2H), 7.85 (d, J = 8.4 Hz, 2H), 7.64 (d, J = 8.4 Hz, 2H), 5.06-5.00 (m, 1H), 4.88-4.68 (m, 6H), 4.47 (s, 3H), 3.21 (q, J = 7.2 Hz, 2H), 2.20-2.10 (m, 1H), 1.22 (t, J = 7.2 Hz, 3H), 1.19 (d, J = 6.4 Hz, 3H), 0.95 (d, J = 6.4 Hz, 3H). |

TABLE 5-continued

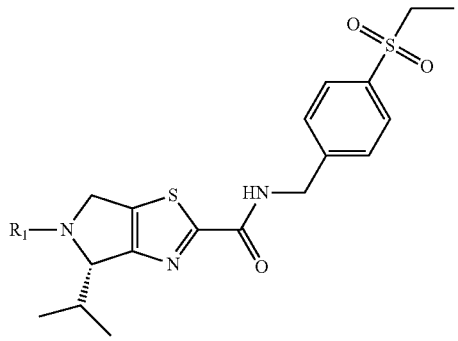

| Compound Number | R₁ | PREP method | LC/MS | 1H NMR (400 MHz) |
|---|---|---|---|---|
| I-J4 | F₃C-pyridyl-CH₂- (structure) | A | m/z 553.1 [M + H]⁺ | (CD₃OD) δ 9.46 (t, J = 5.2 Hz, 1H), 9.04 (s, 1H), 8.29 (dd, J = 2.4, 8.4 Hz, 1H), 7.90 (d, J = 6.4 Hz, 2H), 7.79 (d, J = 8.4 Hz, 1H), 7.64 (d, J = 8.4 Hz, 2H), 5.11-5.06 (m, 1H), 5.02-4.98 (m, 2H), 4.85-4.77 (m, 2H), 4.70 (s, 2H), 3.22 (q, J = 7.6 Hz, 2H), 2.53-2.48 (m, 1H), 1.27 (d, J = 6.8 Hz, 3H), 1.22 (t, J = 7.2 Hz, 3H), 1.02 (d, J = 6.8 Hz, 3H). |
| I-J5 | Boc-N-morpholinyl-CH₂- (structure) | C | m/z 593.1 [M + H]⁺ | (CD₃OD) δ 7.88 (d, J = 8.4 Hz, 2H), 7.62 (d, J = 8.4 Hz, 2H), 4.72-4.63 (m, 3H), 3.97-3.86 (m, 5H), 3.55-3.45 (m, 2H), 3.18 (q, J = 7.2 Hz, 2H), 3.04-2.95 (m, 4H), 2.03-1.95 (m, 1H), 1.47 (s, 9H), 1.21 (t, J = 7.6 Hz, 3H), 1.16 (d, J = 6.8 Hz, 3H), 0.87 (d, J = 6.8 Hz, 3H). |
| I-J6 | OCHF₂-phenyl-CH₂- (structure) | A | m/z 550.5 [M + H]⁺ | (CDCl₃) δ 7.88 (d, J = 8.4 Hz, 2H), 7.65 (d, J = 8.4 Hz, 2H), 7.62 (d, J = 8.4 Hz, 2H), 7.28 (d, J = 8.4 Hz, 2H), 6.92 (t, J = 73 Hz, 1H, CHF₂), 4.81-4.68 (m, 5H), 4.64 (s, 2H), 3.19 (q, J = 7.2 Hz, 2H), 2.21-2.13 (m, 1H), 1.20 (t, J = 7.2 Hz, 3H), 1.17 (d, J = 7.2 Hz, 3H), 0.92 (d, J = 7.2 Hz, 3H). |

(S)-5-((5-chloropyridin-2-yl)methyl)-4-isopropyl-N-(4-(methylsulfonyl)benzyl)-5,6-dihydro-4H-pyrrolo[3,4-d]thiazole-2-carboxamide (I-K1)

Compound I-K1 was prepared by following the synthetic step shown in Scheme 66.

Scheme 66.

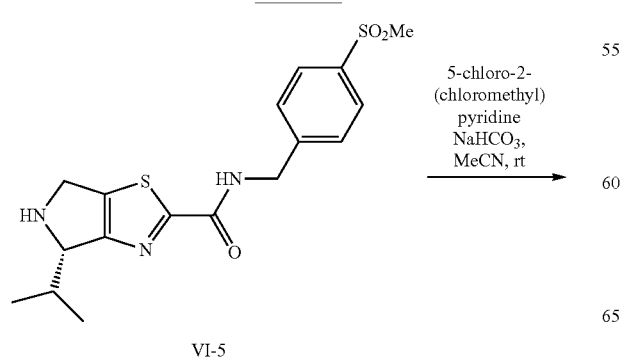

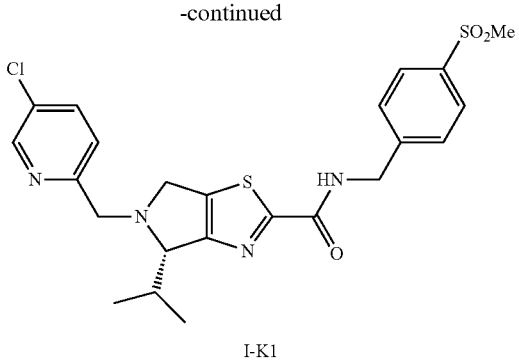

To a solution of VI-5 (which is deprotected VI-3) (crude 36 mg, 0.076 mmol) in CH₃CN (4 mL) was added 5-chloro-2-(chloromethyl)pyridine (15 mg, 0.091 mmol) and NaHCO₃ (32 mg, 0.38 mmol). The mixture was stirred at rt overnight. The mixture was concentrated under reduced pressure. Water (10 mL) and ethyl acetate (10 mL) were added to the mixture. After partition, the aqueous layer was extracted with ethyl acetate (3×10 mL). The combined organic layers were washed with brine (15 mL), dried over anhydrous sodium sulfate, filtered and concentrated under reduced pressure. The residue was purified by preparative TLC with petroleum ether/ethyl acetate 1/1 to afford 1-K1 (3.90 mg, 10%) as a white solid. LC-MS $t_R$=0.744 min in 5-95AB_1.5 min chromatography (Welch MK RP-18e 25-2 mm), MS (ESI) m/z 504.9 [M+H]$^+$. $^1$H NMR (CD$_3$OD): δ 8.48 (d, J=2.4 Hz, 1H), 7.92 (d, J=8.4 Hz, 2H), 7.74 (dd, J=2.4, 8.4 Hz, 1H), 7.63 (t, J=8.4 Hz, 3H), 4.67 (s, 2H), 4.33 (dd, J=4.0, 10.8 Hz, 1H), 4.24 (d, J=15.2 Hz, 1H), 4.07-4.01 (m, 2H), 3.84 (dd, J=2.4, 14.8 Hz, 1H), 3.10 (s, 3H), 2.08-2.03 (m, 1H), 1.13 (d, J=6.8 Hz, 3H), 0.92 (d, J=6.8 Hz, 3H). Isomer SFC $t_R$=4.209 min in 8 min chromatography (Column: AS-H; Method Name: AS-H_S_5_5_40_3 ML_8 MIN_15 C, ee=100%).

The following compounds in Table 6 were prepared from compound VI-5 using the appropriate (het)arylalkyl halide by the method shown in Scheme 66.

TABLE 6

| Compound Number | R$_1$ | LC/MS | 1H NMR (400 MHz) |
|---|---|---|---|
| I-K2 | 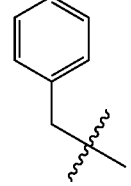 | m/z 536.0 [M + H]$^+$ | (CDCl$_3$) δ 7.94 (d, J = 6.8 Hz, 2H), 7.64 (t, J = 6.0 Hz, 1H), 7.59 (d, J = 8.4 Hz, 2H), 7.42 (d, J = 8.4 Hz, 2H), 7.12 (d, J = 8.8 Hz, 2H), 6.53 (t, J = 73.6 Hz, 1H), 4.83-4.63 (m, 2H), 4.20 (dd, J = 3.6, 8.8 Hz, 2H), 7.42 (d, J = 8.4 Hz, 2H), 3.97-3.95 (m, 1H), 3.81 (d, J = 13.6 Hz, 1H), 3.68 (dd, J = 2.8, 14.4 Hz, 1H), 3.06 (s, 3H), 2.11-2.07 (m, 1H), 1.14 (d, J = 6.8 Hz, 3H), 0.95 (d, J = 6.8 Hz, 3H). |
| I-K3 | 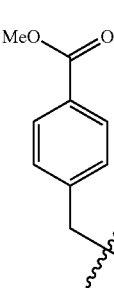 | m/z 528.0 (M + H) | (CD$_3$OD) δ 8.00 (d, J = 7.6 Hz, 2H), 7.93 (d, J = 8.0 Hz, 2H) 7.62 (d, J = 8.4 Hz, 2H), 7.55 (d, J = 7.6 Hz, 2H), 4.76-4.53 (m, 4H), 4.23-4.22 (m, 2H), 4.01-3.85 (m, 4H), 3.10 (s, 2H), 2.12-1.97 (m, 1H), 1.16 (d, J = 6.4 Hz, 3H), 0.95 (d, J = 6.4 Hz, 3H). |

(S)-5-(4-chlorobenzyl)-N-((5-(ethylsulfonyl)pyridin-2-yl)methyl)-4-isopropyl-5,6-dihydro-4H-pyrrolo[3,4-d]thiazole-2-carboxamide (I-L1)

Compound I-L1 was prepared by following the synthetic step shown in Scheme 67.

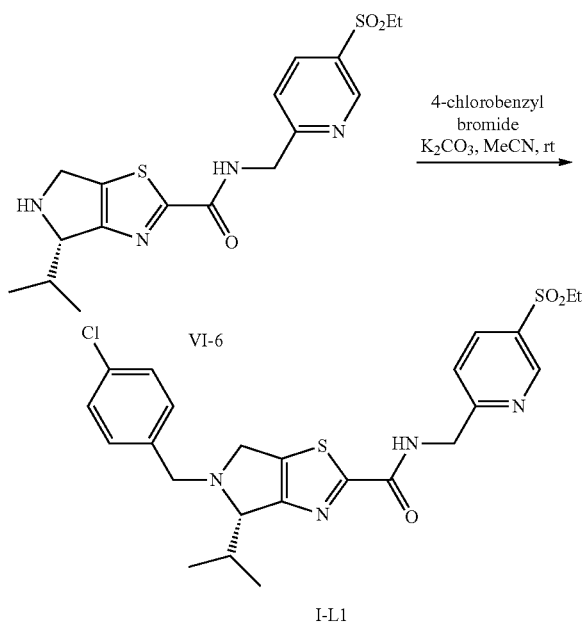

To a solution of compound VI-6 (which is deprotected VI-4) (12 mg, 0.023 mmol) in CH₃CN (2 mL) was added 4-chlorobenzyl bromide (10 mg, 0.05 mmol) and K₂CO₃ (7 mg, 0.05 mmol). The mixture was stirred at rt overnight. The mixture was concentrated under reduced pressure. Water (10 mL) and ethyl acetate (10 mL) were added to the mixture. After partition, the aqueous layer was extracted with ethyl acetate (3×10 mL). The combined organic layers were washed with brine (15 mL), dried over anhydrous sodium sulfate, filtered and concentrated under reduced pressure. Purification on reverse phase prep-HPLC afforded compound I-L1. LC-MS $t_R$=1.234 min in 2 min chromatography, MS (ESI) m/z 519.53 [M+H]⁺. ¹H NMR (CD₃OD): δ 8.97 (d, J=2.4 Hz, 1H), 8.27 (dd, J=7.0, 2.4 Hz, 1H), 7.64 (d, J=8.4 Hz, 1H), 7.65 (d, J=8.4 Hz, 2H), 7.54 (d, J=8.4 Hz, 2H), 4.81 (s, 2H), 4.80-4.65 (m, 5H), 3.28 (q, J=7.2 Hz, 2H), 2.20-2.07 (m, 1H), 1.24 (t, J=7.2 Hz, 3H), 1.19 (d, J=6.8 Hz, 3H), 0.94 (d, J=6.8 Hz, 3H).

The following compounds in Table 7 were prepared from compound VI-6 using the appropriate (het)arylalkyl halide by method shown in Scheme 67.

TABLE 7

| Compound Number | R₁ | LC/MS | 1H NMR (400 MHz) |
|---|---|---|---|
| I-L2 | (4-CF₃-benzyl) | m/z 554.5 [M + H]⁺ $t_R$ = 1.44 min | (CD₃OD) δ 0.98 (d, J = 2.4 Hz, 1H), 8.27 (dd, J = 8.4, 2.4 Hz, 1H), 7.85 s, 4H), 7.65 d, J = 8.4 Hz, 1H), 4.81 (s, 2H), 4.80-4.70 (m, 5H), 3.28 (q, J = 7.2 Hz, 2H), 2.31-2.19 (m, 1H) 1.25 (t, J = 7.2 Hz, 3H), 1.22 (d, J = 6.8 Hz, 3H), 0.96 (d, J = 6.8 Hz, 3H). |

TABLE 7-continued

| Compound Number | R₁ | LC/MS | 1H NMR (400 MHz) |
|---|---|---|---|
| I-L3 | (difluorobenzodioxole-CH₂) | m/z 565.5 [M + H]⁺ $t_R$ = 1.34 min | (CD₃OD) δ 8.98 (s, 1H), 8.27 (dd, J = 8.4, 2.4 Hz, 1H), 7.65 (d, J = 8.4 Hz, 1H), 7.57 (s, 1H), 7.48 (d, J = 8.4 Hz, 1H), 7.38 (d, J = 8.4 Hz, 1H), 4.81 (s, 2H), 4.80-4.70 (m, 5H), 3.28 (q, J = 7.2 Hz, 2H), 2.29-2.19 (m, 1H), 1.25 (t, J = 7.2 Hz, 3H), 1.22 (d, J = 6.8 Hz, 3H), 0.96 (d, J = 6.8 Hz, 3H). |

(S)—N-(5-(4-cyanobenzyl)-4-isopropyl-5,6-dihydro-4H-pyrrolo[3,4-d]thiazol-2-yl)-2-(2-fluoro-4-(methylsulfonyl)phenyl)acetamide (I-M1)

Compound I-M1 was prepared by following the synthetic step shown in Scheme 68.

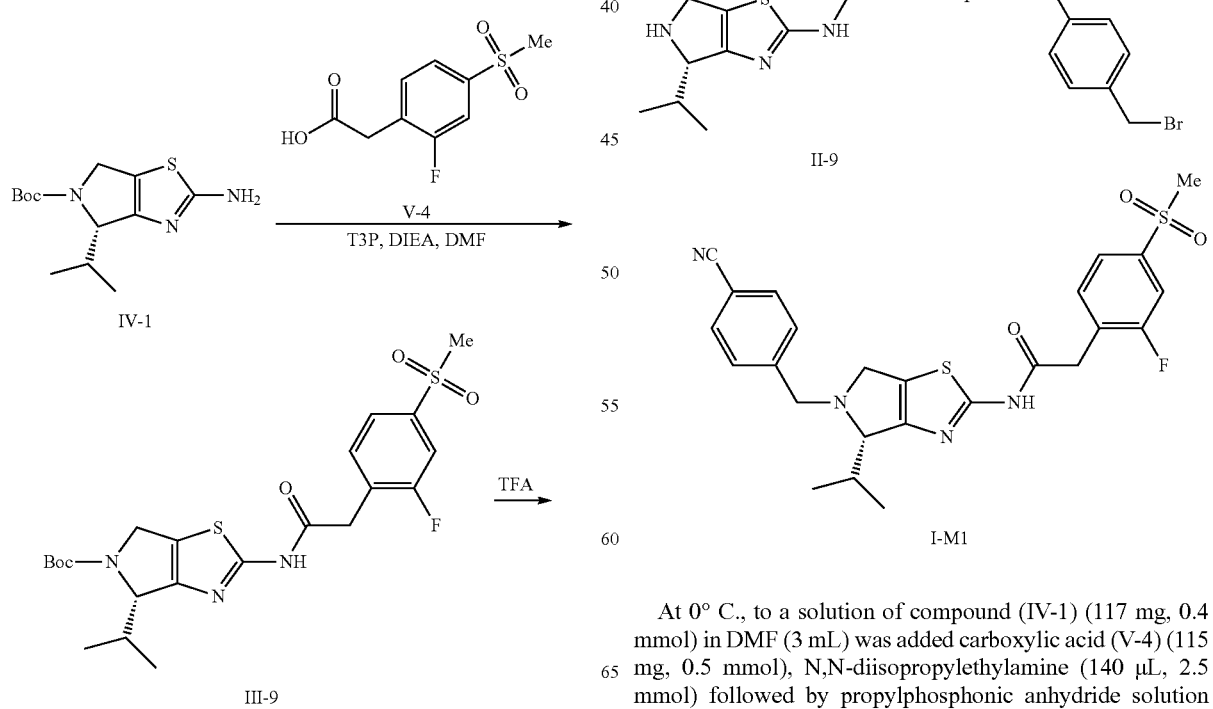

Scheme 68.

At 0° C., to a solution of compound (IV-1) (117 mg, 0.4 mmol) in DMF (3 mL) was added carboxylic acid (V-4) (115 mg, 0.5 mmol), N,N-diisopropylethylamine (140 μL, 2.5 mmol) followed by propylphosphonic anhydride solution (T3P, 50 wt. % in ethyl acetate, 0.4 mL, 0.65 mmol). The mixture was allowed to stir at rt for 6 h and diluted with H$_2$O (20 mL) and ethyl acetate (30 mL). The aqueous phase was extracted with ethyl acetate (3×20 mL). The combined organic layers were washed with brine (30 mL), dried over anhydrous Na$_2$SO$_4$, filtered and concentrated under reduced pressure. The residue was purified by column chromatography on silica gel eluting with Hexanes/ethyl acetate (1/1) to afford compound (III-9) (140 mg, 70%) as a white solid. LC-MS $t_R$=1.59 min in 2 min chromatography, MS (ESI) m/z 498.4 [M+H]$^+$.

To a solution of compound III-9 (150 mg, 0.3 mmol) in CH$_2$Cl$_2$ (5 mL) was added TFA (1 mL). The mixture was stirred at rt for 2 h and neutralized with sat. NaHCO$_3$ solution. The separated aqueous phase was extracted with CH$_2$Cl$_2$ (3×15 mL). The organic layer was dried over anhydrous Na$_2$SO$_4$, filtered and concentrated under reduced pressure to afford crude compound II-9 as a brown oil, which was used directly for the next step without further purification. LC-MS $t_R$=0.66 min in 2 min chromatography, MS (ESI) m/z 398.3 [M+H]$^+$.

To a solution of compound II-9 (10 mg) in CH$_3$CN (0.5 mL) was added 4-(bromomethyl)benzonitrile (1.3 equiv.) and N,N-diisopropylethylamine (2.5 equiv.). The mixture was stirred at rt for 2 h. The solvent was removed in vacuo to give the crude product which was purified on reverse phase prep-HPLC to yield the final compound I-M1. LC-MS $t_R$=1.01 min in 2 min chromatography, MS (ESI) m/z 513.5 [M+H]$^+$. $^1$H NMR (CD$_3$OD, 400 MHz): δ 7.92-7.86 (m, 4H), 7.80-7.72 (m, 2H), 7.68-7.64 (m, 1H), 4.94-4.70 (m, 5H), 4.00 (s, 2H), 3.16 (s, 3H), 2.09-2.01 (m, 1H), 1.18-1.13 (m, 3H), 0.90 (d, J=6.8 Hz, 3H).

BIOLOGICAL ASSAYS

Radio-Ligand RORγ Binding Assay (Assay 1)

Compounds of the present invention were tested for ability to bind to RORγ in a cell-free competition assay with commercially available radio-ligand (RL), 25-hydroxy [26, 27-$^3$H]— cholesterol (PerkinElmer, Cat. # NET674250UC), for a ligand binding site on a recombinant RORγ Ligand Binding Domain (LBD) protein expressed as a 6×His-Glutathione-S-Transferase (GST) fusion ("6×His" disclosed as SEQ ID NO: 2). The assay was performed in 96-well SPA plates (PerkinElmer, Cat. #1450-401) in 50 mM HEPES buffer, pH 7.4, containing 150 mM NaCl, 5 mM MgCl$_2$, 10% (v/v) glycerol, 2 mM CHAPS, 0.5 mM β-octylglucopyranoside and 5 mM DTT. Tested compounds were dissolved in DMSO, and semi-log (3.162×) serial dilutions of the compounds were prepared in the same solvent. Two μL of the DMSO solutions were mixed with 28 μL of 8.6 nM 25-hydroxy [26,27-$^3$H]— cholesterol and 50 μL of 24 nM RORγ LBD. The plate was shaken at 700 rpm for 20 min and incubated for 10 min at rt, after which 40 μL of poly-Lys YSi SPA beads (PerkinElmer, Cat. # RPNQ0010) were added to achieve 50 μg of the beads per well. The plate was incubated on an orbital shaker for 20 min and then for 10 min without agitation at rt. SPA signal for tritium beta radiation was registered on PerkinElmer Microbeta plate reader. Percent inhibition values were calculated based on the high signal obtained with DMSO control and the low signal observed with 10 μM standard RORγ inverse agonist T0901317 (SigmaAldrich, Cat. # T2320). The percent inhibition vs. concentration data were fit into a four-parameter model, and 1050 values were calculated from the fit as the concentrations corresponding to the inflection points on the dose-response curves. Inhibitory constants (Ki) were calculated using the following equation, where [RL] is the concentration in the assay and K$_D$ is a dissociation constant of 25-hydroxy [26,27-$^3$H]-cholesterol:

$$K_i = \frac{IC_{50}}{\left(1 + \frac{[RL]}{K_D}\right)}.$$

RORγt 5xRORE Assay in Jurkat Cells (Assay 2)

Compounds of the present invention were tested for RORγ inverse agonist activity in a cell-based, transcriptional activity assay. Secreted Nanoluc® luciferase was used as a reporter for transcriptional activity of the full-length RORγt in Jurkat cells (ATCC, Cat. # TIB-152). A reporter plasmid was constructed by inserting 5 repeats of the ROR Response Element (RORE) AAAGTAGGTCA (SEQ ID NO:1) into a commercially available promoterless plasmid pNL1.3[secN-luc] (Promega, Cat. # N1021) using KpnI and HindIII restriction sites. The expression plasmid for RORγt was purchased (Geneocopoeia, Cat. # EX-T6988-M02). Jurkat cells (30 million cells) were transfected with 11 μg of EX-T6988-MO2 and 26 μg of the reporter plasmid in OptiMEM® media using Lipofectamine® LTX and Plus™ reagents (Life Technologies, Cat. #15338-100). After 5-6 h of incubation at 37° C./5% CO$_2$, the cells were collected, resuspended in phenol-red free RPMI media containing 10% (v/v) delipidated FBS (Hyclone, Cat. # SH30855.03) and dispensed into 96-well clear bottom tissue culture plates (CoStar, Cat. #3603), at 80,000 cells per well. Tested compounds were added to the cells in the same media (final concentration of DMSO was 0.1% (v/v)), and the plates were incubated at 37° C./5% CO$_2$ for 16-18 hrs. Luciferase activity in the conditioned supernatants was determined with NanoGlo® assay reagents (Promega, Cat. # N1130). Percent inhibition values were calculated based on the fully inhibited and non-inhibited (DMSO) controls, and the values were regressed against concentrations of the tested compounds to derive IC50 values using a four-parameter non-linear fitting model.

The results of assays 1 and 2 are shown in Table 8.

TABLE 8

| Compound Number | RORγ Binding Ki Range* (nM) | RORγt5X IC50 Range* (nM) |
|---|---|---|
| I-A1 | +++ | +++ |
| I-A2 | +++ | +++ |
| I-A3 | +++ | +++ |
| I-A4 | +++ | +++ |
| I-A5 | +++ | +++ |
| I-A6 | +++ | +++ |
| I-A7 | +++ | + |
| I-A8 | +++ | + |
| I-A9 | +++ | + |
| I-A10 | +++ | +++ |
| I-A11 | +++ | +++ |
| I-A12 | +++ | +++ |
| I-A13 | +++ | +++ |
| I-A14 | +++ | + |
| I-A15 | +++ | +++ |
| I-A16 | +++ | +++ |
| I-A17 | +++ | +++ |
| I-A18 | +++ | +++ |
| I-A19 | +++ | +++ |
| I-A20 | +++ | +++ |
| I-A21 | +++ | +++ |
| I-A22 | +++ | +++ |
| I-A23 | +++ | +++ |
| I-A24 | +++ | +++ |
| I-A25 | +++ | +++ |

TABLE 8-continued

| Compound Number | RORγ Binding Ki Range* (nM) | RORγt5X IC50 Range* (nM) |
|---|---|---|
| I-A26 | +++ | +++ |
| I-A27 | +++ | +++ |
| I-A28 | +++ | +++ |
| I-A29 | +++ | +++ |
| I-A30 | +++ | +++ |
| I-A31 | +++ | +++ |
| I-A32 | +++ | +++ |
| I-A33 | +++ | +++ |
| I-A34 | +++ | +++ |
| I-A35 | +++ | +++ |
| I-A36 | +++ | +++ |
| I-A37 | +++ | +++ |
| I-A38 | +++ | +++ |
| I-A39 | +++ | +++ |
| I-A40 | +++ | +++ |
| I-A41 | +++ | +++ |
| I-A42 | +++ | +++ |
| I-A43 | +++ | +++ |
| I-A44 | +++ | +++ |
| I-A45 | +++ | +++ |
| I-A46 | +++ | +++ |
| I-A47 | +++ | +++ |
| I-A48 | +++ | +++ |
| I-A49 | +++ | +++ |
| I-A50 | +++ | +++ |
| I-A51 | +++ | +++ |
| I-A53 | +++ | +++ |
| I-A54 | +++ | +++ |
| I-A58 | +++ | +++ |
| I-A59 | +++ | +++ |
| I-A60 | +++ | +++ |
| I-A61 | +++ | +++ |
| I-A62 | +++ | +++ |
| I-A63 | +++ | +++ |
| I-A64 | +++ | +++ |
| I-B1 | +++ | +++ |
| I-B2 | +++ | +++ |
| I-B3 | +++ | +++ |
| I-B4 | +++ | +++ |
| I-B5 | +++ | +++ |
| I-B6 | +++ | +++ |
| I-B7 | +++ | +++ |
| I-B8 | +++ | +++ |
| I-B9 | +++ | +++ |
| I-B10 | +++ | +++ |
| I-B11 | +++ | +++ |
| I-B12 | +++ | +++ |
| I-B13 | +++ | +++ |
| I-B14 | +++ | +++ |
| I-B15 | +++ | +++ |
| I-B16 | +++ | +++ |
| I-B17 | +++ | +++ |
| I-B18 | +++ | +++ |
| I-B19 | +++ | +++ |
| I-C1 | +++ | +++ |
| I-C2 | +++ | +++ |
| I-C3 | +++ | +++ |
| I-C4 | +++ | +++ |
| I-C5 | +++ | +++ |
| I-C6 | +++ | +++ |
| I-C7 | +++ | +++ |
| I-C8 | +++ | +++ |
| I-C9 | +++ | +++ |
| I-C10 | +++ | +++ |
| I-C11 | +++ | +++ |
| I-D1 | +++ | + |
| I-D2 | +++ | + |
| I-D3 | + | |
| I-E1 | +++ | ++ |
| I-F1 | +++ | + |
| I-F2 | +++ | +++ |
| I-F3 | +++ | +++ |
| I-G1 | +++ | +++ |
| I-H1 | +++ | +++ |
| I-H2 | +++ | +++ |
| I-H3 | +++ | +++ |
| I-I1 | +++ | +++ |
| I-J1 | +++ | +++ |
| I-J2 | +++ | +++ |
| I-J3 | +++ | +++ |
| I-J4 | +++ | +++ |
| I-J5 | +++ | +++ |
| I-J6 | +++ | +++ |
| I-K1 | +++ | ++ |
| I-K2 | +++ | +++ |
| I-K3 | +++ | +++ |
| I-L1 | +++ | +++ |
| I-L2 | +++ | +++ |
| I-L3 | +++ | +++ |
| I-M1 | +++ | +++ |

*+ means >1000 nM; ++ means 100 nM – 1000 nM; +++ means < 100 nM.

Additional compounds of the present invention were synthesized in accordance with the general procedures listed above. The results of of assays 1 and 2 for these compounds are shown in Table 9.

TABLE 9

| Compound | RORγ Binding Ki Range* (nM) | RORγt5X IC50 Range* (nM) |
|---|---|---|
| 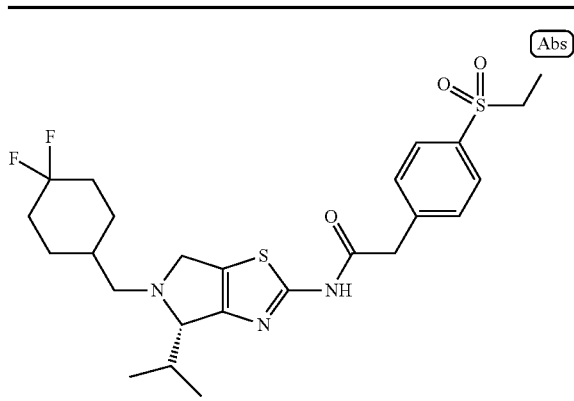 | +++ | |

TABLE 9-continued

| Compound | RORγ Binding Ki Range* (nM) | RORγt5X IC50 Range* (nM) |
|---|---|---|
| (structure) | +++ | +++ |
| (structure) | +++ | + |
| (structure) | +++ | + |
| (structure) | +++ | ++ |

TABLE 9-continued
| Compound | RORγ Binding Ki Range* (nM) | RORγt5X IC50 Range* (nM) |
|---|---|---|
| 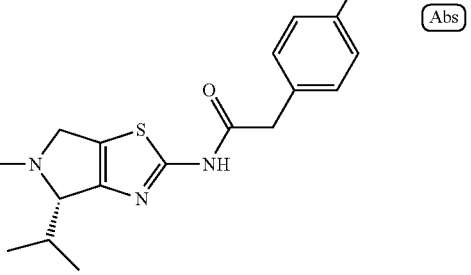 | +++ | ++ |
| 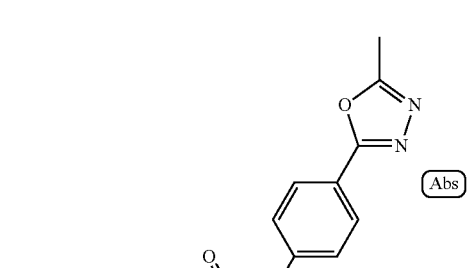 | ++ | |
| 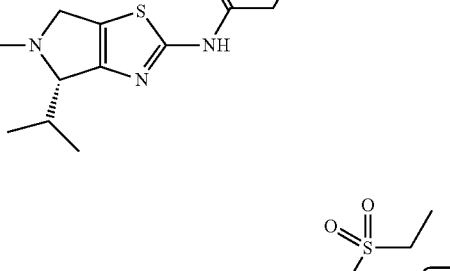 | +++ | +++ |
| 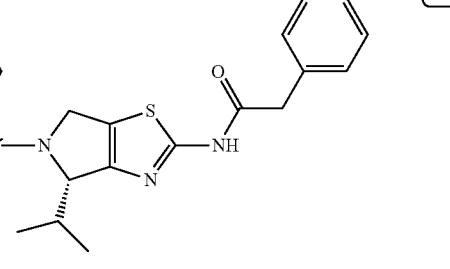 | +++ | + |

TABLE 9-continued
| Compound | RORγ Binding Ki Range* (nM) | RORγt5X IC50 Range* (nM) |
|---|---|---|
| 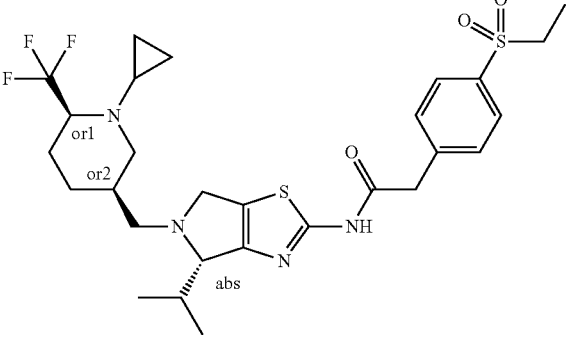 | +++ | + |
| 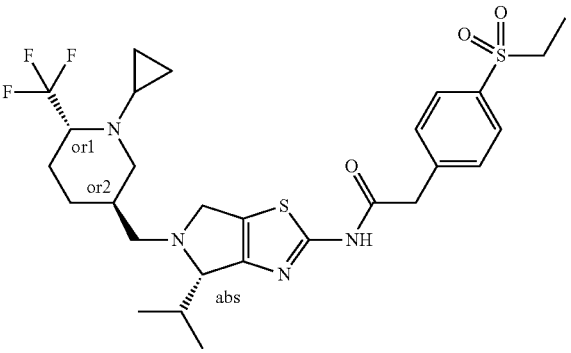 [SMILES: CCS(=O)(=O)c1ccc(CC(=O)Nc2nc3c(s2)CN(C[C@H]2CC[C@H](C(F)(F)F)N(C4CC4)C2)[C@H]3C(C)C)cc1] | +++ | + |
| 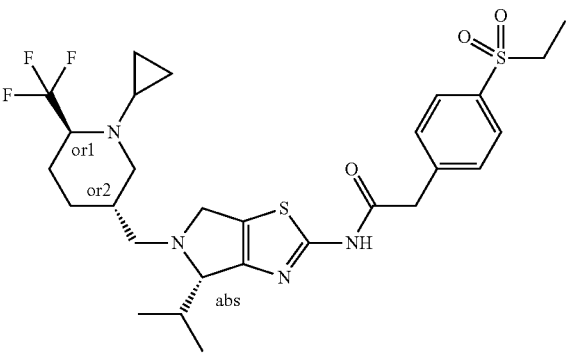 [SMILES: CCS(=O)(=O)c1ccc(CC(=O)Nc2nc3c(s2)CN(C[C@@H]2CC[C@@H](C(F)(F)F)N(C4CC4)C2)[C@H]3C(C)C)cc1] | +++ | + |
| 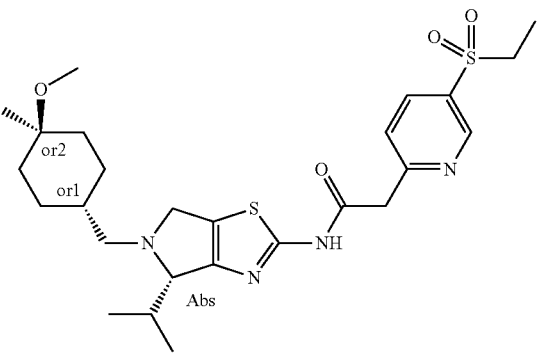 [SMILES: CCS(=O)(=O)c1ccc(CC(=O)Nc2nc3c(s2)CN(C[C@H]2CC[C@](C)(OC)CC2)[C@H]3C(C)C)nc1] | +++ | +++ |

TABLE 9-continued

| Compound | RORγ Binding Ki Range* (nM) | RORγt5X IC50 Range* (nM) |
|---|---|---|
| [structure] | +++ | +++ |
| [structure] | +++ | ++ |
| [structure] | +++ | +++ |
| [structure] | +++ | + |

TABLE 9-continued
| Compound | RORγ Binding Ki Range* (nM) | RORγt5X IC50 Range* (nM) |
|---|---|---|
| 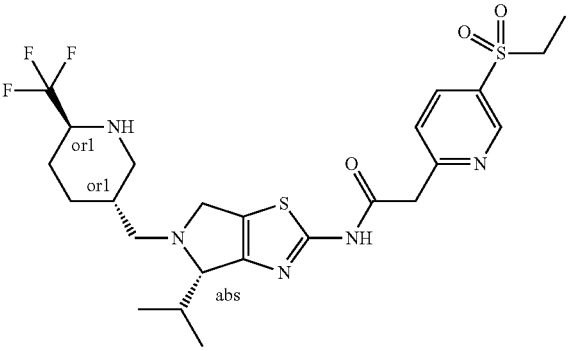 [SMILES: CCS(=O)(=O)c1ccc(CC(=O)Nc2nc3c(s2)CN(C[C@@H]2CC[C@@H](C(F)(F)F)NC2)[C@H]3C(C)C)nc1] | ++ | |
| 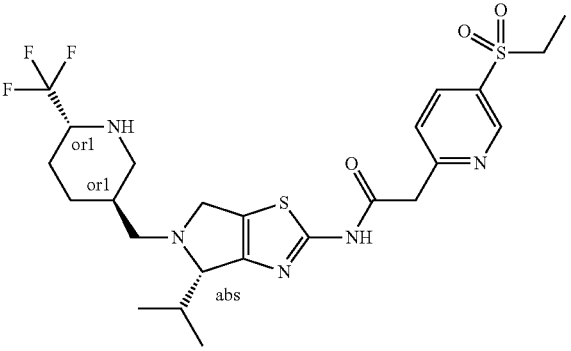 [SMILES: CCS(=O)(=O)c1ccc(CC(=O)Nc2nc3c(s2)CN(C[C@H]2CC[C@H](C(F)(F)F)NC2)[C@H]3C(C)C)nc1] | ++ | ++ |
| 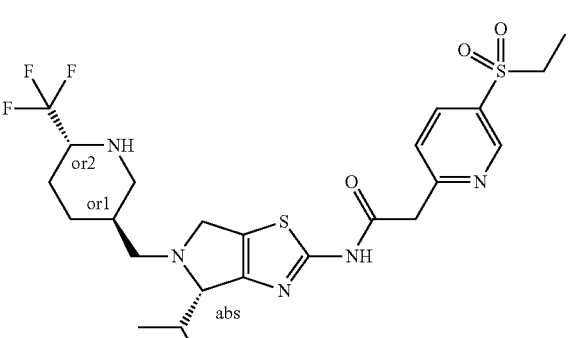 | +++ | + |
| 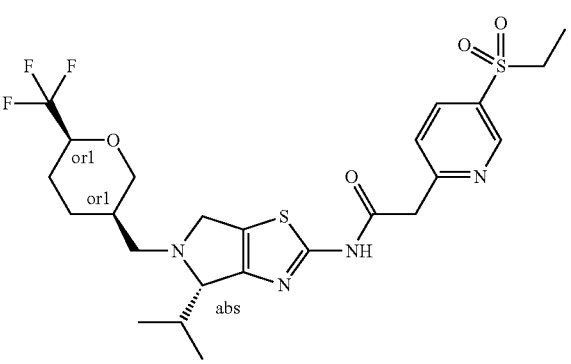 [SMILES: CCS(=O)(=O)c1ccc(CC(=O)Nc2nc3c(s2)CN(C[C@H]2CC[C@@H](C(F)(F)F)OC2)[C@H]3C(C)C)nc1] | +++ | ++ |

TABLE 9-continued

| Compound | RORγ Binding Ki Range* (nM) | RORγt5X IC50 Range* (nM) |
|---|---|---|
| | +++ | + |
| | +++ | + |
| | +++ | + |
| | +++ | + |

TABLE 9-continued
| Compound | RORγ Binding Ki Range* (nM) | RORγt5X IC50 Range* (nM) |
|---|---|---|
| 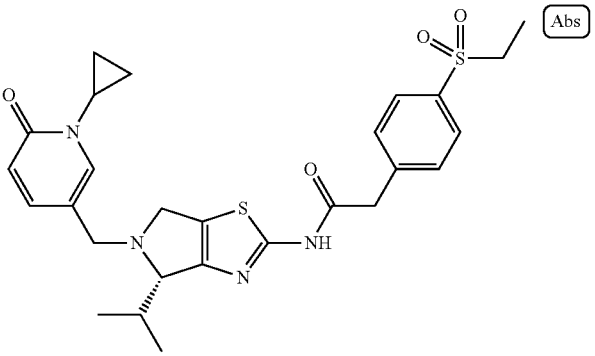 [SMILES: CCS(=O)(=O)c1ccc(CC(=O)Nc2nc3c(s2)CN(Cc2ccc(=O)n(C4CC4)c2)[C@H]3C(C)C)cc1] | +++ | ++ |
| 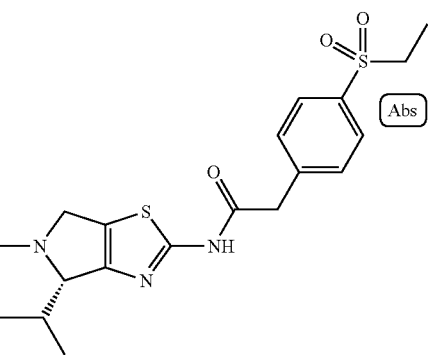 | + | |
| 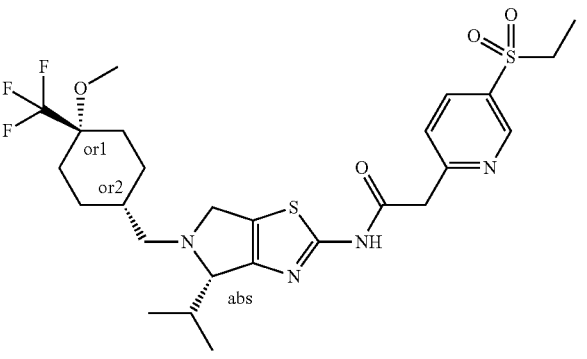 [SMILES: CCS(=O)(=O)c1ccc(CC(=O)Nc2nc3c(s2)CN(C[C@H]2CC[C@](OC)(C(F)(F)F)CC2)[C@H]3C(C)C)nc1] | +++ | +++ |
| 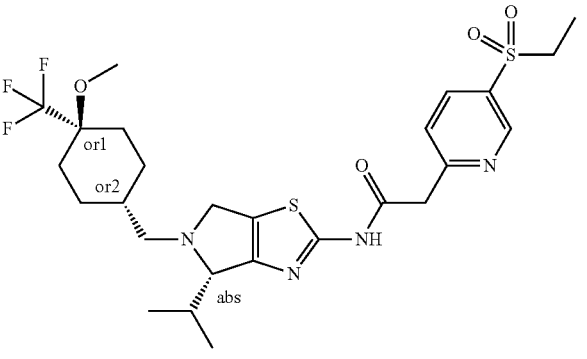 [SMILES: CCS(=O)(=O)c1ccc(CC(=O)Nc2nc3c(s2)CN(C[C@H]2CC[C@@](OC)(C(F)(F)F)CC2)[C@H]3C(C)C)nc1] | +++ | ++ |

TABLE 9-continued
| Compound | RORγ Binding Ki Range* (nM) | RORγt5X IC50 Range* (nM) |
|---|---|---|
| 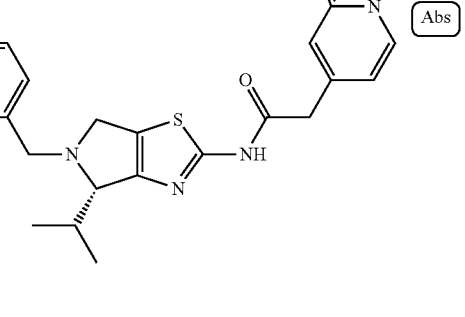 | ++ | |
| 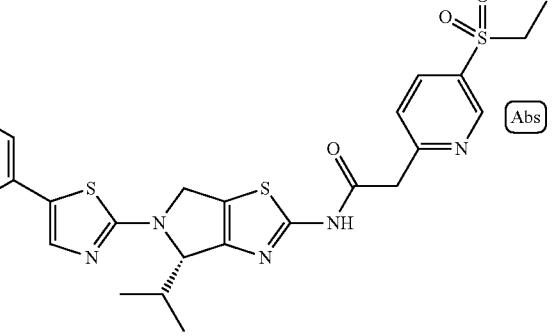 | + | |
| 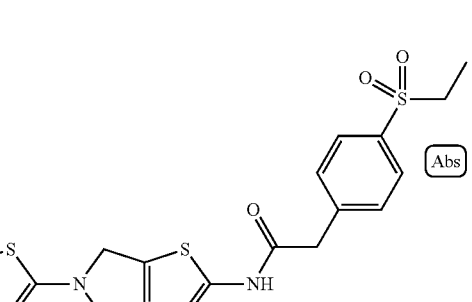 | +++ | + |
| 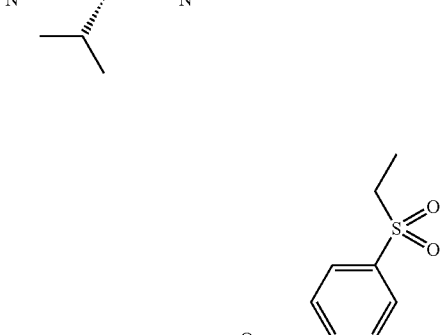 | +++ | +++ |

TABLE 9-continued

| Compound | RORγ Binding Ki Range* (nM) | RORγt5X IC50 Range* (nM) |
|---|---|---|
| (structure) | +++ | + |
| (structure) | +++ | +++ |
| (structure) | +++ | + |
| (structure) | +++ | + |

TABLE 9-continued

| Compound | RORγ Binding Ki Range* (nM) | RORγt5X IC50 Range* (nM) |
|---|---|---|
| | +++ | +++ |
| | +++ | + |
| | ++ | |
| | +++ | + |

TABLE 9-continued

| Compound | RORγ Binding Ki Range* (nM) | RORγt5X IC50 Range* (nM) |
|---|---|---|
| [structure] | +++ | + |
| [structure] | +++ | +++ |
| [structure] | ++ | ++ |
| [structure] | +++ | + |

TABLE 9-continued

| Compound | RORγ Binding Ki Range* (nM) | RORγt5X IC50 Range* (nM) |
|---|---|---|
| (structure) | +++ | + |
| (structure) | +++ | ++ |
| (structure) | +++ | + |
| (structure) | ++ | ++ |

TABLE 9-continued
| Compound | RORγ Binding Ki Range* (nM) | RORγt5X IC50 Range* (nM) |
|---|---|---|
| 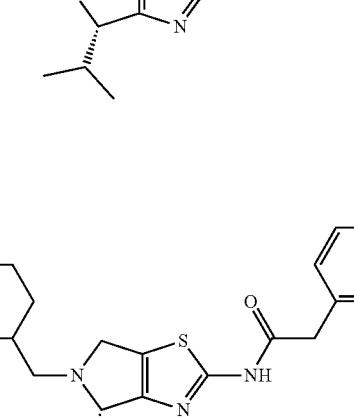 | ++ | |
| 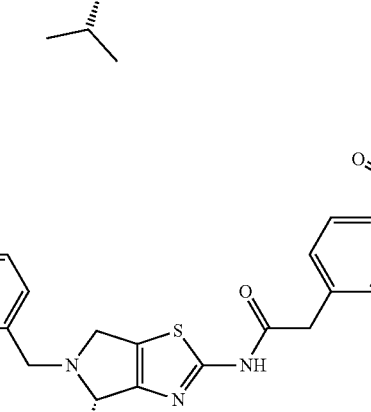 | ++ | + |
| 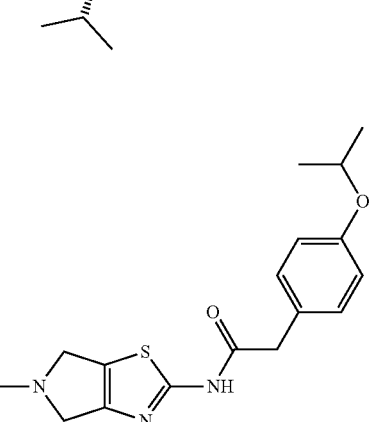 | +++ | +++ |
|  | ++ | + |

TABLE 9-continued

| Compound | RORγ Binding Ki Range* (nM) | RORγt5X IC50 Range* (nM) |
|---|---|---|
| (structure) | +++ | +++ |
| (structure) | +++ | +++ |
| (structure) | +++ | +++ |
| (structure) | +++ | +++ |

TABLE 9-continued

| Compound | RORγ Binding Ki Range* (nM) | RORγt5X IC50 Range* (nM) |
|---|---|---|
| (structure) | +++ | +++ |
| (structure) | ++ | ++ |
| (structure) | ++ | + |
| (structure) | ++ | + |

TABLE 9-continued

| Compound | RORγ Binding Ki Range* (nM) | RORγt5X IC50 Range* (nM) |
|---|---|---|
| | +++ | + |
| | +++ | + |
| | +++ | + |
| | ++ | + |

TABLE 9-continued

| Compound | RORγ Binding Ki Range* (nM) | RORγt5X IC50 Range* (nM) |
|---|---|---|
| (structure) | +++ | ++ |
| (structure) | +++ | +++ |
| (structure) | +++ | ++ |
| (structure) | +++ | + |

TABLE 9-continued

| Compound | RORγ Binding Ki Range* (nM) | RORγt5X IC50 Range* (nM) |
| --- | --- | --- |
| (structure) | +++ | + |
| (structure) | +++ | + |
| (structure) | ++ | + |
| (structure) | +++ | + |

TABLE 9-continued

| Compound | RORγ Binding Ki Range* (nM) | RORγt5X IC50 Range* (nM) |
|---|---|---|
| (structure) | +++ | ++ |
| (structure) | ++ | |
| (structure) | ++ | |
| (structure) | +++ | ++ |

TABLE 9-continued

| Compound | RORγ Binding Ki Range* (nM) | RORγt5X IC50 Range* (nM) |
|---|---|---|
| [structure] | +++ | +++ |
| [structure] | +++ | +++ |
| [structure] | +++ | ++ |
| [structure] | +++ | ++ |

TABLE 9-continued

| Compound | RORγ Binding Ki Range* (nM) | RORγt5X IC50 Range* (nM) |
|---|---|---|
| (structure) | +++ | + |
| (structure) | +++ | +++ |
| (structure) | +++ | ++ |
| (structure) | +++ | +++ |

TABLE 9-continued

| Compound | RORγ Binding Ki Range* (nM) | RORγt5X IC50 Range* (nM) |
|---|---|---|
| | ++ | |
| | ++ | |
| | +++ | +++ |
| | +++ | ++ |

TABLE 9-continued
| Compound | RORγ Binding Ki Range* (nM) | RORγt5X IC50 Range* (nM) |
| --- | --- | --- |
| 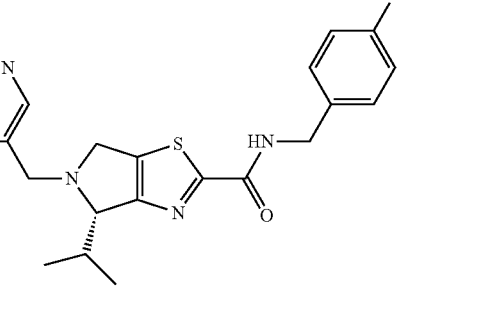 | ++ | ++ |
| 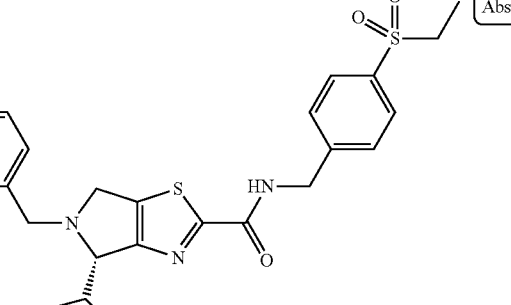 | ++ | ++ |
| 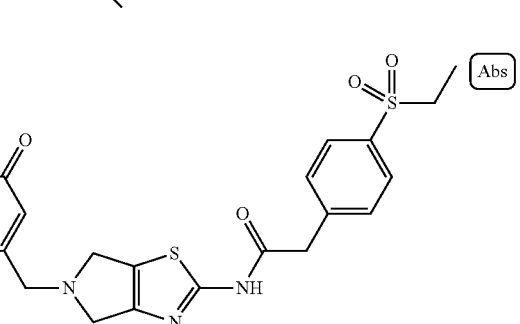 | +++ | ++ |
| | ++ | + |
| 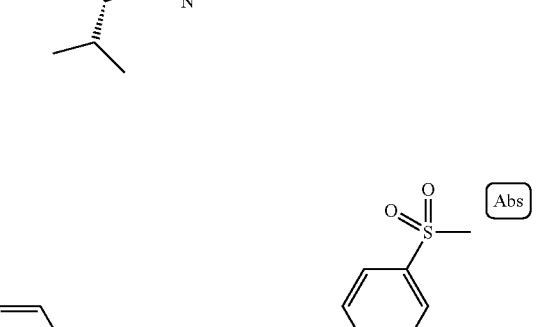 | | |

TABLE 9-continued

| Compound | RORγ Binding Ki Range* (nM) | RORγt5X IC50 Range* (nM) |
| --- | --- | --- |
| *(structure)* | +++ | ++ |
| *(structure)* | ++ | + |
| *(structure)* | +++ | ++ |
| *(structure)* | ++ | |

TABLE 9-continued

| Compound | RORγ Binding Ki Range* (nM) | RORγt5X IC50 Range* (nM) |
|---|---|---|
| [structure] | +++ | +++ |
| [structure] | + | |
| [structure] | ++ | ++ |
| [structure] | +++ | + |

TABLE 9-continued

| Compound | RORγ Binding Ki Range* (nM) | RORγt5X IC50 Range* (nM) |
|---|---|---|
| [structure] | +++ | +++ |
| [structure] | +++ | +++ |
| [structure] | +++ | ++ |
| [structure] | +++ | ++ |

TABLE 9-continued

| Compound | RORγ Binding Ki Range* (nM) | RORγt5X IC50 Range* (nM) |
|---|---|---|
| [structure] | +++ | + |
| [structure] | ++ | |
| lp;2p [structure] | +++ | ++ |
| [structure] | +++ | ++ |

TABLE 9-continued

| Compound | RORγ Binding Ki Range* (nM) | RORγt5X IC50 Range* (nM) |
|---|---|---|
| (structure) | +++ | + |
| (structure) | +++ | + |
| (structure) | +++ | ++ |
| (structure) | ++ | |

TABLE 9-continued

| Compound | RORγ Binding Ki Range* (nM) | RORγt5X IC50 Range* (nM) |
|---|---|---|
| (structure) | +++ | + |
| (structure) | +++ | +++ |
| (structure) | +++ | ++ |
| (structure) | +++ | + |

TABLE 9-continued

| Compound | RORγ Binding Ki Range* (nM) | RORγt5X IC50 Range* (nM) |
|---|---|---|
| *(structure: 4-chlorobenzyl pyrrolo-thiazole with isopropyl, amide-CH2-phenyl-SO2Et)* | +++ | +++ |
| *(structure: 4-cyanobenzyl pyrrolo-thiazole with isopropyl, amide-CH2-pyrimidine-SO2Et)* | +++ | ++ |
| *(structure: 4-cyanobenzyl pyrrolo-thiazole with ethyl/methyl, amide-CH2-phenyl-SO2Et)* | +++ | ++ |
| *(structure: 4-chlorobenzyl pyrrolo-thiazole with ethyl/methyl, amide-CH2-phenyl-SO2Et)* | +++ | +++ |

TABLE 9-continued
| Compound | RORγ Binding Ki Range* (nM) | RORγt5X IC50 Range* (nM) |
|---|---|---|
| 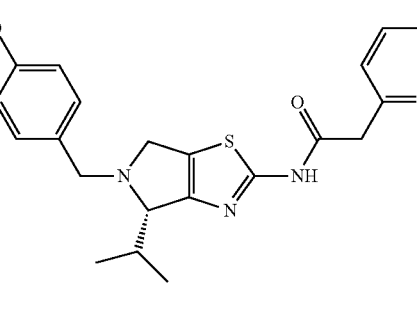 | +++ | +++ |
| 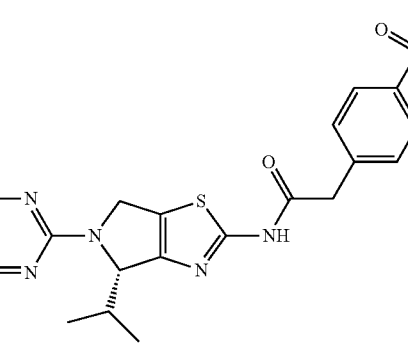 | +++ | + |
| 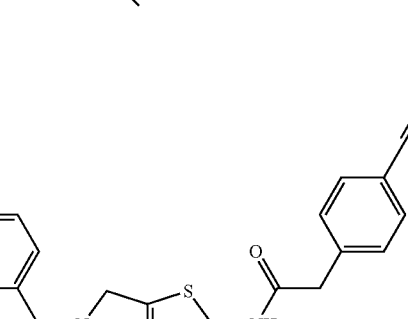 | +++ | ++ |
| 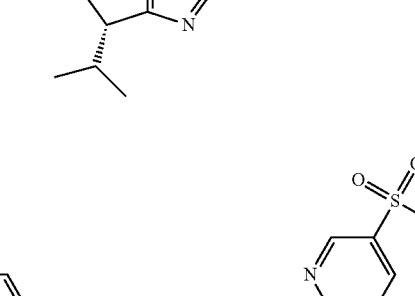 | +++ | ++ |

TABLE 9-continued

| Compound | RORγ Binding Ki Range* (nM) | RORγt5X IC50 Range* (nM) |
|---|---|---|
| | ++ | |
| | ++ | |
| | +++ | ++ |
| | +++ | |

TABLE 9-continued
| Compound | RORγ Binding Ki Range* (nM) | RORγt5X IC50 Range* (nM) |
|---|---|---|
| 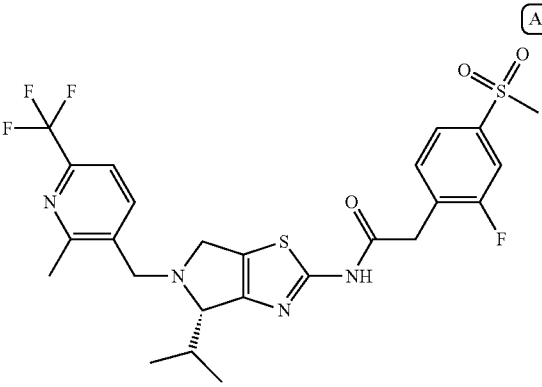 | +++ | +++ |
| 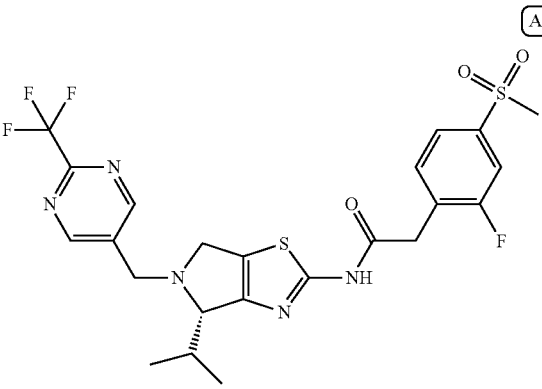 | ++ | |
| 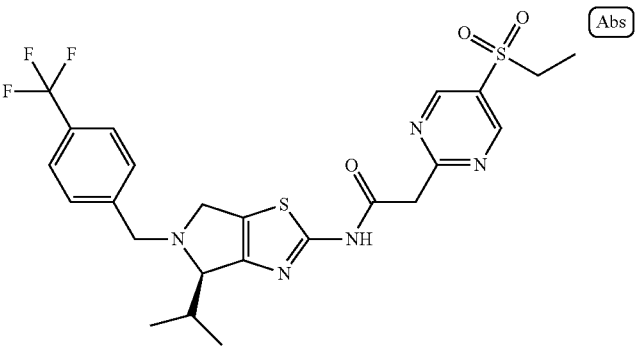 [SMILES: CCS(=O)(=O)c1cnc(CC(=O)Nc2nc3c(s2)CN(Cc2ccc(C(F)(F)F)cc2)[C@@H]3C(C)C)nc1] | + | |
| 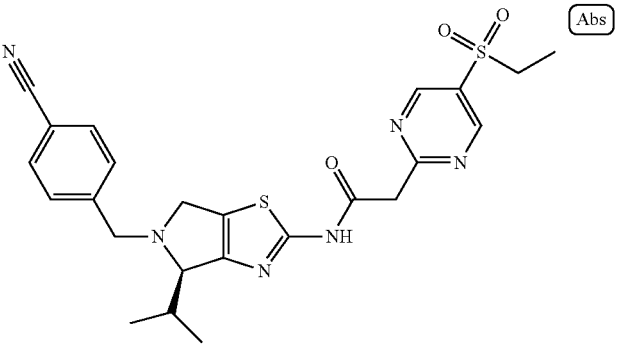 [SMILES: CCS(=O)(=O)c1cnc(CC(=O)Nc2nc3c(s2)CN(Cc2ccc(C#N)cc2)[C@@H]3C(C)C)nc1] | + | |

TABLE 9-continued

| Compound | RORγ Binding Ki Range* (nM) | RORγt5X IC50 Range* (nM) |
|---|---|---|
| [structure: 2-aminopyrimidine-CH2-pyrrolo-thiazole-isopropyl, amide linker to phenyl-SO2-ethyl] (Abs) | ++ | |
| [structure: 6-aminopyridine-CH2-pyrrolo-thiazole-isopropyl, amide linker to phenyl-SO2-ethyl] (Abs) | +++ | + |
| [structure: 2-methylpyrimidine-CH2-pyrrolo-thiazole-isopropyl, amide linker to phenyl-SO2-ethyl] (Abs) | +++ | ++ |
| [structure: 4-chlorophenyl-CH2-pyrrolo-thiazole-ethyl, amide linker to phenyl-CH2-OH] (Abs) | +++ | ++ |

TABLE 9-continued

| Compound | RORγ Binding Ki Range* (nM) | RORγt5X IC50 Range* (nM) |
|---|---|---|
| (structure: 4-chlorobenzyl pyrrolo-thiazole with ethyl, methyl benzoate) [Abs] | ++ | |
| (structure: 4-chlorobenzyl pyrrolo-thiazole with isopropyl, benzoic acid) [Abs] | +++ | ++ |
| (structure: 1-methyltetrazol-5-yl phenyl pyrrolo-thiazole with isopropyl, methylsulfonyl phenyl) [Abs] | +++ | +++ |
| (structure: 5-methyl-1,3,4-oxadiazol-2-yl phenyl pyrrolo-thiazole with isopropyl, methylsulfonyl phenyl) [Abs] | +++ | +++ |

TABLE 9-continued

| Compound | RORγ Binding Ki Range* (nM) | RORγt5X IC50 Range* (nM) |
| --- | --- | --- |
| | + | |
| | ++ | |
| | +++ | + |
| | + | |

TABLE 9-continued
| Compound | RORγ Binding Ki Range* (nM) | RORγt5X IC50 Range* (nM) |
|---|---|---|
| 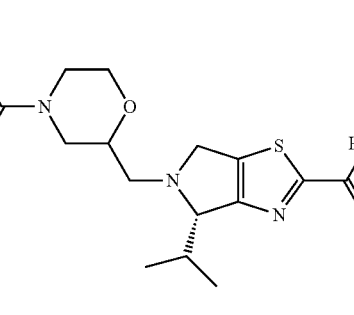 | +++ | +++ |
| 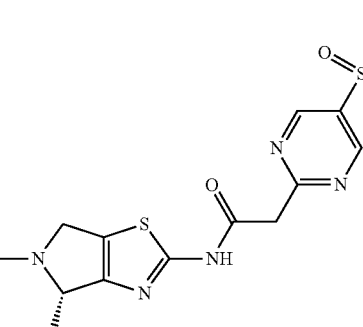 | +++ | ++ |
| 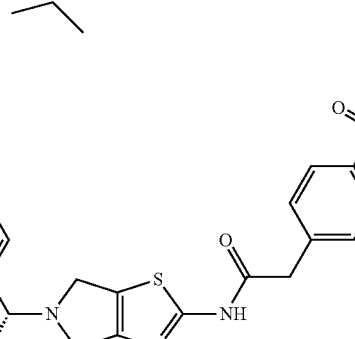 | +++ | ++ |
| 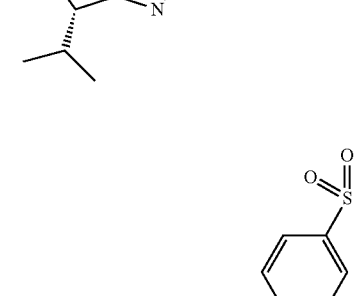 | +++ | + |

TABLE 9-continued

| Compound | RORγ Binding Ki Range* (nM) | RORγt5X IC50 Range* (nM) |
|---|---|---|
| (structure: 4-(hydroxymethyl)benzyl pyrrolo-thiazole with isopropyl, N-H amide linked to 4-(ethylsulfonyl)phenylacetyl) [Abs] | +++ | ++ |
| (structure: 1H-benzotriazol-5-ylmethyl pyrrolo-thiazole with isopropyl, carboxamide N-H-CH2-4-(methylsulfonyl)phenyl) [Abs] | ++ | |
| (structure: 1H-benzotriazol-5-ylmethyl pyrrolo-thiazole with ethyl, NH-C(O)-CH2-4-(methylsulfonyl)phenyl) [Abs] | +++ | ++ |
| (structure: (2-methylpyrimidin-5-yl)methyl pyrrolo-thiazole with isopropyl, NH-C(O)-CH2-4-(methylsulfonyl)phenyl) [Abs] | ++ | |

TABLE 9-continued

| Compound | RORγ Binding Ki Range* (nM) | RORγt5X IC50 Range* (nM) |
|---|---|---|
| (structure) | ++ | |
| (structure) | ++ | |
| (structure) | +++ | + |
| (structure) | +++ | + |

TABLE 9-continued

| Compound | RORγ Binding Ki Range* (nM) | RORγt5X IC50 Range* (nM) |
|---|---|---|
| [structure] | +++ | + |
| [structure] | ++ | |
| [structure] | +++ | +++ |
| [structure] | +++ | ++ |

TABLE 9-continued

| Compound | RORγ Binding Ki Range* (nM) | RORγt5X IC50 Range* (nM) |
|---|---|---|
| (structure) | +++ | +++ |
| (structure) | +++ | +++ |
| (structure) | ++ | |
| (structure) | +++ | + |

TABLE 9-continued

| Compound | RORγ Binding Ki Range* (nM) | RORγt5X IC50 Range* (nM) |
|---|---|---|
| [structure] | +++ | ++ |
| [structure] | + | |
| [structure] | +++ | ++ |
| [structure] | +++ | +++ |

TABLE 9-continued

| Compound | RORγ Binding Ki Range* (nM) | RORγt5X IC50 Range* (nM) |
|---|---|---|
| [structure] | +++ | ++ |
| [structure] | +++ | + |
| [structure] | +++ | +++ |
| [structure] | ++ | |

TABLE 9-continued

| Compound | RORγ Binding Ki Range* (nM) | RORγt5X IC50 Range* (nM) |
|---|---|---|
| (structure) | + | |
| (structure) | + | |
| (structure) | + | |
| (structure) | ++ | |

TABLE 9-continued
| Compound | RORγ Binding Ki Range* (nM) | RORγt5X IC50 Range* (nM) |
|---|---|---|
| 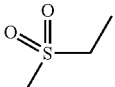 | +++ | ++ |
| 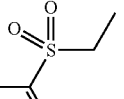 | +++ | + |
| 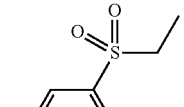 | ++ | |
| 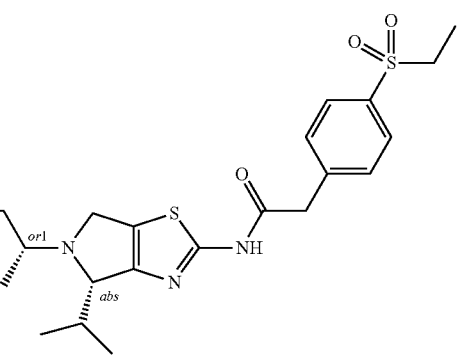 | +++ | + |

TABLE 9-continued
| Compound | RORγ Binding Ki Range* (nM) | RORγt5X IC50 Range* (nM) |
|---|---|---|
| 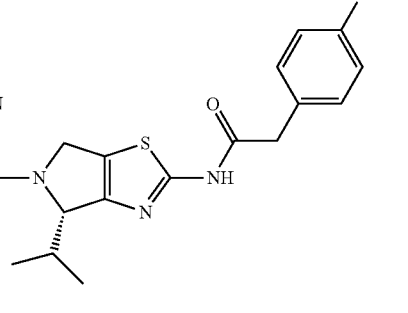 | ++ | |
| 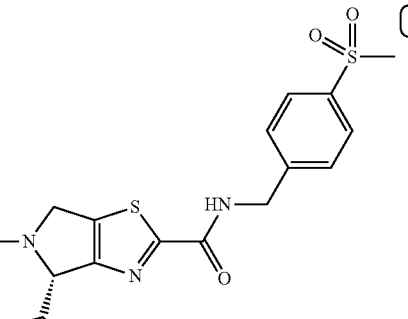 | +++ | + |
| 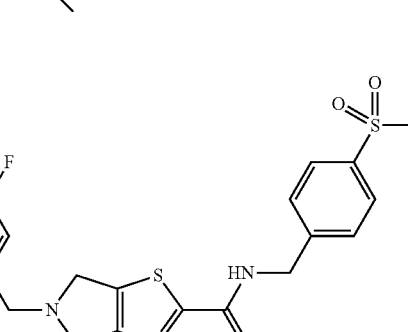 | +++ | ++ |
| 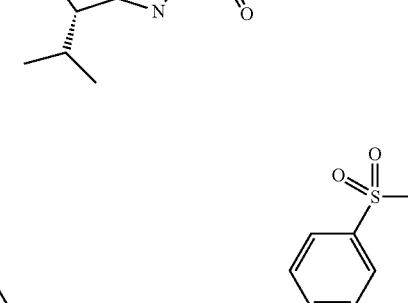 | ++ | |

TABLE 9-continued

| Compound | RORγ Binding Ki Range* (nM) | RORγt5X IC50 Range* (nM) |
|---|---|---|
| (5-chloropyridin-2-yl methyl / isopropyl / methylsulfonylbenzyl amide pyrrolothiazole) | +++ | ++ |
| (4-trifluoromethylbenzyl / isopropyl / methylsulfonylbenzyl amide pyrrolothiazole) | +++ | +++ |
| (4-cyano-2-fluorobenzyl / isopropyl / methylsulfonylbenzyl amide pyrrolothiazole) | +++ | ++ |
| (4-trifluoromethylpyrimidin-2-yl / dimethyl / methylsulfonylphenylacetamide pyrrolothiazole) | ++ | + |

TABLE 9-continued
| Compound | RORγ Binding Ki Range* (nM) | RORγt5X IC50 Range* (nM) |
|---|---|---|
| 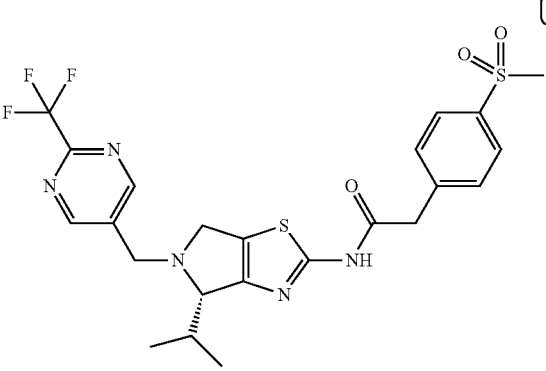 | +++ | +++ |
| 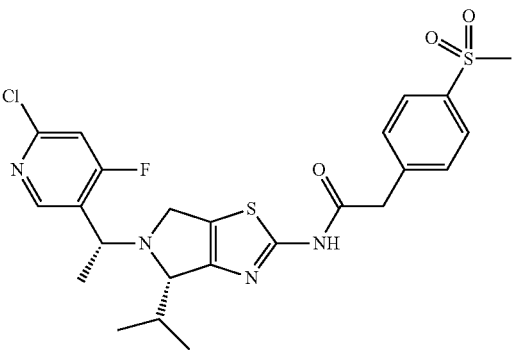 [SMILES: CC(C)[C@H]1c2nc(NC(=O)Cc3ccc(S(C)(=O)=O)cc3)sc2CN1[C@H](C)c1cnc(Cl)cc1F] | +++ | ++ |
| 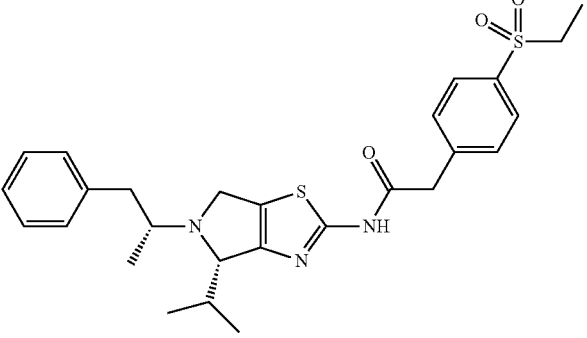 | +++ | + |
| 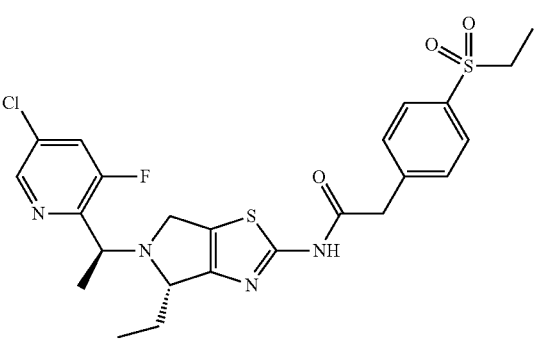 [SMILES: CC[C@H]1c2nc(NC(=O)Cc3ccc(S(=O)(=O)CC)cc3)sc2CN1[C@@H](C)c1ncc(Cl)cc1F] | +++ | ++ |

TABLE 9-continued
| Compound | RORγ Binding Ki Range* (nM) | RORγt5X IC50 Range* (nM) |
|---|---|---|
| 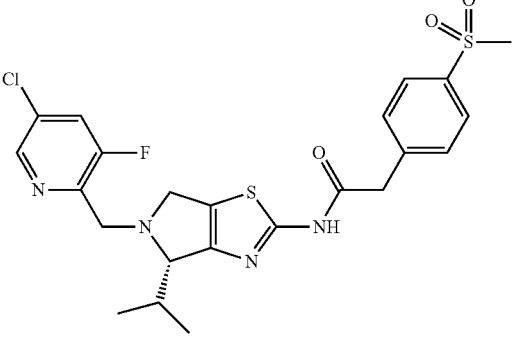 | ++ | |
| 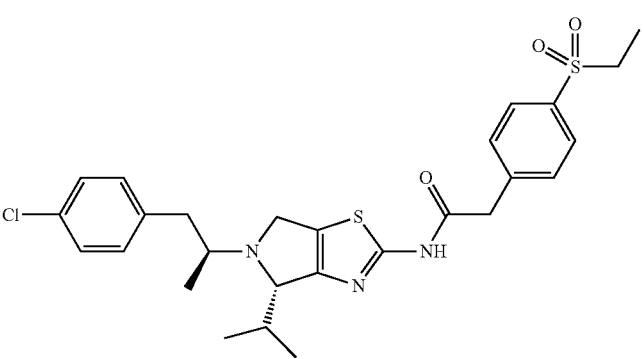 [SMILES: CCS(=O)(=O)c1ccc(CC(=O)Nc2nc3c(s2)CN([C@@H](C)Cc2ccc(Cl)cc2)[C@H]3C(C)C)cc1] | +++ | ++ |
| 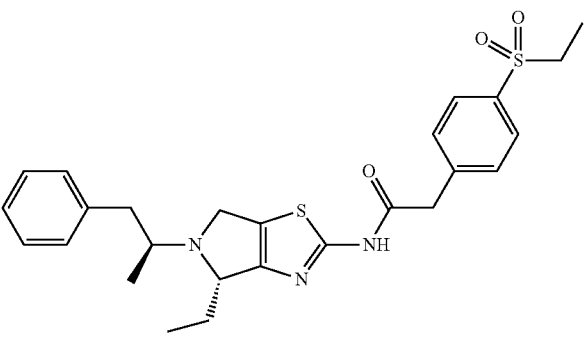 [SMILES: CC[C@H]1c2nc(NC(=O)Cc3ccc(S(=O)(=O)CC)cc3)sc2CN1[C@@H](C)Cc1ccccc1] | +++ | + |
| 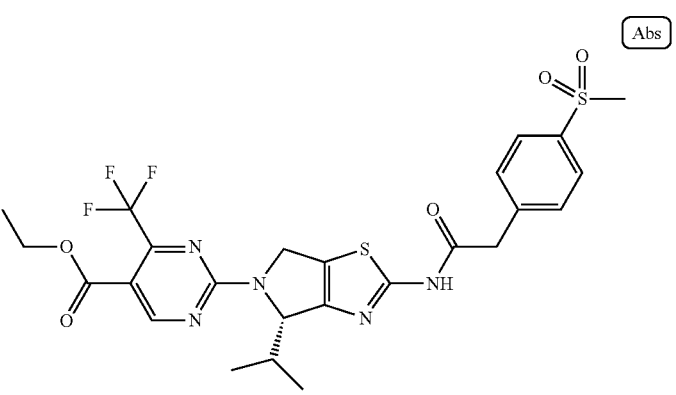 [SMILES: CCOC(=O)c1cnc(N2Cc3sc(NC(=O)Cc4ccc(S(C)(=O)=O)cc4)nc3[C@@H]2C(C)C)nc1C(F)(F)F] | ++ | |

TABLE 9-continued
| Compound | RORγ Binding Ki Range* (nM) | RORγt5X IC50 Range* (nM) |
|---|---|---|
| 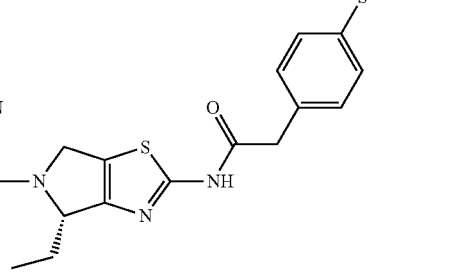 | ++ | +++ |
| 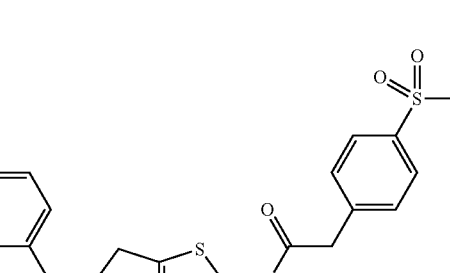 | +++ | +++ |
| 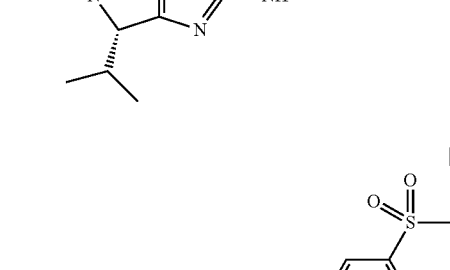 | +++ | ++ |
| 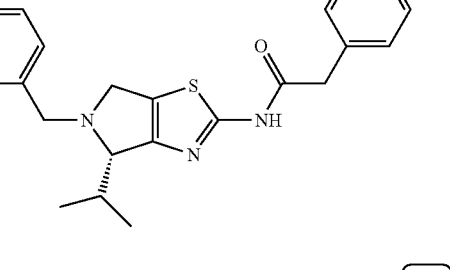 | ++ | |

TABLE 9-continued
| Compound | RORγ Binding Ki Range* (nM) | RORγt5X IC50 Range* (nM) |
|---|---|---|
| 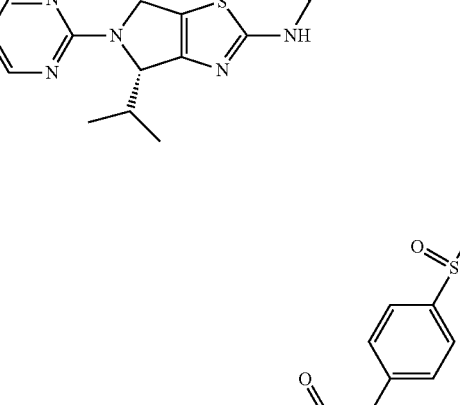 | ++ | |
| 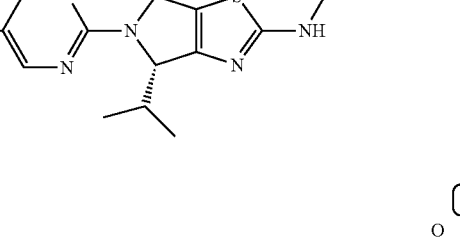 | + | |
| 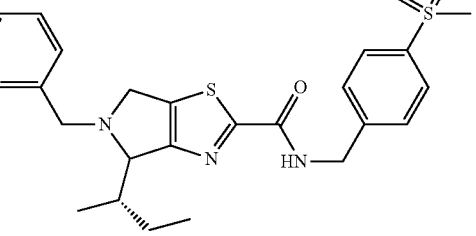 | +++ | ++ |
| | +++ | ++ |
|  | | |

TABLE 9-continued
| Compound | RORγ Binding Ki Range* (nM) | RORγt5X IC50 Range* (nM) |
|---|---|---|
| 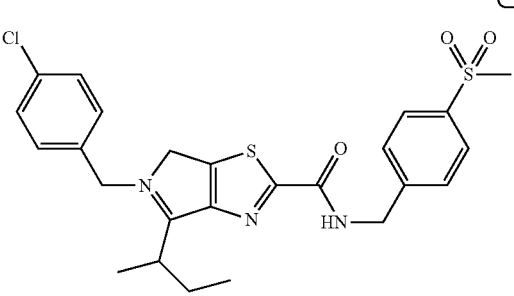 | +++ | ++ |
| 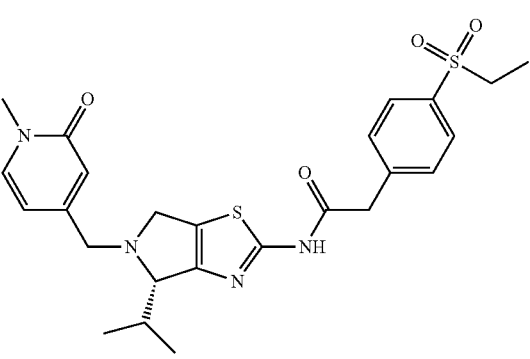 | ++ | + |
| 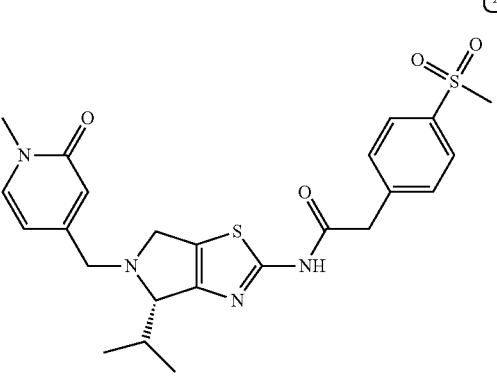 | ++ | + |
| 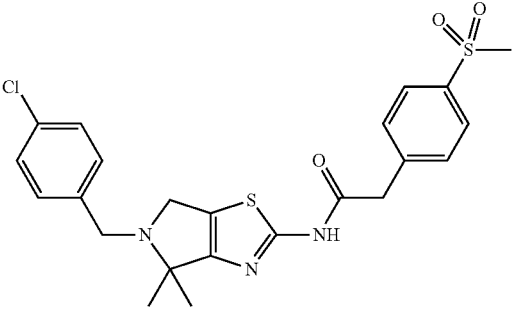 [SMILES: CC1(C)c2nc(NC(=O)Cc3ccc(S(C)(=O)=O)cc3)sc2CN1Cc1ccc(Cl)cc1] | ++ | + |

TABLE 9-continued
| Compound | RORγ Binding Ki Range* (nM) | RORγt5X IC50 Range* (nM) |
|---|---|---|
| 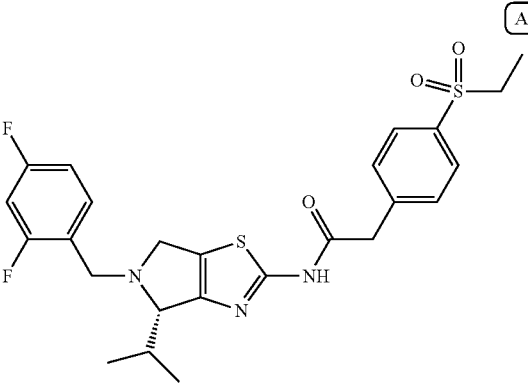 | +++ | + |
| 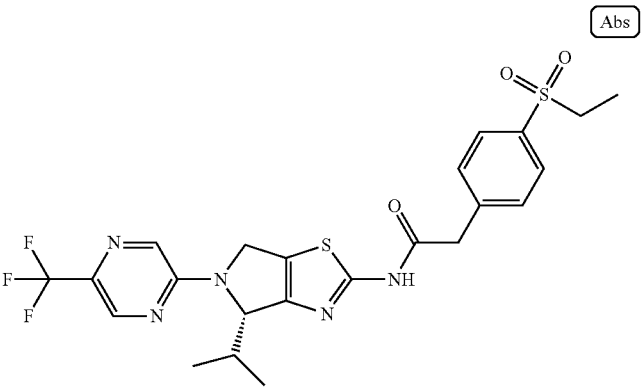 [SMILES: CCS(=O)(=O)c1ccc(CC(=O)Nc2nc3c(s2)CN(c2cnc(C(F)(F)F)cn2)[C@H]3C(C)C)cc1] | +++ | + |
| 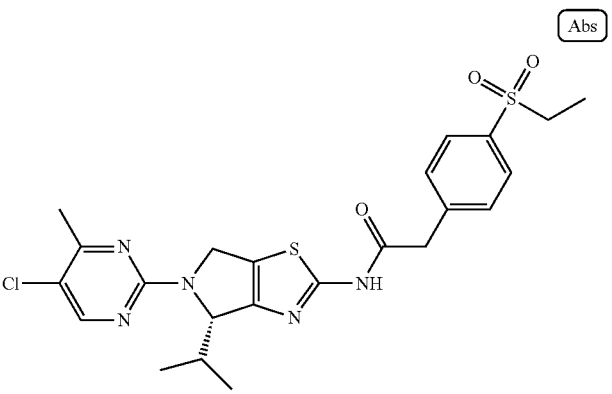 [SMILES: CCS(=O)(=O)c1ccc(CC(=O)Nc2nc3c(s2)CN(c2ncc(Cl)c(C)n2)[C@H]3C(C)C)cc1] | +++ | + |
| 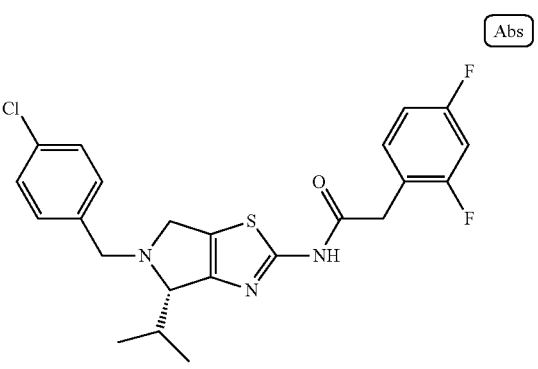 [SMILES: CC(C)[C@H]1c2nc(NC(=O)Cc3ccc(F)cc3F)sc2CN1Cc1ccc(Cl)cc1] | ++ | |

TABLE 9-continued

| Compound | RORγ Binding Ki Range* (nM) | RORγt5X IC50 Range* (nM) |
|---|---|---|
| [structure: 4-Cl-benzyl, ethyl pyrrolothiazole, 4-F-phenylacetamide] | +++ | ++ |
| [structure: 4-F-benzyl, isopropyl pyrrolothiazole, 4-(methylsulfonyl)phenylacetamide] | +++ | + |
| [structure: 3,4-diF-benzyl, isopropyl pyrrolothiazole, 4-(ethylsulfonyl)phenylacetamide] | +++ | + |
| [structure: 4-Br-benzyl, isopropyl pyrrolothiazole, 4-(ethylsulfonyl)phenylacetamide] | +++ | +++ |

TABLE 9-continued
| Compound | RORγ Binding Ki Range* (nM) | RORγt5X IC50 Range* (nM) |
|---|---|---|
| 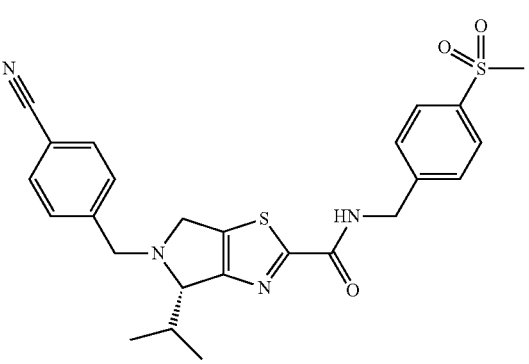 | +++ | ++ |
| 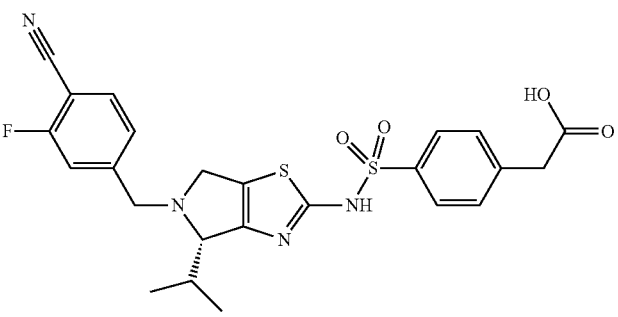 | +++ | + |
| 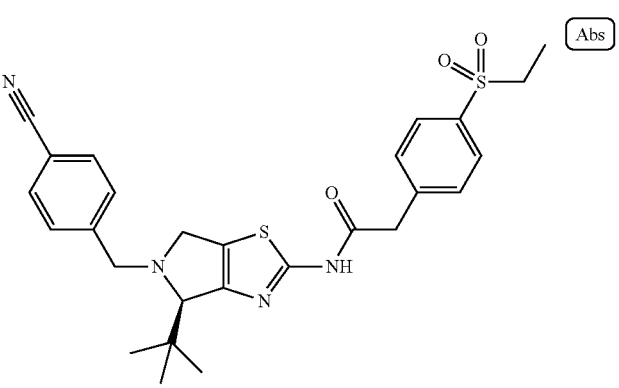 [SMILES: CCS(=O)(=O)c1ccc(CC(=O)Nc2nc3c(s2)CN(Cc2ccc(C#N)cc2)[C@@H]3C(C)(C)C)cc1] | +++ | ++ |
| 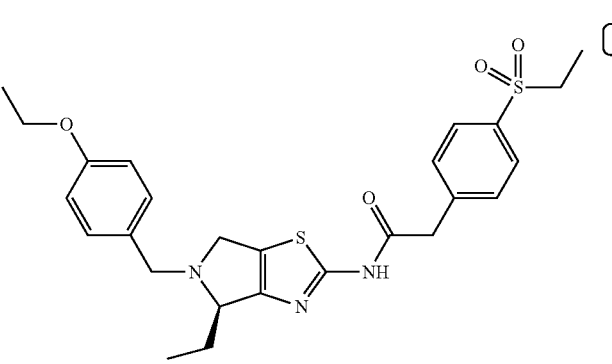 | +++ | ++ |

TABLE 9-continued
| Compound | RORγ Binding Ki Range* (nM) | RORγt5X IC50 Range* (nM) |
|---|---|---|
| 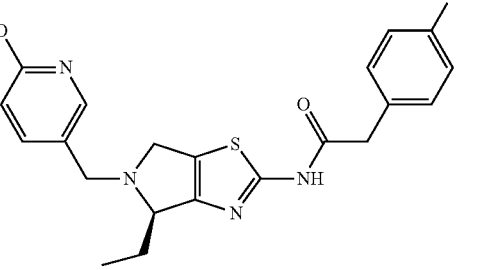 | ++ | |
| 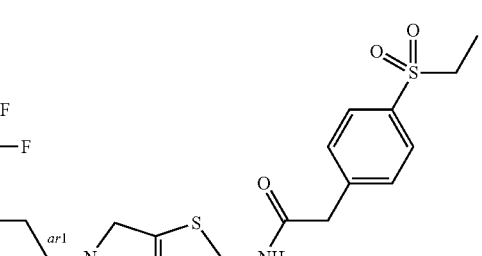 | +++ | + |
| 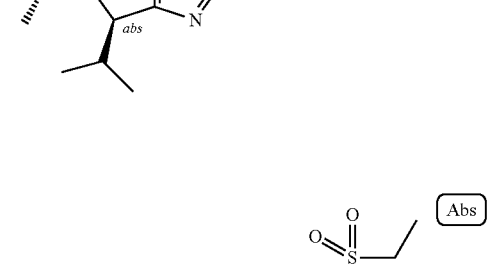 | ++ | |
| 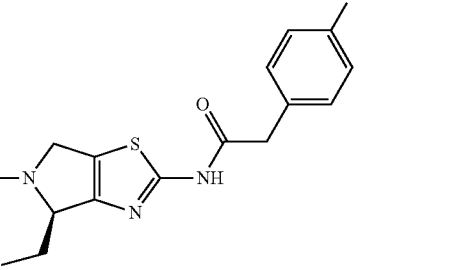 | +++ | + |
| 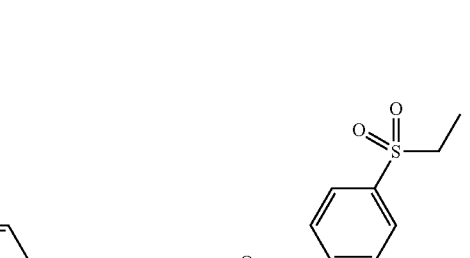 | | |

TABLE 9-continued

| Compound | RORγ Binding Ki Range* (nM) | RORγt5X IC50 Range* (nM) |
|---|---|---|
| [structure: 3-fluoro-4-(trifluoromethyl)benzyl pyrrolothiazole isopropyl, ethylsulfonyl phenyl acetamide] | +++ | ++ |
| [structure: 4-isopropoxybenzyl pyrrolothiazole ethyl, ethylsulfonyl phenyl acetamide] | +++ | + |
| [structure: 2-fluoro-4-(trifluoromethoxy)benzyl pyrrolothiazole ethyl, methylsulfonyl phenyl acetamide] | ++ | |
| [structure: 4-bromobenzyl pyrrolothiazole isopropyl, methylsulfonyl phenyl acetamide] | ++ | |

TABLE 9-continued

| Compound | RORγ Binding Ki Range* (nM) | RORγt5X IC50 Range* (nM) |
|---|---|---|
| | +++ | + |
| | +++ | + |
| | +++ | + |
| | +++ | + |

TABLE 9-continued

| Compound | RORγ Binding Ki Range* (nM) | RORγt5X IC50 Range* (nM) |
|---|---|---|
| (structure) | ++ | |
| (structure) | ++ | |
| (structure) | +++ | + |
| (structure) | +++ | + |

TABLE 9-continued

| Compound | RORγ Binding Ki Range* (nM) | RORγt5X IC50 Range* (nM) |
|---|---|---|
| (structure) | ++ | ++ |
| (structure) | ++ | + |
| (structure) | +++ | + |
| (structure) | ++ | ++ |

TABLE 9-continued

| Compound | RORγ Binding Ki Range* (nM) | RORγt5X IC50 Range* (nM) |
|---|---|---|
| *(structure)* | ++ | ++ |
| *(structure)* | ++ | + |
| *(structure)* | ++ | |
| *(structure)* | ++ | |

TABLE 9-continued

| Compound | RORγ Binding Ki Range* (nM) | RORγt5X IC50 Range* (nM) |
|---|---|---|
| *[structure: 4-isopropylbenzyl pyrrolo-thiazole with 4-(methylsulfonyl)phenylacetamide, Abs]* | +++ | + |
| *[structure: (1-phenylethyl) pyrrolo-thiazole with 4-(ethylsulfonyl)phenylacetamide, or1/abs]* | +++ | + |
| | ++ | |
| *[structure: 4-(trifluoromethyl)pyrimidin-2-ylmethyl pyrrolo-thiazole with 4-(ethylsulfonyl)phenylacetamide, Abs]* | +++ | + |
| *[structure: 3-cyclopropylbenzyl pyrrolo-thiazole with 4-(ethylsulfonyl)phenylacetamide, Abs]* | | |

TABLE 9-continued

| Compound | RORγ Binding Ki Range* (nM) | RORγt5X IC50 Range* (nM) |
|---|---|---|
| *(structure)* | ++ | + |
| *(structure)* | ++ | |
| *(structure)* | + | |
| *(structure)* | ++ | ++ |

TABLE 9-continued
| Compound | RORγ Binding Ki Range* (nM) | RORγt5X IC50 Range* (nM) |
|---|---|---|
| 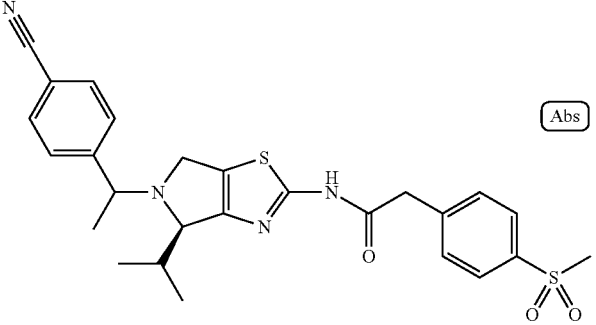 [SMILES: CC(C)[C@@H]1c2nc(NC(=O)Cc3ccc(S(C)(=O)=O)cc3)sc2CN1C(C)c1ccc(C#N)cc1] | ++ | |
| 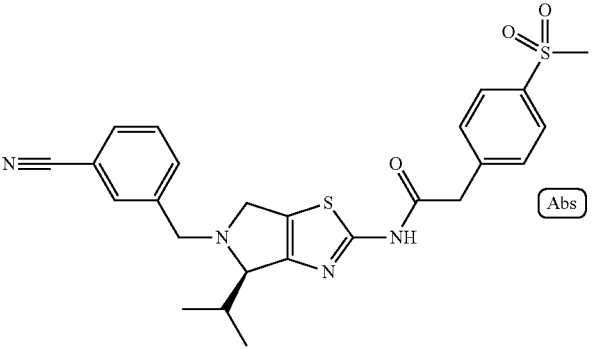 [SMILES: CC(C)[C@@H]1c2nc(NC(=O)Cc3ccc(S(C)(=O)=O)cc3)sc2CN1Cc1cccc(C#N)c1] | ++ | + |
| 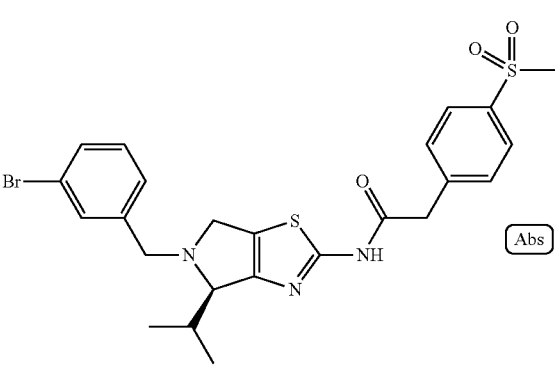 [SMILES: CC(C)[C@@H]1c2nc(NC(=O)Cc3ccc(S(C)(=O)=O)cc3)sc2CN1Cc1cccc(Br)c1] | +++ | + |
| 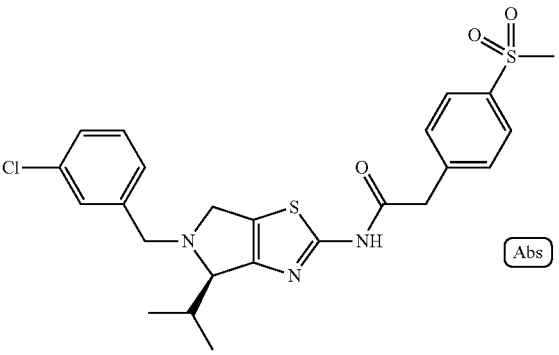 [SMILES: CC(C)[C@@H]1c2nc(NC(=O)Cc3ccc(S(C)(=O)=O)cc3)sc2CN1Cc1cccc(Cl)c1] | +++ | + |

TABLE 9-continued

| Compound | RORγ Binding Ki Range* (nM) | RORγt5X IC50 Range* (nM) |
|---|---|---|
| *(structure: 3-fluorobenzyl pyrrolo-thiazole isopropyl, 4-methylsulfonylphenyl acetamide)* [Abs] | +++ | + |
| *(structure: 4-methylbenzyl pyrrolo-thiazole isopropyl, 4-methylsulfonylphenyl acetamide)* [Abs] | ++ | |
| *(structure: 4-chlorobenzyl pyrrolo-thiazole isopropyl, 4-methylsulfonylphenyl acetamide)* [Abs] | ++ | ++ |
| *(structure: phenethyl pyrrolo-thiazole isopropyl, 4-ethylsulfonylphenyl acetamide)* [Abs] | +++ | + |

TABLE 9-continued

| Compound | RORγ Binding Ki Range* (nM) | RORγt5X IC50 Range* (nM) |
|---|---|---|
| [structure, Abs] | ++ | |
| [structure, Abs] | +++ | + |
| [structure, Abs] | +++ | ++ |
| [structure, Abs] | ++ | ++ |

TABLE 9-continued

| Compound | RORγ Binding Ki Range* (nM) | RORγt5X IC50 Range* (nM) |
|---|---|---|
| (structure, Abs) | ++ | |
| (structure, Abs) | ++ | ++ |
| (structure, Abs) | +++ | + |
| (structure, Abs) | +++ | + |

TABLE 9-continued

| Compound | RORγ Binding Ki Range* (nM) | RORγt5X IC50 Range* (nM) |
|---|---|---|
| *[structure: 3-fluorobenzyl, isopropyl, ethylsulfonyl phenyl]* | +++ | + |
| *[structure: 3-trifluoromethylbenzyl, ethyl, methylsulfonyl phenyl]* | +++ | + |
| *[structure: benzyl, isopropyl, ethylsulfonyl phenyl]* | +++ | + |
| *[structure: 4-cyclopropylpyrimidin-2-yl, isopropyl, ethylsulfonyl phenyl]* | +++ | + |

TABLE 9-continued

| Compound | RORγ Binding Ki Range* (nM) | RORγt5X IC50 Range* (nM) |
|---|---|---|
| [structure: 5-(trifluoromethoxy)-2-fluorobenzyl pyrrolothiazole isopropyl, N-[4-(ethylsulfonyl)phenylacetyl], Abs] | +++ | + |
| [structure: 4-cyanobenzyl pyrrolothiazole isopropyl, N-[4-(ethylsulfonyl)phenylacetyl], Abs] | ++ | ++ |
| [structure: 6-(trifluoromethyl)pyridin-3-ylmethyl pyrrolothiazole isopropyl, N-[4-(ethylsulfonyl)phenylacetyl], Abs] | ++ | |
| [structure: 1-(3-(trifluoromethyl)phenyl)ethyl pyrrolothiazole isopropyl, N-[4-(ethylsulfonyl)phenylacetyl], Abs] | +++ | + |
| [structure: (tetrahydro-2H-pyran-4-yl)methyl pyrrolothiazole isopropyl, N-[4-(ethylsulfonyl)phenylacetyl], Abs] | ++ | |

TABLE 9-continued
| Compound | RORγ Binding Ki Range* (nM) | RORγt5X IC50 Range* (nM) |
|---|---|---|
| 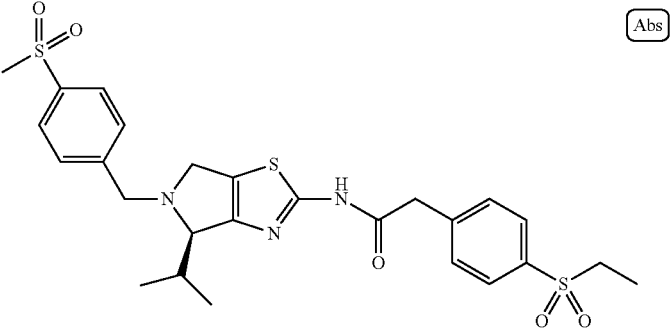 [SMILES: CCS(=O)(=O)c1ccc(CC(=O)Nc2nc3c(s2)CN(Cc2ccc(S(C)(=O)=O)cc2)[C@@H]3C(C)C)cc1] | ++ | |
| 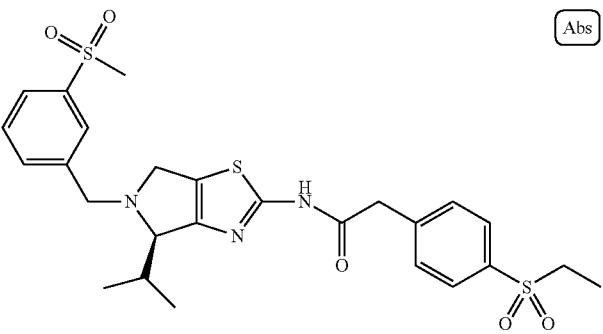 [SMILES: CCS(=O)(=O)c1ccc(CC(=O)Nc2nc3c(s2)CN(Cc2cccc(S(C)(=O)=O)c2)[C@@H]3C(C)C)cc1] | ++ | + |
| 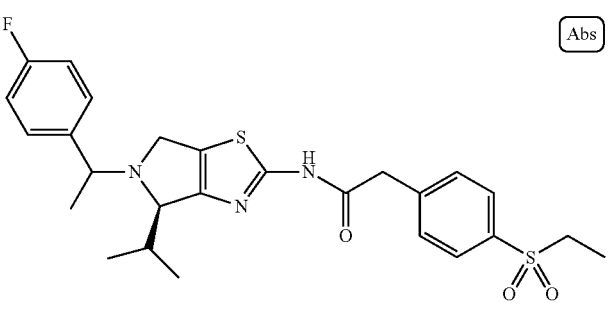 [SMILES: CCS(=O)(=O)c1ccc(CC(=O)Nc2nc3c(s2)CN(C(C)c2ccc(F)cc2)[C@@H]3C(C)C)cc1] | +++ | + |
| 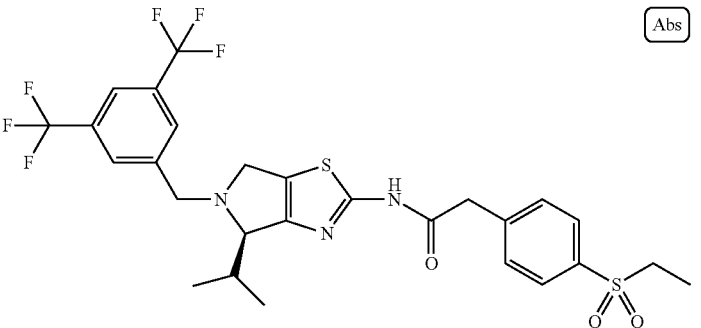 [SMILES: CCS(=O)(=O)c1ccc(CC(=O)Nc2nc3c(s2)CN(Cc2cc(C(F)(F)F)cc(C(F)(F)F)c2)[C@@H]3C(C)C)cc1] | +++ | + |

TABLE 9-continued

| Compound | RORγ Binding Ki Range* (nM) | RORγt5X IC50 Range* (nM) |
|---|---|---|
| [structure: 3,5-dimethoxybenzyl pyrrolothiazole isopropyl, phenyl ethylsulfonyl acetamide] (Abs) | +++ | + |
| [structure: 2,5-dichlorobenzyl pyrrolothiazole isopropyl, phenyl ethylsulfonyl acetamide] (Abs) | +++ | + |
| [structure: 4-trifluoromethoxybenzyl pyrrolothiazole isopropyl, phenyl ethylsulfonyl acetamide] (Abs) | +++ | ++ |
| [structure: 3-chloro-4-trifluoromethylbenzyl pyrrolothiazole isopropyl, phenyl ethylsulfonyl acetamide] (Abs) | +++ | ++ |
| [structure: 4-fluorobenzyl pyrrolothiazole isopropyl, phenyl ethylsulfonyl acetamide] (Abs) | +++ | + |

TABLE 9-continued
| Compound | RORγ Binding Ki Range* (nM) | RORγt5X IC50 Range* (nM) |
|---|---|---|
| 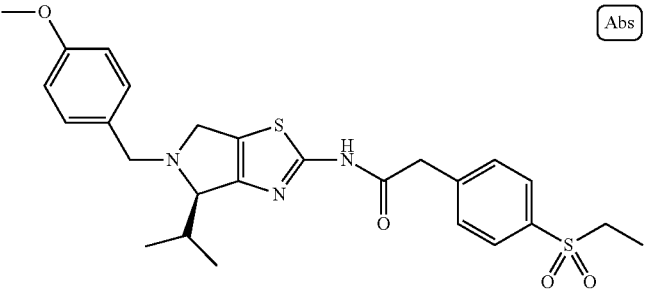 [SMILES: CCS(=O)(=O)c1ccc(CC(=O)Nc2nc3c(s2)CN(Cc2ccc(OC)cc2)[C@@H]3C(C)C)cc1] | +++ | + |
| 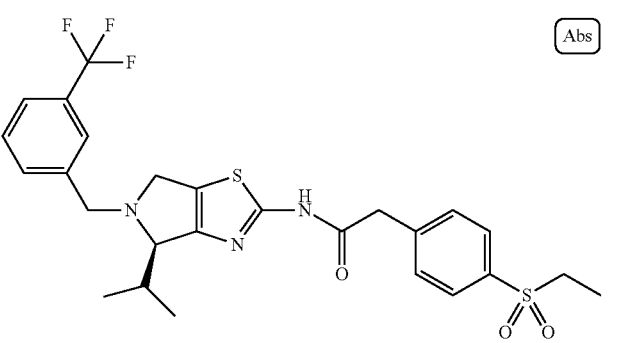 [SMILES: CCS(=O)(=O)c1ccc(CC(=O)Nc2nc3c(s2)CN(Cc2cccc(C(F)(F)F)c2)[C@@H]3C(C)C)cc1] | +++ | + |
| 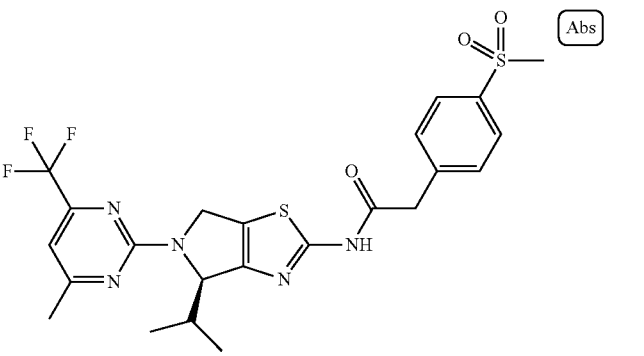 [SMILES: Cc1cc(C(F)(F)F)nc(N2Cc3sc(NC(=O)Cc4ccc(S(C)(=O)=O)cc4)nc3[C@H]2C(C)C)n1] | ++ | + |
| 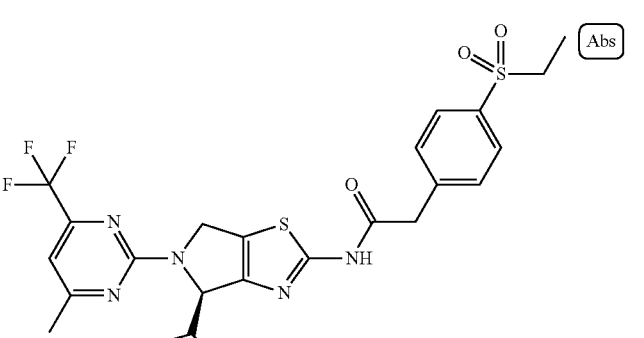 | +++ | + |
| 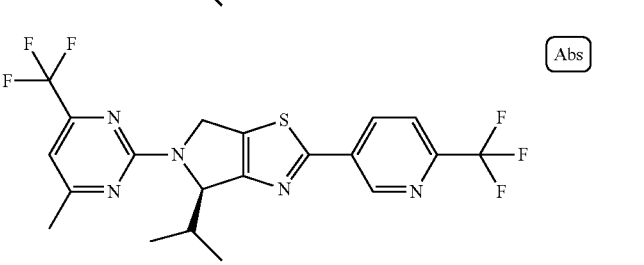 | | + |

TABLE 9-continued

| Compound | RORγ Binding Ki Range* (nM) | RORγt5X IC50 Range* (nM) |
|---|---|---|
| [structure with tetrazole, Abs] | ++ | |
| [structure with nitrile, Abs] | + | |

*+ means >1000 nM; ++ means 100 nM-1000 nM; +++ means <100 nM.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A compound of Formula (I):

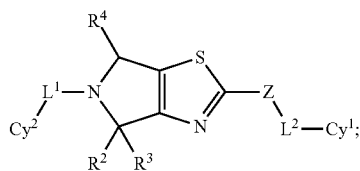

or a pharmaceutically acceptable salt thereof, wherein:

Z is —C(O)NR$^1$—, —NR$^1$C(O)—, —NR$^1$—, or NR$^1$SO$_2$;

R$^1$ is hydrogen or (C$_1$-C$_3$)alkyl;

L$^1$ and L$^2$ are each independently a bond or (C$_1$-C$_3$) alkylene optionally substituted with (C$_1$-C$_2$)alkyl or spirocyclopropane;

R$^2$ is (C$_1$-C$_6$)alkyl, halo(C$_1$-C$_6$)alkyl, phenyl, benzyl, heteroaryl, monocyclic cycloalkyl or monocyclic heterocyclyl, each optionally substituted with 1 to 2 groups independently selected from CN, halo, hydroxyl, (C$_1$-C$_6$)alkyl, halo(C$_1$-C$_6$)alkyl, (C$_1$-C$_6$)alkoxy, oxo, and halo(C$_1$-C$_6$)alkoxy;

R$^3$ is hydrogen or (C$_1$-C$_3$)alkyl;

Cy$^1$ is aryl or heteroaryl, each of which is optionally substituted with 1 to 3 groups independently selected from R$^5$;

R$^4$ is hydrogen or (C$_1$-C$_3$)alkyl; and

Cy$^2$ is aryl, heteroaryl, monocyclic cycloalkyl, or monocyclic heterocyclyl, wherein the aryl and heteroaryl are each optionally fused with a monocyclic heterocyclyl or monocyclic cycloalkyl, and wherein Cy$^2$ is optionally substituted with 1 to 3 groups independently selected from R$^6$; and R$^5$ and R$^6$ are each independently selected from halo, cyano, nitro, amino, hydroxy, carboxy, (C$_1$-C$_6$)alkyl, heterocyclyl, hydroxy(C$_1$-C$_6$)alkyl, CO$_2$H, (CH$_2$)$_{1-3}$COOH, (C$_3$-C$_6$)cycloalkyl, hydroxy(C$_3$-C$_6$) cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$) alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$) cycloalkoxy, halo(C$_4$-C$_7$)cycloalkylalkoxy, (C$_1$-C$_6$) alkylthio, (C$_3$-C$_6$)cycloalkythio, (C$_4$-C$_7$) cycloalkylalkylthio, halo(C$_1$-C$_6$)alkylthio, halo(C$_3$-C$_6$) cycloalkythio, halo(C$_4$-C$_7$)cycloalkylalkylthio, (C$_1$-C$_6$)alkylsulfonyl, (C$_3$-C$_6$)cycloalkylsulfinyl, (C$_4$-C$_7$) cycloalkylalkylsulfinyl, halo(C$_1$-C$_6$)alkylsulfonyl, halo (C$_3$-C$_6$)cycloalkylsulfinyl, halo(C$_4$-C$_7$) cycloalkylalkylsulfinyl, (C$_1$-C$_6$)alkylsulfonyl, (C$_3$-C$_6$) cycloalkylsulfonyl, (C$_4$-C$_7$)cycloalkylalkylsulfonyl, halo(C$_1$-C$_6$)alkylsulfonyl, halo(C$_3$-C$_6$)cycloalkylsulfonyl, halo(C$_4$-C$_7$)cycloalkylalkylsulfonyl, (C$_1$-C$_6$)alkylamino, di(C$_1$-C$_6$)alkylamino, (C$_1$-C$_6$)alkoxy(C$_1$-C$_6$) alkoxy, halo(C$_1$-C$_6$)alkoxy(C$_1$-C$_6$)alkoxy, (C$_1$-C$_6$) alkoxycarbonyl, H$_2$NCO, H$_2$NSO$_2$, (C$_1$-C$_6$) alkylaminocarbonyl, di(C$_1$-C$_6$)alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$) alkylaminosulfonyl, heterocyclylsulfonyl, (C$_1$-C$_6$) alkylcarbonylamino, (C$_1$-C$_6$)alkylcarbonylamino(C$_1$-C$_6$)alkyl, (C$_1$-C$_6$)alkylsulfonylamino, (C$_1$-C$_6$) alkylsulfonylamino(C$_1$-C$_6$)alkyl, (C$_1$-C$_6$) alkoxycarbonyl(C$_1$-C$_6$)alkoxy, (C$_1$-C$_6$)alkoxy(C$_1$-C$_6$) alkyl, halo(C$_1$-C$_6$)alkoxy(C$_1$-C$_6$)alkyl, hydroxy(C$_1$-C$_6$)alkoxy, aryl, heteroaryl, oxo, amino(C$_1$-C$_6$)alkyl, (C$_1$-C$_6$)alkylamino(C$_1$-C$_6$)alkyl, di(C$_1$-C$_6$)alkylamino (C$_1$-C$_6$)alkyl amino(C$_2$-C$_6$)alkoxy, (C$_1$-C$_6$)alkylamino (C$_2$-C$_6$)alkoxy, di(C$_1$-C$_6$)alkylamino(C$_2$-C$_6$)alkoxy, (C$_1$-C$_6$)alkylcarbonyl, (C$_3$-C$_6$)cycloalkylcarbonyl, (C$_3$-C$_6$)cycloalkylaminocarbonyl, {(C$_3$-C$_6$)cycloalkyl}{(C$_1$-C$_6$)alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$) alkyl}aminosulfonyl, di(C$_3$-C$_6$) cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$) alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl (C$_1$-C$_6$)alkyl and di(C$_3$-C$_6$)cycloalkylaminocarbonyl (C$_1$-C$_6$)alkyl.

2. The compound of claim 1, wherein the compound is of Formula (Ia):

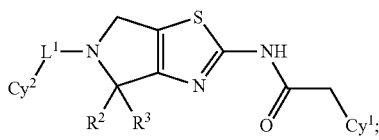

or a pharmaceutically acceptable salt thereof.

3. The compound of claim 2, wherein the compound is of Formula (Ib):

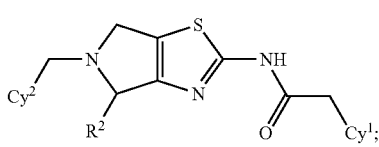

or a pharmaceutically acceptable salt thereof.

4. The compound of claim 3, wherein the compound is of Formula (Ib'):

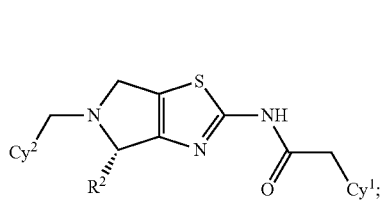

(Ib')

or a pharmaceutically acceptable salt thereof.

5. The compound of claim 4, wherein $Cy^1$ is phenyl, pyridinyl, or pyrimidinyl, each of which is optionally substituted with 1 to 3 groups independently selected from $R^5$.

6. The compound of claim 5, wherein $Cy^2$ is phenyl, pyridinyl, pyrimidinyl, cyclohexyl, or oxadiazolyl, each of which are optionally substituted with 1 to 3 groups independently selected from $R^6$.

7. The compound of claim 6, wherein $R^5$ is selected from halo, cyano, $(C_1-C_3)$alkyl, halo$(C_1-C_3)$alkyl, hydroxy$(C_1-C_3)$alkyl, $(C_1-C_6)$alkoxy, halo$(C_1-C_6)$alkoxy, $CO_2H$, $(CH_2)_{1-3}COOH$, and $(C_1-C_3)$alkylsulfonyl.

8. The compound of claim 7, wherein $R^2$ is isopropyl, isobutyl, sec-butyl, phenyl, benzyl, cyclopropyl, tetrahydrofuranyl, or tetrahydropyranyl, wherein the phenyl and benzyl are each optionally substituted with 1 to 2 groups independently selected from CN, halo, $(C_1-C_6)$alkyl, halo$(C_1-C_6)$alkyl, $(C_1-C_6)$alkoxy, and halo$(C_1-C_6)$alkoxy.

9. The compound of claim 8, wherein:
$Cy^1$ is phenyl, 2-pyridinyl, or 2-pyrimidinyl, each of which is optionally substituted with 1 to 2 groups independently selected from halo, $(C_1-C_3)$alkyl, $(CH_2)_{1-3}COOH$, $(C_1-C_3)$alkylsulfonyl, cyano, or hydroxy$(C_1-C_3)$alkyl; and
$R^2$ is isopropyl, isobutyl, sec-butyl, phenyl, benzyl, or cyclopropyl, wherein the phenyl and benzyl are each optionally substituted with 1 to 2 groups independently selected from CN, halo, $(C_1-C_3)$alkyl, and $(C_1-C_3)$alkoxy.

10. The compound of claim 9, wherein:
$Cy^1$ is phenyl optionally substituted with 1 to 2 groups independently selected from halo, $(C_1-C_3)$alkyl, $CH_2COOH$, $(C_1-C_3)$alkanesulfonyl, cyano, or hydroxy$(C_1-C_3)$alkyl; and
$R^2$ is isopropyl, isobutyl, sec-butyl, phenyl, benzyl, or cyclopropyl, wherein the phenyl and benzyl are each optionally substituted with 1 to 2 groups independently selected from CN, halo, $(C_1-C_3)$alkyl, and $(C_1-C_3)$alkoxy.

11. The compound of claim 10, wherein the compound is of Formula (Ic):

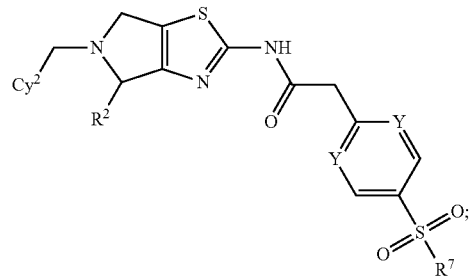

(Ic)

or a pharmaceutically acceptable salt thereof, wherein:
each Y is independently CH, $CR^5$, or N; and
$R^7$ is $(C_1-C_3)$alkyl.

12. The compound of claim 11, wherein the compound is of Formula (Id):

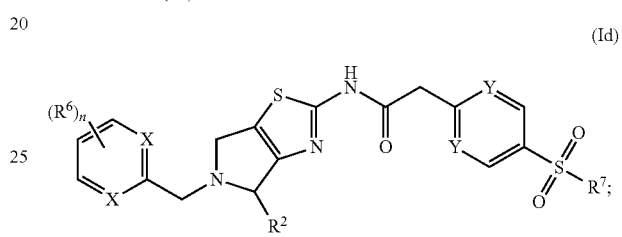

(Id)

or a pharmaceutically acceptable salt thereof, wherein:
each X is independently CH, $CR^6$, or N;
each Y is independently CH, $CR^5$, or N;
n is 0, 1, or 2; and
$R^7$ is $(C_1-C_3)$alkyl.

13. The compound of claim 12, wherein $R^2$ is isopropyl, cyclopropyl, isobutyl or sec-butyl.

14. The compound of claim 13, wherein $R^2$ is isopropyl.

15. The compound of claim 14, wherein $R^6$ is selected from halo, cyano, nitro, amino, hydroxy, carboxy, $(C_1-C_6)$alkyl, hydroxy$(C_1-C_6)$alkyl, $H_2NCO$, $(C_2-C_6)$alkenyl, halo$(C_2-C_6)$alkenyl, hydroxy$(C_2-C_6)$alkenyl, halo$(C_1-C_6)$alkyl, $(C_1-C_6)$alkoxy, halo$(C_1-C_6)$alkoxy, $(C_1-C_6)$alkylsulfinyl, halo$(C_1-C_6)$alkylsulfinyl $(C_1-C_6)$alkylsulfonyl, halo$(C_1-C_6)$alkylsulfonyl, oxo, amino$(C_1-C_6)$alkyl, $(C_1-C_6)$alkylcarbonyl, and aminocarbonyl$(C_1-C_6)$alkyl.

16. The compound of claim 15, wherein $R^6$ is selected from halo, cyano, nitro, amino, hydroxy, carboxy, $(C_1-C_6)$alkyl, hydroxy$(C_1-C_6)$alkyl, $(C_2-C_6)$alkenyl, halo$(C_1-C_6)$alkyl, $(C_1-C_6)$alkoxy, and halo$(C_1-C_6)$alkoxy.

17. The compound of claim 16, wherein $R^6$ is halo, cyano, halo$(C_1-C_3)$alkyl, or halo$(C_1-C_3)$alkoxy.

18. A pharmaceutical composition comprising the compound of claim 1, or a pharmaceutically acceptable salt thereof, and a pharmaceutically acceptable carrier.

19. A method of treating one or more diseases or disorders selected from ankylosing spondylitis, psoriasis and psoriatic arthritis (PsA).

* * * * *